US009840724B2

(12) United States Patent
Anthony et al.

(10) Patent No.: US 9,840,724 B2
(45) Date of Patent: Dec. 12, 2017

(54) PRODUCTION OF RENEWABLE HYDROCARBON COMPOSITIONS

(71) Applicant: Butamax Advanced Biofuels LLC, Wilmington, DE (US)

(72) Inventors: Larry Cameron Anthony, Aston, PA (US); Tyler T. Ames, Wilmington, DE (US); Keith H. Burlew, Middletown, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 158 days.

(21) Appl. No.: 14/428,197

(22) PCT Filed: Sep. 20, 2013

(86) PCT No.: PCT/US2013/060871
§ 371 (c)(1),
(2) Date: Mar. 13, 2015

(87) PCT Pub. No.: WO2014/047421
PCT Pub. Date: Mar. 27, 2014

(65) Prior Publication Data
US 2015/0240267 A1    Aug. 27, 2015

Related U.S. Application Data

(60) Provisional application No. 61/704,295, filed on Sep. 21, 2012.

(51) Int. Cl.
| | | |
|---|---|---|
| *C12P 7/16* | (2006.01) | |
| *C10L 1/18* | (2006.01) | |
| *C12N 9/10* | (2006.01) | |
| *C12N 9/88* | (2006.01) | |
| *C12P 5/00* | (2006.01) | |
| *F02D 19/08* | (2006.01) | |
| *C10L 1/183* | (2006.01) | |

(52) U.S. Cl.
CPC ..... *C12P 7/16* (2013.01); *C10L 1/18* (2013.01); *C12N 9/1025* (2013.01); *C12N 9/88* (2013.01); *C12P 5/00* (2013.01); *C12Y 206/00* (2013.01); *C10L 1/1832* (2013.01); *C10L 2200/0423* (2013.01); *C10L 2200/0469* (2013.01); *C10L 2290/24* (2013.01); *C10L 2290/26* (2013.01); *C10L 2290/543* (2013.01); *C12P 2201/00* (2013.01); *C12Y 203/03013* (2013.01); *C12Y 403/01019* (2013.01); *F02D 19/084* (2013.01); *Y02E 50/10* (2013.01); *Y02T 10/36* (2013.01)

(58) Field of Classification Search
CPC .................................................. C12P 7/16
USPC ................................................ 435/252.3, 206
See application file for complete search history.

(56) References Cited

U.S. PATENT DOCUMENTS

| | | |
|---|---|---|
| 5,231,017 A | 7/1993 | Lantero et al. |
| 7,541,173 B2 | 6/2009 | Bramucci et al. |
| 7,659,104 B2 | 2/2010 | Bramucci et al. |
| 7,851,188 B2 | 12/2010 | Donaldson et al. |
| 7,910,342 B2 | 3/2011 | Liao et al. |
| 7,993,889 B1 | 8/2011 | Donaldson et al. |
| 8,017,364 B2 | 9/2011 | Bramucci et al. |
| 8,129,162 B2 | 3/2012 | Li et al. |
| 8,178,328 B2 | 5/2012 | Donaldson et al. |
| 8,188,250 B2 | 5/2012 | Bramucci et al. |
| 8,206,970 B2 | 6/2012 | Eliot et al. |
| 8,222,017 B2 | 7/2012 | Li et al. |
| 8,241,878 B2 | 8/2012 | Anthony et al. |
| 8,273,558 B2 | 9/2012 | Donaldson et al. |
| 8,283,144 B2 | 10/2012 | Donaldson et al. |
| 8,372,612 B2 | 2/2013 | Larossa et al. |
| 8,389,252 B2 | 3/2013 | Larossa |
| 8,455,224 B2 | 6/2013 | Paul |
| 8,455,225 B2 | 6/2013 | Bramucci et al. |
| 8,465,964 B2 | 6/2013 | Anthony |
| 8,518,678 B2 | 8/2013 | Flint et al. |
| 8,557,540 B2 | 10/2013 | Burlew et al. |
| 8,557,562 B2 | 10/2013 | Bramucci et al. |
| 8,614,085 B2 | 12/2013 | Van Dyk |
| 8,637,281 B2 | 1/2014 | Paul et al. |
| 8,637,289 B2 | 1/2014 | Anthony et al. |
| 8,652,823 B2 | 2/2014 | Flint et al. |
| 8,669,094 B2 | 3/2014 | Anthony et al. |
| 8,691,540 B2 | 4/2014 | Bramucci et al. |
| 8,735,114 B2 | 5/2014 | Donaldson et al. |
| 8,765,433 B2 | 7/2014 | Satagopan et al. |
| 8,785,166 B2 | 7/2014 | Anthony |
| 8,795,992 B2 | 8/2014 | Bramucci et al. |
| 8,828,694 B2 | 9/2014 | Anthony et al. |
| 8,828,695 B2 | 9/2014 | Grady et al. |

(Continued)

FOREIGN PATENT DOCUMENTS

| | | |
|---|---|---|
| EP | 0624388 | 1/1998 |
| WO | WO2005040392 | 5/2005 |

(Continued)

OTHER PUBLICATIONS

Huo, et al., Conversion of Proteins into Biofuels by Engineering Nitrogen Flux, Nature Biotechnol. 29:346-351; 2011.
Van Nedervelde, et al., Role of the branched-chain amino acid aminotransferases on the production of volatile compounds by *Saccharomyces cerevisiae*, Proceedings of the Congress European Brewery Convention, 29th Congress, Dublin Dublin 2003 50/1-50/10.
Piddocke, et al., Revealing the beneficial effect of protease supplementation to high gravity beer fermentations using "-omics" techniques, Microbial Cell Factories 10:27, 2011.
Hazelwood, et al., The Ehrlich pathway for fusel alcohol production: a century of research on *Saccharomyces cerevisiae* metabolism, Appl. Environ. Microbiol. 74:2259-2266, 2008.

(Continued)

*Primary Examiner* — Maryam Monshipouri

(57) ABSTRACT

Provided herein are processes and microorganisms which utilize both protein hydrolysates and carbohydrates from biomass feedstocks to produce renewable hydrocarbon compositions. Advantages of the disclosed methods may be recognized in fuel blends comprising such hydrocarbon compositions.

10 Claims, 18 Drawing Sheets

(56) References Cited

U.S. PATENT DOCUMENTS

| | | | |
|---|---|---|---|
| 8,828,704 B2 | 9/2014 | Donaldson et al. |
| 8,871,488 B2 | 10/2014 | Dauner et al. |
| 8,889,385 B2 | 11/2014 | Donaldson et al. |
| 8,895,307 B2 | 11/2014 | Li et al. |
| 8,906,666 B2 | 12/2014 | Alsaker et al. |
| 8,911,981 B2 | 12/2014 | Li et al. |
| 8,940,511 B2 | 1/2015 | Larossa |
| 8,945,859 B2 | 2/2015 | Donaldson et al. |
| 8,945,899 B2 | 2/2015 | Li et al. |
| 8,951,774 B2 | 2/2015 | Donaldson et al. |
| 8,951,937 B2 | 2/2015 | Flint et al. |
| 8,956,850 B2 | 2/2015 | Anthony et al. |
| 8,962,298 B2 | 2/2015 | Donaldson et al. |
| 8,969,065 B2 | 3/2015 | Anthony et al. |
| 8,980,612 B2 | 3/2015 | Donaldson et al. |
| 9,068,190 B2 | 6/2015 | Donaldson et al. |
| 9,080,179 B2 | 7/2015 | Paul |
| 9,109,196 B2 | 8/2015 | Bazzana et al. |
| 9,156,760 B2 | 10/2015 | Zaher |
| 9,163,266 B2 | 10/2015 | Anthony |
| 9,169,467 B2 | 10/2015 | Govindarajan et al. |
| 9,169,499 B2 | 10/2015 | Paul et al. |
| 9,181,566 B2 | 11/2015 | Dauner et al. |
| 9,206,447 B2 | 12/2015 | Anthony et al. |
| 9,238,801 B2 | 1/2016 | Li et al. |
| 9,238,828 B2 | 1/2016 | McElvain et al. |
| 9,260,708 B2 | 2/2016 | Anthony et al. |
| 9,267,157 B2 | 2/2016 | Anthony et al. |
| 9,273,330 B2 | 3/2016 | Bramucci et al. |
| 9,284,612 B2 | 3/2016 | Liao et al. |
| 9,297,016 B2 | 3/2016 | Flint et al. |
| 9,297,028 B2 | 3/2016 | Donaldson et al. |
| 9,297,029 B2 | 3/2016 | Donaldson et al. |
| 9,303,225 B2 | 4/2016 | Donaldson et al. |
| 9,365,872 B2 | 6/2016 | Donaldson et al. |
| 9,388,392 B2 | 7/2016 | Govindarajan et al. |
| 9,404,117 B2 | 8/2016 | Anthony |
| 9,422,582 B2 | 8/2016 | Anthony et al. |
| 9,523,104 B2 | 12/2016 | Fuchs et al. |
| 9,670,511 B2 | 6/2017 | Roesch et al. |
| 2009/0081746 A1 | 3/2009 | Liao et al. |
| 2009/0162911 A1 | 6/2009 | Larossa et al. |
| 2009/0288337 A1 | 11/2009 | Picataggio et al. |
| 2009/0305369 A1 | 12/2009 | Donaldson et al. |
| 2009/0305370 A1 | 12/2009 | Grady et al. |
| 2010/0081154 A1 | 4/2010 | Flint et al. |
| 2010/0081182 A1 | 4/2010 | Paul et al. |
| 2010/0093020 A1 | 4/2010 | Bramucci et al. |
| 2010/0120105 A1 | 5/2010 | Anthony et al. |
| 2010/0129887 A1 | 5/2010 | Anthony |
| 2010/0209986 A1 | 8/2010 | Liao et al. |
| 2011/0195505 A1 | 8/2011 | Euler et al. |
| 2011/0244536 A1 | 10/2011 | Nagarajan et al. |
| 2012/0045809 A1 | 2/2012 | Buelter et al. |
| 2012/0058541 A1 | 3/2012 | Alsaker et al. |
| 2012/0149080 A1 | 6/2012 | Bramucci et al. |
| 2012/0156738 A1 | 6/2012 | Anton et al. |
| 2012/0164302 A1 | 6/2012 | Roesch et al. |
| 2012/0196341 A1 | 8/2012 | Donaldson et al. |
| 2012/0258873 A1 | 10/2012 | Gibson et al. |
| 2013/0035515 A1 | 2/2013 | Dobson et al. |
| 2013/0252296 A1 | 9/2013 | Maggio-Hall |
| 2014/0024064 A1 | 1/2014 | Burlew et al. |
| 2014/0030782 A1 | 1/2014 | Anthony et al. |
| 2014/0030783 A1 | 1/2014 | Anthony et al. |
| 2014/0038263 A1 | 2/2014 | Flint et al. |
| 2014/0038268 A1 | 2/2014 | Flint et al. |
| 2014/0051137 A1 | 2/2014 | Flint et al. |
| 2014/0073820 A1 | 3/2014 | Bazzana et al. |
| 2014/0093930 A1 | 4/2014 | Li et al. |
| 2014/0106419 A1 | 4/2014 | Bazzana et al. |
| 2014/0141479 A1 | 5/2014 | Anthony et al. |
| 2014/0170732 A1 | 6/2014 | Bramucci et al. |
| 2014/0186910 A1 | 7/2014 | Rothman et al. |
| 2014/0186911 A1 | 7/2014 | Anthony et al. |
| 2014/0273116 A1 | 9/2014 | Kelly et al. |
| 2014/0273129 A1 | 9/2014 | Bhalla et al. |
| 2014/0273130 A1 | 9/2014 | Anthony et al. |
| 2014/0349349 A1 | 11/2014 | Dauner et al. |
| 2014/0377824 A1 | 12/2014 | Satagopan et al. |
| 2015/0037855 A1 | 2/2015 | Bhadra et al. |
| 2015/0111269 A1 | 4/2015 | Li et al. |
| 2015/0125920 A1 | 5/2015 | Anthony et al. |
| 2015/0211026 A1 | 7/2015 | Bazzana et al. |
| 2015/0218595 A1 | 8/2015 | Bhadra et al. |
| 2015/0267225 A1 | 9/2015 | Bazzana et al. |
| 2016/0024534 A1 | 1/2016 | Anthony et al. |
| 2016/0130612 A1 | 5/2016 | Anthony et al. |
| 2016/0138050 A1 | 5/2016 | Bramucci |
| 2016/0222370 A1 | 8/2016 | Anthony et al. |
| 2016/0319307 A1 | 11/2016 | Nagarajan et al. |
| 2016/0326551 A1 | 11/2016 | Van Dyk et al. |
| 2016/0326552 A1 | 11/2016 | Dauner et al. |

FOREIGN PATENT DOCUMENTS

| | | |
|---|---|---|
| WO | WO2007032522 | 3/2007 |
| WO | WO2008098227 | 8/2008 |
| WO | WO2011019894 | 2/2011 |
| WO | WO2011041415 | 4/2011 |
| WO | WO2013003545 | 1/2013 |

OTHER PUBLICATIONS

Schoondermark-Stolk, et al., Bat2p is essential in *Saccharomyces cerevisiae* for fusel alcohol production on the non-fermentable carbon source ethanol, FEMS Yeast Res. 5:757-766, 2005.

Holmberg M.M. et al., Regulation of isoleucine-valine biosynthesis in *Saccharomyces cerevisiae*,Curr. Genetics 13:207-217, 1988.

International Search Report for for corresponding PCT/US2013/060871, dated Mar. 5, 2014.

International Preliminary Report on Patentability for corresponding PCT/US2013/060871, dated Mar. 24, 2015.

Dickinson, et al., An Investigation o f the Metabolism of Valine to isobutyl Alcohol in *Saccharornyces cerevisiae*, J. Biol. Chem. 273:25751-25756, 1998.

Lilly, et al., The effect of increased branched-chainamino acid transaminase activity in yeast on the production of higher alcohols and on the flavour profiles of wine and distillates, FEMS Yeast Res, 6:7.26-743, 2006.

Chen, et al., Increased isobutanol production in *Saccharomyces cerevisiae* by overexpression of genes in valine metabolism, Biotechnology for Biofuels 4:21, 2011.

Yoshimoto, et al., Genetic and physiological analysis of branched-chain alcohols and isoamyl acetate production in *Saccharomyces cerevisiae*, Appl. Microbiol. Biotechnol. 59:501-508, 2002.

Lynd, et al., Microbial Cellulose Utilization: Fundamentals and Biotechnology, Microbiol. Mol. Biol, Rev. 66:506-577, 2002.

Guymon, et al., The formation of n-propyl alcohol by *Saccharomyces cerevisiae*, Arch. Biochem. Bophys. 95:163-168, 1961 Abstract only.

Guymon, et al., Influence of Aeration upon the formation of Higher Alcohols by Yeasts, American J. Enology and Viticulture 12:60-66, 1961 Abstract only.

Hazelwood, et al., A new physiological role for Pdr12p in *Saccharomyces cerevisiae*: export of aromatic and branched-chain organic acids produced in amino acid catabolism, FEMS Yeast Res. 6:937-945, 2006.

Durre, New insights and novel developments in clostridial acetoneibutanollisopropanol fermentation, Appl. Microbiol. Biotechnol. 49: 639-648, 1998.

Groot, et al., Technologies for Butanol Recovery Integrated with Fermentations, Process Biochem. 27:61-75, 1992.

Aden, et al., Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, Jun. 2002.

Guo, et al., Pervaporation study on the dehydration of aqueous butanol solutions: a comparison of flux vs. perrneance, separation factor vs. selectivity, J. Mernbr. Sci. 245:199-210, 2004.

PRODUCTION OF RENEWABLE HYDROCARBON COMPOSITIONS

CROSS-REFERENCE TO RELATED APPLICATIONS

This application is related to and claims the benefit of priority of U.S. Provisional Application Ser. No. 61/704,295, filed on Sep. 21, 2012, the entirety of which is herein incorporated herein by reference.

REFERENCE TO SEQUENCE LISTING SUBMITTED ELECTRONICALLY

The content of the electronically submitted sequence listing in ASCII text file (Name:, 20130920_CL5716WOPCT_SeqList_ST25.txt; Size: 509,049 bytes; Date of Creation: Sep. 19, 2013) filed with the application is incorporated herein by reference in its entirety.

FIELD OF THE INVENTION

The invention relates to methods for fermentative co-production of butanol and fusel alcohols, as well as recombinant host cells thereof.

BACKGROUND OF THE INVENTION

Butanol is an important industrial chemical, useful as a fuel, fuel component and fuel additive, as a chemical solvent, feedstock in various chemical markets, such as the plastics industry, and as a food grade extractant in the food and flavor industry. Each year 10 to 12 billion pounds of butanol are produced by petrochemical means and the need for this commodity chemical will likely increase in the future.

Methods for the chemical synthesis of isobutanol are known, such as oxo synthesis, catalytic hydrogenation of carbon monoxide (Ullmann's Encyclopedia of Industrial Chemistry, 6th edition, 2003, Wiley-VCH Verlag GmbH and Co., Weinheim, Germany, Vol. 5, pp. 716-719) and Guerbet condensation of methanol with n-propanol (Carlini et al., *J. Molec. Catal. A. Chem.*, 220:215-220 (2004)). These processes use starting materials derived from petrochemicals. The production of isobutanol from plant-derived raw materials would represent an advance in the art.

Isobutanol is produced biologically as a by-product of yeast fermentation. It is a component of "fusel oil" that forms as a result of the incomplete metabolism of amino acids by fungi. Isobutanol is specifically produced from catabolism of L-valine. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.*, 273:25752-25756, 1998). U.S. Pat. Nos. 7,851,188 and 7,993,889 describe enzymatic pathways for the production of isobutanol in recombinant microorganisms.

An increase in the yield of C3-C5 alcohols from carbohydrates was shown when amino acids leucine, isoleucine, and/or valine were added to the growth medium as the nitrogen source (Internat'l. Patent Pub. No. WO 2005/040392). Similarly, Lilly et al. (*FEMS Yeast Res.*, 6(5):726-743 (2006)) have demonstrated that the addition of a high concentration of valine to a fermentation medium increased *Saccharomyces cerevisiae* production of isobutanol, isobutyric acid, propanol and propionic acid concentrations.

Nako et al (Internat'l. Patent Pub. No. WO 2007/032522) note that amyl alcohol and/or isobutanol and/or isoamyl acetate levels in yeast used for the production of alcoholic beverages may be altered via manipulation of the BAT1 and BAT2 genes. See also, Chen, X. et al. (*Biotechnology for Biofuels*, 4:21 (2011)) and Yoshimoto, H., et al. (*Appl. Microbial. Biotechnol.*, 59:501-508 (2002)).

U.S. Pat. Pub. No. 20100209986 describes means to produce metabolically-modified microorganisms useful for producing biofuels (e.g., isobutanol, 1-butanol, 1-propanol, 2-methyl-1-butanol, 3-methyl-1-butanol and 2-phenylethanol) from a suitable substrate. The methodology utilizes the organism's native metabolites in the amino acid biosynthetic pathway to produce biofuels by increasing flux towards the production of a 2-keto acid. The microorganism may comprise a 2-keto-acid decarboxylase, preferably selected from the group consisting of Pdc, Pdc1, Pdc5, Pdc6, Aro10, Thi3, KivD, and KdcA.

U.S. Pat. Pub. No. 20120045809 describes a recombinant eukaryotic microorganism capable of producing isobutanol from a carbon source, said recombinant eukaryotic microorganism comprising an isobutanol producing metabolic pathway, wherein said recombinant eukaryotic microorganism may overexpress a valine transaminase (encoded, e.g. by BAT1 or BAT2).

Enzymatic saccharification of cellulosic and/or lignocellulosic biomass may be employed to break down cellulose and hemicellulose to produce a hydrolysate containing sugars suitable for consumption by microorganisms (Lynd, et al., *Microbiol. Mol. Biol. Rev.*, 66:506-577 (2002)). U.S. Pat. No. 5,231,017 describes a process for producing ethanol from raw materials, wherein a protease is utilized in combination with alpha-amylase and glucoamylase, to increase the rate and yield of ethanol production. Huo, Y.-X., et al. (*Nature Biotechnol*, 29(4):346-352 (2011)) suggest that a nitrogen-centric metabolic engineering strategy could be utilized to utilize proteins as feedstock for the production of biofuels.

Improvements and alternatives for the biosynthesis of butanol directly from plant-derived raw materials would improve economic viability and would represent an advance in the art.

SUMMARY OF THE INVENTION

Provided herein are methods for producing a renewable hydrocarbon composition comprising isobutanol, the methods comprising: a) providing a biomass feedstock; b) processing the biomass feedstock to produce a processed feedstock slurry comprising protein hydrolysates and fermentable carbohydrate; c) adding the processed feedstock slurry to a fermentation medium; d) contacting the fermentation medium comprising processed feedstock slurry with a recombinant yeast host cell modified to produce a fermentation composition comprising isobutanol from carbohydrate and from protein hydrolysate; and (e) recovering a renewable hydrocarbon composition from the fermentation composition by distillation; whereby the renewable hydrocarbon composition comprising at least about 90% isobutanol is produced. In embodiments, processing the biomass feedstock to produce a processed feedstock slurry comprising protein hydrolysates and oligosaccharides comprises liquefying the biomass feedstock in the presence of at least one protease. In embodiments, processing the biomass feedstock to produce a processed feedstock slurry comprising protein hydrolysates and oligosaccharides comprises: liquefying the biomass feedstock to create a feedstock slurry comprising oligosaccharides, undissolved solids, and water; separating at least a portion of the undissolved solids from the feedstock slurry of step (a) to generate: 1) an aqueous solution comprising oligosaccharides; and 2) a wet cake co-product comprising solids; hydrolyzing the wet cake co-product to produce protein hydrolysates; and, mixing the aqueous solution comprising oligosaccharides with the protein hydrolysates to produce a processed feedstock slurry comprising protein hydrolysates and oligosaccharides. In embodiments, the wet cake co-product is hydrolyzed by a means selected from the group consisting of: acid hydrolysis, base hydrolysis and enzymatic hydrolysis. In embodiments, the recombinant yeast host cell modified to produce isobutanol from carbohydrate and from protein hydrolysate comprises: a heterologous isobutanol biosynthetic pathway for production of isobutanol; and, at least one upregulated Ehrlich pathway gene for production of fusel oil. In embodiments, the recovered renewable hydrocarbon composition comprises at least about 90% isobutanol and further comprises greater than about 0.3% isoamyl alcohol. In embodiments, the recombinant yeast host cell modified to produce isobutanol from carbohydrate and from protein hydrolysate further comprises: at least one downregulated Ehrlich pathway gene for production of fusel oil. In embodiments, the recovered renewable hydrocarbon composition comprises less than about 0.3% isoamyl alcohol. In embodiments, the renewable hydrocarbon composition comprises higher total carbon content than a composition consisting essentially of isobutanol.

In embodiments, the methods provided herein further comprise blending an amount of the renewable hydrocarbon composition with gasoline whereby a fuel blend is produced. In embodiments, the fuel blend comprises at least one of increased volumetric energy density or decreased vapor pressure as compared to a blend comprising an equivalent amount of a composition consisting essentially of isobutanol. In embodiments, the fuel blend further comprises ethanol. In embodiments, the fuel blend comprising ethanol comprises decreased phase separation when contacted by water as compared to a fuel blend comprising ethanol and an equivalent amount of a composition consisting essentially of isobutanol.

Also provided herein are methods of producing a butanol and fusel oil mixture from a biomass feedstock comprising: providing a biomass feedstock; processing the biomass feedstock to produce a processed feedstock slurry comprising protein hydrolysates and oligosaccharides; saccharifying the oligosaccharides of the processed feedstock slurry to produce a fermentation composition comprising fermentable sugars and protein hydrolysates; fermenting a recombinant yeast in the presence of the fermentation composition, said recombinant yeast comprising: a heterologous butanol biosynthetic pathway for production of butanol; and, at least one upregulated Ehrlich pathway gene for production of fusel oil; whereby a butanol and fusel oil mixture is produced; and, recovering the butanol and fusel oil mixture; wherein the yield of the butanol and fusel oil mixture per unit weight of biomass feedstock is improved. In embodiments, processing the biomass feedstock to produce a processed feedstock slurry comprising protein hydrolysates and oligosaccharides comprises liquefying the biomass feedstock in the presence of at least one protease. In embodiments, processing the biomass feedstock to produce a processed feedstock slurry comprising protein hydrolysates and oligosaccharides comprises: liquefying the biomass feedstock to create a feedstock slurry comprising oligosaccharides, undissolved solids, and water; separating at least a portion of the undissolved solids from the feedstock slurry step to generate: an aqueous solution comprising oligosaccharides and a wet cake co-product comprising solids; hydrolyzing the wet cake co-product of step (2)(ii) to produce protein hydrolysates; and mixing the aqueous solution comprising oligosaccharides with the protein hydrolysates to produce a processed feedstock slurry comprising protein hydrolysates and oligosaccharides.

In embodiments, the undissolved solids are separated from the feedstock slurry by decanter bowl centrifugation, tricanter centrifugation, disk stack centrifugation, filtering centrifugation, decanter centrifugation, filtration, vacuum filtration, beltfilter, pressure filtration, screen filtration, microfiltration, screen separation, grating, porous grating, flotation, hydroclone, filter press, screwpress, gravity settler, vortex separator, or combinations thereof. In embodiments, the wet cake co-product is hydrolyzed by a means selected from the group consisting of: acid hydrolysis, base hydrolysis and enzymatic hydrolysis.

In embodiments provided herein, the feedstock in the fermentation process comprises one or more fermentable sugars derived from corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, and mixtures thereof. In embodiments provided herein, the recombinant yeast is *Saccharomyces, Schizosaccharomyces, Hansenula, Candida, Kluyveromyces, Yarrowia, Issatchenkia,* or *Pichia*. In embodiments, the recombinant yeast is *Saccharomyces cerevisiae.*

In embodiments of the methods provided herein, the at least one upregulated Ehrlich pathway gene is selected from the group consisting of: a gene encoding a polypeptide having aromatic aminotransferase activity, said polypeptide having at least about 90% identity to ARO8 (SEQ ID NO:2) or ARO9 (SEQ ID NO:4); a gene encoding a polypeptide having branched chain amino acid transferase activity, said polypeptide having at least about 90% identity to BAT1 (SEQ ID NO:8) or BAT2 (SEQ ID NO:10); a gene encoding a polypeptide having phenylpyruvate decarboxylase activity, said polypeptide having at least about 90% identity to ARO10 (SEQ ID NO:6); a gene encoding a polypeptide having Pyruvate decarboxylase activity, said polypeptide having at least about 90% identity to PDC1 (SEQ ID NO:12), PDC5 (SEQ ID NO:14) or PDC6 (SEQ ID NO:16); a gene encoding a polypeptide having Alpha-ketoisocaproate decarboxylase activity, said polypeptide having at least about 90% identity to THI3 (SEQ ID NO:18); a gene encoding a polypeptide having Alcohol dehydrogenase activity, said polypeptide having at least about 90% identity to ADH1 (SEQ ID NO:20), ADH2 (SEQ ID NO:22), ADH3 (SEQ ID NO:24), ADH4 (SEQ ID NO:26), ADH5 (SEQ ID NO:28), ADH6 (SEQ ID NO:30) or SFA1 (SEQ ID NO:32); a gene encoding a polypeptide having aryl-alcohol dehydrogenase activity, said polypeptide having at least about 90% identity to AAD3 (SEQ ID NO:34), AAD4 (SEQ ID NO:36), AAD6 (SEQ ID NO:30), AAD10 (SEQ ID NO:40), AAD14 (SEQ ID NO:42), AAD15 (SEQ ID NO:44), AAD16 (SEQ ID NO:46) or YPL088W (SEQ ID NO:48); a gene encoding a polypeptide having Aldehyde dehydrogenase activity, said polypeptide having at least about 90% identity to ALD2 (SEQ ID NO:52), ALD3 (SEQ ID NO:54), ALD4 (SEQ ID NO:56), ALD5 (SEQ ID NO:58) or ALD6

(SEQ ID NO:60); and, a gene encoding a polypeptide having ATP-binding ATP transporter activity, said polypeptide having at least about 90% identity to PDR12 (SEQ ID NO:50).

In embodiments of the methods provided herein, the butanol biosynthetic pathway is selected from the group consisting of: an isobutanol biosynthetic pathway comprising the following substrate to product conversions: pyruvate to acetolactate, acetolactate to 2,3-dihydroxyisovalerate, 2,3-dihydroxyisovalerate to α-ketoisovalerate, α-ketoisovalerate to isobutyraldehyde, and isobutyraldehyde to isobutanol; an isobutanol biosynthetic pathway comprising the following substrate to product conversions: pyruvate to acetolactate, acetolactate to 2,3-dihydroxyisovalerate, 2,3-dihydroxyisovalerate to α-ketoisovalerate, α-ketoisovalerate to isobutyryl-CoA, isobutyryl-CoA to isobutyraldehyde, and isobutyraldehyde to isobutanol; an isobutanol biosynthetic pathway comprising the following substrate to product conversions: pyruvate to acetolactate, acetolactate to 2,3-dihydroxyisovalerate, 2,3-dihydroxyisovalerate to α-ketoisovalerate, α-ketoisovalerate to valine, valine to isobutylamine, isobutylamine to isobutyraldehyde, and isobutyraldehyde to isobutanol; a 1-butanol biosynthetic pathway comprising the following substrate to product conversions: acetyl-CoA to acetoacetyl-CoA, acetoacetyl-CoA to 3-hydroxybutyryl-CoA, 3-hydroxybutyryl-CoA to crotonyl-CoA, crotonyl-CoA to butyryl-CoA, butyryl-CoA to butyraldehyde, and butyraldehyde to 1-butanol; a 2-butanol biosynthetic pathway comprising the following substrate to product conversions: pyruvate to alpha-acetolactate, alpha-acetolactate to acetoin, acetoin to 2,3-butanediol, 2,3-butanediol to 2-butanone, and 2-butanone to 2-butanol. In embodiments, the yield of butanol in the butanol and fusel oil mixture is increased. In embodiments, the yield of fusel oil in the butanol and fusel oil mixture is increased. In embodiments, the saccharifying and the fermenting occur in the same vessel. In embodiments, the saccharifying and the fermenting occur concurrently.

BRIEF DESCRIPTION OF THE FIGURES AND SEQUENCE DESCRIPTIONS

The invention can be more fully understood from the following detailed description, the Figures, and the accompanying sequence descriptions, which form part of this application.

FIG. 1, illustrates the Ehrlich pathway, wherein branched-chain amino acids (i.e., leucine, valine and isoleucine), aromatic amino acids (i.e., phenyl-alanine, tyrosine and tryptophan) and a sulfur-containing amino acid (i.e., methionine) lead to the formation of fusel acids and fusel alcohols. Genes encoding enzymes for each step are indicated.

FIG. 2 schematically shows a portion of the *Saccharomyces cerevisiae* pathway for degradation of: (A) valine; and, (B) isoleucine.

FIG. 3 schematically shows a portion of the *Saccharomyces cerevisiae* pathway for degradation of: (A) leucine; and, (B) tyrosine.

FIG. 4 schematically shows a portion of the *Saccharomyces cerevisiae* pathway for degradation of: (A) phenyl-alanine; and, (B) tryptophan.

FIG. 5 schematically illustrates example methods and systems of the present invention, in which: (A) undissolved solids are removed in a centrifuge after liquefaction and before fermentation; or (B) feedstock is milled.

FIG. 6 schematically illustrates example methods and systems of the present invention, in which: (A) the centrifuge discharges an oil stream; or (B) a saccharification vessel is placed between the centrifuge and the fermentor.

FIG. 7 schematically illustrates alternative exemplary methods and systems of the present invention, in which: (A) a saccharification vessel is placed between the liquefaction vessel and the centrifuge; or (B) two centrifuges are utilized in series to remove the undissolved solids.

FIG. 8 shows different isobutanol biosynthetic pathways. The steps labeled "a", "b", "c", "d", "e", "f", "g", "h", "i", "j" and "k" represent the substrate to product conversions described herein. Step "a" may be catalyzed, for example, by acetolactate synthase. Step "b" may be catalyzed, for example, by acetohydroxy acid isomeroreductase. Step "c" may be catalyzed, for example, by acetohydroxy acid dehydratase. Step "d" may be catalyzed, for example, by branched-chain keto acid decarboxylase. Step "e" may be catalyzed, for example, by branched chain alcohol dehydrogenase. Step "f" may be catalyzed, for example, by branched chain keto acid dehydrogenase. Step "g" may be catalyzed, for example, by an acetylating aldehyde dehydrogenase. Step ""h" may be catalyzed, for example, by a transaminase. Step "i" may be catalyzed, for example, by a valine decarboxylase. Step "j" may be catalyzed, for example, by an omega transaminase.

FIG. 9 shows four different pathways for biosynthesis of 1-butanone and 1-butanol. The steps labeled "a", "b", "c", "d", "e" and "f" represent the substrate to product conversions described herein. Step "a" may be catalyzed, for example, by acetyl-CoA acetyl transferase. Step "b" may be catalyzed, for example, by 3-hydroxybutyryl-CoA dehydrogenase. Step "c" may be catalyzed, for example, by crotonase. Step "d" may be catalyzed, for example, by butyryl-CoA dehydrogenase. Step "e" may be catalyzed, for example, by butyraldehyde dehydrogenase. Step "f" may be catalyzed, for example, by butanol dehydrogenase.

FIG. 10 shows four different pathways for biosynthesis of 2-butanone and 2-butanol. The steps labeled "a", "b", "c", "d", "e", "f", "g", "h", "i", "j", "k", "l" and "m" represent the substrate to product conversions described herein. Step "a" may be catalyzed, for example, by acetolactate synthase. Step "b" may be catalyzed, for example, by acetolactate decarboxylase. Step "c" may be catalyzed, for example, by acetoin aminase. Step "d" may be catalyzed, for example, by aminobutanol kinase. Step "e" may be catalyzed, for example, by aminobutanol phosphate phospholyase. Step "f" may be catalyzed, for example, by butanol dehydrogenase. Step "g" may be catalyzed, for example, by a dihydroxyacetone kinase. Step ""h" may be catalyzed, for example, by a serinol aphophate aminotransferase. Step "i" may be catalyzed, for example, by a butanediol dehydrogenase. Step "j" may be catalyzed, for example, by a diol dehydratase or glycerol dehydratase.

TABLE 1

Figure 1:
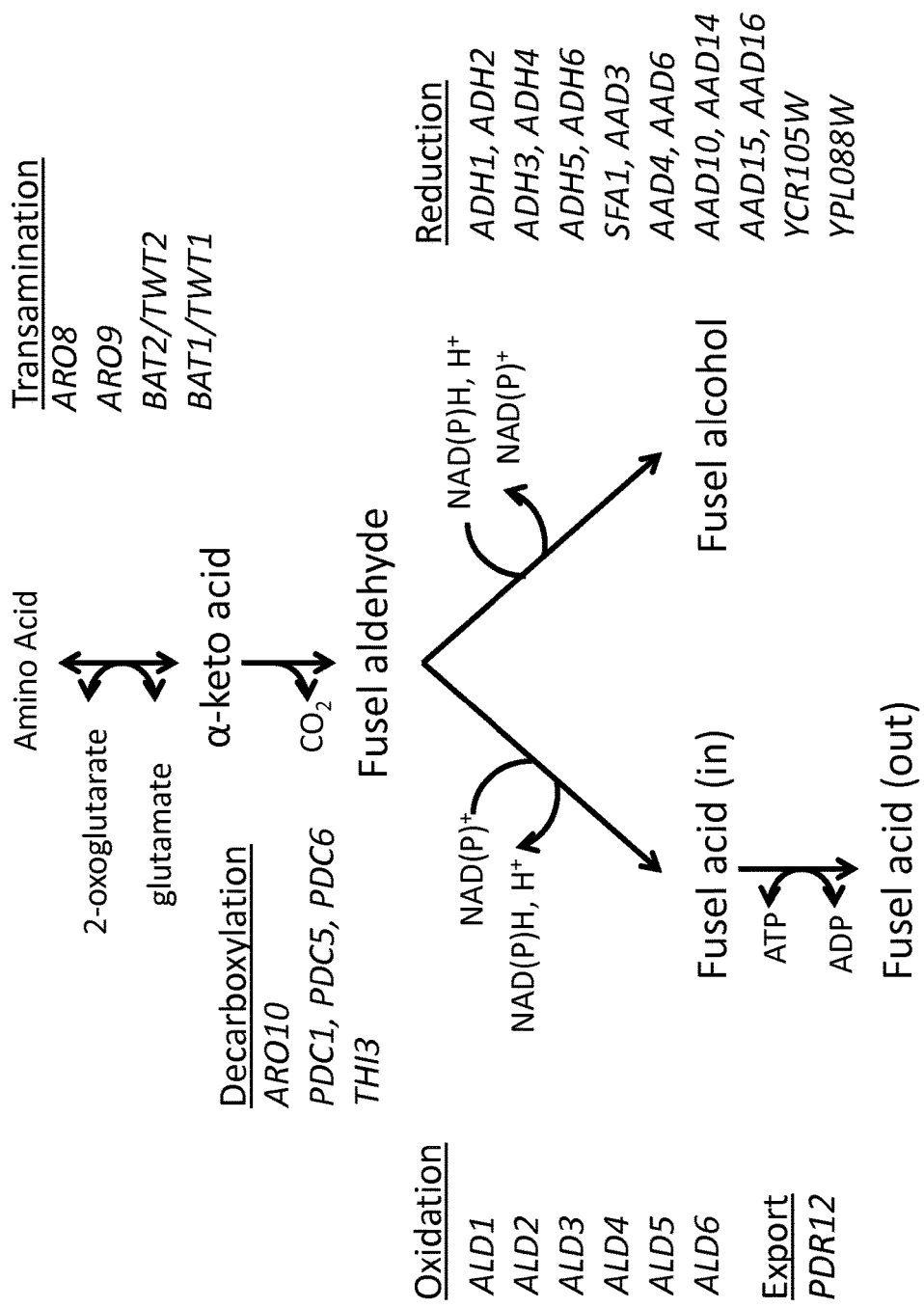

Summary of Gene and Protein SEQ ID Numbers

| Gene | DNA SEQ ID NO | Protein SEQ ID NO |
|---|---|---|
| *Saccharomyces cerevisiae* Aromatic aminotransferase I (GenBank Accession No. NM_001181067) ("ARO8") | 1 (1503 bp) | 2 (500 AA) |
| *Saccharomyces cerevisiae* Aromatic aminotransferase II (GenBank Accession No. NM_001179267) ("ARO9") | 3 (1542 bp) | 4 (513 AA) |
| *Saccharomyces cerevisiae* Phenylpyruvate decarboxylase (GenBank Accession No. NM_001180688) ("ARO10") | 5 (1908 bp) | 6 (635 AA) |
| *Saccharomyces cerevisiae* Mitochondrial branched chain amino acid transferase (GenBank Accession No. X78961) ("BAT1") | 7 (1835 bp) | 8 (393 AA) |
| *Saccharomyces cerevisiae* Cytosolic branched chain amino acid transferase (GenBank Accession No. NM_001181806) ("BAT2") | 9 (1131 bp) | 10 (376 AA) |
| *Saccharomyces cerevisiae* Pyruvate decarboxylase (GenBank Accession No. NM_001181931) ("PDC1") | 11 (1692 bp) | 12 (563 AA) |
| *Saccharomyces cerevisiae* Pyruvate decarboxylase (GenBank Accession No. NM_001182021) ("PDC5") | 13 (1692 bp) | 14 (563 AA) |
| *Saccharomyces cerevisiae* Pyruvate decarboxylase (GenBank Accession No. NM_001181216) ("PDC6") | 15 (1692 bp) | 16 (563 AA) |
| *Saccharomyces cerevisiae* Alpha-ketoisocaproate decarboxylase ("THI3") (GenBank Accession No. D21880) | 17 (3169 bp) | 18 (568 AA) |
| *Saccharomyces cerevisiae* Alcohol dehydrogenase (GenBank Accession No. V01291) ("ADH1") | 19 (360 bp) | 20 (120 AA) |
| *Saccharomyces cerevisiae* Alcohol dehydrogenase (GenBank Accession No. NM_001182812) ("ADH2") | 21 (1047 bp) | 22 (348 AA) |
| *Saccharomyces cerevisiae* Alcohol dehydrogenase (GenBank Accession No. NM_001182582) ("ADH3") | 23 (1128 bp) | 24 (375 AA) |
| *Saccharomyces cerevisiae* Alcohol dehydrogenase (GenBank Accession No. X05992) ("ADH4") | 25 (2160 bp) | 26 (382 AA) |
| *Saccharomyces cerevisiae* Alcohol dehydrogenase (GenBank Accession No. NM_001178493) ("ADH5") | 27 (1056 bp) | 28 (351 AA) |
| *Saccharomyces cerevisiae* Alcohol dehydrogenase (GenBank Accession No. NM_001182831) ("ADH6") | 29 (1083 bp) | 30 (360 AA) |
| *Saccharomyces cerevisiae* Alcohol dehydrogenase (class III) (GenBank Accession No. NM_001180228) ("SFA1") | 31 (1161 bp) | 32 (386 AA) |
| *Saccharomyces cerevisiae* Putative aryl-alcohol dehydrogenase (GenBank Accession No. NM_001178814) ("AAD3") | 33 (1092 bp) | 34 (363 AA) |
| *Saccharomyces cerevisiae* Putative aryl-alcohol dehydrogenase (GenBank Accession No. NM_001180303) ("AAD4") | 35 (990 bp) | 36 (329 AA) |
| *Saccharomyces cerevisiae* Putative aryl-alcohol dehydrogenase (GenBank Accession No. NM_001179911) ("AAD6") | 37 (639 bp) | 38 (212 AA) |
| *Saccharomyces cerevisiae* Putative aryl-alcohol dehydrogenase (GenBank Accession No. NM_001181813) ("AAD10") | 39 (867 bp) | 40 (288 AA) |
| *Saccharomyces cerevisiae* Putative aryl-alcohol dehydrogenase (GenBank Accession No. NM_001183169) ("AAD14") | 41 (1131 bp) | 42 (376 AA) |
| *Saccharomyces cerevisiae* Putative aryl-alcohol dehydrogenase (GenBank Accession No. NM_001183418) ("AAD15") | 43 (432 bp) | 44 (143 AA) |
| *Saccharomyces cerevisiae* Putative aryl-alcohol dehydrogenase (GenBank Accession No. NM_001179910) ("AAD16") | 45 (459 bp) | 46 (152 AA) |
| *Saccharomyces cerevisiae* Putative aryl-alcohol dehydrogenase (GenBank Accession No. NM_001183902) ("YPL088W") | 47 (1029 bp) | 48 (342 AA) |
| *Saccharomyces cerevisiae* ATP-binding ATP transporter (GenBank Accession No. NM_001183872) ("PDR12") | 49 (4536 bp) | 50 (1511 AA) |
| *Saccharomyces cerevisiae* Aldehyde dehydrogenase (GenBank Accession No. NM_001182674) ("ALD2") | 51 (1521 bp) | 52 (506 AA) |
| *Saccharomyces cerevisiae* Aldehyde dehydrogenase (GenBank Accession No. NM_001182673) ("ALD3") | 53 (1521 bp) | 54 (506 AA) |
| *Saccharomyces cerevisiae* Aldehyde dehydrogenase (GenBank Accession No. NM_001183794) ("ALD4") | 55 (1560 bp) | 56 (519 AA) |
| *Saccharomyces cerevisiae* Aldehyde dehydrogenase (GenBank Accession No. NM_001178964) ("ALD5") | 57 (1563 bp) | 58 (520 AA) |
| *Saccharomyces cerevisiae* Aldehyde dehydrogenase (GenBank Accession No. NM_001183875) ("ALD6") | 59 (1503 bp) | 60 (500 AA) |
| Plasmid pLA54 | 61 (4519 bp) | — |
| Primers BK505 and BK506 | 62-63 | — |
| Primers LA468 and LA492 | 64-65 | — |

TABLE 1-continued

Summary of Gene and Protein SEQ ID Numbers

| Gene | DNA SEQ ID NO | Protein SEQ ID NO |
|---|---|---|
| Primers AK109-1, AK109-2, and AK109-3 | 66-68 | — |
| Primers oBP452, oBP453, oBP454, oBP455, oBP456, oBP457, oBP458, oBP459, oBP460, , LA135, oBP461 and LA92 | 69-80 | — |
| Plasmid pLA59 | 81 (4242 bp) | — |
| Primers LA678, LA679, LA337, LA692 and LA693 | 82-86 | — |
| Plasmid pLA34 | 87 (7523 bp) | — |
| Primers LA722, LA733, LA453, LA694 and LA695 | 88-92 | — |
| Primers oBP594, oBP595, oBP596, oBP597, oBP598, OBP599, 0BP6OO, oBP601, oBP602, and oBP603 | 93-102 | — |
| 2-micron plasmid fragments LA811 and LA817 | 103-104 | — |
| 2-micron plasmid fragments LA812 and LA818 | 105-106 | — |
| Primers LA512, LA513, LA516, LA514 and LA515 | 107-111 | — |
| Plasmid pLA71 | 112 (6903 bp) | — |
| Primers LA829, LA834, N1257, LA830 | 113-116 | — |
| Plasmid pLA59::FBA1p-BAT1-CYC1t | 117 (6369 bp) | — |
| Plasmid pLA59::FBA1p-BAT2-CYC1t | 118 (6318 bp) | — |
| Plasmid pLA59::TDH3p-ARO8-ADH1t | 119 (6682 bp) | — |
| Plasmid pLA59::TDH3p-ARO9-ADHt1 | 120 (6721 bp) | — |
| Plasmid pLA59::TDH3p-ARO10-ADH1t | 121 (7087 bp) | — |
| Plasmid pHR81-ILV5p-K9SB2 | 122 (9613 bp) | — |
| Plasmid pLA84 | 123 (13022 bp) | — |
| *Anaerostipes caccae* ketol-acid reductoisomerase, variant K9SB2 | — | 124 (343 AA) |
| *Streptococcus mutans* dihydroxyacid dehydratase (ilvD) | 125 (1713 bp) | 126 (571 AA) |
| *Listeria grayi* branched-chain α-keto acid decarboxylase (kivD) | 127 (1647 bp) | 128 (548 AA) |
| *Beijerinkia indica* alcohol dehydrogenase (ADH) | — | 129 (347 AA) |
| *Lactococcus lactis* dihydroxyacid dehydratase | 130 (1713 bp) | 131 (570 AA) |
| *Macrococcus caseolyticus* 2-ketoisovalerate decarboxylase | 132 (1641 bp) | 133 (546 AA) |
| *Achromobacter xylosoxidans* alcohol dehydrogenase | — | 134 (348 AA) |
| *Bacillus subtilis* AlsS | — | 135 (571 AA) |
| *Escherichia coli* ketol-acid reductoisomerase | — | 136 (491 AA) |
| *Pseudomonas fluorescens* ketol-acid reductoisomerase | — | 137 (338 AA) |

DETAILED DESCRIPTION

The Applicants have provided herein processes and recombinant microorganisms which permit improved yields of fermentation products by capitalizing on both carbohydrates and amino acids present in feedstocks. While recombinant host cells capable of converting carbohydrates to butanol have been described (see, for example, U.S. Pat. No. 7,851,188, incorporated herein by reference), the present application describes processes and recombinant microorganisms which may be employed to provide increased production of butanol and/or fusel alcohols. For some purposes, it may be desireable to minimize non-isobutanol fusels to increase yield of isobutanol, while for other purposes, it may be desireable to maximize production of a particular non-isobutanol fusel alcohol or a subset of non-isobutanol fusel alcohols in conjunction with production of butanol. Equipped with this specification, one of skill in the art will be able to employ the appropriate combination of feedstock processing steps and recombinant microorganism to produce the desired combination of fermentation product alcohols.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned in this specification are indicative of the level of skill of those skilled in the art to which this invention pertains, and are herein incorporated by reference in their entireties for all purposes to the same extent whether or not each individual publication or patent application is specifically and individually indicated to be incorporated by reference, unless only specific sections of patents or patent publications are indicated to be incorporated by reference.

Although methods and materials similar or equivalent to those disclosed herein can be used in practice or testing of the present invention, suitable methods and materials are disclosed below. The materials, methods and examples are illustrative only and are not intended to be limiting. Other features and advantages of the invention will be apparent from the detailed description and from the claims.

In order to further define this invention, the following terms, abbreviations and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, that is, occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolyzable polysaccharides that provide fermentable sugars including any sugars and starch derived from natural resources such as corn, cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass can comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, waste sugars, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation such as by milling, treating, and/or liquefying and comprises fermentable sugar and may comprise water. For example, cellulosic and/or lignocellulosic biomass may be processed to obtain a hydrolysate containing fermentable sugars by any method known to one skilled in the art. A low ammonia pretreatment is disclosed in U.S. Patent Pub. No. 2007/0031918A1, which is herein incorporated by reference. Enzymatic saccharification of cellulosic and/or lignocellulosic biomass typically makes use of an enzyme consortium for breaking down cellulose and hemicellulose to produce a hydrolysate containing sugars including glucose, xylose, and arabinose. (Saccharification enzymes suitable for cellulosic and/or lignocellulosic biomass are reviewed in Lynd, et al. (*Microbiol. Mol. Biol. Rev.*, 66:506-577 (2002)).

Mash, juice, molasses, or hydrolysate may include feedstock 12 and feedstock slurry 16 as described herein. An aqueous feedstream may be derived or formed from biomass by any processing known in the art for processing the biomass for purposes of fermentation such as by milling, treating, and/or liquefying and comprises fermentable carbon substrate (e.g., sugar) and may comprise water. An aqueous feedstream may include feedstock 12 and feedstock slurry 16 as described herein.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the break down of complex sugars by further processing such as by liquefaction, saccharification, or other process. Feedstock includes or is derived from a biomass. Suitable feedstocks include, but are not limited to, rye, wheat, corn, corn mash, cane, cane mash, barley, cellulosic material, lignocellulosic material, or mixtures thereof. Where reference is made to "feedstock oil," it will be appreciated that the term encompasses the oil produced from a given feedstock.

"Processed feedstock slurry" refers to a slurry comprising feedstock that has been processed in a manner to produce protein hydrolysates and fermentable carbohydrate substrate. This processing will typically comprises steps resulting in liquefaction, saccharification and protein hydrolysis.

"Renewable hydrocarbon composition comprising butanol" as used herein refers to the butanol and fusel oil mixture produced from biomass by the action of microorganisms during fermentation.

"Fermentation medium" as used herein means the mixture of water, sugars, dissolved solids, optionally microorganisms producing alcohol, product alcohol, and all other constituents of the material held in the fermentation vessel in which product alcohol is being made by the reaction of sugars to alcohol, water, and carbon dioxide ($CO_2$) by the microorganisms present. From time to time, as used herein the term "fermentation broth" and "fermented mixture" can be used synonymously with "fermentation medium." "Fermentable carbon source" or "fermentable carbon substrate" as used herein means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; and mixtures thereof.

"Fermentable sugar" as used herein refers to one or more sugars capable of being metabolized by the microorganisms disclosed herein for the production of fermentative alcohol.

"Fermentation vessel" as used herein means the vessel in which the fermentation reaction is carried out whereby product alcohol such as butanol is made from sugars.

"Liquefaction vessel" as used herein means the vessel in which liquefaction is carried out. Liquefaction is the process in which oligosaccharides are liberated from the feedstock. In some embodiments where the feedstock is corn, oligosaccharides are liberated from the corn starch content during liquefaction.

"Saccharification vessel" as used herein means the vessel in which saccharification (i.e., the break down of oligosaccharides into monosaccharides) is carried out. Where fermentation and saccharification occur simultaneously, the saccharification vessel and the fermentation vessel may be one in the same vessel. "Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

As used herein, "saccharification enzyme" means one or more enzymes that are capable of hydrolyzing polysaccharides and/or oligosaccharides, for example, alpha-1,4-glucosidic bonds of glycogen, or starch. Saccharification enzymes may include enzymes capable of hydrolyzing cellulosic or lignocellulosic materials as well.

"Undissolved solids" as used herein means non-fermentable portions of feedstock, for example, germ, fiber, and gluten. For example, the non-fermentable portions of feedstock include the portion of feedstock that remains as solids and can absorb liquid from the fermentation broth.

Dried Distillers' Grains with Solubles (DDGS) as used herein refers to a co-product or by-product from a fermentation of a feedstock or biomass (e.g., fermentation of grain or grain mixture that produces a product alcohol). In some embodiments, DDGS may also refer to an animal feed product produced from a process of making a product alcohol (e.g., butanol, isobutanol, etc.).

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In some embodiments, the product alcohols are $C_3$ to $C_8$ alkyl alcohols. In other embodiments, the product alcohols are $C_2$ to $C_5$ alkyl alcohols. In other embodiments, the product alcohols are $C_3$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. "Alcohol" is also used herein with reference to a product alcohol.

"Butanol" as used herein refers with specificity to the butanol isomers 1-butanol (1-BuOH), 2-butanol (2-BuOH), tert-butanol (t-BuOH), and/or isobutanol (iBuOH or i-BuOH or I—BUOH, also known as 2-methyl-1-propanol), either individually or as mixtures thereof. From time to time, when referring to esters of butanol, the terms "butyl esters" and "butanol esters" may be used interchangeably.

The term "fusel alcohols" refers to aliphatic and aromatic alcohols comprising more than two carbon atoms that are formed by fermentation with yeast and are components of "fusel oils", As used herein, "fusel alcohols" refer to isobutanol, 2-methyl-1-butanol, 3-methyl-1-butanol, 2-phenylethanol, and 1-propanol. Fusel alcohols are derived from amino acid catabolism via a pathway that was first proposed a century ago by F. Ehrlich (*Über die Bedingungen der Fuselölbildung und über ihren Zusammenhang mit dem Eiweissaufbau der Hefe. Ber. Dtsch. Chem. Ges.* 40:1027-1047 (1907)). Amino acids that are assimilated by the Ehrlich pathway (i.e., valine, leucine, isoleucine, methionine, and phenylalanine) are initially transaminated, and the resulting α-keto acid cannot be redirected into central carbon metabolism. Thus, these α-keto acids may be converted into fusel alcohols or acids via the Ehrlich pathway (see FIG. 1; Hazelwood, et al., *Appl. Environ. Microbiol.*, 74(8):2259-2266 (2008)). "Non-isobutanol fusel alcohols" refers to the fusel alcohols independent of isobutanol.

The term "separation" as used herein is synonymous with "recovery" and refers to removing a chemical compound from an initial mixture to obtain the compound in greater purity or at a higher concentration than the purity or concentration of the compound in the initial mixture.

The term "yield" refers to the amount of product per amount of biomass source in g/kg. While determinations of yield often only consider the available carbon (e.g., glucose) in the biomass source, in the present invention, yield is based on the available energy that can be extracted from both carbon (e.g., glucose) and nitrogen (e.g., amino acids) containing compounds in the biomass. The yield may be exemplified for corn as the biomass source. It is understood unless otherwise noted that yield is expressed as a percentage of the theoretical yield. In reference to a microorganism or metabolic pathway, "theoretical yield" is defined as the maximum amount of product that can be generated per total amount of substrate as dictated by the stoichiometry of the metabolic pathway used to make the product. For example, the theoretical yield for one typical conversion of glucose to isopropanol is 0.33 g/g. As such, a yield of isopropanol from glucose of 0.297 g/g would be expressed as 90% of theoretical or 90% theoretical yield. One skilled in the art will appreciate that the yield may vary depending on the biomass source used. One skilled in the art can calculate yields on various biomass sources.

As used herein, "recombinant microorganism" refers to microorganisms, such as bacteria or yeast, that are modified by use of recombinant DNA techniques, such as by engineering a host cell to comprise a biosynthetic pathway such as butanol. For example, a recombinant host cell comprising an "engineered alcohol production pathway" (such as an engineered butanol or isobutanol production pathway) refers to a host cell containing a modified pathway that produces alcohol in a manner different than that normally present in the host cell. Such differences include production of an alcohol not typically produced by the host cell, or increased or more efficient production.

The term "butanologen" as used herein refers to a microorganism capable of producing a butanol isomer. Such microorganisms are typically recombinant microorganisms comprising an engineered butanol biosynthetic pathway. The term "isobutanologen" as used herein refers to a microorganism capable of producing isobutanol isomers. Such microorganisms are typically recombinant microorganisms comprising an engineered isobutanol biosynthetic pathway.

The term "butanol biosynthetic pathway" as used herein refers to an enzyme pathway to produce 1-butanol, 2-butanol, or isobutanol.

The term "1-butanol biosynthetic pathway" as used herein refers to an enzyme pathway to produce 1-butanol from acetyl-coenzyme A (acetyl-CoA).

The term "2-butanol biosynthetic pathway" as used herein refers to an enzyme pathway to produce 2-butanol from pyruvate.

The term "isobutanol biosynthetic pathway" as used herein refers to an enzyme pathway to produce isobutanol from pyruvate. For example, isobutanol biosynthetic pathways are disclosed in U.S. Pat. No. 7,851,188, which is incorporated by reference herein. Certain isobutanol biosynthetic pathways are illustrated in FIG. 1 and described herein. Isobutanol is also known as 2-methyl-1-propanol.

The term "Ehrlich pathway" refers to a pathway for catabolism of branched-chain amino acids, aromatic amino acids and the sulfur containing amino acid, as first proposed a century ago by F. Ehrlich (supra). As used herein, "Ehrlich pathway gene" refers to any gene encoding a polypeptide that catalyzes a reaction of the Ehrlich pathway, i.e., transamination (e.g., ARO8, ARO9, BAT1, BAT2), decarboxylation (e.g., ARO10, THI3, PDC1, PDC5, PDC6), oxidation (e.g., ALD1, ALD2, ALD3, ALD4, ALD5, ALD6), reduction (e.g., ADH1, ADH2, ADH3, ADH4, ADH5, ADH6, SFA1, AAD3, AAD4, AAD6, AAD10, AAD14, AAD15, AAD16, YPL088W) and export (e.g., PDR12) for production of fusel oil (see FIG. 1; Hazelwood, et al., *Appl. Environ. Microbiol.*, 74(8):2259-2266 (2008)). Sequences encoding ARO8, ARO9, BAT1, BAT2, ARO10, PDC1, PDC5, PDC6, ALD1, ALD2, ALD3, ALD4, ALD5, ALD6, THI3, ADH1, ADH2, ADH3, ADH4, ADH5, ADH6, SFA1, AAD3, AAD4, AAD6, AAD10, AAD14, AAD15, AAD16, YPL088W and PDR12 are available in the art from a variety of yeast; for example, the sequences encoding these Ehrlich pathway genes from *Saccharomyces cerevisiae* are provided herein as SEQ ID NOs:1-60, although the invention is by no means limited thereto.

The term "heterologous biosynthetic pathway" as used herein refers to an enzyme pathway to produce a product in which at least one of the enzymes is not endogenous to the host cell containing the biosynthetic pathway.

Figure 11:
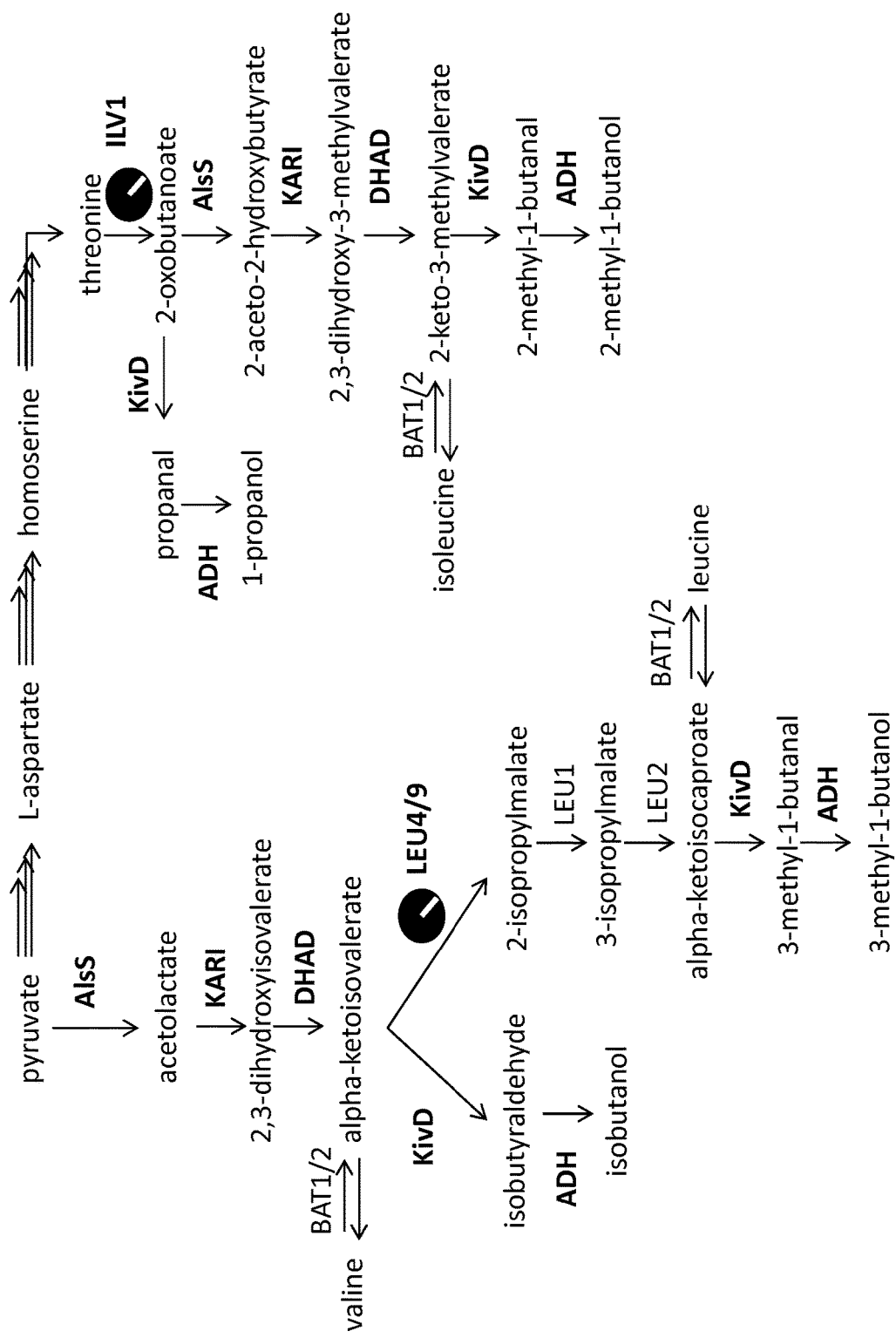
FIG. 11 depicts a biosynthetic production matrix comprising an isobutanol production pathway, a 3-methyl-1-butanol production pathway, a 2-methyl-1-butanol pathway and a 1-propanol production pathway. The steps catalyzed by LEU4/9 and ILV1 are indicated as branchpoints for production of 3-methyl-1-butanol and 2-methyl-1-butanol/1-propanol, respectively, in the biosynthetic production matrix.

The term "biosynthetic production matrix" as used herein refers to a network of production pathways introduced in the cell by heterologous expression of at least two, at least three, at least four, or all of α-ketoisovalerate decarboxylase, alcohol dehydrogenase, acetolactate synthase, ketol-acid reductoisomerase, and dihydroxyacid dehydratase. As shown in FIG. 11, a biosynthetic production matrix so engineered is capable of production of isobutanol, 2-methyl-1-butanol, 3-methyl-1-butanol, 1-propanol, or combinations thereof.

The term "production matrix branchpoint" as used herein refers to the pathway steps wherein more than one product can be produced depending on the enzyme catalyzing the substrate to product conversion. For example, in FIG. 11, α-ketoisovalerate may be converted to either isobutyraldehyde or 2-isopropylmalate. Thus, such point in the matrix is a production matrix branchpoint.

The term "production matrix branchpoint enzyme" as used herein refers to the endogenous pathway enzymes which may be targeted to increase or decrease activity, ultimately resulting in increased or decreased production of a given matrix product. For example, in FIG. 11, alteration of LEU4 or LEU9 activity would so alter 2-methyl-1-butanol production. Likewise, alteration of ILV1 activity would alter production of 1-propanol and 3-methyl-1-butanol.

Polypeptides and Polynucleotides for Use in the Invention

The term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides", "dipeptides", "tripeptides", "oligopeptides", "protein", "amino acid chain" or any other term used to refer to a chain or chains of two or more amino acids, are included within the definition of "polypeptide", and the term "polypeptide" may be used instead of, or interchangeably with any of these terms. A polypeptide may be derived from a natural biological source or produced by recombinant technology, but is not necessarily translated from a designated nucleic acid sequence. It may be generated in any manner, including by chemical synthesis. The polypeptides used in this invention comprise full-length polypeptides and fragments thereof.

The term "polynucleotide" is intended to encompass a singular nucleic acid as well as plural nucleic acids, and refers to a nucleic acid molecule or construct, for example, messenger RNA (mRNA) or plasmid DNA (pDNA). As used herein, a "gene" is a polynucleotide. A polynucleotide can contain the nucleotide sequence of the full-length cDNA sequence or a fragment thereof, including the untranslated 5' and 3' sequences and the coding sequences. The polynucleotide can be composed of any polyribonucleotide or polydeoxyribonucleotide, which may be unmodified RNA or DNA or modified RNA or DNA (e.g., heterologous DNA). For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. "Polynucleotide" embraces chemically, enzymatically, or metabolically modified forms.

A polynucleotide sequence may be referred to as "isolated," in which it has been removed from its native environment. For example, a heterologous polynucleotide encoding a polypeptide or polypeptide fragment having dihydroxy-acid dehydratase activity contained in a vector is considered isolated for the purposes herein. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA may be comprised of one or more segments of cDNA, genomic DNA, or synthetic DNA.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposes of the invention, as are native or recombinant polypeptides which have been separated, fractionated, or partially or substantially purified by any suitable technique.

As used herein, "native" refers to the form of a polynucleotide, gene, or polypeptide as found in nature with its own regulatory sequences, if present.

The term "endogenous," when used in reference to a polynucleotide, a gene, or a polypeptide refers to a native polynucleotide or gene in its natural location in the genome of an organism, or for a native polypeptide, is transcribed and translated from this location in the genome.

The term "heterologous" when used in reference to a polynucleotide, a gene, or a polypeptide refers to a polynucleotide, gene, or polypeptide not normally found in the host organism or is found natively but is modified in some way as compared to its native state. "Heterologous" also includes a native coding region, or portion thereof, that is reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region with non-native regulatory regions that is reintroduced into the native host. A "transgene" is a gene that has been introduced into the genome by a transformation procedure.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene (i.e., it is modified from its native state or is from another source) comprising regulatory and coding sequences that are not found together in nature. Accordingly, a chimeric gene may comprise regulatory sequences and coding sequences that are derived from different sources or regulatory sequences and coding sequences derived from the same source, but arranged in a manner different than that found in nature. "Endogenous gene" refers to a native gene in its natural location in the genome of an organism. A "foreign gene" or "heterologous gene" refers to a gene not normally found as a native gene in the host organism, but that is introduced into the host organism by gene transfer. Foreign genes can comprise native genes inserted into a non-native organism or chimeric genes.

As used herein, a "coding region" refers to a DNA sequence that codes for a specific amino acid sequence. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' non-translated regions, and the like, are not part of a coding region.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences can include promoters, enhancers, operators, repressors, transcription termination signals, translation leader sequences, introns, polyadenylation recognition sequences, RNA processing sites, effector binding sites and stem-loop structures.

The term "promoter" refers to a nucleic acid sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic nucleic acid segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters". "Inducible promoters," on the other hand, cause a gene to be expressed when the promoter is induced or turned on by a promoter-specific signal or molecule. It is further recognized that since in most cases the exact boundaries of regulatory sequences have not been completely defined, DNA fragments of different lengths can have identical promoter activity. For example, it will be understood that "FBA1 promoter" can be used to refer to a fragment derived from the promoter region of the FBA1 gene.

The term "terminator" as used herein refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence. It is recognized that since in most cases the exact boundaries of regulatory sequences have not been completely defined, DNA fragments of different lengths can have identical terminator activity. For example, it will be understood that "CYC1 terminator" can be used to refer to a fragment derived from the terminator region of the CYC1 gene.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "recombinant genetic expression element" refers to a nucleic acid fragment that expresses one or more specific proteins, including regulatory sequences preceding (5' non-coding sequences) and following (3' termination sequences) coding sequences for the proteins. A chimeric gene is a recombinant genetic expression element. The coding regions of an operon can form a recombinant genetic expression element, along with an operably linked promoter and termination region.

The term "expression", as used herein, refers to the transcription and stable accumulation of sense (mRNA) or antisense RNA derived from a particular nucleic acid fragment. Expression may also refer to translation of mRNA into a polypeptide. The process includes any manifestation of the functional presence of the expressed polynucleotide, gene, or polypeptide within the cell including, without limitation, gene knockdown as well as both transient expression and stable expression.

The term "overexpression" or "up-regulated" as used herein, refers to expression that is higher than endogenous expression of the same or related gene. A heterologous gene is overexpressed if its expression is higher than that of a comparable endogenous gene. Thus, the term overexpression refers to an increase in the level of nucleic acid or protein in a host cell. Overexpression can result from increasing the level of transcription or translation of an endogenous sequence in a host cell or can result from the introduction of a heterologous sequence into a host cell. Overexpression can also result from increasing the stability of a nucleic acid or protein sequence. Expression or overexpression of a polypeptide in a recombinant host cell can be quantified according to any number of methods known to the skilled artisan and can be represented, e.g., by a percent of total cell protein. The percent of total protein can be an amount selected from greater than about 0.001% of total cell protein; greater than about 0.01% of total cell protein; greater than about 0.1% of total cell protein; greater than about 0.5% of total cell protein; greater than about 1.0% of total cell protein; greater than about 2.0% of total cell protein; greater than about 3% of total cell protein; greater than about 4.0% of total cell protein; greater than about 5% of total cell protein; greater than about 6.0% of total cell protein; greater than about 7.0% of total cell protein; greater than about 8.0% of total cell protein; greater than about 9.0% of total cell protein; greater than about 10% of total cell protein; or greater than about 20% of total cell protein.

The term "reduced activity" in connection with an Ehrlich pathway enzyme refers to down-regulation, whether partial or total, of the activity of at least one of the Ehrlich pathway enzymes, as compared to the activity of the wildtype Ehrlich pathway enzyme. Likewise, the term "reduced activity" in connection with a production matrix branch point enzyme refers to down-regulation, whether partial or total, of the activity of at least one of the production matrix branch point enzymes. Down-regulation may occur when a native gene has a "disruption" or "modification", referring to an insertion, deletion, or targeted mutation within a portion of that gene, that results in e.g., a complete gene knockout such that the gene is deleted from the genome and no protein is translated or a translated subunit protein having an insertion, deletion, amino acid substitution or other targeted mutation. The location of the modification in the protein may be, for example, within the N-terminal portion of the protein or within the C-terminal portion of the protein. The modified protein will have impaired activity with respect to the protein that was not disrupted, and can be non-functional. Reduced activity in an Ehrlich pathway enzyme could also result via manipulating the upstream regulatory proteins or regulatory domains, altering a downstream protein regulated by the Ehrlich pathway enzyme, transcription and translation factors and/or signal transduction pathways or by use of sense, antisense or RNAi technology, etc. Another mechanism of reducing activity of an enzyme is introduction of a mutation that alters kinetic properties of the enzyme (e.g. reducing the affinity for a substrate, lowering the $k_{cat}$, etc.)

The term "increased activity" with a production matrix branch point enzyme refers to up-regulation, whether partial or total, of the activity of at least one of the matrix branch point enzymes. Increased activity may occur when a gene encoding an enzyme is overexpressed or when a mutation is introduced into the gene or into a regulator of the gene resulting in increased transcription or translation of the gene or alteration of the kinetic properties of the enzyme.

The term "alters activity" refers to any of the aforementioned modifications resulting in increased activity or decreased activity of an indicated enzyme.

As used herein the term "transformation" refers to the transfer of a nucleic acid fragment into the genome of a host microorganism, resulting in genetically stable inheritance. Host microorganisms containing the transformed nucleic acid fragments are referred to as "transgenic" or "recombinant" or "transformed" microorganisms.

The terms "plasmid", "vector" and "cassette" refer to an extra chromosomal element often carrying genes which are not part of the central metabolism of the cell, and usually in the form of circular double-stranded DNA fragments. Such elements can be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

"Transformation cassette" refers to a specific vector containing a foreign gene and having elements in addition to the foreign gene that facilitates transformation of a particular host cell.

"Expression cassette" refers to a specific vector containing a foreign gene and having elements in addition to the foreign gene that allow for enhanced expression of that gene in a foreign host.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

A polynucleotide or nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. Molecular Cloning: A Laboratory Manual, 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50 9.51). For hybridizations with shorter nucleic acids, i.e., oligonucleotides, the position of mismatches becomes more important, and the length of the oligonucleotide determines its specificity (see Sambrook et al., supra, 11.7 11.8). In one embodiment the length for a hybridizable nucleic acid is at least about 10 nucleotides. In one embodiment, a minimum length for a hybridizable nucleic acid is at least about 15 nucleotides; at least about 20 nucleotides; or the length is at least about 30 nucleotides. Furthermore, the skilled artisan will recognize that the temperature and wash solution salt concentration can be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides can be used in sequence-dependent methods of gene identification (e.g., Southern hybridization) and isolation (e.g., in situ hybridization of bacterial colonies or bacteriophage plaques). In addition, short oligonucleotides of 12-15 bases can be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, can now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenine is complementary to thymine and cytosine is complementary to guanine, and with respect to RNA, adenine is complementary to uracil and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Methods to determine identity are designed to give the best match between the sequences tested. Methods to determine identity and similarity are codified in publicly available computer programs. Sequence alignments and percent identity calculations can be performed using the MegAlign™ program of the LASERGENE bioinformatics computing suite (DNASTAR Inc., Madison, Wis.). Multiple alignments of the sequences are performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191(1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, such as polypeptides from other species or variants of a polypeptide, wherein such polypeptides have the same or similar function or activity, or in describing the corresponding polynucleotides. Useful examples of percent identities include, but are not limited to: 60%, 65%, 70%, 75%, 80%, 85%, 90%, or 95%, or any integer percentage from 60% to 100% can be useful in describing the present invention, such as 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable polynucleotide fragments not only have the above homologies but typically comprise a polynucleotide having at least 50 nucleotides, at least 100 nucleotides, at least 150 nucleotides, at least 200 nucleotides, or at least 250 nucleotides. Further, suitable polynucleotide fragments having the above homologies encode a polypeptide having at least 50 amino acids, at least 100 amino acids, at least 150 amino acids, at least 200 amino acids, or at least 250 amino acids.

The term "sequence analysis software" refers to any computer algorithm or software program that is useful for the analysis of nucleotide or amino acid sequences. "Sequence analysis software" can be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987). Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.).

Methods for Producing Butanol and Fusel Alcohol Mixtures in Recombinant Yeast—an Overview Traditional recombinant fermentations utilizing various feedstocks rely on available carbon substrates to enable production of the product of interest, while various protein by-products often accumulate and are used for animal feeds. Huo, Y.-X., et al. (*Nature Biotechnol*, 29(4):346-352 (2011)) suggest that a nitrogen-centric metabolic engineering strategy could be utilized to utilize proteins (versus carbon) as feedstock for the production of biofuels and they engineer an *Escherichia coli* that can deaminate protein hydrolysates (via introduction of three exogenous transamination and deamination cycles), enabling the cells to convert proteins to C4 and C5 alcohols (including ethanol, isobutanol, 2-methyl-1-butanol and 3-methyl-1-butanol) at 56% of the theoretical yield. Huo, et al. report that *Saccharomyces cerevisiae, E. coli, Bacillus subtilis* and microalgae were useful protein sources, producing up to 4,035 mg/L of alcohols from biomass containing ~22 g/L of amino acids.

Recombinant yeast engineered to produce butanol as the primary product may co-produce fusel alcohols as minor by-products, based on pathways within the yeast and the substrates present. However, the present invention is an improvement thereof, since the yield of butanol (and optionally, the fusel alcohol) per kilogram of biomass feedstock is improved with respect to previously engineered yeast.

Specifically, the processes and/or recombinant yeast comprising butanol biosynthetic pathways herein may capitalize on both the carbon and nitrogen (via amino acids derived from the biomass protein) available in a biomass feedstock to produce butanol in a fermentation process. In one embodiment, biomass feedstock is processed such that the protein content is hydrolyzed, providing an increase in free amino acids liberated from the biomass as compared to butanol fermentation processes known in the art. In one embodiment, the excess branched chain amino acids valine, leucine, and isoleucine as well as the phenylalanine so produced are substrates for pathways in the yeast to produce fusel alcohols isobutanol, isoamyl alcohol (3-methyl-1-butanol), active amyl alcohol (2-methyl-1-butanol), and 2-phenylethanol, respectively. Increased production of one or more such fusels from previously non-utilized substrates would advantageously lead to increased yield of butanol and fusel oil mixtures per unit of biomass.

To further increase yield of hydrocarbons including butanol per unit biomass, a recombinant microorganism comprising a heterologous butanol biosynthetic pathway may be modified to utilize amino acid substrates more efficiently. In one embodiment, such modification is achieved by modification of the activity of at least one Ehrlich pathway gene (thereby affecting production of fusel alcohols). Together, the processing and host cell modifications may result in increased production of butanol and/or fusel alcohols with respect to the theoretical yield from a particular biomass feedstock, as compared to the production of butanol and/or fusel alcohols obtained from utilization of only fermentable sugars or only protein hydrolysates within the particular biomass feedstock.

Thus, in one embodiment, the present invention is drawn to a method for producing a butanol and fusel alcohol mixture from a biomass feedstock comprising:
  a) providing a biomass feedstock;
  b) processing the biomass feedstock to produce a processed feedstock slurry comprising protein hydrolysates and oligosaccharides;
  c) saccharifying the oligosaccharides of the processed feedstock slurry to produce a fermentation composition comprising fermentable sugars and protein hydrolysates;

d) fermenting a recombinant yeast in the presence of the fermentation composition, said recombinant yeast comprising:
   (i) a heterologous butanol biosynthetic pathway for production of butanol; and,
   (ii) at least one upregulated Ehrlich pathway gene for production of fusel alcohol;
   whereby a butanol and fusel alcohol mixture is produced; and,
e) recovering the butanol and fusel alcohol mixture;
wherein the yield of the butanol and fusel alcohol mixture per kilogram of biomass feedstock is increased.

Fusel Alcohol Production Pathways in Yeast

Processes for the preparation of fusel alcohols are known; see, for example, EP 624 388. Composition of fusel alcohols can vary according to the processes and according to the plant fermented.

In yeasts, under certain conditions, fusel alcohols are produced through the metabolization of nitrogenous compounds, such as amino acids. This pathway for amino acid catabolism was first proposed a century ago by F. Ehrlich (*Über die Bedingungen der Fuselölbildung und über ihren Zusammenhang mit dem Eiweissaufbau der Hefe. Ber. Dtsch. Chem. Ges.* 40:1027-1047 (1907)). Fusel alcohols are formed by all the yeast species that have been examined (Guymon, J. F., et al., *Archives of Biochemistry and Biophysics* 95:163-168 (1961); Guymon, J. F., et al.,. *American J. Enology and Viticulture* 12:60-66 (1961)). Hazelwood, L. A. et al. provide a useful Minireview entitled "The Ehrlich Pathway for Fusel Alcohol Production: A Century Of Research On *Saccharomyces cerevisiae* Metabolism" ((*Appl. Environ. Microbiol.*, 74(8):2259-2266 (2008)). In brief, the Ehrlich Pathway is initiated by transamination of branched-chain amino acids (i.e., leucine, valine and isoleucine), aromatic amino acids (i.e., phenylalanine, tyrosine and tryptophan) and/or the sulfur-containing amino acid (i.e., methionine), which results in formation of an α-keto acid that cannot be redirected into central carbon metabolism. The α-keto acid then is decarboxylated to produce a "fusel aldehyde", and oxidation or reduction of fusel aldehydes then occur, thereby producing fusel acids and/or fusel alcohols, respectively. These products are then either passively or actively exported from the cell into the fermentation medium.

Figure 2A:
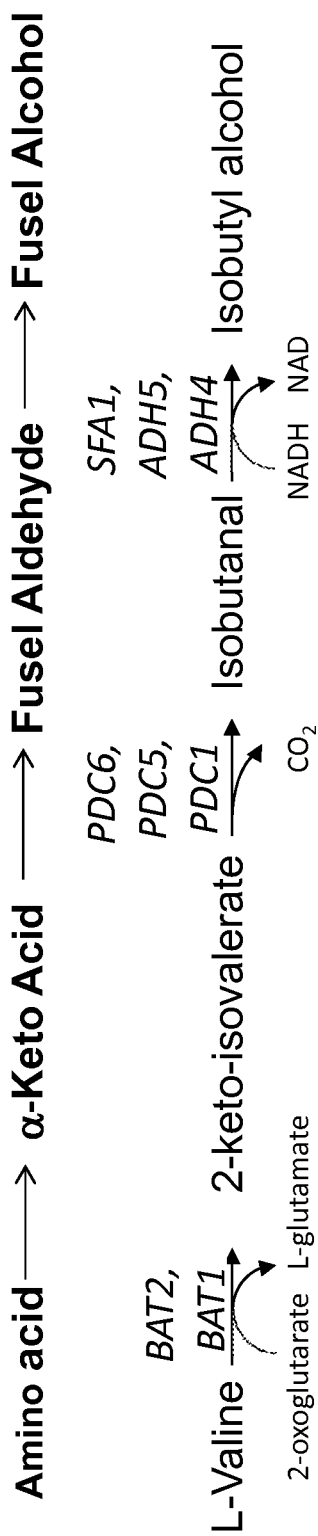
Figure 2B:
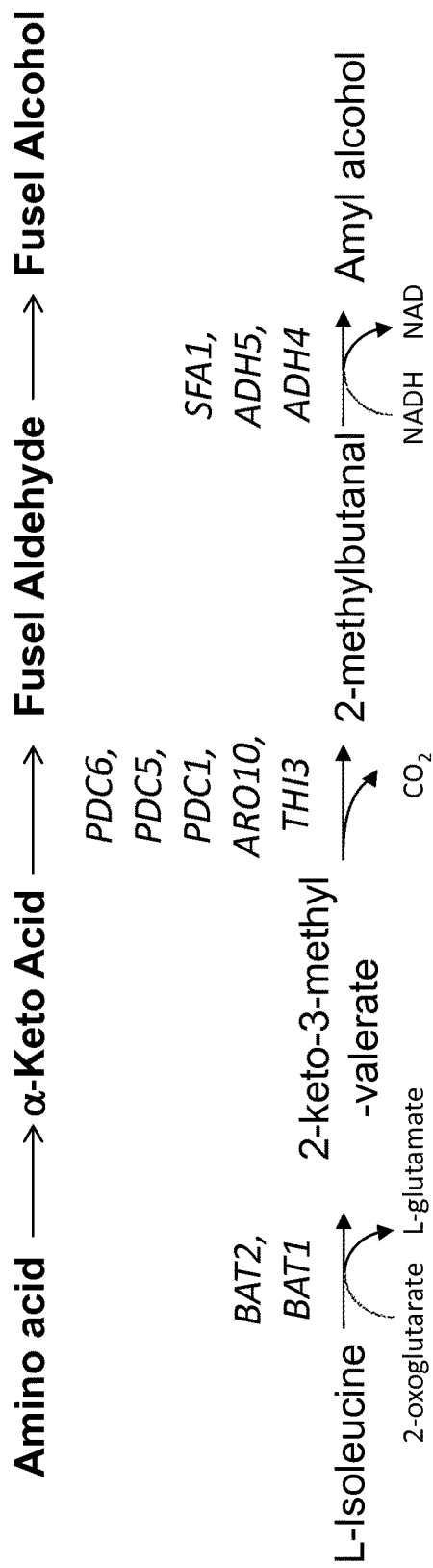
Figure 3A:
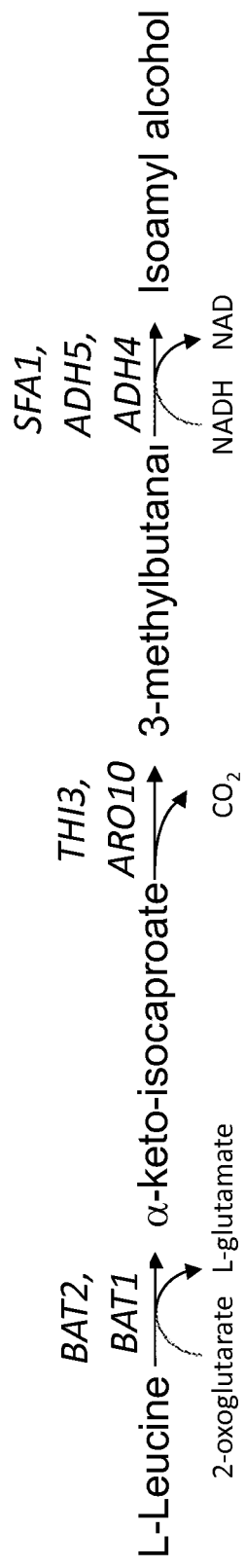
Figure 3B:
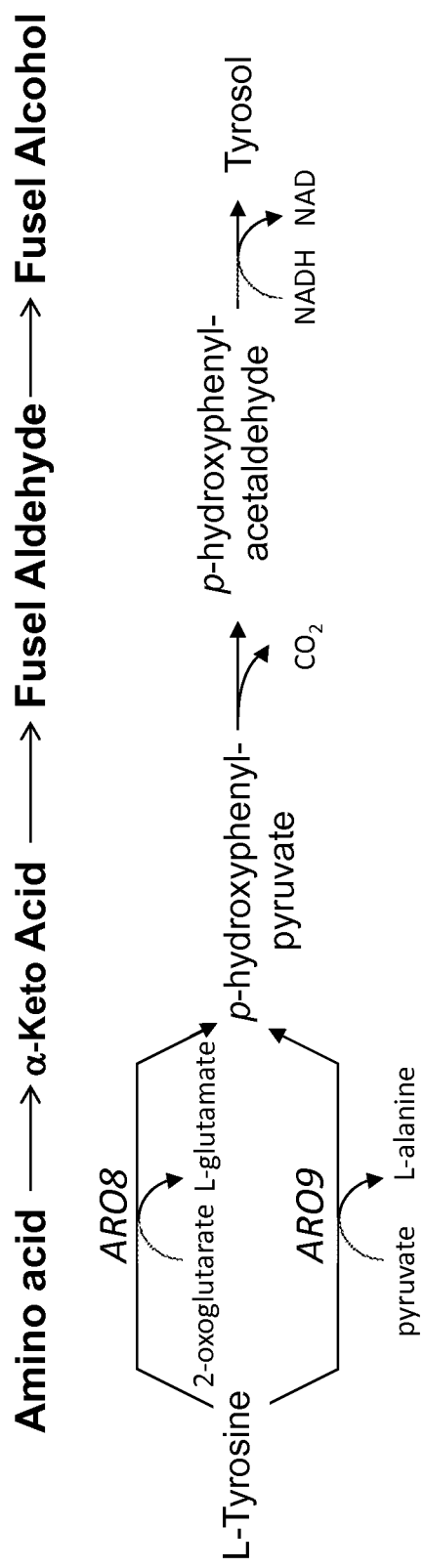
Figure 4A:
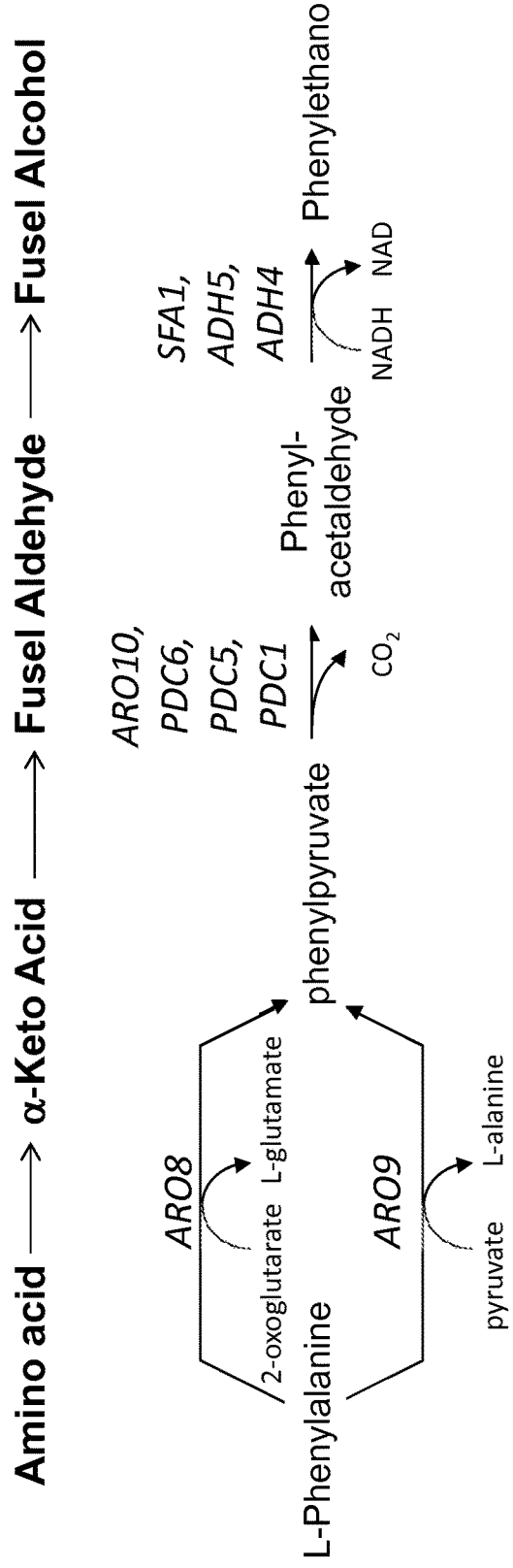
Figure 4B:
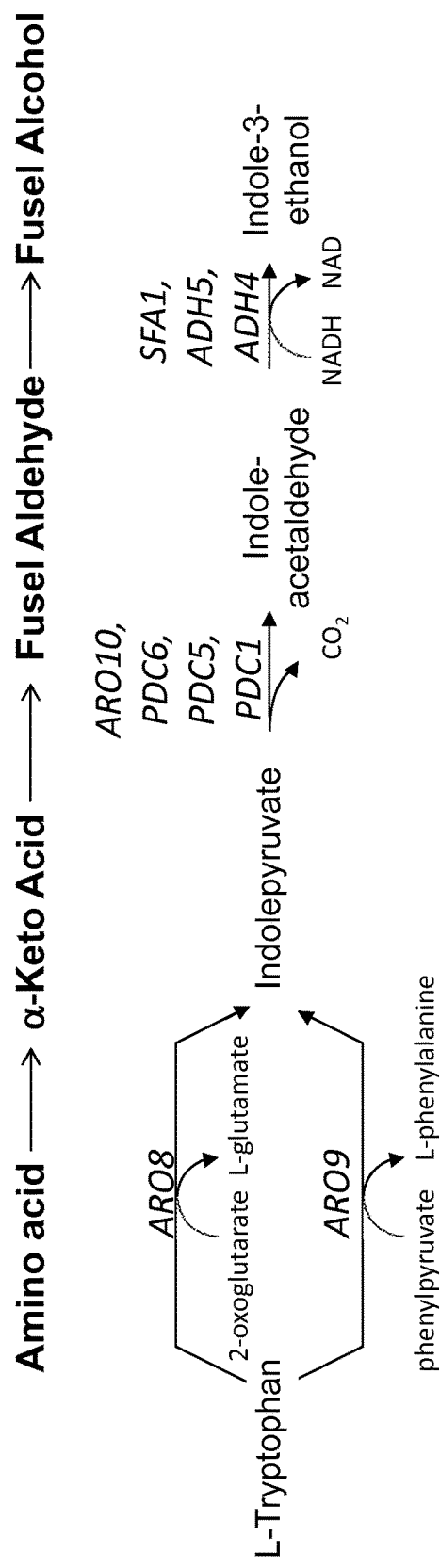

Although the Ehrlich pathway was proposed over a century ago, experimental verification of the role of the pathway in amino acid catabolism wasn't obtained until the late 1990s, via $^{13}C$ labeling studies. Ehrlich pathway intermediates (i.e., α-keto acids and fusel aldehydes) were confirmed. Of particular interest herein, valine is transaminated to 3-methyl-2-oxo-butanoate ("α-ketoisovalerate"), decarboxylated to 2-methylpropanal ("isobutanal" or "isovaleraldehyde"), and oxidized to produce the fusel acid 2-methylpropanoate ("isobutyrate") or reduced to produce the fusel alcohol 2-methylpropanol ("isobutanol" or "isobutyl alcohol") (FIG. 2A). Similarly, isoleucine is catabolized to produce 3-methyl-2-oxo-pentanoate ("α-ketomethylvalerate"), 2-methylbutanal ("methylvaleraldehyde"), the fusel acid 2-methylbutanoate ("methylvalerate") and/or the fusel alcohol 2-methylbutanol ("active amyl alcohol") (FIG. 2B). Leucine is transaminated to produce 4-methyl-2-oxo-pentanoate ("α-keotisocaproate"), decarboxylated to produce 3-methylbutanal ("isoamylaldehyde"), and reduced to produce 3-methylbutanoate ("isovalerate") or oxidized to produce 3-methylbutanol ("isoamyl alcohol") (FIG. 3A). Tyrosine is catabolized to produce p-hydroxyphenylpyruvate, p-hydroxyphenylacetylaldehyde, the fusel acid 2-(4-hydroxyphenyl) ethanoate ("p-hydroxyphenylacetate") and/or the fusel alcohol 2-(4-hydroxyphenyl) ethanol ("tyrosol" or "p-hydroxyphenylethanol") (FIG. 3B). Phenylalanine is transaminated to produce 3-phenyl-2-oxo-propanoate ("phenylpyruvate"), decarboxylated to produce 2-phenylethanal ("2-phenylacetaldehyde"), and reduced to produce 2-phenylethanoate ("2-phenylacetate") or oxidized to produce 2-phenylethanol (FIG. 4A). Tryptophan is catabolized to produce 3-(indol-3-yl)-2-oxopropanoate ("3-indole pyruvate"), 2-(indol-3-yl)-2-ethanal ("3-indole acetaldehyde"), the fusel acid 2-(indol-3-yl)-2-ethanoate and/or the fusel alcohol 2-(indol-3-yl)ethanol ("tryptophol" or "indole-3-ethanol") (FIG. 4B).

A variety of proteins play roles in the Ehrlich pathway, as shown in FIG. 1 herein and summarized in Table 2. (See Hazelwood, L. A. et al., supra.) In general, ARO8 and ARO9 are through to be minor transaminases for isoleucine and leucine catabolism, while BAT1 and BAT2 function for isoleucine, leucine and valine catabolism. ARO10 functions as a broad-substrate specificity decarboxylase for isoleucine and leucine catabolism, while PDC1, PDC5 and PDC6 typically participate in valine catabolism. Finally, recent studies with THI3 indicate that this enzyme may play a regulatory role in the Ehrlich pathway (as opposed to a catalytic role) (reviewed in Hazelwood, L. A. et al., supra).

TABLE 2

Ehrlich Pathway Proteins For Formation Of Fusel Acids And Fusel Alcohols

| Reaction | Enzyme | EC Number | Enzyme Name | *Saccharomyces cerevisiae* Protein |
|---|---|---|---|---|
| Transamination | Aromatic aminotransferase | 2.6.1.39 or 2.6.1.57 | ARO8 | GenBank Accession No. NM_001181067 (SEQ ID NO: 2) |
| | Aromatic aminotransferase | 2.6.1.57 | ARO9 | GenBank Accession No. NM_001179267 (SEQ ID NO: 4) |
| | Mitochondrial branched chain amino acid transferase | 2.6.1.42 | BAT1 | GenBank Accession No. X78961 (SEQ ID NO: 8) |
| | Cytosolic branched chain amino acid transferase | 2.6.1.42 | BAT2 | GenBank Accession No. NM_001181806 (SEQ ID NO: 10) |
| Decarboxylation | Phenylpyruvate decarboxylase | 4.1.1.— | ARO10 | GenBank Accession No. NM_001180688 (SEQ ID NO: 6) |

TABLE 2-continued

Ehrlich Pathway Proteins For Formation Of Fusel Acids And Fusel Alcohols

| Reaction | Enzyme | EC Number | Enzyme Name | *Saccharomyces cerevisiae* Protein |
|---|---|---|---|---|
| | Pyruvate decarboxylase | 4.1.1.1 | PDC1 | GenBank Accession No. NM_001181931 (SEQ ID NO: 12) |
| | Pyruvate decarboxylase | 4.1.1.1 | PDC5 | GenBank Accession No. NM_001182021 (SEQ ID NO: 14) |
| | Pyruvate decarboxylase | 4.1.1.1 | PDC6 | GenBank Accession No. NM_001181216 (SEQ ID NO: 16) |
| | Alpha-ketoisocaproate decarboxylase | 4.1.1.— | THI3 | GenBank Accession No. D21880 (SEQ ID NO: 18) |
| Reduction (for synthesis of fusel alcohols) | Alcohol dehydrogenase | 1.1.1.1 | ADH1 | GenBank Accession No. V01291 (SEQ ID NO: 20) |
| | Alcohol dehydrogenase | 1.1.1.1 | ADH2 | GenBank Accession No. NM_001182812 (SEQ ID NO: 22) |
| | Alcohol dehydrogenase | 1.1.1.1 | ADH3 | GenBank Accession No. NM_001182582 (SEQ ID NO: 24) |
| | Alcohol dehydrogenase | 1.1.1.1 | ADH4 | GenBank Accession No. X05992 (SEQ ID NO: 26) |
| | Alcohol dehydrogenase | 1.1.1.1 | ADH5 | GenBank Accession No. NM_001178493 (SEQ ID NO: 28) |
| | Alcohol dehydrogenase | 1.1.1.2 | ADH6 | GenBank Accession No. NM_001182831 (SEQ ID NO: 30) |
| | Alcohol dehydrogenase (class III) | | SFA1 | GenBank Accession No. NM_001180228 (SEQ ID NO: 32) |
| | Putative aryl-alcohol dehydrogenase | 1.1.1.— | AAD3 | GenBank Accession No. NM_001178814 (SEQ ID NO: 34) |
| | Putative aryl-alcohol dehydrogenase | 1.1.1.— | AAD4 | GenBank Accession No. NM_001180303 (SEQ ID NO: 36) |
| | Putative aryl-alcohol dehydrogenase | 1.1.1.— | AAD6 | GenBank Accession No. NM_001179911 (SEQ ID NO: 38) |
| | Putative aryl-alcohol dehydrogenase | 1.1.1.— | AAD10 | GenBank Accession No. NM_001181813 (SEQ ID NO: 40) |
| | Putative aryl-alcohol dehydrogenase | 1.1.1.— | AAD14 | GenBank Accession No. NM_001183169 (SEQ ID NO: 42) |
| | Putative aryl-alcohol dehydrogenase | 1.1.1.— | AAD15 | GenBank Accession No. NM_001183418 (SEQ ID NO: 44) |
| | Putative aryl-alcohol dehydrogenase | 1.1.1.— | AAD16 | GenBank Accession No. NM_001179910 (SEQ ID NO: 46) |
| | Putative aryl-alcohol dehydrogenase | 1.1.1.— | YPL088W | GenBank Accession No. NM_001183902 (SEQ ID NO: 48) |
| Oxidation (for synthesis of fusel acids) | Aldehyde dehydrogenase | 1.2.1.5 | ALD2 | GenBank Accession No. NM_001182674 (SEQ ID NO: 52) |
| | Aldehyde dehydrogenase | 1.2.1.5 | ALD3 | GenBank Accession No. NM_001182673 (SEQ ID NO: 54) |
| | Aldehyde dehydrogenase | 1.2.1.3 | ALD4 | GenBank Accession No. NM_001183794 (SEQ ID NO: 56) |
| | Aldehyde dehydrogenase | 1.2.1.3 or 1.2.1.4 | ALD5 | GenBank Accession No. NM_001178964 (SEQ ID NO: 58) |
| | Aldehyde dehydrogenase | 1.2.1.3 | ALD6 | GenBank Accession No. NM_001183875 (SEQ ID NO: 60) |

TABLE 2-continued

Ehrlich Pathway Proteins For Formation Of Fusel Acids And Fusel Alcohols

| Reaction | Enzyme | EC Number | Enzyme Name | *Saccharomyces cerevisiae* Protein |
|---|---|---|---|---|
| Export (for fusel acids) | ATP-binding ATP transporter | — | PDR12 | GenBank Accession No. NM_001183872 (SEQ ID NO: 50) |

Note:
Suitable polypeptide sequences that encode enzymes which catalyze the reactions set forth above, as well as E.C. numbers corresponding to the substrate to product conversions indicated include, but are not limited to, those set forth above. Suitable enzymes capable of performing the substrate to product conversions associated with the given E.C. numbers will be readily available to those of skill in the art, for example, through online public databases such as the BRENDA database (http://www.brenda-enzymes.org/).

Although the *Saccharomyces cerevisiae* proteins shown in Table 2 are exemplary of useful Ehrlich pathway polypeptides, one of skill in the art will recognize that the present invention is not limited thereto. Thus, preferably, the polypeptide sequence encoding an Ehrlich pathway gene is selected from the group consisting of SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, and 60. In alternate embodiments, the polypeptide sequence encoding an Ehrlich pathway gene has at least 85% sequence identity based on the CLUSTALW method of alignment, when compared to any one of SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, and 60, i.e., the polypeptide may have at least 85%, 86%, 87%, 88%, 89%, 90%, 91%, 92%, 93%, 94%, 95%, 96%, 97%, 98%, 99%, or 100% identity when compared thereto. In alternate embodiments, the sequences set forth in Table 2, or homologs or codon-optimized derivatives thereof, may be used in the present invention.

In other embodiments, a polynucleotide, gene and/or polypeptide encoding ARO8, ARO9, BAT1, BAT2, ARO10, PDC1, PDC5, PDC6, ALD2, ALD3, ALD4, ALD5, ALD6, THI3, ADH1, ADH2, ADH3, ADH4, ADH5, ADH6, SFA1, AAD3, AAD4, AAD6, AAD10, AAD14, AAD15, AAD16, YPL088W and PDR12 can be used to identify homologs in other cells. Such Ehrlich pathway sequences can be identified, for example, in the literature and/or in bioinformatics databases well known to the skilled person. For example, the identification of ARO8, ARO9, BAT1, BAT2, ARO10, PDC1, PDC5, PDC6, ALD1, ALD2, ALD3, ALD4, ALD5, ALD6, THI3, ADH1, ADH2, ADH3, ADH4, ADH5, ADH6, SFA1, AAD3, AAD4, AAD6, AAD10, AAD14, AAD15, AAD16, YPL088W and PDR12 encoding sequences in other cell types using bioinformatics can be accomplished through BLAST searching of publicly available databases with known Ehrlich pathway encoding DNA and polypeptide sequences, such as those provided herein as the query. Identities are based on the Clustal W method of alignment using the default parameters of GAP PENALTY=10, GAP LENGTH PENALTY=0.1, and Gonnet 250 series of protein weight matrix.

As shown in FIG. 1, only the fusel acid is exported from inside the cell ("in") to outside in the culture medium ("out"). PDR12, an ATP-dependent transporter, has been confirmed to catalyze this active transport of the fusel acid (Hazelwood, L. A., et al., *FEMS Yeast Res.*, 6:937-945 (2006)), while fusel alcohols are thought to passively diffuse across the cells' lipid bilayer into the medium (Lipinski, C. A., *Adv. Drug Deliv. Rev.*, 46:3-26 (2001)).

It has been reported that the addition of a high concentration of valine to a fermentation medium increased *Saccharomyces cerevisiae* production of isobutanol, isobutyric acid, propanol and propionic acid concentrations (Lilly et al., *FEMS Yeast Res.*, 6(5):726-743 (2006)). Overexpression of Bat2p has been reported to result in increases in isobutanol concentrations (Lilly et al., supra; Chen, X. et al., *Biotechnology for Biofuels*, 4:21 (2011)); similarly, overexpression of Bat1p has been reported to result in increases in isoamyl alcohol concentrations (Yoshimoto, H., et al., *Appl. Microbiol. Biotechnol.*, 59:501-508 (2002); Lilly et al., supra).

The recombinant yeast of the present invention comprises at least one modification to an Ehrlich pathway gene, thereby changing the expression or activity of a polypeptide encoded by the Erhlich pathway genes by deleting, mutating, substituting, up-regulating, down-regulating, altering the cellular location, altering the state of the protein, and/or adding a cofactor.

Thus, in one embodiment, the recombinant yeast of the present invention comprises at least one upregulated Ehrlich pathway gene, wherein said upregulation increases the rate and/or yield of fusel alcohol production. For example, since BAT1 and BAT2 are capable of catalyzing conversion of the branched chain amino acids to their α-keto acid counterparts (i.e., L-isoleucine→2-keto-3-methyl-valerate, L-leucine→α-ketoisocaproate and L-valine→2-keto-isovalerate, respectively), it is expected that upregulation of either of these transaminases (or both in combination) will lead to increased flux through the Ehrlich pathway resulting in an increased concentration of fusel alcohol from these amino acids. When performed in combination with processing methods to increase the availability of these branched chain amino acids in the fermentation medium, this may increase the overall butanol and fusel alcohol yield per unit of biomass. If the recombinant yeast is engineered to function as an isobutanologen, isobutanol is produced through the isobutanol biosynthetic pathway introduced into the yeast and as a result of increased conversion of valine to isobutanol through the Ehrlich pathway when BAT2 is upregulated, thereby resulting in increased product yield.

Similarly, since ARO8 and ARO9 are capable of catalyzing conversion of the aromatic amino acids to their α-keto acid counterparts (i.e., L-tyrosine→p-hydroxyphenylpyruvate, L-phenylalanine→phenylpyruvate, L-tryptophan→indolepyruvate, respectively), it is expected that upregulation of either of these aromatic aminotransferase will lead to increased flux through the Ehrlich pathway resulting in an increased concentration of fusel alcohol from these amino acids.

In another embodiment, the recombinant yeast of the present invention may comprise at least one down-regulated Ehrlich pathway gene, thereby minimizing the rate and/or yield of fusel alcohol production. This may be advantageous if it is desirable to increase the purity of the primary product of the butanol biosynthetic pathway (i.e., 1-butanol, 2-butanol, isobutanol) and minimize co-production of fusel alcohol, primarily non-isobutanol fusel alcohol. Thus, one of skill in the art will be able to envision means to partially or completely down-regulate the activity of at least one of the Ehrlich pathway enzymes, by creating an insertion, deletion, or targeted mutation within a portion of e.g., BAT1, BAT2, ARO8, ARO9, ARO10, that results in e.g., a complete gene knockout such that the gene is deleted from the genome and no protein is translated.

In an alternate embodiment, expression of one or more of the transaminases BAT1 or BAT2 is up-regulated while expression of the transaminases ARO8 or ARO9 are reduced or eliminated. Gene deletion cassettes causing reduced or eliminated expression are well-known in the art, and are available for purchase from ATCC (i.e. aro8D; ATCC #4004569).

Butanol Biosynthetic Pathways

TABLE 3

Summary Of Substrate to Product Conversions In An Example 1-Butanol Biosynthetic Pathway

| Reaction | Substrate To Product Conversion | Enzyme [Example E.C. number associated with substrate to product conversion] |
|---|---|---|
| A | acetyl-CoA → acetoacetyl-CoA | acetyl-CoA acetyltransferase [E.C. 2.3.1.9] |
| b | acetoacetyl-CoA → 3-hydroxybutyryl-CoA | 3-hydroxybutyryl-CoA dehydrogenase [E.C. 1.1.1.35, E.C. 1.1.1.30, E.C. 1.1.1.157 and E.C. 1.1.1.36] |
| c | 3-hydroxybutyryl-CoA → crotonyl-CoA | Crotonase [E.C. 4.2.1.17 and E.C. 4.2.1.55] |
| d | crotonyl-CoA → butyryl-CoA | butyryl-CoA dehydrogenase [E.C. 1.3.1.44 and E.C. 1.3.1.38] |
| e | butyryl-CoA → butyraldehyde | butyraldehyde dehydrogenase [E.C. 1.2.1.57] |
| f | butyraldehyde → 1-butanol | 1-butanol dehydrogenase |

Note:
Suitable polypeptide sequences that encode enzymes which catalyze the substrate to product conversions of the pathway as well as E.C. numbers corresponding to substrate to product conversions for the indicated pathway steps include, but are not limited to, those set forth above. Suitable enzymes associated with the given E.C. numbers will be readily available to those of skill in the art, for example, through online public databases such as the BRENDA database (www.brenda-enzymes.org/) and in the art (for example, in U.S. Pat. Appn. Pub. No. 20080182308A1, incorporated herein by reference).

TABLE 4

Summary Of Substrate to Product Conversions In Example 2-Butanol Biosynthetic Pathways

| | Pathway I | | Pathway III | |
|---|---|---|---|---|
| Reaction | Substrate To Product Conversion | Enzyme | Substrate To Produc Conversion [Example E.C. number associated with substrate to product conversion] | Enzyme |
| A | pyruvate → alpha-acetolactate | acetolactate synthase EC 2.2.1.6 | pyruvate → alpha-acetolactate | acetolactate synthase EC 2.2.1.6 |
| B | alpha-acetolactate → acetoin | acetolactate decarboxylase [EC 4.1.1.5] | alpha-acetolactate → acetoin | acetolactate decarboxylase [EC 4.1.1.5] |
| C | acetoin → 3-amino-2-butanol | acetoin aminase | — | — |
| D | 3-amino-2-butanol → 3-amino-2-butanol O-phosphate | aminobutanol kinase | — | — |
| E | 3-amino-2-butanol phosphate → butanone | aminobutanol phosphate phospho-lyase | — | — |
| I | — | — | acetoin → 2,3-butanediol | butanediol dehydrogenase |

TABLE 4-continued

Summary Of Substrate to Product Conversions In Example 2-Butanol Biosynthetic Pathways

| | Pathway I | | Pathway III | |
|---|---|---|---|---|
| Reaction | Substrate To Product Conversion | Enzyme | Substrate To Produc Conversion [Example E.C. number associated with substrate to product conversion] | Enzyme |
| J | — | — | 2,3-butanediol → 2-butanone | butanediol dehydratase [EC 4.2.1.28 and EC 4.2.1.30] |
| F | 2-butanone → 2-butanol | butanol dehydrogenase | 2-butanone → 2-butanol | butanol dehydrogenase |

Note:
Suitable polypeptide sequences that encode enzymes which catalyze the substrate to product conversions of the pathway as well as E.C. numbers corresponding to substrate to product conversions for indicated pathway steps include, but are not limited to, those set forth above. Suitable enzymes capable of catalyzing the substrate to product conversions associated with the given E.C. numbers will be readily available to those of skill in the art, for example, through online public databases such as the BRENDA database (www.brenda-enzymes.org/) and in the art (for example, in U.S. Pat. No. 8,206,970 and U.S. Pat. Appn. Pub. 2007-0292927-A1, each incorporated herein by reference).

TABLE 5

Summary Of Substrate to Product Conversions In Example Isobutanol Biosynthetic Pathways

| | Pathway I | | Pathway II | | Pathway III | |
|---|---|---|---|---|---|---|
| Reaction | Substrate To Product Conversion | Enzyme | Substrate To Product Conversion | Enzyme [Example E.C. number associated with substrate to product conversion] | Substrate To Product Conversion | Enzyme |
| A | pyruvate → acetolactate | acetolactate synthase [EC 2.2.1.6] | pyruvate → acetolactate | acetolactate synthase [EC 2.2.1.6] | pyruvate → acetolactate | acetolactate synthase [EC 2.2.1.6] |
| B | acetolactate → 2,3-dihydroxy-isovalerate | acetohydroxy acid isomer-reductase [EC 1.1.1.86] | acetolactate → 2,3-dihydroxy-isovalerate | acetohydroxy acid isomer-reductase [EC 1.1.1.86] | acetolactate → 2,3-dihydroxy-isovalerate | acetohydroxy acid isomer-reductase [EC 1.1.1.86] |
| C | 2,3-dihydroxy-isovalerate → α-ketoisovalerate | acetohydroxy acid dehydratase [EC 4.2.1.9] | 2,3-dihydroxy-isovalerate → α-ketoisovalerate | acetohydroxy acid dehydratase [EC 4.2.1.9] | 2,3-dihydroxy-isovalerate → α-ketoisovalerate | acetohydroxy acid dehydratase [EC 4.2.1.9] |
| D | α-ketoisovalerate → isobutyraldehyde | branched-chain keto acid decarboxylase [EC 4.1.1.72 or EC 4.1.1.1] | — | — | — | — |
| F | — | — | α-ketoisovalerate → isobutyryl-CoA | branched-chain keto acid dehydrogenase | — | — |
| G | — | — | isobutyryl-CoA → isobutyraldehyde | acylating aldehyde dehydrogenase | — | — |
| H | — | — | — | — | α-ketoisovalerate → valine | valine dehydrogenase or transaminase |
| I | — | — | — | — | valine to isobutylamine | valine decarboxylase |
| J | — | — | — | — | isobutylamine to isobutyraldehyde | omega transaminase |
| E | isobutyraldehyde → isobutanol | branched-chain alcohol dehydrogenase [EC 1.1.1.265, EC 1.1.1.1 or EC 1.1.1.2] | isobutyraldehyde → isobutanol | branched-chain alcohol dehydrogenase [EC 1.1.1.265, EC 1.1.1.1 or EC 1.1.1.2] | isobutyraldehyde → isobutanol | branched-chain alcohol dehydrogenase [EC 1.1.1.265, EC 1.1.1.1 or EC 1.1.1.2] |

Note:
Suitable polypeptide sequences that encode enzymes which catalyze the substrate to product conversions of the pathway as well as E.C. numbers corresponding to substrate to product conversions for indicated pathway steps include, but are not limited to, those set forth above. Suitable enzymes capable of catalyzing the substrate to product conversions associated with the given E.C. numbers will be readily available to those of skill in the art, for example, through online public databases such as the BRENDA database (http://www.brenda-enzymes.org/), and in the art (for example in U.S. Pat. Nos. 7,851,188; 7,993,889; and 8,178,328, each incorporated herein by reference).

In one embodiment, the invention produces butanol from recently-living plant derived carbon sources, avoiding the negative environmental impact associated with the standard petrochemical processes for butanol production. In one embodiment, the invention provides a method for the production of butanol using recombinant industrial host cells comprising an engineered butanol biosynthetic pathway.

In some embodiments, the butanol biosynthetic pathway comprises at least one polynucleotide, at least two polynucleotides, at least three polynucleotides, at least four polynucleotides, etc. that is/are heterologous to the host cell. In some embodiments, each substrate to product conversion of a butanol biosynthetic pathway in a recombinant host cell is catalyzed by a heterologous polypeptide. In embodiments, the polypeptide catalyzing the substrate to product conversions of acetolactate to 2,3-dihydroxyisovalerate and/or the polypeptide catalyzing the substrate to product conversion of isobutyraldehyde to isobutanol are capable of utilizing NADH as a cofactor.

In some embodiments, the engineered butanol pathway of the butanologen comprises at least one polypeptide selected from the group of enzymes having the following Enzyme Commission Numbers: EC 2.2.1.6, EC 1.1.1.86, EC 4.2.1.9, EC 4.1.1.72, EC 1.1.1.1, EC 1.1.1.265, EC 1.1.1.2, EC 1.2.4.4, EC 1.3.99.2, EC 1.2.1.10, EC 2.3.1.9, EC 2.3.1.16, EC 1.1.1.35, EC 1.1.1.157, EC 1.1.1.36, EC 4.2.1.17, EC 4.2.1.55, EC 1.3.1.44, EC 1.3.1.38, EC 4.1.1.8, EC 4.2.1.28, EC 4.2.1.30, and EC 1.2.1.57.

In some embodiments, the engineered butanol pathway of the butanologen comprises at least one polypeptide selected from the following group of enzymes: acetolactate synthase, acetohydroxy acid isomeroreductase, acetohydroxy acid dehydratase, branched-chain alpha-keto acid decarboxylase, branched-chain alcohol dehydrogenase, acylating aldehyde dehydrogenase, branched-chain keto acid dehydrogenase, butyryl-CoA dehydrogenase, butyraldehyde dehydrogenase, acetyl-CoA acetyltransferase, 3-hydroxybutyryl-CoA dehydrogenase, crotonase, butanol dehydrogenase, acetolactate decarboxylase, acetoin aminase, aminobutanol kinase, aminobutanol phosphate pholyase, dihydroxyacetone kinase, serinol phophate aminotransferase, butanediol dehydrogenase, diol dehydratase and glycerol dehydratase.

The terms "acetohydroxyacid synthase," "acetolactate synthase" and "acetolactate synthetase" (abbreviated "ALS") are used interchangeably herein to refer to a polypeptide(s) having an enzyme activity that catalyzes the conversion of two molecules of pyruvic acid to one molecule of alpha-acetolactate. Example acetolactate synthases are known by the EC number 2.2.1.6 [formerly EC 4.1.3.18] (Enzyme Nomenclature 1992, Academic Press, San Diego, Calif.). Acetolactate synthase may utilize the cofactor thiamin pyrophosphate. These unmodified enzymes are available from a number of sources, including, but not limited to, *Bacillus subtilis* (GenBank Nos: CAB15618 and Z99122, NCBI (National Center for Biotechnology Information) amino acid sequence, NCBI nucleotide sequence, respectively), *Klebsiella pneumoniae* (GenBank Nos: AAA25079 and M73842), and *Lactococcus lactis* (GenBank Nos: AAA25161 and L16975). A suitable *B. subtilis* acetolactate synthase is set forth herein as SEQ ID NO:135.

The terms "ketol-acid reductoisomerase" ("KARI"), "acetohydroxy acid isomeroreductase" and "acetohydroxy acid reductoisomerase" will be used interchangeably and refer to any polypeptide having a biological function of a ketol-acid reductoisomerase. Such polypeptides include a polypeptide capable of catalyzing the reaction of (S)-acetolactate to 2,3-dihydroxyisovalerate. Example KARI enzymes may be classified as EC number 1.1.1.86 and are available from a vast array of microorganisms, including, but not limited to, *Escherichia coli* (SEQ ID NO:136) (GenBank Nos: NP_418222 and NC_000913), *Saccharomyces cerevisiae* (GenBank Nos: NP_013459 and NC_001144), *Methanococcus maripaludis* (GenBank Nos: CAF30210 and BX957220), *Pseudomonas fluorescens* (SEQ ID NO:137) and *Bacillus subtilis* (GenBank Nos: CAB14789 and Z99118). KARIs include *Anaerostipes caccae* KARI variants "K9G9" and "K9D3" and variants thereof. Ketol-acid reductoisomerase (KARI) enzymes are described in U.S. Pat. Nos. 7,910,342, and 8,129,162; U.S. Patent Appl. Pub. No. 20100197519; and International Appl. Pub. No. WO 2011/041415, all of which are incorporated herein by reference. Examples of KARIs disclosed therein are those from *Lactococcus lactis, Vibrio cholera, Pseudomonas aeruginosa* PAO1 and *Pseudomonas fluorescens* PF5 mutants. U.S. Appl. Pub. No. US20130071898A1, incorporated herein by reference, further describes KARI variants useful in the present invention, and is incorporated herein by reference. An example *A. caccae* KARI (i.e., variant "K9SB2") is set forth herein as SEQ ID NO:124.

The terms "acetohydroxy acid dehydratase" and "dihydroxyacid dehydratase" ("DHAD") refer to any polypeptide having a biological function of a dihydroxyacid dehydratase. Such polypeptides include a polypeptide that catalyzes the conversion of 2,3-dihydroxyisovalerate to α-ketoisovalerate. Example acetohydroxy acid dehydratases are known by the EC number 4.2.1.9. Such enzymes are available from a vast array of microorganisms, including, but not limited to, *E. coli* (GenBank Nos: YP_026248 and NC_000913), *S. cerevisiae* (GenBank Nos: NP_012550 and NC_001142), *M. maripaludis* (GenBank Nos: CAF29874 and BX957219), *B. subtilis* (GenBank Nos:CAB14105 and Z99115), *Lactococcus lactis* (SEQ ID NO:131), *Streptococcus mutans* (SEQ ID NO:X126) and *N. crassa*. US Appl. Pub. No. 20100081154 A1 and U.S. Pat. No. 7,993,889, both of which are incorporated herein by reference, describe dihydroxyacid dehydratases (DHADs), including a DHAD from *Streptococcus mutans* and a DHAD from *Lactococcus lactis*. The term "branched-chain α-keto acid decarboxylase" or "α-ketoacid decarboxylase" or "α-ketoisovalerate decarboxylase" or "2-ketoisovalerate decarboxylase" ("KIVD") refers to any polypeptide having a biological function of a 2-ketoisovalerate decarboxylase. Such polypeptides include a polypeptide that catalyzes the conversion of α-ketoisovalerate to isobutyraldehyde and $CO_2$. Example branched chain α-keto acid decarboxylases are known by the EC number 4.1.1.72 and are available from a number of sources, including, but not limited to, *Lactococcus lactis* (GenBank Nos: AAS49166, AY548760, CAG34226 and AJ746364), *Salmonella typhimurium* (GenBank Nos: NP_461346 and NC_003197), *Clostridium acetobutylicum* (GenBank Nos: NP_149189 and NC_001988), *Macrococcus caseolyticus* (SEQ ID NO:133), and *Listeria grayi* (SEQ ID NO:128).

The terms "branched-chain alcohol dehydrogenase" or "alcohol dehydrogenase" ("ADH") refer to any polypeptide having a biological function of an alcohol dehydrogenase. Such polypeptides include a polypeptide that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Such enzymes are available from a number of sources, including, but not limited to, *S. cerevisiae* (GenBank Nos: NP_010656, NC_001136, NP_014051 and NC_001145), *E.* coli (GenBank Nos: NP_417484 and NC_000913), *C. acetobutylicum* (GenBank Nos: NP_349892, N_003030, NP_349891 and NC_003030), *Beijerinkia indica* (SEQ ID NO:129) and *Achromobacter xylosoxidans* (SEQ ID NO:134). U.S. Pat. No. 8,188,250, incorporated herein by reference, describes SadB, an alcohol dehydrogenase (ADH) from *A. xylosoxidans*. Alcohol dehydrogenases also include horse liver ADH and *B. indica* ADH (as described by U.S. Appl. Publ. No. 20110269199, incorporated herein by reference).

The term "butanol dehydrogenase" refers to any polypeptide having a biological function of a butanol dehydrogenase. Such polypeptides include a polypeptide that catalyzes the conversion of isobutyraldehyde to isobutanol or the conversion of 2-butanone to 2-butanol. Butanol dehydrogenases are a subset of a broad family of alcohol dehydrogenases. Example enzymes are known as EC 1.1.1.1 and are available, for example, from *Rhodococcus ruber* (GenBank Nos: CAD36475 and AJ491307). Other example enzymes are known as EC 1.1.1.2 and are available, for example, from *Pyrococcus furiosus* (GenBank Nos: AAC25556 and AF013169). Additionally, a butanol dehydrogenase is available from *Escherichia coli* (GenBank Nos: NP_417484 and NC_000913) and a cyclohexanol dehydrogenase is available from *Acinetobacter* sp. (GenBank Nos: AAG10026 and AF282240). The term "butanol dehydrogenase" also refers to an enzyme that catalyzes the conversion of butyraldehyde to 1-butanol, using either NADH or NADPH as cofactor. Butanol dehydrogenases are available from, for example, *C. acetobutylicum* (GenBank Nos: NP_149325 and NC_001988 (note: this enzyme possesses both aldehyde and alcohol dehydrogenase activity), NP_349891, NC_003030, NP_349892 and NC_003030) and *E. coli* (GenBank Nos: NP_417484 and NC_000913).

The term "branched-chain keto acid dehydrogenase" refers to any polypeptide having a biological function of a branched-chain keto acid dehydrogenase. Such polypeptides include a polypeptide that catalyzes the conversion of α-ketoisovalerate to isobutyryl-CoA (isobutyryl-coenzyme A), typically using NAD+(nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms, including, but not limited to, *B. subtilis* (GenBank Nos: CAB14336, Z99116, CAB14335, Z99116, CAB14334, Z99116, CAB14337 and Z99116) and *Pseudomonas putida* (GenBank Nos: AAA65614, M57613, AAA65615, M57613, AAA65617, M57613, AAA65618 and M57613).

The term "acylating aldehyde dehydrogenase" refers to any polypeptide having a biological function of an acylating aldehyde dehydrogenase. Such polypeptides include a polypeptide that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources, including, but not limited to, *Clostridium beijerinckii* (GenBank Nos: AAD31841 and AF157306), *C. acetobutylicum* (GenBank Nos: NP_149325, NC_001988, NP_149199 and NC 001988), *P. putida* (GenBank Nos: AAA89106 and U13232), and *Thermus thermophilus* (GenBank Nos: YP_145486 and NC_006461).

The term "acetyl-CoA acetyltransferase" refers to any polypeptide having a biological function of an acetyl-CoA acetyltransferase. Such polypeptides include a polypeptide that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9; although, enzymes with a broader substrate range (E.C. 2.3.1.16) will be functional as well. Acetyl-CoA acetyltransferases are available from a number of sources, for example, *Escherichia coli* (GenBank Nos: NP_416728 and NC_000913), *Clostridium acetobutylicum* (GenBank Nos: NP_349476.1, NC_003030, NP_149242 and NC_001988, *Bacillus subtilis* (GenBank Nos: NP_390297 and NC_000964), and *Saccharomyces cerevisiae* (GenBank Nos: NP_015297 and NC_001148).

The term "3-hydroxybutyryl-CoA dehydrogenase" refers to any polypeptide having a biological function of a 3-hydroxybutyryl-CoA dehydrogenase. Such polypeptides include a polypeptide that catalyzes the conversion of acetoacetyl-CoA to 3-hydroxybutyryl-CoA. Example 3-hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank Nos: NP_349314 and NC_003030), *B. subtilis* (GenBank Nos: AAB09614 and U29084), *Ralstonia eutropha* (GenBank Nos:YP_294481 and NC_007347), and *Alcaligenes eutrophus* (GenBank Nos: AAA21973 and J04987).

The term "crotonase" refers to any polypeptide having a biological function of acrotonase. Such polypeptides include a polypeptide that catalyzes the conversion of 3-hydroxybutyryl-CoA to crotonyl-CoA and H2O. Example crotonases may have asubstrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *E. coli* (GenBank Nos: NP_415911 and NC_000913), *C. acetobutylicum* (GenBank Nos: NP_349318 and NC_003030), *B. subtilis* (GenBank Nos: CAB13705 and Z99113), and *Aeromonas caviae* (GenBank Nos:BAA21816 and D88825).

The term "butyryl-CoA dehydrogenase" refers to any polypeptide having abiological function of a butyryl-CoA dehydrogenase. Such polypeptides include a polypeptide that catalyzes the conversion of crotonyl-CoA to butyryl-CoA. Example butyryl-CoA dehydrogenases may be NADH-dependent, NADPH-dependent, or flavin dependent and may be classified as E.C. 1.3.1.44, E.C. 1.3.1.38, and E.C. 1.3.99.2, respectively. Butyryl-CoA dehydrogenases are available from a number of sources, for example, *C. acetobutylicum* (GenBank Nos: NP_347102 and NC_003030), *Euglenagracilis* (GenBank Nos: Q5EU90 and AY741582), *Streptomyces collinus* (GenBank Nos: AAA92890 and U37135), and *Streptomyces coelicolor* (GenBank Nos: CAA22721 and AL939127). The term "butyraldehyde dehydrogenase" refers to any polypeptide having abiological function of a butyraldehyde dehydrogenase. Such polypeptides include apolypeptide that catalyzes the conversion of butyryl-CoA to butyraldehyde, using NADH or NADPH as cofactor. Butyraldehyde dehydrogenases with a preference for NADH are known as E.C.

1.2.1.57 and are available from, for example, *Clostridium beijerinckii* (GenBank Nos: AAD31841 and AF157306) and *C. acetobutylicum* (GenBank Nos:NP_149325 and NC_001988).

The term "transaminase" refers to an enzyme that catalyzes the conversion of α-ketoisovalerate to L-valine, using either alanine or glutamate as amine donor. Example transaminases are known by the EC numbers 2.6.1.42 and 2.6.1.66. These enzymes are available from a number of sources. Examples of sources for alanine-dependent enzymes include, but are not limited to, *E. coli* (GenBank Nos: YP_026231, NC_000913) and *Bacillus licheniformis* (GenBank Nos: YP_093743, NC_006322). Examples of sources for glutamate-dependent enzymes include, but are not limited to, *E. coli* (GenBank Nos: YP_026247, NC_000913), *S. cerevisiae* (GenBank Nos: NP_012682, NC_001142) and *Methanobacterium thermoautotrophicum* (GenBank Nos: NP_276546, NC_000916).

The term "valine dehydrogenase" refers to an enzyme that catalyzes the conversion of α-ketoisovalerate to L-valine, using NAD(P)H as electron donor and ammonia as amine donor. Example valine dehydrogenases are known by the EC numbers 1.4.1.8 and 1.4.1.9 and are available from a number of sources, including, but not limited to, *Streptomyces coelicolor* (GenBank Nos: NP_628270, NC_003888) and *B. subtilis* (GenBank Nos: CAB14339, Z99116).

The term "valine decarboxylase" refers to an enzyme that catalyzes the conversion of L-valine to isobutylamine and $CO_2$. Example valine decarboxylases are known by the EC number 4.1.1.14. These enzymes are found in Streptomycetes, such as for example, *Streptomyces viridifaciens* (GenBank Nos: AAN10242, AY116644).

The term "omega transaminase" refers to an enzyme that catalyzes the conversion of isobutylamine to isobutyraldehyde using a suitable amino acid as amine donor. Example omega transaminases are known by the EC number 2.6.1.18 and are available from a number of sources, including, but not limited to, *Alcaligenes denitrificans* (AAP92672, AY330220), *Ralstonia eutropha* (GenBank Nos: YP_294474, NC 007347), *Shewanella oneidensis* (GenBank Nos: NP_719046, NC_004347), and *P. putida* (GenBank Nos: AAN66223, AE016776).

The term "isobutyryl-CoA mutase" refers to an enzyme that catalyzes the conversion of butyryl-CoA to isobutyryl-CoA. This enzyme uses coenzyme $B_{12}$ as cofactor. Example isobutyryl-CoA mutases are known by the EC number 5.4.99.13. These enzymes are found in a number of Streptomycetes.

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* [GenBank Nos: AAA22223, L04470], *Klebsiella terrigena* [GenBank Nos: AAA25054, L04507] and *Klebsiella pneumoniae* [GenBank Nos: AAU43774, AY722056].

The term "acetoin aminase" or "acetoin transaminase" refers to a polypeptide (or polypeptides) having an enzyme activity that catalyzes the conversion of acetoin to 3-amino-2-butanol. An example acetoin aminase, also known as amino alcohol dehydrogenase, is described by Ito et al. (U.S. Pat. No. 6,432,688). Another example is the amine:pyruvate aminotransferase (also called amine:pyruvate transaminase) described by Shin and Kim (*J. Org. Chem.* 67:2848-2853 (2002)).

The term "aminobutanol phosphate phospho-lyase", also called "amino alcohol O-phosphate lyase", refers to a polypeptide (or polypeptides) having an enzyme activity that catalyzes the conversion of 3-amino-2-butanol O-phosphate to 2-butanone. U.S. Pat. Pub. No. 2007-0259410 describes an aminobutanol phosphate phospho-lyase from the *Erwinia carotovora* subsp. *atroseptica*.

The term "aminobutanol kinase" refers to a polypeptide (or polypeptides) having an enzyme activity that catalyzes the conversion of 3-amino-2-butanol to 3-amino-2-butanol O-phosphate. Aminobutanol kinase may utilize ATP as the phosphate donor. U.S. Pat. Pub. No. 20070259410 describes an amino alcohol kinase of *Erwinia carotovora* subsp. *atroseptica*.

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of (R)- or (S)-stereochemistry in the alcohol product. Example (S)-specific butanediol dehydrogenases are known as EC 1.1.1.76 and are available, for example, from *Klebsiella pneumoniae* (GenBank Nos: BBA13085, D86412). Example (R)-specific butanediol dehydrogenases are known as EC 1.1.1.4 and are available, for example, from *Bacillus cereus* [GenBank Nos. NP_830481, NC_004722, AAP07682, AE017000], and *Lactococcus lactis* [GenBank Nos. AAK04995, AE006323].

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (vitamin B12). Adenosyl cobalamin-dependent enzymes are known as EC 4.2.1.28 and are available, for example, from *Klebsiella oxytoca* [GenBank Nos: BAA08099 (alpha subunit), D45071; BAA08100 (beta subunit), D45071; and BBA08101 (gamma subunit), D45071 (Note all three subunits are required for activity)], and *Klebsiella pneumoniae* [GenBank Nos: AAC98384 (alpha subunit), AF102064; GenBank Nos: AAC98385 (beta subunit), AF102064, GenBank Nos: AAC98386 (gamma subunit), AF102064]. Other suitable diol dehydratases include, but are not limited to, B12-dependent diol dehydratases available from *Salmonella typhimurium* [GenBank Nos: AAB84102 (large subunit), AF026270; GenBank Nos: AAB84103 (medium subunit), AF026270; GenBank Nos: AAB84104 (small subunit), AF026270]; and *Lactobacillus collinoides* [GenBank Nos: CAC82541 (large subunit), AJ297723; GenBank Nos: CAC82542 (medium subunit); AJ297723; GenBank Nos: CAD01091 (small subunit), AJ297723]; and enzymes from *Lactobacillus brevis* (particularly strains CNRZ 734 and CNRZ 735, Speranza et al., supra), and nucleotide sequences that encode the corresponding enzymes. Methods of diol dehydratase gene isolation are well known in the art (e.g., U.S. Pat. No. 5,686, 276).

The term "glycerol dehydratase" refers to a polypeptide (or polypeptides) having an enzyme activity that catalyzes the conversion of glycerol to 3-hydroxypropionaldehyde. Adenosyl cobalamin-dependent glycerol dehydratases are known as EC 4.2.1.30. The glycerol dehydratases of EC 4.2.1.30 are similar to the diol dehydratases in sequence and in having three subunits. The glycerol dehydratases can also be used to convert 2,3-butanediol to 2-butanone. Some examples of glycerol dehydratases of EC 4.2.1.30 include those from *Klebsiella pneumoniae*; from *Clostridium pasteurianum* [GenBank Nos: 3360389 (alpha subunit), 3360390 (beta subunit), and 3360391 (gamma subunit)]; from *Escherichia blattae* [GenBank Nos: 60099613 (alpha subunit), 57340191 (beta subunit), and 57340192 (gamma subunit)]; and from *Citrobacter freundii* [GenBank Nos: 1169287 (alpha subunit), 1229154 (beta subunit), and 1229155 (gamma subunit)]. Note that all three subunits are required for activity.

Methods for Producing a Recombinant Yeast Containing an Engineered Isobutanol Biosynthetic Pathway Containing a Modified Biosynthetic Production Matrix In embodiments, the recombinant yeast containing an engineered isobutanol biosynthetic pathway contains a biosynthetic production matrix for the production of isobutanol and other fusel alcohols. The biosynthetic production matrix contains various branch points where the production of one or more fusel alcohols can be modulated. This modulation can occur through genetic modification of the yeast chromosome so that specific genes or regulatory elements involved in the fusel alcohol production pathways are altered.

For example, in one embodiment, the recombinant yeast with engineered isobutanol biosynthetic pathway contains genomic modifications resulting in reduced or eliminated 1-propanol, 2-methyl-1-butanol, and 3-methyl-1-butanol production, and enhanced production of isobutanol. One non-limiting example of such a recombinant yeast is a yeast cell comprising a complete or partial deletion of the LEU4, LEU9, and ILV1 genes (optionally BAT1 and BAT2). Reduced or eliminated expression of the LEU4, LEU9, and ILV1 genes can be achieved by methods known in the art, such as deletions, frameshift mutations, point mutations which disrupt enzyme activity/structure, or modification of regulatory elements (e.g. promoters) that reduce or eliminate expression.

For example, in one embodiment, the recombinant yeast with engineered isobutanol biosynthetic pathway contains genomic modifications resulting in enhanced 1-propanol, 2-methyl-1-butanol, 3-methyl-1-butanol, and isobutanol production. One non-limiting example of such a recombinant yeast is a yeast cell comprising upregulation of the LEU4, LEU9, ILV1, BAT1, and BAT2 genes. Upregulation of these genes, for example LEU4, can be achieved by methods known in the art, such as by promoter replacement with a strong promoter (for example, FBA1), or by introducing multiple copies of the LEU4 gene into the chromosome.

In another embodiment, the recombinant yeast with engineered isobutanol biosynthetic pathway contains genomic modifications resulting in reduced or eliminated 1-propanol and 2-methyl-1-butanol production, but enhanced production of isobutanol and 3-methyl-1-butanol production. One non-limiting example of such a recombinant yeast is a yeast cell comprising upregulation of the LEU4 and LEU9 genes (optionally BAT1 and BAT2) and a complete or partial deletion of the ILV1 gene. Upregulation of these genes, for example LEU4, can be achieved by methods known in the art, such as by promoter replacement with a strong promoter (for example, FBA1), or by introducing multiple copies of the LEU4 gene into the chromosome. Reduced or eliminated expression of the ILV1 gene can be achieved by methods known in the art, such as deletions, frameshift mutations, point mutations which disrupt enzyme activity/structure, or modification of regulatory elements (e.g. promoters) that reduce or eliminate expression.

Yeast Host Cells for Butanol Production

Host cells for butanol production in the present invention comprise yeast. In general, suitable host cells include any yeast cell useful for genetic modification and recombinant gene expression. The criteria for selection of suitable microbial hosts include the following: intrinsic tolerance to the butanol isomer being produced, high rate of glucose utilization, availability of genetic tools for gene manipulation, and the ability to generate stable chromosomal alterations.

The ability to genetically modify the host is a consideration for the production of any recombinant microorganism. The mode of gene transfer technology may be by electroporation, conjugation, transduction or natural transformation. A broad range of host conjugative plasmids and drug resistance markers are available. The cloning vectors are tailored to the host organisms based on the nature of antibiotic resistance markers that can function in that host.

The microbial host also has to be manipulated in order to inactivate competing pathways for carbon flow by deleting various genes. This requires the availability of either transposons to direct inactivation or chromosomal integration vectors. Additionally, the production host should be amenable to chemical mutagenesis so that mutations to improve intrinsic butanol tolerance may be obtained.

The microbial host cell used for the production butanol isomers is preferably tolerant to the butanol isomer that is being produced so that the yield of the butanol isomer is not limited by the toxicity of the butanol isomer. In one embodiment, the host used for the isobutanol production is tolerant to isobutanol. Suitable host strains with a tolerance for isobutanol may be identified by a screening method based on the intrinsic tolerance of the strain as described in U.S. Pat. No. 7,993,889 (incorporated herein by reference).

The microbial host for isobutanol production should also utilize carbohydrates, including monosaccharides, oligosaccharides and polysaccharides, at a high rate. Most microbes are capable of utilizing carbohydrates. However, certain environmental microbes cannot utilize carbohydrates to high efficiency, and therefore would not be suitable hosts.

Based on the criteria described above, suitable yeasts for the production of butanol in the present invention include, but are not limited to, crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii*, and *Candida glabrata*.

In some embodiments, the host cell is *Saccharomyces cerevisiae*. *S. cerevisiae* yeast are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

Recombinant yeast containing the genes necessary to encode the enzymatic pathway for conversion of a fermentable carbon substrate to butanol isomers may be constructed using techniques well known in the art. In the present invention, genes encoding the enzymes of one of the butanol biosynthetic pathways, for example, acetolactate synthase, acetohydroxy acid isomeroreductase, acetohydroxy acid dehydratase, branched-chain α-keto acid decarboxylase, and branched-chain alcohol dehydrogenase, may be isolated from various sources, as described, for example, herein, and in U.S. Pat. No. 7,993,889 and U.S. App. Pub. No. US20130071898A1, both incorporated by reference.

Relevant enzymes of the butanol biosynthetic pathway may be introduced into yeast cells, as described, for example, in U.S. Pat. No. 7,993,889, incorporated by reference, to produce butanologens. The butanologens generated comprise an engineered butanol biosynthetic pathway. In some embodiments, the butanologen is an isobutanologen, which comprises an engineered isobutanol biosynthetic pathway. In some embodiments, the butanologen is *Saccharomyces cerevisiae*.

In some embodiments, enzymes of the butanol biosynthetic pathway are not localized to the mitochondria. In some embodiments, enzymes of the engineered butanol biosynthetic pathway are localized to the cytosol. In some embodiments, an enzyme of the biosynthetic pathway is localized to the cytosol by removing the mitochondrial targeting sequence. In some embodiments, mitochondrial targeting is eliminated by generating new start codons as described in for example, U.S. Pat. No. 7,993,889, incorporated herein by reference. In some embodiments, an enzyme of the biosynthetic pathway that is localized to the cytosol is DHAD. In some embodiments, an enzyme from the biosynthetic pathway that is localized to the cytosol is KARI.

Additional Modifications within Butanologens

The butanologens as provided herein may further comprise one or more additional modifications. Such modifications, for example, may include disruption of the activity of the genes involved in the production of by-products during the fermentative production of butanol isomers via the engineered butanol biosynthetic pathway. The disruption of the activity of the genes involved in the production of by-products during the fermentative production of butanol isomers reduces yield loss from the competing pathways for carbon flow and increases butanol production. In some embodiments, such modifications include disruption of the activity of pyruvate decarboxylase, aldehyde dehydrogenase or both.

The term "pyruvate decarboxylase" refers to any polypeptide having a biological function of a pyruvate decarboxylase. Such polypeptides include a polypeptide that catalyzes the decarboxylation of pyruvic acid to acetaldehyde and $CO_2$. Pyruvate decarboxylases are known by the EC number 4.1.1.1. Such polypeptides can be determined by methods well known in the art and disclosed in U.S. Patent Appl. No. US 20130071898A1, incorporated herein by reference. These enzymes are found in a number of yeast, including *Saccharomyces cerevisiae* (GenBank Nos: CAA97575, CAA97705 and CAA97091). Additional examples of PDC are provided in U.S. Appl. Pub. No. 2009035363, which is incorporated herein by reference.

In some embodiments, a butanologen disclosed herein can comprise a modification or disruption of an endogenous polynucleotide and/or gene encoding a polypeptide having pyruvate decarboxylase activity and/or an endogenous polypeptide having pyruvate decarboxylase activity. In some embodiments, a butanologen disclosed herein can comprise a deletion, mutation, and/or substitution in an endogenous polynucleotide or gene encoding a polypeptide having PDC activity, or in an endogenous polypeptide having PDC activity. Such modifications, disruptions, deletions, mutations, and/or substitutions can result in PDC activity that is reduced or eliminated, resulting, for example, in a PDC knock-out (PDC-KO) phenotype.

Endogenous pyruvate decarboxylase in yeast converts pyruvate to acetaldehyde, which is then converted to ethanol or to acetyl-CoA via acetate. Yeast may have one or more genes encoding pyruvate decarboxylase. For example, there is one gene encoding pyruvate decarboxylase in *Candida glabrata, Schizosaccharomyces pombe* and *Kluyveromyces lactis*, while there are three isozymes of pyruvate decarboxylase encoded by the PDC1, PCD5 and/or PDC6 genes in *Saccharomyces*. In some embodiments, in the present yeast cells at least one PDC gene is inactivated. If the yeast cell used has more than one expressed (active) PDC gene, then each of the active PDC genes may be modified or inactivated thereby producing a pdc-cell. For example, in *S. cerevisiae* the PDC1, PDC5 and PDC6 genes may be modified or inactivated. If a PDC gene is not active under the fermentation conditions to be used then such a gene would not need to be modified or inactivated. In some embodiments, the pyruvate decarboxylase that is deleted or downregulated is selected from the group consisting of: PDC1, PDC5, PDC6 and combinations thereof. U.S. Patent Appl. Pub. No. 20090305363 and U.S. Patent Appl. No. US20130071898A1 (both incorporated herein by reference) further describe the modifications in the endogenous pyruvate decarboxylase, and are incorporated herein by reference. U.S. Appl. Pub. No. 20090305363 (incorporated herein by reference) discloses increased conversion of pyruvate to acetolactate by engineering yeast for expression of a cytosol-localized acetolactate synthase and substantial elimination of pyruvate decarboxylase activity. Yeast having a reduced enzymatic activity can be identified using various methods. For example, yeast having reduced pyruvate decarboxylase activity can be identified using common methods, including, for example, measuring ethanol formation via gas chromatography.

Other target genes, such as those encoding pyruvate decarboxylase proteins having at least about 70-75%, at least about 75-85%, at least about 80-85%, at least about 85%-90%, at least about 90%-95%, or at least about 96%, at least about 97%, at least about 98%, or at least about 99% sequence identity to the pyruvate decarboxylases may be identified in the literature and in bioinformatics databases well known to the skilled person. The methods for disruption of pyruvate decarboxylase activity along with the methods for identification of butanologens with modified or deleted pyruvate decarboxylase are described in detail in U.S. Patent Appl. Pub. No. 20090305363 and U.S. Patent Appl. No. US 20130071898 A1, incorporated herein by reference.

In some embodiments, a butanologen comprises modifications to reduce glycerol-3-phosphate dehydrogenase activity and/or disruption of at least one gene encoding a polypeptide having PDC activity or a disruption in at least one gene encoding a regulatory element controlling PDC gene expression as described in U.S. Patent Appl. Pub. Nos. 20090305363 and US20130071898A1, both incorporated by reference, the modifications that would provide for an increased carbon flux through Entner-Doudoroff Pathway, or reducing equivalents balance as described in U.S. Patent Appl. Pub. No. 20100120105 (incorporated by reference). Yeast cells with inactivated endogenous PDC gene and an engineered biosynthethic pathway having improved growth and product yield when glucose repression was reduced are described in U.S. Appl. Publication No. 20110124060, incorporated herein by reference.

The term "aldehyde dehydrogenases" refers to any polypeptide having a biological function of an aldehyde dehydrogenase. Such polypeptides include a polypeptide that catalyzes the oxidation (dehydrogenation) of aldehydes (Wang et al., *J. Bacteriol*. 180:822-30, 1998; Navarro-Avino et al., *Yeast* 15:829-42, 1999; and Saint-Prix et al., *Microbiology* 150:2209-20, 2004). Such polypeptides include a polypeptide that catalyzes the conversion of isobutyraldehyde to isobutyric acid. Such polypeptides also include a polypeptide that corresponds to EC Numbers 1.2.1.3, EC 1.2.1.4 or 1.2.1.5. Such polypeptides can be determined by methods well known in the art and are disclosed in U.S. Patent Appl. No. US20130071898A1, incorporated by reference.

In some embodiments, a butanologen can comprise deletion, mutation and/or substitution in an endogenous polynucleotide or gene encoding a polypeptide having aldehyde dehydrogenase (ALD) and/or aldehyde oxidase activity or deletion, mutation and/or substitution in an endogenous polypeptide having aldehyde dehydrogenase activity and/or aldehyde oxidase activity. In some embodiments, a recombinant host cell of the invention can be *S. cerevisiae*, and a polypeptide having aldehyde dehydrogenase activity can be ALD2, ALD3, ALD4, ALD5, ALD6, or combinations thereof.

In some embodiments, the polypeptide having aldehyde dehydrogenase activity is ALD6 in *Saccharomyces cerevisiae* or a homolog thereof. Such modifications, disruptions, deletions, mutations, and/or substitutions can result in ALD activity that is reduced or eliminated, resulting, for example, in an ALD6 knock-out (ALD6-KO) phenotype. Examples of aldehyde dehydrogenase polynucleotides, genes and polypeptides that can be targeted for modification or inactivation in a recombinant host cell are provided in further detail in U.S. Patent Appl. Pub. No. US 20130071898A1.

The disruption of a particular aldehyde dehydrogenase could be confirmed, for example, with PCR screening using primers internal and external to the aldehyde dehydrogenase gene or by Southern blot using a probe designed to the aldehyde dehydrogenase gene sequence. Alternatively, one could utilize gas chromatography-mass spectroscopy or liquid chromatography to screen strains exposed to isobutyraldehyde for decreased formation of isobutyric acid. For example, a method of screening for strains with decreased isobutyric acid formation can comprise: a) providing a strain comprising a modification in a polynucleotide encoding a polypeptide having aldehyde dehydrogenase activity and/or a modification in a polynucleotide encoding a polypeptide having aldehyde oxidase activity; b) contacting the cell with isobutyraldehyde; and c) measuring isobutyric acid formation; wherein isobutyric acid formation is reduced as compared to a control strain without the modification. In some embodiments, the measuring is carried out using gas chromatography-mass spectroscopy. The methods for deletion, mutation and/or substitution of polynucleotide, gene or polypeptide for aldehyde dehydrogenase and methods for identifying disruption of aldehyde dehydrogenase activity are described in detail, e.g., in U.S. Patent Appl. Pub. No. US 20130071898A1.

Other target genes, such as those encoding aldehyde dehydrogenase proteins having at least about 70-75%, at least about 75-85%, at least about 80-85%, at least about 85%-90%, at least about 90%-95%, or at least about 96%, at least about 97%, at least about 98%, or at least about 99% sequence identity to the aldehyde dehydrogenase may be identified in the literature and in bioinformatics databases well known to the skilled person.

In some embodiments, butanologens described herein can comprise a reduced or eliminated aldehyde dehydrogenase and/or aldehyde oxidase activity, as described in U.S. Patent Appl. Pub. No. US 20130071898 A1. In some embodiments, a butanologen with reduced or eliminated aldehyde dehydrogenase activity can produce a butanol isomer via the engineered biosynthetic pathway at a greater yield or amount than the yield or amount of the same isomer produced by a butanologen that does not comprise reduced or eliminated aldehyde dehydrogenase activity.

In some embodiments, a butanologen as described herein can comprise a deletion, mutation, and/or substitution in an endogenous polynucleotide or gene encoding a polypeptide involved in the pathways for the production of by-products during the fermentative production of butanol isomers. In some embodiments, a butanogen can comprise one or more deletions, mutations, and/or substitutions in an endogenous polypeptide that is involved in the pathways for the production of by-products during the fermentative production of butanol isomers. In some embodiments, butanologens provided herein comprise modifications in genes or polynucleotides encoding URA3 (orotidine-5'-phosphate (OMP) decarboxylase), HIS3 (imidazoleglycerol-phosphate dehydratase), FRA2 (iron repressor protein), CCC1 (putative vacuolar Fe2+/Mn2+ transporter) or GPD2 (glycerol-2-phosphate dehydrogenase) or polypeptides having URA3, HIS3, FRA2, CCC1 or GPD2 activity or combinations thereof as described, for example, in US Appl. Pub. No. 20120064561A1, incorporated herein by reference.

In other embodiments, modifications include integration of at least one polynucleotide encoding a polypeptide that catalyzes a step in a pyruvate-utilizing biosynthetic pathway. Other modifications include at least one deletion, mutation, and/or substitution in an endogenous polynucleotide encoding a polypeptide having acetolactate reductase activity. In embodiments, the polypeptide having acetolactate reductase activity is YMR226C of *Saccharomyces cerevisae* or a homolog thereof. In other embodiments, a butanogen may comprise modifications including integration of at least one polynucleotide encoding a polypeptide that catalyzes the conversion of xylulose-5-phosphate into glyceraldehyde-3-phosphate and acetyl-phosphate and/or at least one polynucleotide encoding a polypeptide that catalyzes conversion of fructose-6-phosphate into erythrose-4-phosphate and acetyl-phosphate, as described in Internat'l. Pat. Pub. No, WO 2011/159853. More specifically, it has been found that expression of enzymes associated with the phosphoketolase pathway (e.g., phosphoketolase [EC 4.1.2.9] and/or phosphotransacetylase [EC 2.3.1.8]) results in a reduced or eliminated requirement for exogenous two-carbon substrate supplementation for growth of PDC-KO cells. Numerous examples of polynucleotides, genes and polypeptides encoding phosphoketolase activity are known in the art and can be used in the recombinant host cells disclosed herein. In embodiments, the phosphoketolase may be xpkl from *Lactobacillus plantarum* (ATCC No. BAA-793) (GenBank GI number 28379168). In embodiments, the phosphotransacetylase can be EutD from *Lactobacillus plantarum* (ATCC No. BAA-793) (GenBank GI number 28377658).

Protein Hydrolysates

Protein hydrolysates (i.e., mixtures of peptides and amino acids) are typically produced from polypeptides during processes of chemical hydrolysis or enzymatic hydrolysis, as described further below. According to the processes of the present invention, protein hydrolysates can be produced via hydrolysis of various process streams (e.g., feedstock slurry 16, wet cake, 24, within the fermentor 30, whole stillage wet cake, thin stillage, syrup).

Chemical Hydrolysis: Polypeptides can be completely hydrolyzed by chemical methods, for example, those that are used for amino acid analysis. These include liquid phase and vapor phase acid hydrolysis using 6 N HCl at 110° C. or at higher temperature for shorter times. Polypeptide hydrolysis may also be accelerated by use of microwave heating. Hydrolyses are typically performed as a function of time as serine and threonine are labile and peptide bonds where P1 is isoleucine or valine and P1' is isoleucine or valine cleave slowly. Following a time course allows one to determine the rate of degradation of serine and threonine and the rate of cleavage of isoleucine and valine. Asparagine and glutamine are hydrolyzed to the respective aspartic and glutamic acids. Cysteine is oxidized to cystine and some oxidation of methionine will occur to the sulfone. Tryptophan is particularly labile to oxidation but can be stabilized to some extent in the presence of thiol reagents (e.g., mercaptoethanesulfonic acid, thioglycolic acid).

Enzymatic Hydrolysis: Complete conversion of a polypeptide to its component amino acids is often more difficult than acid hydrolysis, owing to the specificity of different proteases. Treatment by broad spectrum proteases (e.g., proteinase K, papain, subtilisin) or consortia of endopeptidases (e.g., pepsin, trypsin, chymotrypsin, and elastase), followed by a combination of exopeptidases (e.g., carboxypeptidases and aminopeptidases) and dipeptidyl and tripeptidyl peptidases are likely to yield a fairly complete hydrolysis, though there may be at the same time some autoproteolysis or cross proteolysis of the added proteases. Pronase, a mixture of proteases secreted by *Streptomyces griseus* will give a complete or nearly complete hydrolysis of many polypeptides. The choice and concentration of the proteases used may need to be tailored to the polypeptide to be hydrolyzed.

Described in U.S. Pat. No. 5,231,017 is a process for producing ethanol from raw materials that contain fermentable sugars or constituents which can be converted to sugars, comprising the steps of: (a) liquefaction of the raw materials in the presence of an alpha-amylase for obtaining liquefied mash; (b) saccharification of the liquefied mash in the presence of a glucoamylase for obtaining hydrolyzed starch and sugars; (c) fermentation of the hydrolyzed starch and sugars by yeast for obtaining ethanol; (d) recovering alcohol; wherein a protease is introduced in the liquefied mash during the saccharification and/or in the hydrolyze starch and sugars during the fermentation. The yeast advantageously has an increased rate and yield of ethanol production, presumably as a result of increased availability of energy for the yeast's consumption.

According to U.S. Pat. No. 5,231,017, incorporated herein by reference, acid fungal protease may be derived from *Aspergillus, Mucor, Rhizopus, Candida, Coriolus, Endothia, Enthomophtora, lrpex, Penicillium, Sclerotium* and *Torulopsis*. In embodiments, the acid fungal protease chosen is thermally stable and is derived from *Aspergillus*, such as *A. niger, A. saitoi* or *A. oryzae*, from *Mucor* such as *M. pusillus* or *M. miehei*, from *Endothia*, such as *E. parasitica*, or from *Rhizopus*. Most preferably, the acid fungal protease is derived from *Aspergillus niger* (for example, one acid fungal protease from *Aspergillus niger*, var. is available under the trade mark AFP-2000 through Solvay Enzymes, Inc.).

The quantity of the acid fungal protease for use in the process herein will depend on the enzymatic activity of the protease, as appreciated by one of skill in the art.

Also available in the art are preparations of glucoamylase and protease blends for simultaneous starch and protein hydrolysis. For example, Fermenzyme L-400 provides a mixture of ~10-15% glucoamylase and <1% protease (Genencor®, Palo Alto, Calif.).

Protease use in ethanol production from dry fractionated cornhas been studied (Bernardo, Jr., C. Vidal, Ph.D. Thesis, Univ. of Illinois at Urbana-Champaign, 2010). Of particular note, protease NS50045 (Novozymes, Franklinton, N.C.) treatment was reported to result in at least 1% increase in the molar content of all amino acids (except cysteine) in a corn slurry produced from endosperm and germ. For example, a ~9.3% and ~7.5% increase in leucine content was measured after protease treatment of the endosperm and germ, respectively.

Methods for Production of Butanol and Fusel Alcohol Mixtures

International Pat. Pub. No. WO 2011/160030, herein incorporated by reference in its entirety, is directed to a method comprising providing a biomass feedstock slurry comprising fermentable carbon source, undissolved solids, and water; separating at least a portion of the undissolved solids from said slurry whereby (i) an aqueous solution comprising fermentable carbon source and (ii) a wet cake co-product comprising solids are generated; and adding the aqueous solution to a fermentation broth comprising recombinant microorganisms in a fermentation vessel whereby a fermentative product is produced; wherein the biomass processing productivity is improved. In some embodiments of the disclosure therein, the method further comprises a step of liquefying a feedstock to create a biomass feedstock slurry; wherein the feedstock is selected from corn grain, corn cobs, crop residues such as corn husks, corn stover, grasses, corn, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, and mixtures thereof. The feedstock may be fractionated or unfractionated, wet milled or dry milled. The wet cake may be washed with water to recover oligosaccharides present in the wet cake, said recovered oligosaccharides optionally added to the fermentation vessel. The fermentative product may be a product alcohol selected from the group consisting of methanol, ethanol, propanol, butanol, pentanol, and isomers thereof and the recombinant microorganism may comprise an engineered butanol biosynthetic pathway.

Figure 12:
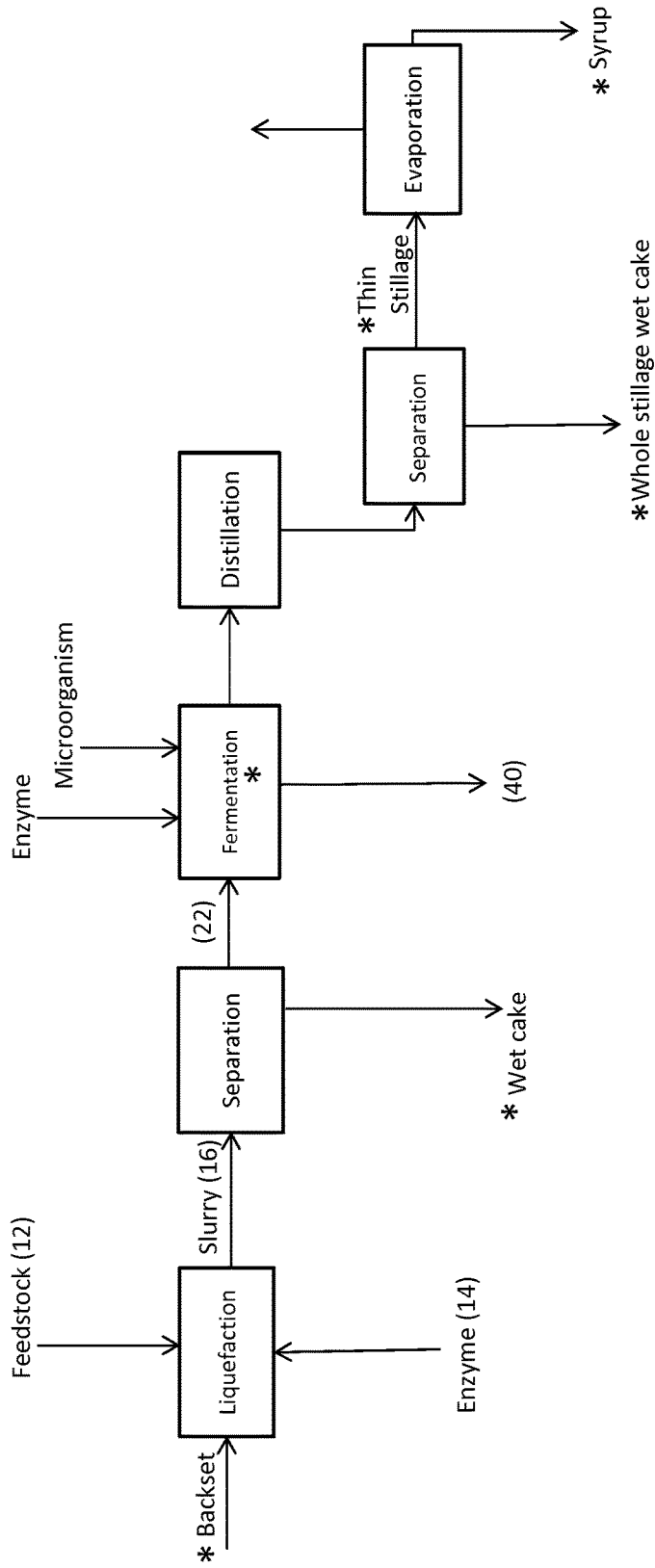
FIG. 12 shows an example alcohol production process. Streams which may contain hydrolysable proteins are depicted with an asterisk.

An alcohol production process wherein substrates containing proteins, for example, feedstock solids, can be modified to include a step wherein the biomass feedstock is subjected to chemical or enzymatic hydrolysis to yield protein hydrolysates for use by the recombinant microorganism. An example alcohol production process is depicted in FIG. 12. Biomass feedstock 12 is contacted with liquefaction enzyme 14 in a liquefaction vessel 10 configured to liquefy a feedstock to create a feedstock slurry 16. Feedstock slurry 16 is optionally introduced into a centrifuge to produce wet cake 24 and a carbohydrate-containing stream 22. At least a carbohydrate-containing portion of feedstock slurry 16 is introduced into fermentation vessel where contact occurs with an enzyme or microorganism For example, as indicated in FIG. 12, protein hydrolysates may be generated from substrates present in the fermentation vessel, in the thin stillage, in the whole stillage wet cake, in the syrup, in the backset, or in the wet cake.

One of skill in the art will envision modifying the methods of International Pat. Pub. No. WO 2011/160030, incorporated herein by reference, to include a step wherein the biomass feedstock is subjected to chemical or enzymatic hydrolysis to yield protein hydrolysates for use by the recombinant microorganism.

Figure 5A:
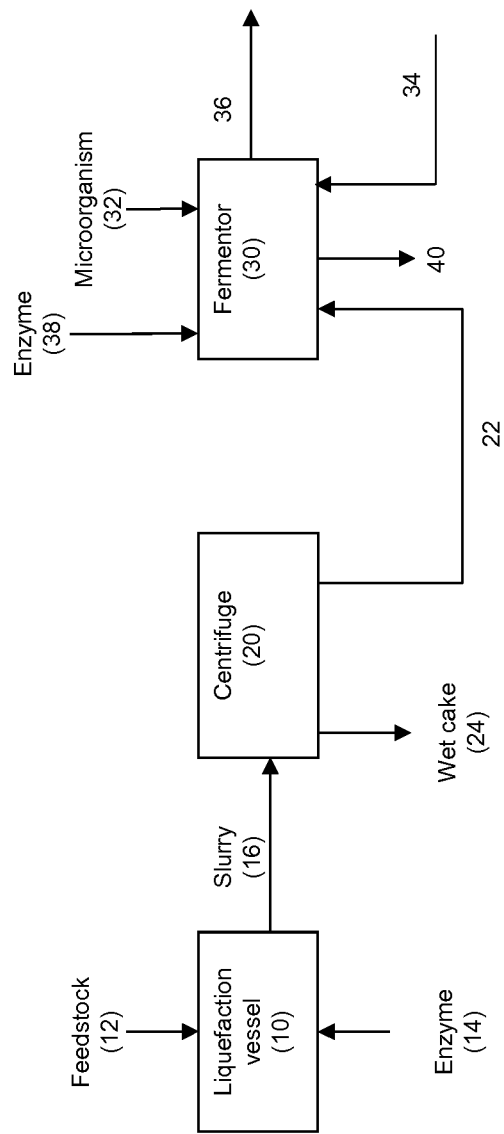
Figure 5B:
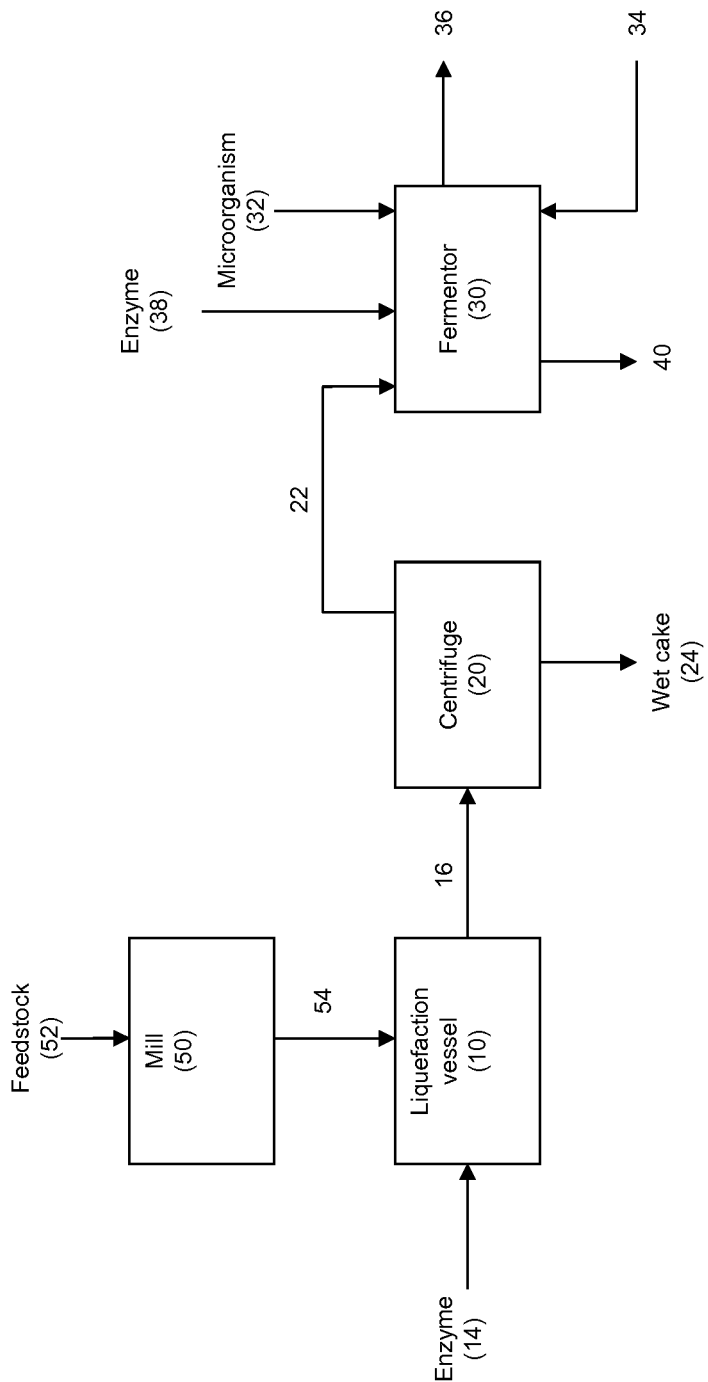
Figure 6A:
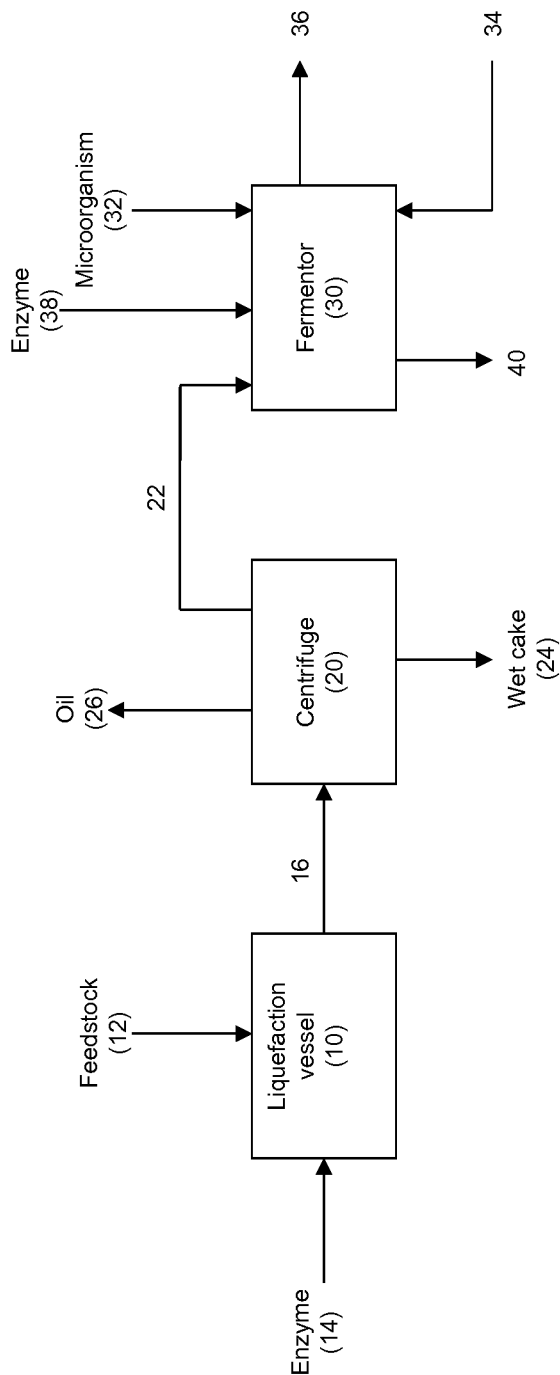
Figure 6B:
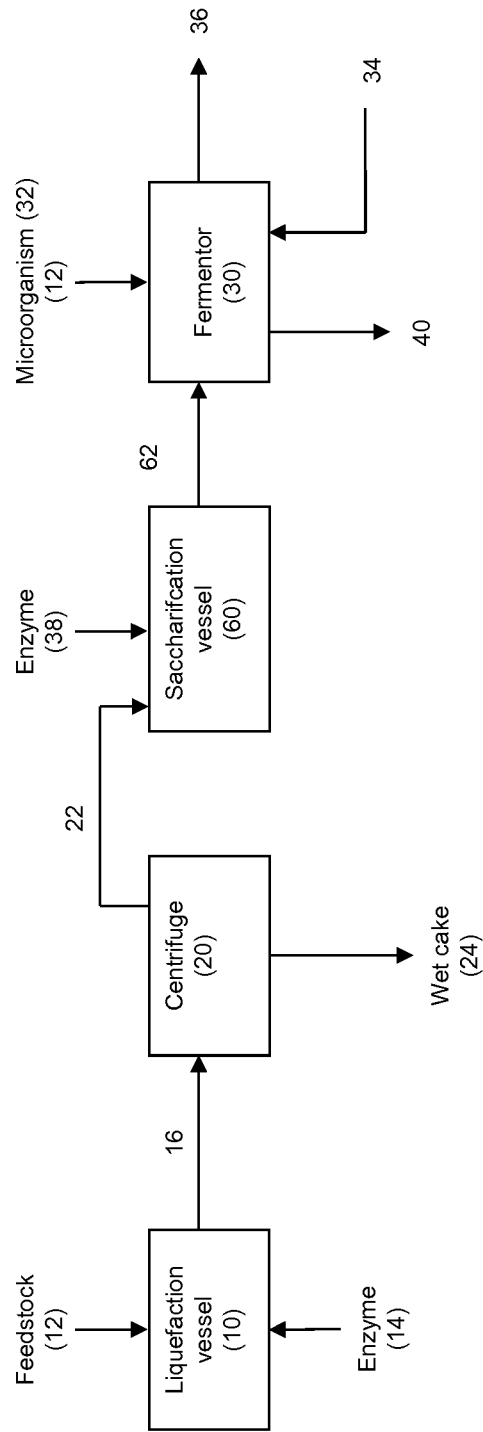
Figure 7A:
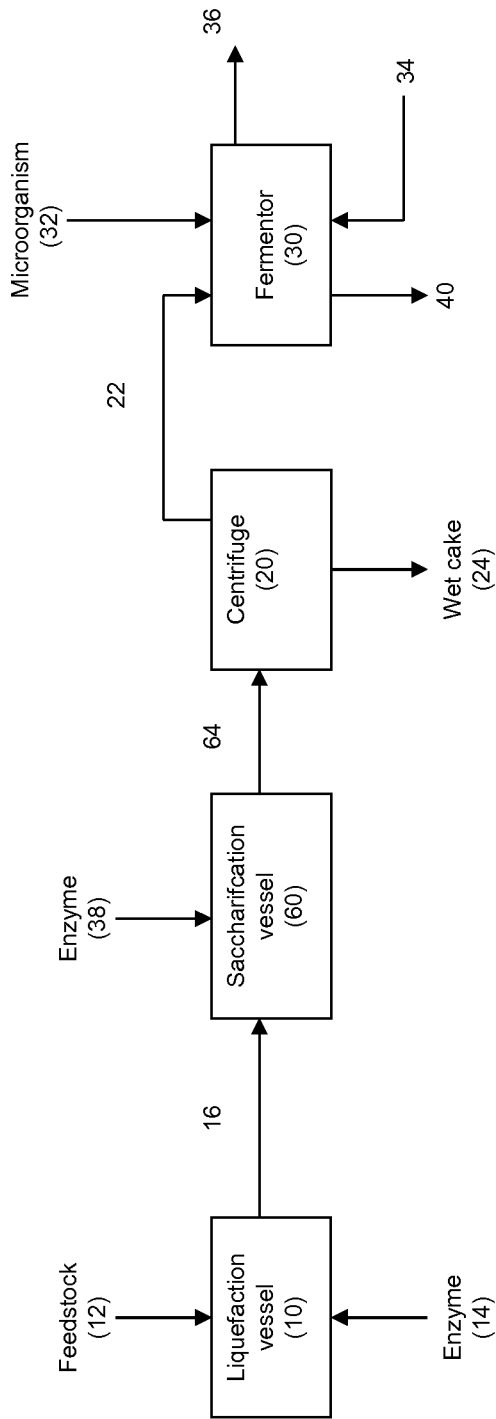
Figure 7B:
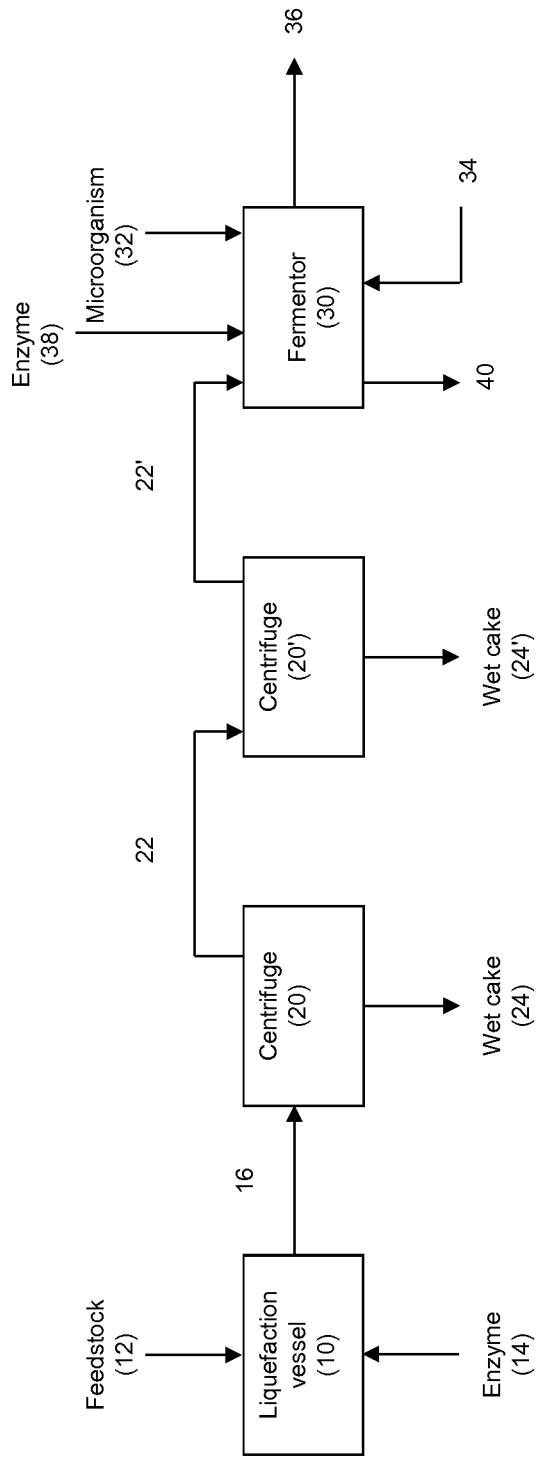
Figure 8:
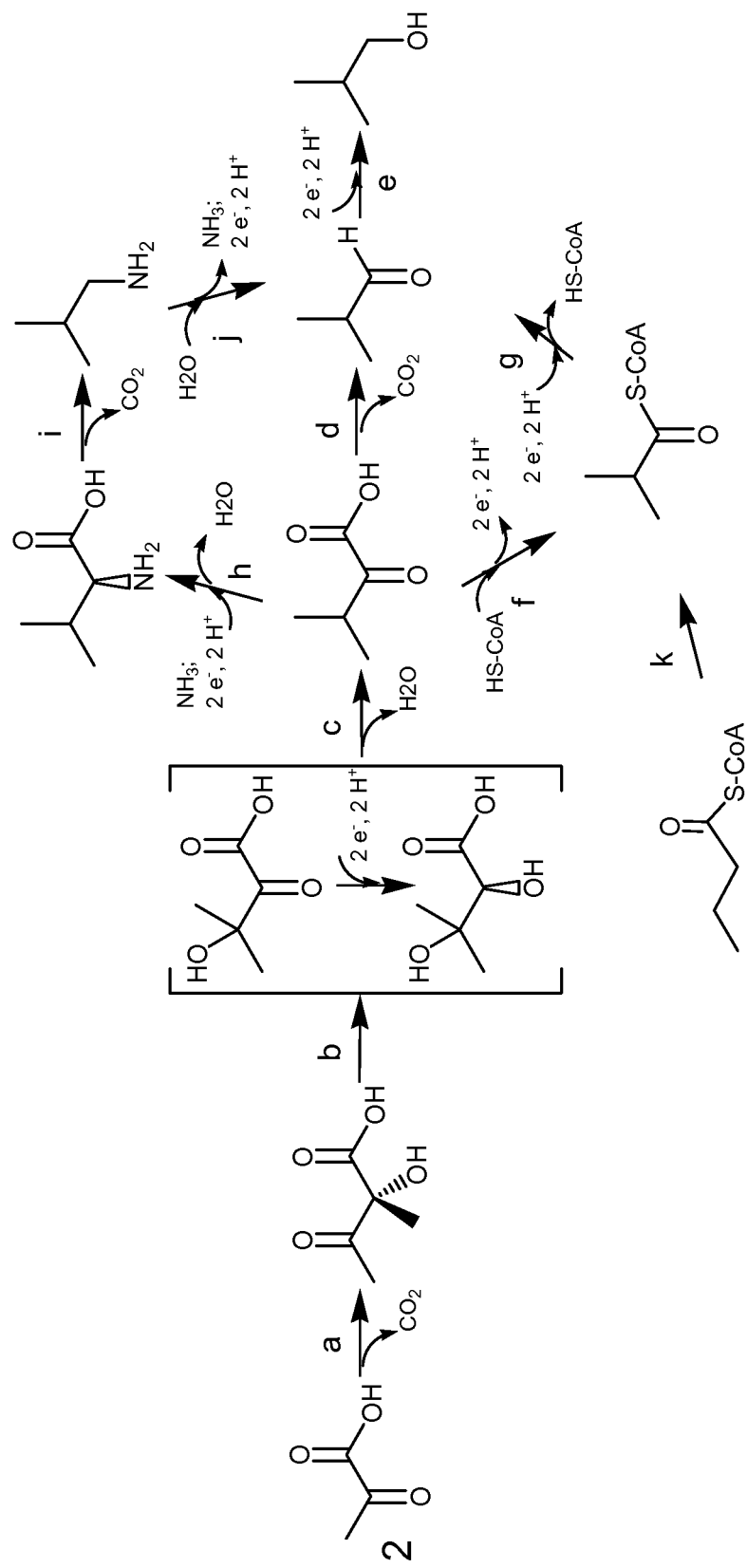
Figure 9:
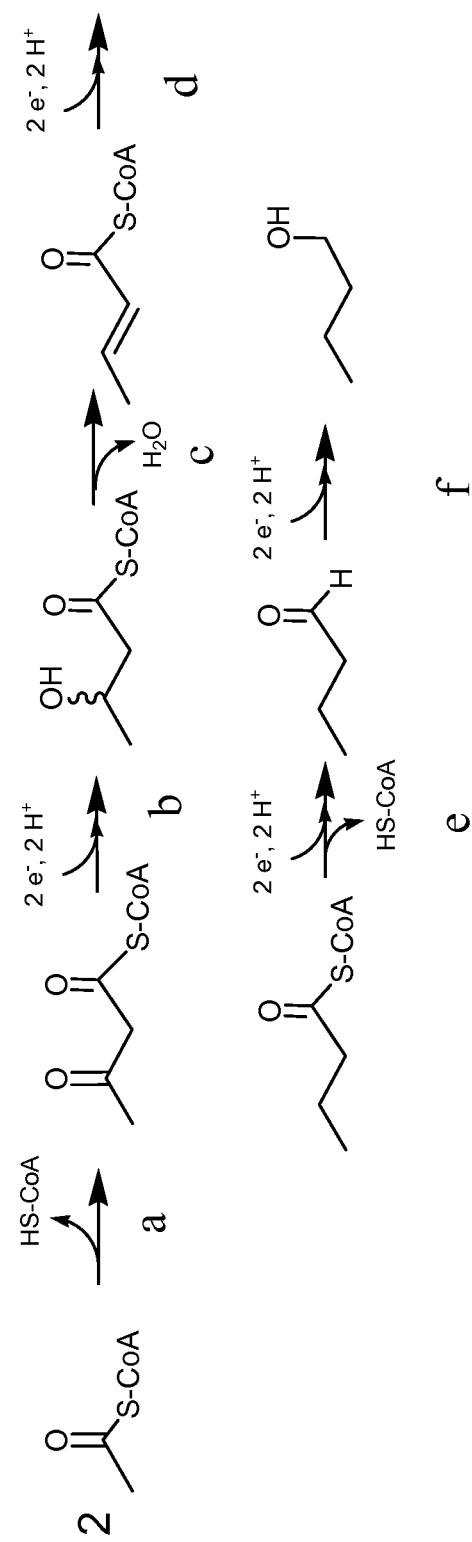
Figure 10:
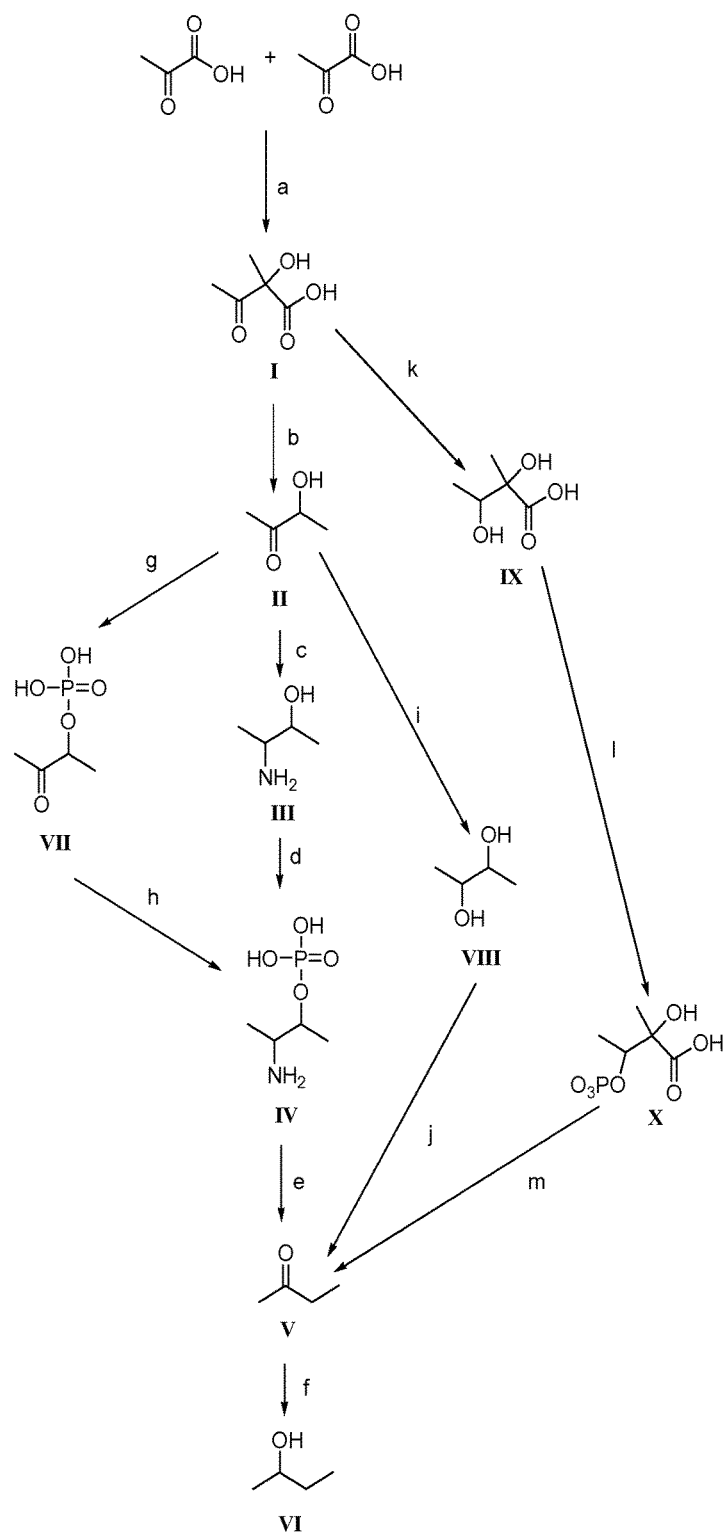

For example, in some embodiments, as shown, for example, in FIG. 5A, the system for use in the methods of the invention will include a liquefaction vessel 10 configured to liquefy a feedstock to create a feedstock slurry. In particular, a feedstock 12 can be introduced to an inlet in liquefaction vessel 10. Feedstock 12 can be any suitable biomass material known in the industry including, but not limited to, rye, wheat, cane, or corn that contains a fermentable carbon source such as starch.

The process of liquefying feedstock 12 involves hydrolysis of starch in feedstock 12 into water-soluble sugars and is a conventional process. Any known liquefying processes, as well as the corresponding liquefaction vessel, normally utilized by the industry can be used including, but not limited to, the acid process, the acid-enzyme process, or the enzyme process. Such processes can be used alone or in combination. In some embodiments, the enzyme process can be utilized and an appropriate enzyme 14, for example, alpha-amylase, is introduced to an inlet in liquefaction vessel 10. Water can also be introduced to the liquefaction vessel 10.

The process of liquefying feedstock 12 creates a feedstock slurry 16 that includes sugar (e.g., fermentable carbon) and undissolved solids from the feedstock or biomass. The undissolved solids are non-fermentable portions of feedstock 12. In some embodiments, feedstock 12 can be corn, such as dry milled, unfractionated corn kernels, and the undissolved particles can include germ, fiber, and gluten. Feedstock slurry 16 can be discharged from an outlet of liquefaction vessel 10. In some embodiments, feedstock 12 is corn or corn kernels and feedstock slurry 16 is a corn mash slurry.

A centrifuge 20 configured to remove the undissolved solids from feedstock slurry 16 has an inlet for receiving feedstock slurry 16. Centrifuge 20 agitates or spins feedstock slurry 16 to create a liquid phase or aqueous solution 22 and a solid phase or wet cake 24.

Aqueous solution 22 can include the sugar, for example, in the form of oligosaccharides, and water. Aqueous solution can comprise at least about 10% by weight oligosaccharides, at least about 20% by weight of oligosaccharides, or at least about 30% by weight of oligosaccharides. Aqueous solution 22 can be discharged out an outlet located near the top of centrifuge 20. Aqueous solution can have a viscosity of less than about 20 centipoise. The aqueous solution can comprise less than about 20 g/L of monomeric glucose, more preferably less than about 10 g/L, or less than about 5 g/L of monomeric glucose. Suitable methodology to determine the amount of monomeric glucose is well known in the art. Such suitable methods known in the art include HPLC.

Wet cake 24 can include the undissolved solids, e.g., typically comprising proteins. Wet cake 24 can be discharged from an outlet located near the bottom of centrifuge 20. Wet cake 24 can also include a portion of the sugar and water. Wet cake 24 can be washed with additional water in centrifuge 20 once aqueous solution 22 has been discharged from centrifuge 20. Alternatively, wet cake 24 can be washed with additional water in a separate centrifuge. Washing wet cake 24 will recover the sugar or sugar source (e.g., oligosaccharides) present in the wet cake, and the recovered sugar and water can be recycled to the liquefaction vessel 10.

Wet cake 24 may optionally be treated via chemical hydrolysis or enzymatic hydrolysis to liberate protein hydrolysates present in the wet cake, and the liberated protein hydrolysates, with or without the residual wet cake, can be directly introduced into the fermentor 30 or added to aqueous stream 22.

Centrifuge 20 can be any conventional centrifuge utilized in the industry, including, for example, a decanter bowl centrifuge, three phase decanter centrifuge, disk stack centrifuge, or filtering centrifuge. In some embodiments, removal of the undissolved solids from feedstock slurry 16 can be accomplished by filtration, vacuum filtration, beltfilter, pressure filtration, filtration using a screen, screen separation, grates or grating, porous grating, flotation, hydrocyclone, filter press, screwpress, gravity settler, vortex separator, or any method that may be used to separate solids from liquids. In one embodiment, undissolved solids may be removed from corn mash to form two product streams, for example, an aqueous solution of oligosaccharides which contains a lower concentration of solids as compared to corn mash and a wet cake which contains a higher concentration of solids as compared to corn mash. In addition, a third stream containing corn oil may be generated if a three phase decanter centrifuge is utilized for solids removal from corn mash. As such, a number of product streams may be generated by using different separation techniques or a combination thereof.

A fermentor 30 configured to ferment aqueous solution 22 and protein hydrolysates to produce butanol has an inlet for receiving aqueous solution 22. Fermentor 30 can include a fermentation broth. A yeast is introduced to fermentor 30 to be included in the fermentation broth. In some embodiments, microorganism 32 can be *S. cerevisiae*. Microorganism 32 consumes the sugar in aqueous solution 22 and the nitrogen in hydrolysates and produces a butanol and fusel alcohol mixture. In some embodiments, microorganism 32 can be a fermentative recombinant microorganism.

The microorganism 32 is engineered to contain a butanol biosynthetic pathway. In some embodiments, the biosynthetic pathway converts pyruvate to a fermentative product. In some embodiments, the biosynthetic pathway comprises at least one heterologous polynucleotide encoding a polypeptide which catalyzes a substrate to product conversion of the biosynthetic pathway. In some embodiments, each substrate to product conversion of the biosynthetic pathway is catalyzed by a polypeptide encoded by a heterologous polynucleotide.

In situ product removal (ISPR) can be utilized to remove the butanol and fusel oil mixture from fermentor 30 as the butanol and fusel oil mixture is produced by the microorganism, for example, by liquid-liquid extraction. Liquid-liquid extraction within the fermentation vessel is described briefly below and can be performed according to the processes described in U.S. Patent Pub. No. 2009/0305370, the disclosure of which is hereby incorporated in its entirety. In embodiments, liquid-liquid extraction is carried out in the same vessel as the fermentation. In other embodiments, liquid-liquid extraction is performed in a separate vessel downstream of the fermentation. In either case, the extraction may be performed concurrently with the fermentation.

Fermentor 30 has an inlet for receiving an extractant 34. Extractant 34 can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof. The extractant may also be an organic extractant selected from the group consisting of saturated, mono-unsaturated, poly-unsaturated (and mixtures thereof) $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, and mixtures thereof. Extractant 34 can be an organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof. Extractant 34 contacts the fermentation broth and the butanol and fusel oil mixture present in the fermentation broth is transferred to extractant 34. A stream 36 of extractant rich with the butanol and fusel oil mixture is discharged through an outlet in fermentor 30. The butanol and fusel oil mixture is subsequently separated from the extractant in stream 36 using conventional techniques. Feed stream may be added to fermentor 30. Fermentor 30 can be any suitable fermentor known in the art.

One of skill in the art will appreciate that the processes described above in conjunction with recombinant microorganisms provided herein can be used to produce renewable hydrocarbon compositions comprising isobutanol and varying amounts of non-isobutanol fusel alcohols. In some embodiments, the processes and microorganisms provided herein are employed to produce a renewable hydrocarbon composition comprising isobutanol and less than about 3% of non-isobutanol fusels by volume. In embodiments, the renewable hydrocarbon composition comprises isobutanol and less than about 2%, less than about 1%, less than about 0.5%, less than about 0.3%, less than about 0.1%, less than about 0.05%, less than about 0.03%, less than about 0.01%, or less than about 0.005% non-isobutanol fusels by volume.

One of skill in the art will also appreciate that it may be desireable to employ the microorganisms and processes provided herein to increase production of non-isobutanol fusels for advantages, but not limited to, those described elsewhere herein for fuel blends. Thus, in embodiments, the renewable hydrocarbon composition comprises isobutanol and greater than about 0.03%, greater than about 0.05%, greater than about 0.07%, greater than about 0.09%, greater than about 1%, greater than about 3%, or greater than about 5% non-isobutanol fusels by volume.

Construction of Recombinant Yeast

Recombinant microorganisms containing the necessary genes that will encode the enzymatic pathway for the conversion of a fermentable carbon substrate to butanol can be constructed using techniques well known in the art (see, for example, U.S. Pat. No. 7,851,188 and US Appl. Pub. No. US20130071898A1, both incorporated by reference).

Methods of obtaining desired genes from a genome are common and well known in the art of molecular biology. For example, if the sequence of the gene is known, suitable genomic libraries can be created by restriction endonuclease digestion and can be screened with probes complementary to the desired gene sequence. Once the sequence is isolated, the DNA can be amplified using standard primer-directed amplification methods such as polymerase chain reaction (U.S. Pat. No. 4,683,202) to obtain amounts of DNA suitable for transformation using appropriate vectors. Tools for codon optimization for expression in a heterologous host are readily available. Some tools for codon optimization are available based on the GC content of the host microorganism. Once the relevant pathway genes are identified and isolated they can be transformed into suitable expression hosts by means well known in the art. Methods for gene expression in recombinant host cells, including, but not limited to, yeast cells are known in the art (see, for example, *Methods in Enzymology*, Volume 194, Guide to Yeast Genetics and Molecular and Cell Biology (Part A, 2004, Christine Guthrie and Gerald R. Fink (Eds.), Elsevier Academic Press, San Diego, Calif.). The coding region may be from the yeast host cell for transformation and combined with regulatory sequences that are not native to the natural gene. Alternatively, the coding region may be from another host cell; in embodiments, the coding region for an Ehrlich pathway gene and/or butanol pathway gene to be expressed can be codon optimized for the target host cell, as well known to one skilled in the art.

Vectors or cassettes useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions can be derived from genes homologous to the transformed host cell, although it is to be understood that such control regions can also be derived from genes that are not native to the specific species chosen as a production host.

Initiation control regions or promoters, which are useful to drive expression of the relevant pathway coding regions in the desired host cell are numerous and familiar to those skilled in the art. For yeast recombinant host cells, a number of promoters can be used in constructing expression cassettes for genes, including, but not limited to, the following constitutive promoters suitable for use in yeast: FBA1, TDH3 (GPD), ADH1, ILV5, and GPM1; and the following inducible promoters suitable for use in yeast: GAL1, GAL10, OLE1, and CUP1. Other yeast promoters include hybrid promoters UAS(PGK1)-FBA1p, UAS(PGK1)-ENO2p, UAS(FBA1)-PDC1p, UAS(PGK1)-PDC1p and UAS(PGK)-OLE1p (Internat'l. Pat. Pub, No, WO 2011/159853, incorporated herein by reference). Suitable transcriptional terminators that can be used in a chimeric gene construct for expression include, but are not limited to, FBA1t, TDH3t, GPM1t, ERG10t, GAL1t, CYC1t, and ADH1t. In embodiments, suitable promoters, transcriptional terminators, and coding regions can be cloned into *E. coli*-yeast shuttle vectors, and transformed into yeast cells. Such vectors allow strain propagation in both *E. coli* and yeast strains, and can contain a selectable marker and sequences allowing autonomous replication or chromosomal integration in the desired host. Typically used plasmids in yeast include, but are not limited to, shuttle vectors pRS423, pRS424, pRS425, and pRS426 (American Type Culture Collection, Rockville, Md.), which contain an *E. coli* replication origin (e.g., pMB1), a yeast 2-micron origin of replication, and a marker for nutritional selection. The selection markers for these four vectors are HIS3 (vector pRS423), TRP1 (vector pRS424), LEU2 (vector pRS425) and URA3 (vector pRS426). In embodiments, construction of expression vectors with a chimeric gene encoding the described Ehrlich pathway gene(s) and/or butanol pathway gene(s) can be performed by the gap repair recombination method in yeast. In embodiments, a yeast vector DNA is digested (e.g., in its multiple cloning site) to create a "gap" in its sequence. A number of insert DNAs of interest are generated that contain an approximately 21 bp sequence at both the 5' and the 3' ends that sequentially overlap with each other, and with the 5' and 3' terminus of the vector DNA. For example, to construct a yeast expression vector for "Gene X," a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 by overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g. TOP10, followed by mini preps and restriction mapping to further verify the plasmid construct. Finally the construct can be verified by sequence analysis.

Like the gap repair technique, integration into the yeast genome also takes advantage of the homologous recombination system in yeast. In embodiments, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y", the promoter-coding region X-terminator construct is PCR amplified from a plasmid DNA construct and joined to an autotrophic marker (such as URA3) by either SOE PCR or by common restriction digests and cloning. The full cassette, containing the promoter-coding regionX-terminator-URA3 region, is PCR amplified with primer sequences that contain 40-70 bp of homology to the regions 5' and 3' of location "Y" on the yeast chromosome. The PCR product is transformed into yeast and selected on growth media lacking uracil. Transformants can be verified either by colony PCR or by direct sequencing of chromosomal DNA. The presence of the introduced enzyme activity in the recombinant host cells disclosed herein can be confirmed using routine methods known in the art. In a non-limiting example, and as described in the Examples herein, transformants can be screened by PCR using primers for the introduced genes. In another non-limiting example, and as described in the Examples herein, transformants can be screened for butanol production.

Promoters, transcriptional terminators, and coding regions can be cloned into a yeast 2 micron plasmid and transformed into yeast cells (Ludwig, et al. Gene, 132: 33-40, 1993; US Appl. Pub. No. 20080261861A1).

Adjusting the amount of gene expression in a given host may be achieved by varying the level of transcription, such as through selection of native or artificial promoters. In addition, techniques such as the use of promoter libraries to achieve desired levels of gene transcription are well known in the art. Such libraries can be generated using techniques known in the art, for example, by cloning of random cDNA fragments in front of gene cassettes (Goh et al. (2002) AEM 99, 17025), by modulating regulatory sequences present within promoters (Ligr et al. (2006) Genetics 172, 2113), or by mutagenesis of known promoter sequences (Alper et al. (2005) PNAS, 12678; Nevoigt et al. (2006) AEM 72, 5266).

Termination control regions can also be derived from various genes native to the hosts. Optionally, a termination site can be unnecessary or can be included.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., Plasmid, 50: 74-79, 2003). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin et al., J. Bacteriol., 174: 5633-5638, 1992). Additionally, in vitro transposomes are available to create random mutations in a variety of genomes from commercial sources such as EPICENTRE®.

Fermentation Media

Fermentation media in the present invention must contain suitable carbon substrates. Suitable substrates can include but are not limited to monosaccharides such as glucose and fructose, oligosaccharides such as lactose, maltose, galactose, sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate can also be one-carbon substrates such as $CO_2$, or methanol for which metabolic conversion into key biochemical intermediates has been demonstrated. In addition to one and two carbon substrates methylotrophic microorganisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. (eds): Murrell, J. Collin; Kelly, Don P. Publisher: Intercept, Andover, UK). Similarly, various species of *Candida* will metabolize alanine or oleic acid (Sulter et al., *Arch. Microbiol.*, 153:485-489, 1990). Hence it is contemplated that the source of carbon utilized in the present invention can encompass a wide variety of carbon containing substrates and will only be limited by the choice of microorganism.

Although it is contemplated that all of the above mentioned carbon substrates and mixtures thereof are suitable in the present invention, in some embodiments, the carbon substrates are glucose, fructose, and sucrose, or mixtures of these with C5 sugars such as xylose and/or arabinose for yeasts cells modified to use C5 sugars. Sucrose can be derived from renewable sugar sources such as sugar cane, sugar beets, cassava, sweet sorghum, and mixtures thereof. Glucose and dextrose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Patent App. Pub. No. 2007/0031918 A1, which is herein incorporated by reference in its entirety. Biomass refers to any cellulosic or lignocellulosic material and includes materials comprising cellulose, and optionally further comprising hemicellulose, lignin, starch, oligosaccharides and/or monosaccharides. Biomass can also comprise additional components, such as protein and/or lipid. Biomass can be derived from a single source, or biomass can comprise a mixture derived from more than one source; for example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for growth of the cultures and promotion of the enzymatic pathway necessary for butanol production described herein.

Fermentation Conditions

Typically cells are grown at a temperature in the range of about 20° C. to about 40° C. in an appropriate medium. In some embodiments, the cells are grown at a temperature of 20° C., 22° C., 25° C., 27° C., 30° C., 32° C., 35° C., 37° C. or 40° C. Certain cells are more thermo-tolerant and may be grown at higher temperatures such as about 42° C., 45° C., 47° C., and even above 50° C. for short periods of time. Suitable growth media in the present invention are common commercially prepared media such as Luria Bertani (LB) broth, Sabouraud Dextrose (SD) broth or Yeast Medium (YM) broth or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media can also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate (cAMP), can also be incorporated into the fermentation medium.

Suitable pH ranges for the fermentation of yeast are typically from about pH 3.0 to about pH 9.0. In one embodiment, about pH 4.0 to about pH 8.0 is used for the initial condition. In another embodiment, about pH 3.5 to about pH 9.0 is used for the initial condition. In one embodiment, about pH 4.5 to about pH 6.5 is used for the initial condition. In one embodiment, about pH 5.0 to about pH 8.0 is used for the initial condition.

In some embodiments, the contacting of the fermentation medium with the recombinant microorganism is performed under anaerobic or microaerobic conditions.

In some embodiments, the butanol is produced in one or more of the following growth phases: high growth log phase, moderate through static lag phase, stationary phase, steady state growth phase, and combinations thereof.

Industrial Batch and Continuous Fermentations

In some embodiments, the butanol isomers may be produced using batch or continuous fermentation. Butanol may be produced using a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH, dissolved oxygen and the partial pressure of waste gases such as $CO_2$. Batch and fed-batch fermentations are common and well known in the art and examples may be found in Thomas D. Brock in *Biotechnology: A Textbook of Industrial Microbiology*, $2^{nd}$ ed., Sinauer Associates, Inc., Sunderland, Mass. (1989) ("Brock"), or Deshpande, Mukund V., *Appl. Biochem. Biotechnol.*, 36:227, (1992), incorporated herein by reference.

In some embodiments, the butanologen is present at a cell density of at least about 0.5 grams dry cell weight per liter (gdcw/L) prior to contacting with the fermentable carbon substrate. In some embodiments, the butanologen is present at a cell density of at least about 6 gdcw/L to 30 gdcw/L during the first contacting with the carbon substrate. In some embodiments, the cell density of the butanologen may be 6.5 gdcw/L, 7 gdcw/L, 7.5 gdcw/L, 8 gdcw/L, 8.5 gdcw/L, 9 gdcw/L, 9.5 gdcw/L, 10 gdcw/L, 10.5 gdcw/L, 12 gdcw/L, 15 gdcw/L, 17 gdcw/L, 20 gdcw/L, 22 gdcw/L, 25 gdcw/L, 27 gdcw/L or 30 gdcw/L during the first contacting with the carbon substrate.

Butanol isomers, such as isobutanol, may also be produced using continuous fermentation methods. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock.

It is contemplated that the production of butanol, including isobutanol, may be practiced using batch, fed-batch or continuous processes and that any known mode of fermentation would be suitable. Additionally, it is contemplated that cells may be immobilized on a substrate as whole cell catalysts and subjected to fermentation conditions for isobutanol production.

Methods for Butanol/Renewable Hydrocarbon Composition Isolation from the Fermentation Medium The bioproduced butanol isomers may be recovered from the fermentation medium using methods known in the art. See, e.g., Durre, *Appl. Microbiol. Biotechnol.* 49:639-648 (1998), Groot et al., *Process. Biochem.* 27:61-75 (1992), and references therein. For example, butanol may be isolated from the fermentation medium using methods such as distillation, liquid-liquid extraction, or membrane-based separation. In situ product removal (ISPR) (also referred to as extractive fermentation) can be used to remove butanol (or other fermentative alcohol) from the fermentation vessel as it is produced, thereby allowing the microorganism to produce butanol at high yields. One method for ISPR for removing fermentative alcohol that has been described in the art is flash-fermentation. Another method for ISPR for removing fermentative alcohol that has been described in the art is liquid-liquid extraction. In general, with regard to butanol fermentation, for example, the fermentation medium, which includes the microorganism, is contacted with an organic extractant at a time before the butanol concentration reaches a toxic level. The organic extractant and the fermentation medium form a biphasic mixture. The butanol partitions into the organic extractant phase, decreasing the concentration in the aqueous phase containing the microorganism, thereby limiting the exposure of the microorganism to the inhibitory butanol.

Liquid-liquid extraction can be performed, for example, according to the processes described in U.S. Patent Appl. Pub. No. 2009/0305370, the disclosure of which is hereby incorporated in its entirety. U.S. Patent Appl. Pub. No. 2009/0305370 describes methods for producing and recovering butanol from a fermentation broth using liquid-liquid extraction, the methods comprising the step of contacting the fermentation broth with a water immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, triglycerides, and mixtures thereof. The extractant(s) for ISPR can be non-alcohol extractants. The ISPR extractant can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof.

In some embodiments, an ester can be formed by contacting the alcohol in a fermentation medium with a carboxylic acid (e.g., fatty acids) and a catalyst capable of esterfiying the alcohol with the carboxylic acid, as described in PCT Pub. No. WO 2011/159998, which is herein incorporated by reference in its entirety. In such embodiments, the carboxylic acid can serve as an ISPR extractant into which the alcohol esters partition. The carboxylic acid can be supplied to the fermentation vessel and/or derived from the biomass supplying fermentable carbon fed to the fermentation vessel. Lipids present in the feedstock can be catalytically hydrolyzed to carboxylic acid, and the same catalyst (e.g., enzymes) can esterify the carboxylic acid with the alcohol. The catalyst can be supplied to the feedstock prior to fermentation, or can be supplied to the fermentation vessel before or contemporaneously with the supplying of the feedstock. When the catalyst is supplied to the fermentation vessel, alcohol esters can be obtained by hydrolysis of the lipids into carboxylic acid and substantially simultaneous esterification of the carboxylic acid with butanol present in the fermentation vessel. Carboxylic acid and/or native oil not derived from the feedstock can also be fed to the fermentation vessel, with the native oil being hydrolyzed into carboxylic acid. Any carboxylic acid not esterified with the alcohol can serve as part of the ISPR extractant. The extractant containing alcohol esters can be separated from the fermentation medium, and the alcohol can be recovered from the extractant. The extractant can be recycled to the fermentation vessel. Thus, in the case of butanol production, for example, the conversion of the butanol to an ester may reduce the free butanol concentration in the fermentation medium, shielding the microorganism from the toxic effect of increasing butanol concentration. In addition, unfractionated grain can be used as feedstock without separation of lipids therein, since the lipids can be catalytically hydrolyzed to carboxylic acid, thereby decreasing the rate of build-up of lipids in the ISPR extractant.

In situ product removal can be carried out in a batch mode or a continuous mode. In a continuous mode of in situ product removal, product is continually removed from the reactor. In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production according to some embodiments of the present invention, the carboxylic acid extractant can contact the fermentation medium at a time before the butanol concentration reaches a toxic level, so as to esterify the butanol with the carboxylic acid to produce butanol esters and consequently reduce the concentration of butanol in the fermentation vessel. The ester-containing organic phase can then be removed from the fermentation vessel (and separated from the fermentation broth which constitutes the aqueous phase) after a desired effective titer of the butanol esters is achieved. In some embodiments, the ester-containing organic phase is separated from the aqueous phase after fermentation of the available fermentable sugar in the fermentation vessel is substantially complete.

Because butanol isomers form a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol isomers may be isolated using azeotropic distillation using an entrainer (see, for example, Doherty and Malone, *Conceptual Design of Distillation Systems*, McGraw Hill, New York (2001)).

When distillation is used in combination with decantation to isolate and purify the butanol, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

When distillation is used in combination with liquid-liquid extraction, the butanol is extracted from the fermentation broth using liquid-liquid extraction with a suitable solvent. The butanol-containing organic phase is then distilled to separate the butanol from the solvent.

When distillation is used in combination with adsorbtion, the fermentation broth containing the butanol is distilled to near the azeotropic composition and then the remaining water is removed by use of an adsorbent, such as molecular sieves (Aden et al., *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

When distillation is used in combination with pervaporation, the fermentation broth containing the butanol is distilled to near the azeotropic composition, and then the remaining water is removed by pervaporation through a hydrophilic membrane (Guo et al., *J. Membr. Sci.*, 245:199-210 (2004)).

Effective Yield

The presence of butanol and various fusel alcohols can be confirmed using methods known in the art, including, but not limited to those described in U.S. Pat. No. 7,993,889, which is incorporated herein by reference. For example, butanol and fusel alcohol production can be measured by employing chromatographic methods such as high pressure liquid chromatography and/or gas chromatography which are known in the art.

In some embodiments, butanol is produced at an increased effective yield per kg of biomass feedstock. In embodiments, effective yield may be increased by at least about 0.5%, at least about 1%, at least about 2%, or at least about 3%.

In some embodiments, renewable hydrocarbon composition comprising butanol is produced at an increased effective yield per kg of biomass feedstock. In embodiments, effective yield may be increased by at least about 2%, at least about 4%, at least about 5%, at least about 8%, at least about 10%, or at least about 15%.

In some embodiments, fusel alcohol is produced at an increased effective yield per kg of biomass feedstock. In embodiments, effective yield may be increased by at least about 1%, at least about 2%, at least about 4%, at least about 5%, or at least about 8%.

Fuel Blends

Advantages of the disclosed methods may be further recognized in fuel blends comprising the resultant biologically-produced renewable hydrocarbon compositions. In some embodiments provided by the processes herein a mixture of butanol and higher-carbon fusel oils (e.g. isoamyl alcohol and active amyl alcohol) is recovered as the renewable hydrocarbon composition gasoline blending component. In such embodiments, the total carbon-content of recovered renewable hydrocarbon composition gasoline blending component is increased per unit weight of biomass, thus, the compositions can be considered to provide higher energy density when incorporated into gasoline blends; the fusel alcohols isoamyl and active amyl alcohol have about 6.5% greater energy per unit volume of liquid fuel. As a result, the volumetric energy density of the resultant liquid fuel blend is increased per unit weight of biomass processed.

Embodiments provided herein may provide further advantages for economical production of renewable gasoline blends with low vapor pressure, which are desirable for reducing evaporative hydrocarbon emissions. As opposed to the increase in vapor pressure which results from use of ethanol in renewable gasoline blends, butanol provides renewable content while reducing vapor pressure of the blend. Inclusion of the fusel oils isoamyl and active amyl alcohol can enhance this blending benefit because the Reid vapor pressure (RVP) of these fusel oils is about 70% lower than the RVP of butanol. Further, higher alcohols are effective as vapor pressure co-solvents in ethanol-blended fuels, effectively suppressing the large, non-linear vapor pressure increase which occurs at low ethanol concentrations in gasoline; the above renewable compositions incorporating isobutanol and fusel oil (i.e., additional higher alcohols) can be considered equally effective as vapor pressure co-solvents for ethanol-blended fuels.

Fusel oils have also been shown to reduce phase separation of ethanol from gasoline blends when contacted by water, as unavoidably occurs in gasoline distribution systems. Thus, the aforementioned embodiments of butanol with fusel oils may be used in combination of with ethanol to form gasoline blends with high renewable content and improved stability to water contact.

While various embodiments of the present invention have been described above, it should be understood that they have been presented by way of example only, and not limitation. It will be apparent to persons skilled in the relevant art that various changes in form and detail can be made therein without departing from the spririt and scope of the invention. Thus, breadth and scope of the present application should not be limited by any of the above-described exemplary embodiments, but should be defined only in accordance with the claims and their equivalents.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Materials and methods suitable for the maintenance and growth of bacterial cultures are well known in the art. Techniques suitable for use in the following examples may be found as set out in *Manual of Methods for General Bacteriology* (Phillipp et al., eds., American Society for Microbiology, Washington, D.C., (1994)) or by in Brock, *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells may be obtained from Sigma-Aldrich Chemicals (St. Louis, Mo.), BD Diagnostic Systems (Sparks, Md.), Invitrogen (Carlsbad, Calif.), HiMedia (Mumbai, India), SD Fine chemicals (India), or Takara Bio Inc. (Shiga, Japan), unless otherwise specified.

Methods for Determining Isobutanol Concentration in Culture Medium

The concentration of isobutanol in the culture medium can be determined by a number of methods known in the art. For example, a specific high performance liquid chromatography (HPLC) method utilized a Shodex SH-1011 column with a Shodex SHG guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Isobutanol had a retention time of 46.6 min under the conditions used. Alternatively, gas chromatography (GC) methods are available. For example, a specific GC method utilized an HP-INNOWax column (30 m×0.53 mm id, 1 µm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of isobutanol was 4.5 min.

The meaning of abbreviations is as follows: "sec" means second(s), "min" means minute(s), "h" means hour(s), "nm" means nanometers, "uL" means microliter(s), "mL" means milliliter(s), "mg/mL" means milligram per milliliter, "L" means liter(s), "nm" means nanometers, "mM" means millimolar, "M" means molar, "mmol" means millimole(s), "µmole" means micromole(s), "kg" means kilogram, "g" means gram(s), "µg" means microgram(s) and "ng" means nanogram(s), "PCR" means polymerase chain reaction, "OD" means optical density, "OD600" means the optical density measured at a wavelength of 600 nm, "kDa" means kilodaltons, "g" can also mean the gravitation constant, "bp" means base pair(s), "kbp" means kilobase pair(s), "kb" means kilobase, "%" means percent, "% w/v" means weight/volume percent, "% v/v" means volume/volume percent, "HPLC" means high performance liquid chromatography, "g/L" means gram per liter, "µg/L" means microgram per liter, "ng/µL" means nanogram per microliter, "pmol/µL" means picomol per microliter, "RPM" means rotation per minute, "pmol/min/mg" means micromole per minute per milligram, "w/v" means weight per volume, "v/v" means volume per volume.

Microbial strains may be obtained from The American Type Culture Collection (ATCC), Manassas, Va., unless otherwise noted. All the oligonucleotide primers are synthesized by Sigma-Genosys (Woodlands, Tex.) or Integrated DNA Technologies (IDT) (Coralville, Iowa).

Example 1

Construction of Strain PNY2061

*Saccharomyces cerevisiae* strain PNY0827 is used as the host cell for further genetic manipulation. PNY0827 refers to a strain derived from *S. cerevisiae* which has been deposited at the ATCC under the Budapest Treaty on Sep. 22, 2011 at the American Type Culture Collection, Patent Depository 10801 University Boulevard, Manassas, Va. 20110-2209 and has the patent deposit designation PTA-12105.

Deletion Of URA3 And Sporulation Into Haploids: In order to delete the endogenous URA3 coding region, a deletion cassette was PCR-amplified from pLA54 (SEQ ID NO:61) which contains a $P_{TEF1}$-kanMX4-TEF1t cassette flanked by loxP sites to allow homologous recombination in vivo and subsequent removal of the KANMX4 marker. PCR was done by using Phusion High Fidelity PCR Master Mix (New England BioLabs; Ipswich, Mass.) and primers BK505 (SEQ ID NO:62) and BK506 (SEQ ID NO:63). The URA3 portion of each primer was derived from the 5' region 180 bp upstream of the URA3 ATG and 3' region 78 bp downstream of the coding region such that integration of the kanMX4 cassette results in replacement of the URA3 coding region. The PCR product was transformed into PNY0827 using standard genetic techniques (Methods in Yeast Genetics, 2005, Cold Spring Harbor Laboratory Press, Cold Spring Harbor, N.Y., pp. 201-202) and transformants were selected on YEP medium supplemented 2% glucose and 100 µg/ml Geneticin at 30° C. Transformants were screened by colony PCR with primers LA468 (SEQ ID NO:64) and LA492 (SEQ ID NO:65) to verify presence of the integration cassette. A heterozygous diploid was obtained: NYLA98, which has the genotype MATa/α URA3/ura3::loxP-kanMX4-loxP. To obtain haploids, NYLA98 was sporulated using standard methods (Codón et al., *Appl. Environ. Microbiol.* 61:630-638 (1995)). Tetrads were dissected using a micromanipulator and grown on rich YPE medium supplemented with 2% glucose. Tetrads containing four viable spores were patched onto synthetic complete medium lacking uracil supplemented with 2% glucose, and the mating type was verified by multiplex colony PCR using primers AK109-1 (SEQ ID NO:66), AK109-2 (SEQ ID NO:67), and AK109-3 (SEQ ID NO:68). The resulting identified haploid strains were called NYLA103, which has the genotype: MATa ura3Δ::loxP-kanMX4-loxP, and NYLA106, which has the genotype: MATa ura3Δ::loxP-kanMX4-loxP.

Deletion of His3: To delete the endogenous HIS3 coding region, a scarless deletion cassette was used. The four fragments for the PCR cassette for the scarless HIS3 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). HIS3 Fragment A was amplified with primer oBP452 (SEQ ID NO:69) and primer oBP453 (SEQ ID NO:70), containing a 5' tail with homology to the 5' end of HIS3 Fragment B. HIS3 Fragment B was amplified with primer oBP454 (SEQ ID NO:71), containing a 5' tail with homology to the 3' end of HIS3 Fragment A, and primer oBP455 (SEQ ID NO:72) containing a 5' tail with homology to the 5' end of HIS3 Fragment U. HIS3 Fragment U was amplified with primer oBP456 (SEQ ID NO:73), containing a 5' tail with homology to the 3' end of HIS3 Fragment B, and primer oBP457 (SEQ ID NO:74), containing a 5' tail with homology to the 5' end of HIS3 Fragment C. HIS3 Fragment C was amplified with primer oBP458 (SEQ ID NO:75), containing a 5' tail with homology to the 3' end of HIS3 Fragment U, and primer oBP459 (SEQ ID NO:76).

PCR products were purified with a PCR Purification kit (Qiagen). HIS3 Fragment AB was created by overlapping PCR by mixing HIS3 Fragment A and HIS3 Fragment B and amplifying with primers oBP452 (SEQ ID NO:69) and oBP455 (SEQ ID NO:72). HIS3 Fragment UC was created by overlapping PCR by mixing HIS3 Fragment U and HIS3 Fragment C and amplifying with primers oBP456 (SEQ ID NO:73) and oBP459 (SEQ ID NO:76). The resulting PCR products were purified on an agarose gel followed by a Gel Extraction kit (Qiagen). The HIS3 ABUC cassette was created by overlapping PCR by mixing HIS3 Fragment AB and HIS3 Fragment UC and amplifying with primers oBP452 (SEQ ID NO:69) and oBP459 (SEQ ID NO:76). The PCR product was purified with a PCR Purification kit (Qiagen).

Competent cells of NYLA106 were transformed with the HIS3 ABUC PCR cassette and were plated on synthetic complete medium lacking uracil supplemented with 2% glucose at 30° C. Transformants were screened to verify correct integration by replica plating onto synthetic complete medium lacking histidine and supplemented with 2% glucose at 30° C. Genomic DNA preps were made to verify the integration by PCR using primers oBP460 (SEQ ID NO:77) and LA135 (SEQ ID NO:78) for the 5' end and primers oBP461 (SEQ ID NO:79) and LA92 (SEQ ID NO:80) for the 3' end. The URA3 marker was recycled by plating on synthetic complete medium supplemented with 2% glucose and 5-FOA at 30° C. following standard protocols. Marker removal was confirmed by patching colonies from the 5-FOA plates onto SD-URA medium to verify the absence of growth. The resulting identified strain, called PNY2003 has the genotype: MATa ura3Δ::loxP-kanMX4-loxP his3Δ.

Deletion of PDC1: To delete the endogenous PDC1 coding region, a deletion cassette was PCR-amplified from pLA59 (SEQ ID NO:81), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA678 (SEQ ID NO:82) and LA679 (SEQ ID NO:83). The PDC1 portion of each primer was derived from the 5' region 50 bp downstream of the PDC1 start codon and 3' region 50 bp upstream of the stop codon such that integration of the URA3 cassette results in replacement of the PDC1 coding region but leaves the first 50 bp and the last 50 bp of the coding region. The PCR product was transformed into PNY2003 using standard genetic techniques and transformants were selected on synthetic complete medium lacking uracil and supplemented with 2% glucose at 30° C. Transformants were screened to verify correct integration by colony PCR using primers LA337 (SEQ ID NO:84), external to the 5' coding region and LA135 (SEQ ID NO:78), an internal primer to URA3. Positive transformants were then screened by colony PCR using primers LA692 (SEQ ID NO:85) and LA693 (SEQ ID NO:86), internal to the PDC1 coding region. The URA3 marker was recycled by transforming with pLA34 (SEQ ID NO:87) containing the CRE recombinase under the GAL1 promoter and plated on synthetic complete medium lacking histidine and supplemented with 2% glucose at 30° C. Transformants were plated on rich medium supplemented with 0.5% galactose to induce the recombinase. Marker removal was confirmed by patching colonies to synthetic complete medium lacking uracil and supplemented with 2% glucose to verify absence of growth. The resulting identified strain, called PNY2008 has the genotype: MATa ura3Δ::loxP-kanMX4-loxP his3Δpdc1Δ::loxP71/66.

Deletion of PDC5: To delete the endogenous PDC5 coding region, a deletion cassette was PCR-amplified from pLA59 (SEQ ID NO:81), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA722 (SEQ ID NO:88) and LA733 (SEQ ID NO:89). The PDC5 portion of each primer was derived from the 5' region 50 bp upstream of the PDC5 start codon and 3' region 50 bp downstream of the stop codon such that integration of the URA3 cassette results in replacement of the entire PDC5 coding region. The PCR product was transformed into PNY2008 using standard genetic techniques and transformants were selected on synthetic complete medium lacking uracil and supplemented with 1% ethanol at 30° C. Transformants were screened to verify correct integration by colony PCR using primers LA453 (SEQ ID NO:90), external to the 5' coding region and LA135 (SEQ ID NO:78), an internal primer to URA3. Positive transformants were then screened by colony PCR using primers LA694 (SEQ ID NO:91) and LA695 (SEQ ID NO:92), internal to the PDC5 coding region. The URA3 marker was recycled by transforming with pLA34 (SEQ ID NO:87) containing the CRE recombinase under the GAL1 promoter and plated on synthetic complete medium lacking histidine and supplemented with 1% ethanol at 30° C. Transformants were plated on rich YEP medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2009 has the genotype: MATa ura3Δ::loxP-kanMX4-loxP his3Δpdc1Δ::loxP71/66 pdc5Δ::loxP71/66.

Deletion Of FRA2: The FRA2 deletion was designed to delete 250 bp from the 3' end of the coding sequence, leaving the first 113 bp of the FRA2 coding sequence intact. An in-frame stop codon was present 7 bp downstream of the deletion. The four fragments for the PCR cassette for the scarless FRA2 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). FRA2 Fragment A was amplified with primer oBP594 (SEQ ID NO:93) and primer oBP595 (SEQ ID NO:94), containing a 5' tail with homology to the 5' end of FRA2 Fragment B. FRA2 Fragment B was amplified with primer oBP596 (SEQ ID NO:95), containing a 5' tail with homology to the 3' end of FRA2 Fragment A, and primer oBP597 (SEQ ID NO:96), containing a 5' tail with homology to the 5' end of FRA2 Fragment U. FRA2 Fragment U was amplified with primer oBP598 (SEQ ID NO:97), containing a 5' tail with homology to the 3' end of FRA2 Fragment B, and primer oBP599 (SEQ ID NO:98), containing a 5' tail with homology to the 5' end of FRA2 Fragment C. FRA2 Fragment C was amplified with primer oBP600 (SEQ ID NO:99), containing a 5' tail with homology to the 3' end of FRA2 Fragment U, and primer oBP601 (SEQ ID NO:100).

PCR products were purified with a PCR Purification kit (Qiagen). FRA2 Fragment AB was created by overlapping PCR by mixing FRA2 Fragment A and FRA2 Fragment B and amplifying with primers oBP594 (SEQ ID NO:93) and oBP597 (SEQ ID NO:96). FRA2 Fragment UC was created by overlapping PCR by mixing FRA2 Fragment U and FRA2 Fragment C and amplifying with primers oBP598 (SEQ ID NO:97) and oBP601 (SEQ ID NO:100). The resulting PCR products were purified on an agarose gel followed by a Gel Extraction kit (Qiagen). The FRA2 ABUC cassette was created by overlapping PCR by mixing FRA2 Fragment AB and FRA2 Fragment UC and amplifying with primers oBP594 (SEQ ID NO:93) and oBP601 (SEQ ID NO:100). The PCR product was purified with a PCR Purification kit (Qiagen).

To delete the endogenous FRA2 coding region, the scarless deletion cassette obtained above was transformed into PNY2009 using standard techniques and plated on synthetic complete medium lacking uracil and supplemented with 1% ethanol. Genomic DNA preps were made to verify the integration by PCR using primers oBP602 (SEQ ID NO:101) and LA135 (SEQ ID NO:78) for the 5' end, and primers oBP602 (SEQ ID NO:101) and oBP603 (SEQ ID NO:102) to amplify the whole locus. The URA3 marker was recycled by plating on synthetic complete medium supplemented with 1% ethanol and 5-FOA (5-Fluoroorotic Acid) at 30° C. following standard protocols. Marker removal was confirmed by patching colonies from the 5-FOA plates onto synthetic complete medium lacking uracil and supplemented with 1% ethanol to verify the absence of growth. The resulting identified strain, PNY2037, has the genotype: MATa ura3Δ::loxP-kanMX4-loxP his3Δpdc1Δ::loxP71/66 pdc5Δ::loxP71/66 fra2Δ.

Addition Of 2 Micron Plasmid Fragments: The loxP71-URA3-loxP66 marker was PCR-amplified using Phusion DNA polymerase (New England BioLabs; Ipswich, Mass.) from pLA59 (SEQ ID NO:81), and transformed along with the LA811 and LA817 (SEQ ID NOs:103 and 104) and LA812 and LA818 (SEQ ID NOs:105 and 106) 2-micron plasmid fragments into strain PNY2037 on SE-URA plates at 30° C. The resulting strain PNY2037 2μ::loxP71-URA3-loxP66 was transformed with pLA34 (pRS423::cre) (SEQ ID NO:87) and selected on SE-HIS-URA plates at 30° C. Transformants were patched onto YP-1% galactose plates and allowed to grow for 48 hrs at 30° C. to induce Cre recombinase expression. Individual colonies were then patched onto SE-URA, SE-HIS, and YPE plates to confirm URA3 marker removal. The resulting identified strain, PNY2050, has the genotype: MATa ura3Δ::loxP-kanMX4-loxP, his3Δpdc1Δ::loxP71/66 pdc5ΔloxP71/66 fra2Δ 2-micron.

Deletion of GPD2: To delete the endogenous GPD2 coding region, a deletion cassette was PCR-amplified from pLA59 (SEQ ID NO:81), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA512 (SEQ ID NO:107) and LA513 (SEQ ID NO:108). The GPD2 portion of each primer was derived from the 5' region 50 bp upstream of the GPD2 start codon and 3' region 50 bp downstream of the stop codon such that integration of the URA3 cassette results in replacement of the entire GPD2 coding region. The PCR product was transformed into PNY2050 using standard genetic techniques and transformants were selected on synthetic complete medium lacking uracil and supplemented with 1% ethanol at 30° C. Transformants were screened to verify correct integration by colony PCR using primers LA516 (SEQ ID NO:109), external to the 5' coding region and LA135 (SEQ ID NO:78), internal to URA3. Positive transformants were then screened by colony PCR using primers LA514 (SEQ ID NO:110) and LA515 (SEQ ID NO:111), internal to the GPD2 coding region. The URA3 marker was recycled by transforming with pLA34 (SEQ ID NO:87) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, PNY2056, has the genotype: MATa ura3Δ::loxP-kanMX4-loxP his3Δpdc1Δ::loxP71/66 pdc5Δ::loxP71/66 fra2Δ 2-micron gpd2Δ.

Deletion Of YMR226 And Integration Of AlsS: To delete the endogenous YMR226C coding region, an integration cassette was PCR-amplified from pLA71 (SEQ ID NO:112), which contains a gene encoding *B. subtilis* acetolactate synthase (amino acid SEQ ID NO:135) with a FBA1 promoter and a CYC1 terminator (i.e., $P_{FBA1}$-alsS_Bs-CYC1t), and a URA3 marker flanked by degenerate loxP sites to allow homologous recombination in vivo and subsequent removal of the URA3 marker. PCR was done by using KAPA HiFi from Kapa Biosystems, Woburn, Mass. and primers LA829 (SEQ ID NO:113) and LA834 (SEQ ID NO:114). The YMR226C portion of each primer was derived from the first 60 bp of the coding sequence and 65 bp that are 409 bp upstream of the stop codon. The PCR product was transformed into PNY2056 using standard genetic techniques and transformants were selected on synthetic complete medium lacking uracil and supplemented with 1% ethanol at 30° C. Transformants were screened to verify correct integration by colony PCR using primers N1257 (SEQ ID NO:115), external to the 5' coding region and LA740, internal to the FBA1 promoter. Positive transformants were then screened by colony PCR using primers N1257 (SEQ ID NO:115) and LA830 (SEQ ID NO:116), internal to the YMR226C coding region, and primers LA830 (SEQ ID NO:116), external to the 3' coding region, and LA92 (SEQ ID NO:80), internal to the URA3 marker. The URA3 marker was recycled by transforming with pLA34 (SEQ ID NO:87) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, PNY2061, has the genotype: MATa ura3Δ::loxP-kanMX4-loxP his3Δpdc1Δ::loxP71/66 pdc5Δ::loxP71/66 fra2Δ 2-micron gpd2Δ ymr226cΔ::$P_{FBA1}$-alsS_Bs-CYC1t-loxP71/66.

Example 2 (Prophetic)

Construction of Strain with Up-Regulated Valine Transaminase Activity

This example describes the construction of a PNY2061-derived strain that has increased expression of the BAT1 and/or BAT2 branched chain transaminases.

In order to integrate a chimeric BAT1 gene (i.e., in addition to the native BAT1 gene) for increased expression, an integration cassette is PCR-amplified from pLA59::FBA1p-BAT1-CYC1t (SEQ ID NO:117), which contains the *S. cerevisiae* BAT1 gene with a FBA1 promoter and a CYC1 terminator, and a URA3 marker flanked by degenerate loxP sites to allow homologous recombination in vivo and subsequent removal of the URA3 marker. PCR is done by using KAPA HiFi from Kapa Biosystems, Woburn, Mass.

with primers designed to add 75 bp of sequence upstream and downstream of the PDC6 locus to allow homologous recombination and replacement of the PDC6 coding region. The PCR product is transformed into PNY2061 using standard genetic techniques and transformants is selected on synthetic complete medium lacking uracil and supplemented with 1% ethanol at 30° C. Transformants are screened to verify correct integration by colony PCR using primers internal to the BAT1 gene and external to the PDC6 locus. The URA3 marker is recycled by transforming with pLA34 (SEQ ID NO:87) containing the CRE recombinase under the GAL1 promoter and plating on synthetic complete medium lacking histidine and supplemented with 1% ethanol at 30° C. Transformants are plated on rich medium supplemented with 1% ethanol and 0.5% galactose to induce the recombinase. Marker removal is confirmed by patching colonies to synthetic complete medium lacking uracil and supplemented with 1% ethanol to verify absence of growth. The resulting identified strain, T0001, has the genotype: MATa ura3Δ::loxP-kanMX4-loxP his3Δpdc1Δ::loxP71/66 pdc5Δ:loxP71/66 fra2Δ 2-micron gpd2Δ ymr226cΔ::$P_{FBA1}$-alsS_Bs-CYC1t-loxP71/66 pdc6Δ:: $P_{FBA1}$-BAT1-CYC1t-loxP71/66.

In order to integrate a chimeric BAT2 gene (i.e., in addition to the native BAT2 gene) for increased expression, an integration cassette is PCR-amplified from pLA59::FBA1p-BAT2-CYC1t (SEQ ID NO:118), which contains the S. cerevisiae BAT2 gene with a FBA1 promoter and a CYC1 terminator, and a URA3 marker flanked by degenerate loxP sites to allow homologous recombination in vivo and subsequent removal of the URA3 marker. PCR is done by using KAPA HiFi (Kapa Biosystems) with primers designed to add 75 bp of sequence upstream and downstream of the ADH1 locus to allow homologous recombination and replacement of the ADH1 coding region. The PCR product is transformed into PNY2061 using standard genetic techniques and transformants is selected on synthetic complete medium lacking uracil and supplemented with 1% ethanol at 30° C. Transformants are screened to verify correct integration by colony PCR using primers internal to the BAT2 gene and external to the ADH1 locus. The URA3 marker is recycled by transforming with pLA34 (SEQ ID NO:87) containing the CRE recombinase under the GAL1 promoter and plating on synthetic complete medium lacking histidine and supplemented with 1% ethanol at 30° C. Transformants are plated on rich medium supplemented with 1% ethanol and 0.5% galactose to induce the recombinase. Marker removal is confirmed by patching colonies to synthetic complete medium lacking uracil and supplemented with 1% ethanol to verify absence of growth. The resulting identified strain, T0002, has the genotype: MATa ura3Δ::loxP-kanMX4-loxP his3Δpdc1Δ::loxP71/66 pdc5Δ::loxP71/66 fra2Δ 2-micron gpd2Δ ymr226cΔ::$P_{FBA1}$-alsS_Bs-CYC1t-loxP71/66 adh1Δ:: $P_{FBA1}$-BAT2-CYC1t-loxP71/66.

Since BAT1 and BAT2 are capable of catalyzing conversion of the branched chain amino acids to their α-keto acid counterparts (i.e., L-isoleucine→2-keto-3-methyl-valerate, L-leucine→α-ketoisocaproate and L-valine→2-keto-isovalerate, respectively), it is expected that upregulation of either of these transaminases will lead to increased flux through the Ehrlich pathway resulting in an increased concentration of fusel oil from these amino acids. Thus, for example, if the PNY2061-derived strain having increased expression of BAT1 and/or BAT2 is grown in a fermentation medium comprising a suitable concentration of protein hydrolysates, an increased concentration of active amyl alcohol and methylvalerate may be produced from L-isoleucine and/or an increased concentration of isoamyl alcohol and isovalerate may be produced from Leucine and/or an increased concentration of isobutanol and isobutyrate may be produced from L-valine (wherein the first product is the fusel alcohol and the second product listed is the fusel acid, respectively).

Example 3 (Prophetic)

Construction of Strain with Up-Regulated Leucine/Isoleucine Transaminase Activity This example describes the construction of a PNY2061-derived strain that has increased expression of the ARO8 and/or ARO9 branched chain transaminases, with optional up-regulation of the ARO10 decarboxylase.

In order to integrate a chimeric ARO8 gene (i.e., in addition to the native ARO8 gene) for increased expression, an integration cassette is PCR-amplified from pLA59::TDH3p-ARO8-ADH1t (SEQ ID NO:119), which contains the S. cerevisiae ARO8 gene with a TDH3 promoter and a ADH1 terminator, and a URA3 marker flanked by degenerate loxP sites to allow homologous recombination in vivo and subsequent removal of the URA3 marker. PCR is done by using KAPA HiFi from Kapa Biosystems, Woburn, Mass. with primers designed to add 75 bp of sequence upstream and downstream of the MET15 locus to allow homologous recombination and replacement of the MET15 coding region. The PCR product is transformed into PNY2061 using standard genetic techniques and transformants is selected on synthetic complete medium lacking uracil and supplemented with 1% ethanol at 30° C. Transformants are screened to verify correct integration by colony PCR using primers internal to the ARO8 gene and external to the MET15 locus. The URA3 marker is recycled by transforming with pLA34 (SEQ ID NO:87) containing the CRE recombinase under the GAL1 promoter and plating on synthetic complete medium lacking histidine and supplemented with 1% ethanol at 30° C. Transformants are plated on rich medium supplemented with 1% ethanol and 0.5% galactose to induce the recombinase. Marker removal are confirmed by patching colonies to synthetic complete medium lacking uracil and supplemented with 1% ethanol to verify absence of growth. The resulting identified strain, T0003, has the genotype: MATa ura3Δ::loxP-kanMX4-loxP his3Δpdc1Δ::loxP71/66 pdc5Δ::loxP71/66 fra2Δ 2-micron gpd2Δ ymr226cΔ::$P_{FBA1}$-alsS_Bs-CYC1t-loxP71/66 met15Δ:: $P_{TDH3}$-ARO8-ADH1t-loxP71/66.

In order to integrate a chimeric ARO9 gene (i.e., in addition to the native ARO9 gene) for increased expression, an integration cassette is PCR-amplified from pLA59::TDH3p-ARO9-ADHt1 (SEQ ID NO:120), which contains the S. cerevisiae ARO9 gene with a TDH3 promoter and a ADH1 terminator, and a URA3 marker flanked by degenerate loxP sites to allow homologous recombination in vivo and subsequent removal of the URA3 marker. PCR is done by using KAPA HiFi from Kapa Biosystems, Woburn, Mass. with primers designed to add 75 bp of sequence upstream and downstream of the BDH1 locus to allow homologous recombination and replacement of the BDH1 coding region. The PCR product is transformed into PNY2061 using standard genetic techniques and transformants is selected on synthetic complete medium lacking uracil and supplemented with 1% ethanol at 30° C. Transformants are screened to verify correct integration by colony PCR using primers internal to the ARO9 gene and external to the BDH1 locus. The URA3 marker is recycled by transforming with pLA34 (SEQ ID NO:87) containing the CRE recombinase under the GAL1 promoter and plating on synthetic complete medium lacking histidine and supplemented with 1% ethanol at 30° C. Transformants are plated on rich medium supplemented with 1% ethanol and 0.5% galactose to induce the recombinase. Marker removal are confirmed by patching colonies to synthetic complete medium lacking uracil and supplemented with 1% ethanol to verify absence of growth. The resulting identified strain, T0004, has the genotype: MATa ura3Δ::loxP-kanMX4-loxP his3Δpdc1Δ::loxP71/66 pdc5Δ::loxP71/66 fra2Δ 2-micron gpd2Δymr226cΔ::$P_{FBA1}$-alsS_Bs-CYC1t-loxP71/66 bdh1Δ:: $P_{TDH3}$-ARO9-ADH1t-loxP71/66.

Optionally, in order to integrate a chimeric ARO10 gene (i.e., in addition to the native ARO10 gene) for increased expression, an integration cassette is PCR-amplified from pLA59::TDH3p-ARO10-ADH1t (SEQ ID NO:121), which contains the *S. cerevisiae* ARO10 gene with a TDH3 promoter and a ADH1 terminator, and a URA3 marker flanked by degenerate loxP sites to allow homologous recombination in vivo and subsequent removal of the URA3 marker. PCR is done by using KAPA HiFi from Kapa Biosystems, Woburn, Mass. with primers designed to add 75 bp of sequence upstream and downstream of the GPD2 locus to allow homologous recombination and replacement of the GPD2 coding region. The PCR product is transformed into PNY2061 using standard genetic techniques and transformants is selected on synthetic complete medium lacking uracil and supplemented with 1% ethanol at 30° C. Transformants are screened to verify correct integration by colony PCR using primers internal to the ARO10 gene and external to the GPD2 locus. The URA3 marker is recycled by transforming with pLA34 (SEQ ID NO:87) containing the CRE recombinase under the GAL1 promoter and plating on synthetic complete medium lacking histidine and supplemented with 1% ethanol at 30° C. Transformants are plated on rich medium supplemented with 1% ethanol and 0.5% galactose to induce the recombinase. Marker removal are confirmed by patching colonies to synthetic complete medium lacking uracil and supplemented with 1% ethanol to verify absence of growth. The resulting identified strain, T0005, has the genotype: MATa ura3Δ::loxP-kanMX4-loxP his3Δpdc1Δ::loxP71/66 pdc5Δ::loxP71/66 fra2Δ 2-micron gpd2Δymr226cΔ::$P_{FBA1}$-alsS_Bs-CYC1 t-loxP71/66 bdh1Δ:: $P_{TDH3}$-ARO9-ADH1t-loxP71/66 gpd2Δ:: $P_{TDH3}$-ARO10-ADH1t-loxP71/66.

Since ARO8 and ARO9 are capable of catalyzing conversion of the aromatic amino acids to their α-keto acid counterparts (i.e., L-tyrosine→p-hydroxyphenylpyruvate, L-phenylalanine→phenylpyruvate, L-tryptophan→indolepyruvate, respectively), it is expected that upregulation of either of these aromatic aminotransferase will lead to increased flux through the Ehrlich pathway resulting in an increased concentration of fusel oil from these amino acids. Thus, for example, if the PNY2061-derived strain having increased expression of ARO8 and/or ARO9 is grown in a fermentation medium comprising a suitable concentration of protein hydrolysates, an increased concentration of p-hydroxyphenylethanol and p-hydroxyphenylacetate may be produced from L-tyrosine and/or an increased concentration of 2-phenylethanol and 2-phenylacetate may be produced from L-phenylalanine and/or an increased concentration of tryptophol and 2-(indol-3-yl)ethanoate may be produced from L-tryptophan.

Similarly, ARO10 catalyzes conversion of α-keto acids to fusel aldehydes (e.g., 2-keto-3-methyl-valerate→2-methylbutanal, α-ketoisocaproate→3-methylbutanal, phenylpyruvate→phenylacetaldehyde, indolepyruvate→indole acetaldehyde, respectively), it is expected that upregulation of this decarboxylase will lead to increased flux through the Ehrlich pathway resulting in an increased concentration of fusel oil from these α-keto acids.

Example 4 (Prophetic)

Construction of Strain with Up-Regulated Valine and Leucine/Isoleucine Transaminase Activity This example describes the construction of a PNY2061-derived strain that has increased expression of a combination of BAT1, BAT2, ARO8, and ARO9 branched chain transaminases, with optional up-regulation of the ARO10 decarboxylase. Using the molecular biology methods outlined in Example 2 and Example 3, the transformation constructs can be sequentially integrated into the genome of PNY2061 (Example 1) with step-wise recycling of the URA3 marker. For example, the genotype of a strain, T0006, with all integrations described in Examples 2-3, would be: MATa ura3Δ::loxP-kanMX4-loxP his3Δpdc1Δ::loxP71/66 pdc5Δ::loxP71/66 fra2Δ 2-micron gpd2Δymr226cΔ::$P_{FBA1}$-alsS_Bs-CYC1t-loxP71/66 pdc6Δ:: $P_{FBA1}$-BAT1-CYC1t-loxP71/66 adh1Δ:: $P_{FBA1}$-BAT2-CYC1t-loxP71/66 met15Δ:: $P_{TDH3}$-ARO8-ADH1t-loxP71/66 bdh1Δ:: $P_{TDH3}$-ARO9-ADH1t-loxP71/66 gpd2Δ:: $P_{TDH3}$-ARO10-ADH1t-loxP71/66.

Example 5 (Prophetic)

Fermentation with Strains Producing Isobutanol and Increased Transaminase Activity This example describes fermentation with a PNY2061-derived strain that produces isobutanol and that has increased expression of a combination of BAT1, BAT2, ARO8, and ARO9 branched chain transaminases, with optional up-regulation of the ARO10 decarboxylase. A protease, such as Fermenzyme L-400, is used to liberate increased amounts of free amino acids from the corn mash fermentation media.

The host strain PNY2061 (Example 1) or PNY2061-derived strain with increased transaminase activity T0006 (Example 4) is transformed with plasmids pHR81-ILV5p-K9SB2 (SEQ ID NO:122) and pLA84 (SEQ ID NO:123), creating the isobutanologens T0007, and T0008, respectively. Plasmids are introduced by lithium acetate transformation method (Methods in Yeast Genetics, 2005, page 113), and transformants are selected on synthetic complete medium, minus histidine and uracil, with 1% ethanol as carbon source. Transformants are then transferred to plates containing synthetic complete medium, minus histidine and uracil, with 2% glucose as carbon source and either ethanol (0.05%) or acetate (2 mM) as a C2 supplement. Freezer vials are made by dilution of log-phase cultures with 45% glycerol to a final glycerol concentration of 15% (w/v).

Plasmid pHR81-ILV5p-K9SB2 (SEQ ID NO:122) contains the *Anaerostipes caccae* K9SB2 KARI gene (SEQ ID NO:124) driven by ILV5 promoter and ILV5 terminator in pHR81 plasmid backbone. Plasmid pLA84 (SEQ ID NO:123) contains the pRS423 plasmid backbone and: (i) the *Streptococcus mutans* ilvD gene (SEQ ID NO:126) driven by the FBA1 promoter and FBA1 terminator; (ii) the *Beijerinkia indica* ADH gene (SEQ ID NO:129) driven by the GPM1 promoter and the ADH1 terminator; and, (iii) the *Listeria grayi* KivD gene (SEQ ID NO:128) driven by the TDH3 promoter And the TDH3 terminator.

Corn mash centrate is produced by removing undissolved solids from the corn mash prior to fermentation. Four extractive fermentations are conducted side-by side, two with liquefied corn mash as the sugar source (solids not removed) and two with liquefied mash centrate (aqueous solution of oligosaccharides) obtained by removing most of the undissolved solids from liquefied corn mash. Oleyl alcohol (OA) is added to extract the product (i-BuOH) from the broth as it is formed.

Approximately 31 kg of liquefied corn mash is prepared in a 30 L jacketed glass resin kettle. The reactor is outfitted with mechanical agitation, temperature control, and pH control. The protocol used is as follows: mix ground corn with tap water (40 wt % corn on a dry basis), heat the slurry to 55° C. while agitating at 250 rpm, adjust pH to 5.8 with either NaOH or $H_2SO_4$, add a dilute aqueous solution of alpha-amylase (0.16 wt % on a dry corn basis), hold at 55° C. for 60 min, heat to 95° C., adjust pH to 5.8, hold at 95° C. for 120 min while maintaining pH at 5.8 to complete liquefaction. The mash is transferred into sterile centrifuge bottles to prevent contamination.

The corn used is whole kernel yellow corn from Pioneer Hi-Bred International, Inc. (Johnston, Iowa). It is ground in a pilot-scale hammer-mill using a 1 mm screen. The moisture content of the ground corn is measured to be about 12 wt %, and the starch content of the ground corn is measured to be about 71.4 wt % on a dry corn basis. The alpha-amylase enzyme used is Spezyme® Fred-L (Genencor®, Palo Alto, Calif.). The amounts of the ingredients used are: 14.1 kg of ground corn (12% moisture), 16.9 kg of tap water, a solution of alpha-amylase consisting of 19.5 g of Spezyme® Fred-L in 2.0 kg of water. The alpha-amylase is sterile filtered. A total of 0.21 kg of NaOH (17 wt %) is added throughout the run to control pH. It is estimated that the liquefied corn mash contained approximately 28 wt % (about 280 g/L) of liquefied starch based on the corn loading used, starch content of the corn, and assuming all the starch is hydrolyzed during liquefaction. The mash is prepared with a higher concentration of oligosaccharides than is desired in the fermentations to allow for dilution when adding the nutrients, inoculum, glucoamylase, and base to the initial fermentation broth. After dilution by addition of nutrients, inoculum, glucoamylase, and base, the expected total initial soluble sugars in the mash (solids not removed) is about 250 g/L.

About 13.9 kg of the liquefied mash is centrifuged using a bottle centrifuge which contained six 1 L bottles. The centrifuge is operated at 5000 rpm (7260 RCF) for 20 min at room temperature. The mash is separated into about 5.5 kg of clarified centrate and about 8.4 kg of wet cake (the pellet at the bottom of the centrifuge bottles). The split, defined as (amount of centrate)/(amount of mash fed), is about (5.5 kg/13.9 kg)=40%. Solids are not removed from the mash charged to the 2010Y034 and 2010Y036 fermentations described below. The centrate charged to fermentations 2010Y033 and 2010Y035 (also described below) is produced by removing (by centrifugation) most of the suspended solids from mash according to the protocols above.

The S. cerevisiae strains T0007 and T0008 are grown to 0.55-1.1 g/L dcw ($OD_{600}$ 1.3-2.6-Thermo Helios a Thermo Fisher Scientific Inc., Waltham, Mass.) in seed flasks from a frozen culture. The culture is grown at 26° C. in an incubator rotating at 300 rpm. The frozen culture is previously stored at −80° C. The composition of the first seed flask medium is: 3.0 g/L dextrose; 3.0 g/L ethanol, anhydrous; 3.7 g/L For-Medium™ Synthetic Complete Amino Acid (Kaiser) Drop-Out:without HIS, without URA (Reference No. DSCKI62CK); and, 6.7 g/L Difco Yeast Nitrogen Base without amino acids (No. 291920).

Twelve milliliters from the first seed flask culture is transferred to a 2 L flask and grown at 30° C. in an incubator rotating at 300 rpm. The second seed flask has 220 mL of the following medium: 30.0 g/L dextrose; 5.0 g/L ethanol, anhydrous; 3.7 g/L ForMedium™ Synthetic Complete Amino Acid (Kaiser) Drop-Out: without HIS, without URA (Reference No. DSCKI62CK); 6.7 g/L Difco Yeast Nitrogen Base without amino acids (No. 291920); and, 0.2 M MES Buffer titrated to pH 5.5-6.0.

The culture is grown to 0.55-1.1 g/L dcw ($OD_{600}$ 1.3-2.6). An addition of 30 mL of a solution containing 200 g/L peptone and 100 g/L yeast extract is added at this cell concentration. Then an addition of 300 mL of 0.2 μM filter sterilized Cognis, 90-95% oleyl alcohol is added to the flask. The culture continues to grow to >4 g/L dcw ($OD_{600}$>10) before being harvested and added to the fermentation.

A glass jacked, 2 L fermentor (Sartorius AG, Goettingen, Germany) is charged with liquefied mash either with or without solids (centrate). A pH probe (Hamilton Easyferm Plus K8, part number: 238627, Hamilton Bonaduz AG, Bonaduz, Switzerland) is calibrated through the Sartorius DCU-3 Control Tower Calibration menu. The zero is calibrated at pH=7. The span is calibrated at pH=4. The probe is then placed into the fermentor, through the stainless steel head plate. A dissolved oxygen probe (P02 probe) is also placed into the fermentor through the head plate. Tubing used for delivering nutrients, seed culture, extracting solvent, and base are attached to the head plate and the ends were foiled. The entire fermentor is placed into a Steris (Steris Corporation, Mentor, Ohio) autoclave and sterilized in a liquid cycle for 30 min. The fermentor is removed from the autoclave and placed on a load cell. The jacket water supply and return line was connected to the house water and clean drain, respectively. The condenser cooling water in and water out lines are connected to a 6-L recirculating temperature bath running at 7° C. The vent line that transfers the gas from the fermentor is connected to a transfer line that is connected to a Thermo mass spectrometer (Prima dB, Thermo Fisher Scientific Inc., Waltham, Mass.). The sparger line is connected to the gas supply line. The tubing for adding nutrients, extract solvent, seed culture, and base is plumbed through pumps or clamped closed. The autoclaved material, 0.9% w/v NaCl is drained prior to the addition of liquefied mash.

7.0 ml/L (post-inoculation volume) of ethanol (200 proof, anhydrous) is added just prior to inoculation. Thiamine (final concentration 20 mg/L) is added just prior to inoculation. Nicotinic acid (100 mg/L) is added just prior to inoculation. The fermentor's p02 probe is calibrated to zero while $N_2$ is being added to the fermentor. The fermentor's $pO_2$ probe is calibrated to its span with sterile air sparging at 300 rpm. The fermentor is inoculated after the second seed flask was >4 g/L dcw. The shake flask is removed from the incubator/shaker for 5 min allowing a phase separation of the oleyl alcohol phase and the aqueous phase. The 55 mL of the aqueous phase is transferred to a sterile, inoculation bottle. The inoculum is pumped into the fermentor through a peristaltic pump. One liter (post-inoculation volume) of oleyl alcohol is added immediately after inoculation.

The fermentor is operated at 30° C. for the entire growth and production stages. The pH is allowed to drop from a pH between 5.7-5.9 to a control set-point of 5.2 without adding any acid. The pH is controlled for the remainder of the growth and production stage at a pH=5.2 with ammonium hydroxide. Sterile air is added to the fermentor, through the sparger, at 0.3 slpm for the remainder of the growth and production stages. The pO2 is set to be controlled at 3.0% by the Sartorius DCU-3 Control Box PID control loop, using stir control only, with the stirrer minimum being set to 300 rpm and the maximum being set to 2000 rpm. The glucose is supplied through simultaneous saccharification and fermentation of the liquified corn mash by adding either Distillase® L-400 (glucoamylase) or Fermenzyme L-400 (glucoamylase plus protease; Genencor®, Palo Alto, Calif.). The glucose is kept excess (1-50 g/L) for as long as starch was available for saccharification.

Process air is analyzed on a Thermo Prima (Thermo Fisher Scientific Inc., Waltham, Mass.) mass spectrometer. This is the same process air that was sterilized and then added to each fermentor. Each fermentor's off-gas is analyzed on the same mass spectrometer. The gases calibrated are: nitrogen, oxygen, isobutanol, argon, and $CO_2$. Based on the analysis of the off-gas of each fermentor, the amount of isobutanol stripped, oxygen consumed, and $CO_2$ respired into the off-gas is measured by using the mass spectrometer's mole fraction analysis and gas flow rates (mass flow controller) into the fermentor. The gassing rate per hour is calculated and used to integrate that rate over the course of the fermentation.

Aqueous samples are refrigerated until ready for processing. Samples are removed from refrigeration for one hr to bring to room temperature. Approximately 300 µL of sample is transferred with a m1000 Variable Channel BioHit pipette with 100-1000 µL BioHit pipette tips into a 0.2 µm centrifuge filter (Nanosep MF modified nylon centrifuge filter), then centrifuged using a Eppendorf 5415C for five min at 14,000 rpm. Approximately 200 uL of filtered sample is transferred into a 1.8 ml auto sampler vial with a 250 µL glass vial insert with polymer feet. A screw cap with PTFE septa, is used to cap the vial before vortexing the sample with a Vortex-Genie® set at 2700 rpm. Samples are then run on Agilent 1200 series LC equipped with binary, isocratic pumps, vacuum degasser, heated column compartment, sampler cooling system, UV DAD detector and RI detector. The column used is an Aminex HPX-87H, 300×7.8 with a Bio-Rad Cation H refill, 30×4.6 guard column. Column temperature is 40° C., with a mobile phase of 0.01 N sulfuric acid, at a flow rate of 0.6 mL/min for 40 min. Samples from the oleyl alcohol phase are refrigerated until ready for processing.

Samples are removed from the refrigerator for one hr to bring to room temperature. Approximately 150 µL of sample is transferred using a m1000 Variable Channel BioHit pipette with 100-1000 µL BioHit pipette tips into a 1.8 ml auto sampler vial with a 250 µL glass vial insert with polymer feet. A screw cap with PTFE septa is used to cap the vial. Samples are then run on Agilent 7890A GC with a 7683B injector and a G2614A auto sampler. The column is a HP-InnoWax column (30 m×0.32 mm ID, 0.25 µm film). The carrier gas is helium at a flow rate of 1.5 mL/min measured at 45° C. with constant head pressure; injector split was 1:50 at 225° C.; oven temperature was 45° C. for 1.5 min, 45° C. to 160° C. at 10° C./min for 0 min, then 230° C. at 35° C./min for 14 min for a run time of 29 min. Flame ionization detection is used at 260° C. with 40 mL/min helium makeup gas.

Increased product yields of fusel alcohols (isobutanol, isoamyl alcohol, and active amyl alcohol) are detected in fermentations using the T0008 strain with increased transaminase activity. Protease addition further increases the product yield of fusel alcohols in T0008 strains with increased transaminase activity.

|  | Relative product yields (expected) | | |
| --- | --- | --- | --- |
|  | Isobutanol | Isoamyl alcohol | Active amyl alcohol |
| without protease addition | | | |
| Strain T0007 | ++ | ++ | ++ |
| Strain T0008 | +++ | +++ | +++ |
| with protease addition | | | |
| Strain T0007 | +++ | +++ | +++ |
| Strain T0008 | ++++ | ++++ | ++++ |

What is claimed is:

1. A method for producing a renewable hydrocarbon composition comprising isobutanol, the method comprising:
   a) providing a feedstock slurry comprising protein hydrolysates and fermentable carbohydrate;
   b) adding the feedstock slurry to a fermentation medium;
   c) contacting the fermentation medium comprising the feedstock slurry with a recombinant yeast host cell capable of producing a renewable hydrocarbon composition from both protein hydrolysates and fermentable carbohydrate; and
   d) recovering a renewable hydrocarbon composition from the fermentation medium by distillation;
   wherein the recombinant yeast host cell comprises:
      i) an isobutanol production pathway comprising enzymes which catalyze the following substrate to product conversions: pyruvate to acetolactate, acetolactate to 2,3-dihydroxyisovalerate, 2,3-dihydroxyisovalerate to α-ketoisovalerate, α-ketoisovalerate to isobutyraldehyde, and isobutyraldehyde to isobutanol;
      ii) at least one heterologous enzyme which catalyzes a substrate to product conversion of i); and
      iii) at least one genetic modification which reduces the activity of LEU4, at least one genetic modification which reduces the activity of LEU9, at least one genetic modification which reduces the activity of ILV1, or a combination of such genetic modifications.

2. The method of claim 1 wherein the at least one heterologous enzyme which catalyzes a substrate to product conversion is acetolactate synthase, ketol-acid reductoisomerase, dihydroxyacid dehydratase, ketoisovalerate decarboxylase, or alcohol dehydrogenase.

3. The method of claim 1, wherein at least two heterologous enzymes catalyze substrate to product conversions of i).

4. The method of claim 1, wherein at least three heterologous enzymes catalyze substrate to product conversions of i).

5. The method of claim 1, wherein the genetic modification which reduces the activity of LEU4, LEU9 or ILV1 comprises a deletion of LEU4, LEU9 or ILV1.

6. The method of claim 1, wherein the recombinant yeast host cell comprises a disruption of an endogenous polynucleotide encoding a polypeptide having pyruvate decarboxylase activity or an endogenous polypeptide having pyruvate decarboxylase activity.

7. The method of claim 6, wherein the recombinant yeast host cell comprises a modification to reduce glycerol-3-phosphate dehydrogenase activity.

8. The method of claim 1, wherein the recombinant yeast host cell comprises modifications in polynucleotides encoding URA3 (orotidine-5'-phosphate decarboxylase), HIS3 (imidazoleglycerol-phosphatedehydratase), FRA2 (iron repressor protein), CCC1 (putative vacuolar Fe2+/Mn2+ transporter), GPD2 (glycerol-2-phosphate dehydrogenase), or acetolactate reductase or polypeptides having URA3, HIS3, FRA2, CCC1, GPD2, or acetolactate reductase activity, or combinations thereof.

9. The method of claim 1, wherein the recombinant yeast host cell is *Saccharomyces, Schizosaccharomyces, Hansenula, Candida, Kluyveromyces, Yarrowia, Issatchenkia,* or *Pichia*.

10. The method of claim 1, wherein the renewable hydrocarbon composition comprises isobutanol.

* * * * *

SEQUENCE LISTING

```
<160> NUMBER OF SEQ ID NOS: 137

<210> SEQ ID NO 1
<211> LENGTH: 1503
<212> TYPE: DNA
<213> ORGANISM: Saccharomyces cerevisiae
<220> FEATURE:
<221> NAME/KEY: CDS
<222> LOCATION: (1)..(1503)
<223> OTHER INFORMATION: GenBank Accession No. NM_001181067

<400> SEQUENCE: 1 atg act tta cct gaa tca aaa gac ttt tct tac ttg ttt tcg gat gaa      48
Met Thr Leu Pro Glu Ser Lys Asp Phe Ser Tyr Leu Phe Ser Asp Glu
1               5                   10                  15 acc aat gct cgt aaa cca tcc cca ttg aaa acc tgc atc cat ctt ttc      96
Thr Asn Ala Arg Lys Pro Ser Pro Leu Lys Thr Cys Ile His Leu Phe
            20                  25                  30 caa gat cct aac att atc ttt ttg ggt ggt ggc ctg cca tta aaa gat     144
Gln Asp Pro Asn Ile Ile Phe Leu Gly Gly Gly Leu Pro Leu Lys Asp
        35                  40                  45 tat ttc cca tgg gat aat cta tct gta gat tca ccc aag cct cct ttt     192
Tyr Phe Pro Trp Asp Asn Leu Ser Val Asp Ser Pro Lys Pro Pro Phe
```

-continued

```
            50                  55                  60
ccc cag ggt att gga gct cca att gac gag cag aat tgc ata aaa tac     240
Pro Gln Gly Ile Gly Ala Pro Ile Asp Glu Gln Asn Cys Ile Lys Tyr
 65                  70                  75                  80 acc gtc aac aaa gat tac gct gat aaa agt gcc aat cct tcc aac gat     288
Thr Val Asn Lys Asp Tyr Ala Asp Lys Ser Ala Asn Pro Ser Asn Asp
                     85                  90                  95 att cct ttg tca aga gct ttg caa tac ggg ttc agt gct ggt caa cct     336
Ile Pro Leu Ser Arg Ala Leu Gln Tyr Gly Phe Ser Ala Gly Gln Pro
                100                 105                 110 gaa cta tta aac ttc att aga gat cat acc aag att atc cac gat ttg     384
Glu Leu Leu Asn Phe Ile Arg Asp His Thr Lys Ile Ile His Asp Leu
            115                 120                 125 aag tat aag gac tgg gac gtt tta gcc act gca ggt aac aca aat gcc     432
Lys Tyr Lys Asp Trp Asp Val Leu Ala Thr Ala Gly Asn Thr Asn Ala
        130                 135                 140 tgg gaa tct act tta aga gtc ttt tgt aac cga ggt gat gtc atc tta     480
Trp Glu Ser Thr Leu Arg Val Phe Cys Asn Arg Gly Asp Val Ile Leu
145                 150                 155                 160 gtt gag gca cat tct ttt tcc tct tca ttg gct tct gca gag gct caa     528
Val Glu Ala His Ser Phe Ser Ser Ser Leu Ala Ser Ala Glu Ala Gln
                165                 170                 175 ggt gtc att acc ttc ccc gtg cca att gac gct gat ggt atc att cct     576
Gly Val Ile Thr Phe Pro Val Pro Ile Asp Ala Asp Gly Ile Ile Pro
            180                 185                 190 gaa aaa tta gct aaa gtc atg gaa aac tgg aca cct ggt gct cct aaa     624
Glu Lys Leu Ala Lys Val Met Glu Asn Trp Thr Pro Gly Ala Pro Lys
        195                 200                 205 cca aag ttg tta tac act att cca acg ggc caa aat cca act ggt act     672
Pro Lys Leu Leu Tyr Thr Ile Pro Thr Gly Gln Asn Pro Thr Gly Thr
    210                 215                 220 tcc att gca gac cat aga aag gag gca att tac aag atc gct caa aag     720
Ser Ile Ala Asp His Arg Lys Glu Ala Ile Tyr Lys Ile Ala Gln Lys
225                 230                 235                 240 tac gac ttc cta att gtg gaa gat gaa cct tat tat ttc tta caa atg     768
Tyr Asp Phe Leu Ile Val Glu Asp Glu Pro Tyr Tyr Phe Leu Gln Met
                245                 250                 255 aat ccc tac atc aaa gac ttg aag gaa aga gag aag gca caa agt tct     816
Asn Pro Tyr Ile Lys Asp Leu Lys Glu Arg Glu Lys Ala Gln Ser Ser
            260                 265                 270 cca aag cag gac cat gac gaa ttt ttg aag tcc ttg gca aac act ttc     864
Pro Lys Gln Asp His Asp Glu Phe Leu Lys Ser Leu Ala Asn Thr Phe
        275                 280                 285 ctt tcc ttg gat aca gaa ggc cgt gtt att aga atg gat tcc ttt tca     912
Leu Ser Leu Asp Thr Glu Gly Arg Val Ile Arg Met Asp Ser Phe Ser
    290                 295                 300 aaa gtt ttg gcc cca ggg aca aga ttg ggt tgg att act ggt tca tcc     960
Lys Val Leu Ala Pro Gly Thr Arg Leu Gly Trp Ile Thr Gly Ser Ser
305                 310                 315                 320 aaa atc ttg aag cct tac ttg agt ttg cat gaa atg acg att caa gcc    1008
Lys Ile Leu Lys Pro Tyr Leu Ser Leu His Glu Met Thr Ile Gln Ala
                325                 330                 335 cca gca ggt ttt aca caa gtt ttg gtc aac gct acg cta tcc agg tgg    1056
Pro Ala Gly Phe Thr Gln Val Leu Val Asn Ala Thr Leu Ser Arg Trp
            340                 345                 350 ggt caa aag ggt tac ttg gac tgg ttg ctt ggc ctg cgt cat gaa tac    1104
Gly Gln Lys Gly Tyr Leu Asp Trp Leu Leu Gly Leu Arg His Glu Tyr
        355                 360                 365 act ttg aaa cgt gac tgt gcc atc gat gcc ctt tac aag tat cta cca    1152
Thr Leu Lys Arg Asp Cys Ala Ile Asp Ala Leu Tyr Lys Tyr Leu Pro
```

```
Thr Leu Lys Arg Asp Cys Ala Ile Asp Ala Leu Tyr Lys Tyr Leu Pro
    370                 375                 380 caa tct gat gct ttc gtg atc aat cct cca att gca ggt atg ttt ttc    1200
Gln Ser Asp Ala Phe Val Ile Asn Pro Pro Ile Ala Gly Met Phe Phe
385                 390                 395                 400 acc gtg aac att gac gca tct gtc cac cct gag ttt aaa aca aaa tac    1248
Thr Val Asn Ile Asp Ala Ser Val His Pro Glu Phe Lys Thr Lys Tyr
                405                 410                 415 aac tca gac cct tac cag cta gaa cag agt ctt tac cac aaa gtg gtt    1296
Asn Ser Asp Pro Tyr Gln Leu Glu Gln Ser Leu Tyr His Lys Val Val
            420                 425                 430 gaa cgt ggt gtt tta gtg gtt ccc ggt tct tgg ttc aag agt gag ggt    1344
Glu Arg Gly Val Leu Val Val Pro Gly Ser Trp Phe Lys Ser Glu Gly
        435                 440                 445 gag acg gaa cct cct caa ccc gct gaa tct aaa gaa gtc agt aat cca    1392
Glu Thr Glu Pro Pro Gln Pro Ala Glu Ser Lys Glu Val Ser Asn Pro
450                 455                 460 aac ata att ttc ttc aga ggt acc tat gca gct gtc tct cct gag aaa    1440
Asn Ile Ile Phe Phe Arg Gly Thr Tyr Ala Ala Val Ser Pro Glu Lys
465                 470                 475                 480 ctg act gaa ggt ctg aag aga tta ggt gat act tta tac gaa gaa ttt    1488
Leu Thr Glu Gly Leu Lys Arg Leu Gly Asp Thr Leu Tyr Glu Glu Phe
                485                 490                 495 ggt att tcc aaa tag                                                1503
Gly Ile Ser Lys
            500

<210> SEQ ID NO 2
<211> LENGTH: 500
<212> TYPE: PRT
<213> ORGANISM: Saccharomyces cerevisiae

<400> SEQUENCE: 2

Met Thr Leu Pro Glu Ser Lys Asp Phe Ser Tyr Leu Phe Ser Asp Glu
1               5                   10                  15

Thr Asn Ala Arg Lys Pro Ser Pro Leu Lys Thr Cys Ile His Leu Phe
            20                  25                  30

Gln Asp Pro Asn Ile Ile Phe Leu Gly Gly Leu Pro Leu Lys Asp
        35                  40                  45

Tyr Phe Pro Trp Asp Asn Leu Ser Val Asp Ser Pro Lys Pro Pro Phe
    50                  55                  60

Pro Gln Gly Ile Gly Ala Pro Ile Asp Glu Gln Asn Cys Ile Lys Tyr
65              70                  75                  80

Thr Val Asn Lys Asp Tyr Ala Asp Lys Ser Ala Asn Pro Ser Asn Asp
            85                  90                  95

Ile Pro Leu Ser Arg Ala Leu Gln Tyr Gly Phe Ser Ala Gly Gln Pro
        100                 105                 110

Glu Leu Leu Asn Phe Ile Arg Asp His Thr Lys Ile Ile His Asp Leu
    115                 120                 125

Lys Tyr Lys Asp Trp Asp Val Leu Ala Thr Ala Gly Asn Thr Asn Ala
        130                 135                 140

Trp Glu Ser Thr Leu Arg Val Phe Cys Asn Arg Gly Asp Val Ile Leu
145                 150                 155                 160

Val Glu Ala His Ser Phe Ser Ser Ser Leu Ala Ser Ala Glu Ala Gln
                165                 170                 175

Gly Val Ile Thr Phe Pro Val Pro Ile Asp Ala Asp Gly Ile Ile Pro
        180                 185                 190
```

-continued

```
Glu Lys Leu Ala Lys Val Met Glu Asn Trp Thr Pro Gly Ala Pro Lys
            195                 200                 205

Pro Lys Leu Leu Tyr Thr Ile Pro Thr Gly Gln Asn Pro Thr Gly Thr
        210                 215                 220

Ser Ile Ala Asp His Arg Lys Glu Ala Ile Tyr Lys Ile Ala Gln Lys
225                 230                 235                 240

Tyr Asp Phe Leu Ile Val Glu Asp Glu Pro Tyr Tyr Phe Leu Gln Met
                245                 250                 255

Asn Pro Tyr Ile Lys Asp Leu Lys Glu Arg Glu Lys Ala Gln Ser Ser
            260                 265                 270

Pro Lys Gln Asp His Asp Glu Phe Leu Lys Ser Leu Ala Asn Thr Phe
        275                 280                 285

Leu Ser Leu Asp Thr Glu Gly Arg Val Ile Arg Met Asp Ser Phe Ser
    290                 295                 300

Lys Val Leu Ala Pro Gly Thr Arg Leu Gly Trp Ile Thr Gly Ser Ser
305                 310                 315                 320

Lys Ile Leu Lys Pro Tyr Leu Ser Leu His Glu Met Thr Ile Gln Ala
                325                 330                 335

Pro Ala Gly Phe Thr Gln Val Leu Val Asn Ala Thr Leu Ser Arg Trp
            340                 345                 350

Gly Gln Lys Gly Tyr Leu Asp Trp Leu Leu Gly Leu Arg His Glu Tyr
        355                 360                 365

Thr Leu Lys Arg Asp Cys Ala Ile Asp Ala Leu Tyr Lys Tyr Leu Pro
    370                 375                 380

Gln Ser Asp Ala Phe Val Ile Asn Pro Pro Ile Ala Gly Met Phe Phe
385                 390                 395                 400

Thr Val Asn Ile Asp Ala Ser Val His Pro Glu Phe Lys Thr Lys Tyr
                405                 410                 415

Asn Ser Asp Pro Tyr Gln Leu Glu Gln Ser Leu Tyr His Lys Val Val
            420                 425                 430

Glu Arg Gly Val Leu Val Val Pro Gly Ser Trp Phe Lys Ser Glu Gly
        435                 440                 445

Glu Thr Glu Pro Pro Gln Pro Ala Glu Ser Lys Glu Val Ser Asn Pro
    450                 455                 460

Asn Ile Ile Phe Phe Arg Gly Thr Tyr Ala Ala Val Ser Pro Glu Lys
465                 470                 475                 480

Leu Thr Glu Gly Leu Lys Arg Leu Gly Asp Thr Leu Tyr Glu Glu Phe
                485                 490                 495

Gly Ile Ser Lys
            500
```

<210> SEQ ID NO 3
<211> LENGTH: 1542
<212> TYPE: DNA
<213> ORGANISM: Saccharomyces cerevisiae
<220> FEATURE:
<221> NAME/KEY: CDS
<222> LOCATION: (1)..(1542)
<223> OTHER INFORMATION: GenBank Accession No. NM_001179267

<400> SEQUENCE: 3

```
atg act gct ggt tct gcc ccc cct gtt gat tac act tcc tta aag aag      48
Met Thr Ala Gly Ser Ala Pro Pro Val Asp Tyr Thr Ser Leu Lys Lys
1               5                   10                  15 aac ttc caa ccg ttt ctc tcc aga aga gta gaa aat aga tct ctg aaa      96
Asn Phe Gln Pro Phe Leu Ser Arg Arg Val Glu Asn Arg Ser Leu Lys
            20                  25                  30
```

| | | |
|---|---|---|
| agc ttt tgg gat gct tct gat atc tca gat gac gtc att gag cta gct<br>Ser Phe Trp Asp Ala Ser Asp Ile Ser Asp Asp Val Ile Glu Leu Ala<br>35　　　　　　　　40　　　　　　　　45 | | 144 |
| ggt gga atg cca aac gag aga ttt ttt cct atc gaa tct atg gat ttg<br>Gly Gly Met Pro Asn Glu Arg Phe Phe Pro Ile Glu Ser Met Asp Leu<br>50　　　　　　　　55　　　　　　　　60 | | 192 |
| aaa ata tca aaa gtt cct ttt aat gat aac cca aaa tgg cat aat tcg<br>Lys Ile Ser Lys Val Pro Phe Asn Asp Asn Pro Lys Trp His Asn Ser<br>65　　　　　　　　70　　　　　　　　75　　　　　　　　80 | | 240 |
| ttt acc acg gcg cat ttg gac ttg gga tcc ccc agt gag cta ccc att<br>Phe Thr Thr Ala His Leu Asp Leu Gly Ser Pro Ser Glu Leu Pro Ile<br>　　　　　　　85　　　　　　　　90　　　　　　　　95 | | 288 |
| gca cgt tct ttc caa tat gca gaa acc aag ggt tta ccc cct ctc tta<br>Ala Arg Ser Phe Gln Tyr Ala Glu Thr Lys Gly Leu Pro Pro Leu Leu<br>　　　　　　　100　　　　　　　　105　　　　　　　110 | | 336 |
| cat ttt gtt aaa gat ttt gtg tcc aga att aat cgc cca gcc ttt tcc<br>His Phe Val Lys Asp Phe Val Ser Arg Ile Asn Arg Pro Ala Phe Ser<br>　　　　　　　115　　　　　　　　120　　　　　　　125 | | 384 |
| gat gag acg gag tct aac tgg gat gtc atc ctt tct ggc ggg tcc aac<br>Asp Glu Thr Glu Ser Asn Trp Asp Val Ile Leu Ser Gly Gly Ser Asn<br>130　　　　　　　　135　　　　　　　　140 | | 432 |
| gat tca atg ttt aag gtt ttt gaa aca att tgc gac gaa tcg acc act<br>Asp Ser Met Phe Lys Val Phe Glu Thr Ile Cys Asp Glu Ser Thr Thr<br>145　　　　　　　　150　　　　　　　　155　　　　　　　160 | | 480 |
| gtg atg att gaa gag ttt act ttc acc ccg gct atg tcc aat gtg gag<br>Val Met Ile Glu Glu Phe Thr Phe Thr Pro Ala Met Ser Asn Val Glu<br>　　　　　　　165　　　　　　　　170　　　　　　　175 | | 528 |
| gct aca gga gca aaa gtc atc ccc atc aag atg aac ctg acc ttc gac<br>Ala Thr Gly Ala Lys Val Ile Pro Ile Lys Met Asn Leu Thr Phe Asp<br>　　　　　　　180　　　　　　　　185　　　　　　　190 | | 576 |
| aga gag tcc cag ggt att gat gtc gaa tat cta acg cag ttg ctc gat<br>Arg Glu Ser Gln Gly Ile Asp Val Glu Tyr Leu Thr Gln Leu Leu Asp<br>　　　　　　　195　　　　　　　　200　　　　　　　205 | | 624 |
| aat tgg tca act gga cca tac aaa gac tta aac aag cca agg gtc cta<br>Asn Trp Ser Thr Gly Pro Tyr Lys Asp Leu Asn Lys Pro Arg Val Leu<br>210　　　　　　　　215　　　　　　　　220 | | 672 |
| tat acc att gca acg ggc caa aat cct acc ggg atg tct gtc ccc cag<br>Tyr Thr Ile Ala Thr Gly Gln Asn Pro Thr Gly Met Ser Val Pro Gln<br>225　　　　　　　　230　　　　　　　　235　　　　　　　240 | | 720 |
| tgg aaa aga gag aaa att tac cag ttg gcc caa aga cac gat ttc ctc<br>Trp Lys Arg Glu Lys Ile Tyr Gln Leu Ala Gln Arg His Asp Phe Leu<br>　　　　　　　245　　　　　　　　250　　　　　　　255 | | 768 |
| att gtt gaa gat gat ccc tac ggt tat ctg tac ttt cct tcc tat aat<br>Ile Val Glu Asp Asp Pro Tyr Gly Tyr Leu Tyr Phe Pro Ser Tyr Asn<br>　　　　　　　260　　　　　　　　265　　　　　　　270 | | 816 |
| ccg caa gag cca tta gaa aac cct tac cat tct agc gac ctg act act<br>Pro Gln Glu Pro Leu Glu Asn Pro Tyr His Ser Ser Asp Leu Thr Thr<br>　　　　　　　275　　　　　　　　280　　　　　　　285 | | 864 |
| gaa cgg tat ttg aat gat ttt tta atg aaa tca ttc ttg act ttg gat<br>Glu Arg Tyr Leu Asn Asp Phe Leu Met Lys Ser Phe Leu Thr Leu Asp<br>290　　　　　　　　295　　　　　　　　300 | | 912 |
| aca gat gcc cgt gtc atc cgt ttg gag act ttt tct aaa att ttt gct<br>Thr Asp Ala Arg Val Ile Arg Leu Glu Thr Phe Ser Lys Ile Phe Ala<br>305　　　　　　　　310　　　　　　　　315　　　　　　　320 | | 960 |
| cct gga tta agg tta tcc ttc atc gtt gct aat aaa ttc ctt ttg caa<br>Pro Gly Leu Arg Leu Ser Phe Ile Val Ala Asn Lys Phe Leu Leu Gln<br>　　　　　　　325　　　　　　　　330　　　　　　　335 | | 1008 |
| aaa atc ttg gat ttg gcc gac att act aca agg gcc ccc agt ggt acc<br>Lys Ile Leu Asp Leu Ala Asp Ile Thr Thr Arg Ala Pro Ser Gly Thr | | 1056 |

```
                              340                 345                 350
tca caa gct att gtt tat tct aca ata aag gca atg gct gag tcc aac        1104
Ser Gln Ala Ile Val Tyr Ser Thr Ile Lys Ala Met Ala Glu Ser Asn
            355                 360                 365 tta tcg tcc tct ctt tct atg aaa gaa gca atg ttt gag ggt tgg ata        1152
Leu Ser Ser Ser Leu Ser Met Lys Glu Ala Met Phe Glu Gly Trp Ile
370                 375                 380 aga tgg ata atg cag att gct tct aaa tac aat cat agg aaa aat ctt        1200
Arg Trp Ile Met Gln Ile Ala Ser Lys Tyr Asn His Arg Lys Asn Leu
385                 390                 395                 400 act ttg aaa gcc tta tac gaa aca gaa tct tac caa gct ggt cag ttt        1248
Thr Leu Lys Ala Leu Tyr Glu Thr Glu Ser Tyr Gln Ala Gly Gln Phe
                405                 410                 415 acc gtt atg gaa ccc tcc gcg ggt atg ttc atc att att aaa atc aat        1296
Thr Val Met Glu Pro Ser Ala Gly Met Phe Ile Ile Ile Lys Ile Asn
            420                 425                 430 tgg ggg aat ttc gat aga cct gac gat ttg ccg caa cag atg gat att        1344
Trp Gly Asn Phe Asp Arg Pro Asp Asp Leu Pro Gln Gln Met Asp Ile
        435                 440                 445 tta gat aag ttc ttg ctg aag aat ggt gtt aaa gta gtg ctt ggt tat        1392
Leu Asp Lys Phe Leu Leu Lys Asn Gly Val Lys Val Val Leu Gly Tyr
450                 455                 460 aaa atg gct gtt tgc cca aat tat tca aag cag aat tca gat ttt cta        1440
Lys Met Ala Val Cys Pro Asn Tyr Ser Lys Gln Asn Ser Asp Phe Leu
465                 470                 475                 480 aga ctc acc atc gcc tat gca agg gat gat gat cag ttg att gaa gct        1488
Arg Leu Thr Ile Ala Tyr Ala Arg Asp Asp Asp Gln Leu Ile Glu Ala
                485                 490                 495 tcc aaa aga atc ggt agt ggc ata aaa gaa ttt ttt gac aac tat aaa        1536
Ser Lys Arg Ile Gly Ser Gly Ile Lys Glu Phe Phe Asp Asn Tyr Lys
            500                 505                 510 agt tga                                                                1542
Ser

<210> SEQ ID NO 4
<211> LENGTH: 513
<212> TYPE: PRT
<213> ORGANISM: Saccharomyces cerevisiae

<400> SEQUENCE: 4

Met Thr Ala Gly Ser Ala Pro Val Asp Tyr Thr Ser Leu Lys Lys
1               5                   10                  15

Asn Phe Gln Pro Phe Leu Ser Arg Arg Val Glu Asn Arg Ser Leu Lys
            20                  25                  30

Ser Phe Trp Asp Ala Ser Asp Ile Ser Asp Asp Val Ile Glu Leu Ala
        35                  40                  45

Gly Gly Met Pro Asn Glu Arg Phe Phe Pro Ile Glu Ser Met Asp Leu
    50                  55                  60

Lys Ile Ser Lys Val Pro Phe Asn Asp Asn Pro Lys Trp His Asn Ser
65                  70                  75                  80

Phe Thr Thr Ala His Leu Asp Leu Gly Ser Pro Ser Glu Leu Pro Ile
                85                  90                  95

Ala Arg Ser Phe Gln Tyr Ala Glu Thr Lys Gly Leu Pro Pro Leu Leu
            100                 105                 110

His Phe Val Lys Asp Phe Val Ser Arg Ile Asn Arg Pro Ala Phe Ser
        115                 120                 125

Asp Glu Thr Glu Ser Asn Trp Asp Val Ile Leu Ser Gly Gly Ser Asn
    130                 135                 140
```

Asp Ser Met Phe Lys Val Phe Glu Thr Ile Cys Asp Glu Ser Thr Thr
145                 150                 155                 160

Val Met Ile Glu Glu Phe Thr Phe Thr Pro Ala Met Ser Asn Val Glu
        165                 170                 175

Ala Thr Gly Ala Lys Val Ile Pro Ile Lys Met Asn Leu Thr Phe Asp
        180                 185                 190

Arg Glu Ser Gln Gly Ile Asp Val Glu Tyr Leu Thr Gln Leu Leu Asp
        195                 200                 205

Asn Trp Ser Thr Gly Pro Tyr Lys Asp Leu Asn Lys Pro Arg Val Leu
210                 215                 220

Tyr Thr Ile Ala Thr Gly Gln Asn Pro Thr Gly Met Ser Val Pro Gln
225                 230                 235                 240

Trp Lys Arg Glu Lys Ile Tyr Gln Leu Ala Gln Arg His Asp Phe Leu
                245                 250                 255

Ile Val Glu Asp Asp Pro Tyr Gly Tyr Leu Tyr Phe Pro Ser Tyr Asn
                260                 265                 270

Pro Gln Glu Pro Leu Glu Asn Pro Tyr His Ser Ser Asp Leu Thr Thr
                275                 280                 285

Glu Arg Tyr Leu Asn Asp Phe Leu Met Lys Ser Phe Leu Thr Leu Asp
290                 295                 300

Thr Asp Ala Arg Val Ile Arg Leu Glu Thr Phe Ser Lys Ile Phe Ala
305                 310                 315                 320

Pro Gly Leu Arg Leu Ser Phe Ile Val Ala Asn Lys Phe Leu Leu Gln
                325                 330                 335

Lys Ile Leu Asp Leu Ala Asp Ile Thr Thr Arg Ala Pro Ser Gly Thr
                340                 345                 350

Ser Gln Ala Ile Val Tyr Ser Thr Ile Lys Ala Met Ala Glu Ser Asn
                355                 360                 365

Leu Ser Ser Ser Leu Ser Met Lys Glu Ala Met Phe Glu Gly Trp Ile
370                 375                 380

Arg Trp Ile Met Gln Ile Ala Ser Lys Tyr Asn His Arg Lys Asn Leu
385                 390                 395                 400

Thr Leu Lys Ala Leu Tyr Glu Thr Glu Ser Tyr Gln Ala Gly Gln Phe
                405                 410                 415

Thr Val Met Glu Pro Ser Ala Gly Met Phe Ile Ile Lys Ile Asn
                420                 425                 430

Trp Gly Asn Phe Asp Arg Pro Asp Asp Leu Pro Gln Gln Met Asp Ile
                435                 440                 445

Leu Asp Lys Phe Leu Leu Lys Asn Gly Val Lys Val Val Leu Gly Tyr
450                 455                 460

Lys Met Ala Val Cys Pro Asn Tyr Ser Lys Gln Asn Ser Asp Phe Leu
465                 470                 475                 480

Arg Leu Thr Ile Ala Tyr Ala Arg Asp Asp Gln Leu Ile Glu Ala
                485                 490                 495

Ser Lys Arg Ile Gly Ser Gly Ile Lys Glu Phe Asp Asn Tyr Lys
                500                 505                 510

Ser

<210> SEQ ID NO 5
<211> LENGTH: 1908
<212> TYPE: DNA
<213> ORGANISM: Saccharomyces cerevisiae
<220> FEATURE:
<221> NAME/KEY: CDS
<222> LOCATION: (1)..(1908)
<223> OTHER INFORMATION: GenBank Accession No. NM_001180688

<400> SEQUENCE: 5

| | | | | | | | | | | | | | | | | |
|---|---|---|---|---|---|---|---|---|---|---|---|---|---|---|---|---|
| atg | gca | cct | gtt | aca | att | gaa | aag | ttc | gta | aat | caa | gaa | gaa | cga | cac | 48 |
| Met | Ala | Pro | Val | Thr | Ile | Glu | Lys | Phe | Val | Asn | Gln | Glu | Glu | Arg | His | |
| 1 | | | | 5 | | | | | 10 | | | | | 15 | | |
| ctt | gtt | tcc | aac | cga | tca | gca | aca | att | ccg | ttt | ggt | gaa | tac | ata | ttt | 96 |
| Leu | Val | Ser | Asn | Arg | Ser | Ala | Thr | Ile | Pro | Phe | Gly | Glu | Tyr | Ile | Phe | |
| | | | 20 | | | | | 25 | | | | | 30 | | | |
| aaa | aga | ttg | ttg | tcc | atc | gat | acg | aaa | tca | gtt | ttc | ggt | gtt | cct | ggt | 144 |
| Lys | Arg | Leu | Leu | Ser | Ile | Asp | Thr | Lys | Ser | Val | Phe | Gly | Val | Pro | Gly | |
| | | | 35 | | | | | 40 | | | | | 45 | | | |
| gac | ttc | aac | tta | tct | cta | tta | gaa | tat | ctc | tat | tca | cct | agt | gtt | gaa | 192 |
| Asp | Phe | Asn | Leu | Ser | Leu | Leu | Glu | Tyr | Leu | Tyr | Ser | Pro | Ser | Val | Glu | |
| 50 | | | | | 55 | | | | | 60 | | | | | | |
| tca | gct | ggc | cta | aga | tgg | gtc | ggc | acg | tgt | aat | gaa | ctg | aac | gcc | gct | 240 |
| Ser | Ala | Gly | Leu | Arg | Trp | Val | Gly | Thr | Cys | Asn | Glu | Leu | Asn | Ala | Ala | |
| 65 | | | | | 70 | | | | | 75 | | | | | 80 | |
| tat | gcg | gcc | gac | gga | tat | tcc | cgt | tac | tct | aat | aag | att | ggc | tgt | tta | 288 |
| Tyr | Ala | Ala | Asp | Gly | Tyr | Ser | Arg | Tyr | Ser | Asn | Lys | Ile | Gly | Cys | Leu | |
| | | | | 85 | | | | | 90 | | | | | 95 | | |
| ata | acc | acg | tat | ggc | gtt | ggt | gaa | tta | agc | gcc | ttg | aac | ggt | ata | gcc | 336 |
| Ile | Thr | Thr | Tyr | Gly | Val | Gly | Glu | Leu | Ser | Ala | Leu | Asn | Gly | Ile | Ala | |
| | | | | 100 | | | | | 105 | | | | | 110 | | |
| ggt | tcg | ttc | gct | gaa | aat | gtc | aaa | gtt | ttg | cac | att | gtt | ggt | gtg | gcc | 384 |
| Gly | Ser | Phe | Ala | Glu | Asn | Val | Lys | Val | Leu | His | Ile | Val | Gly | Val | Ala | |
| | | | 115 | | | | | 120 | | | | | 125 | | | |
| aag | tcc | ata | gat | tcg | cgt | tca | agt | aac | ttt | agt | gat | cgg | aac | cta | cat | 432 |
| Lys | Ser | Ile | Asp | Ser | Arg | Ser | Ser | Asn | Phe | Ser | Asp | Arg | Asn | Leu | His | |
| | | | 130 | | | | | 135 | | | | | 140 | | | |
| cat | ttg | gtc | cca | cag | cta | cat | gat | tca | aat | ttt | aaa | ggg | cca | aat | cat | 480 |
| His | Leu | Val | Pro | Gln | Leu | His | Asp | Ser | Asn | Phe | Lys | Gly | Pro | Asn | His | |
| 145 | | | | | 150 | | | | | 155 | | | | | 160 | |
| aaa | gta | tat | cat | gat | atg | gta | aaa | gat | aga | gtc | gct | tgc | tcg | gta | gcc | 528 |
| Lys | Val | Tyr | His | Asp | Met | Val | Lys | Asp | Arg | Val | Ala | Cys | Ser | Val | Ala | |
| | | | | 165 | | | | | 170 | | | | | 175 | | |
| tac | ttg | gag | gat | att | gaa | act | gca | tgt | gac | caa | gtc | gat | aat | gtt | atc | 576 |
| Tyr | Leu | Glu | Asp | Ile | Glu | Thr | Ala | Cys | Asp | Gln | Val | Asp | Asn | Val | Ile | |
| | | | | 180 | | | | | 185 | | | | | 190 | | |
| cgc | gat | att | tac | aag | tat | tct | aaa | cct | ggt | tat | att | ttt | gtt | cct | gca | 624 |
| Arg | Asp | Ile | Tyr | Lys | Tyr | Ser | Lys | Pro | Gly | Tyr | Ile | Phe | Val | Pro | Ala | |
| | | | 195 | | | | | 200 | | | | | 205 | | | |
| gat | ttt | gcg | gat | atg | tct | gtt | aca | tgt | gat | aat | ttg | gtt | aat | gtt | cca | 672 |
| Asp | Phe | Ala | Asp | Met | Ser | Val | Thr | Cys | Asp | Asn | Leu | Val | Asn | Val | Pro | |
| | | 210 | | | | | 215 | | | | | 220 | | | | |
| cgt | ata | tct | caa | caa | gat | tgt | ata | gta | tac | cct | tct | gaa | aac | caa | ttg | 720 |
| Arg | Ile | Ser | Gln | Gln | Asp | Cys | Ile | Val | Tyr | Pro | Ser | Glu | Asn | Gln | Leu | |
| 225 | | | | | 230 | | | | | 235 | | | | | 240 | |
| tct | gac | ata | atc | aac | aag | att | act | agt | tgg | ata | tat | tcc | agt | aaa | aca | 768 |
| Ser | Asp | Ile | Ile | Asn | Lys | Ile | Thr | Ser | Trp | Ile | Tyr | Ser | Ser | Lys | Thr | |
| | | | | 245 | | | | | 250 | | | | | 255 | | |
| cct | gcg | atc | ctt | gga | gac | gta | ctg | act | gat | agg | tat | ggt | gtg | agt | aac | 816 |
| Pro | Ala | Ile | Leu | Gly | Asp | Val | Leu | Thr | Asp | Arg | Tyr | Gly | Val | Ser | Asn | |
| | | | 260 | | | | | 265 | | | | | 270 | | | |
| ttt | ttg | aac | aag | ctt | atc | tgc | aaa | act | ggg | att | tgg | aat | ttt | tcc | act | 864 |
| Phe | Leu | Asn | Lys | Leu | Ile | Cys | Lys | Thr | Gly | Ile | Trp | Asn | Phe | Ser | Thr | |
| | | | 275 | | | | | 280 | | | | | 285 | | | |
| gtt | atg | gga | aaa | tct | gta | att | gat | gag | tca | aac | cca | act | tat | atg | ggt | 912 |
| Val | Met | Gly | Lys | Ser | Val | Ile | Asp | Glu | Ser | Asn | Pro | Thr | Tyr | Met | Gly | |

```
                 290                 295                 300
caa tat aat ggt aaa gaa ggt tta aaa caa gtc tat gaa cat ttt gaa     960
Gln Tyr Asn Gly Lys Glu Gly Leu Lys Gln Val Tyr Glu His Phe Glu
305                 310                 315                 320 ctg tgc gac ttg gtc ttg cat ttt gga gtc gac atc aat gaa att aat    1008
Leu Cys Asp Leu Val Leu His Phe Gly Val Asp Ile Asn Glu Ile Asn
                325                 330                 335 aat ggg cat tat act ttt act tat aaa cca aat gct aaa atc att caa    1056
Asn Gly His Tyr Thr Phe Thr Tyr Lys Pro Asn Ala Lys Ile Ile Gln
            340                 345                 350 ttt cat ccg aat tat att cgc ctt gtg gac act agg cag ggc aat gag    1104
Phe His Pro Asn Tyr Ile Arg Leu Val Asp Thr Arg Gln Gly Asn Glu
        355                 360                 365 caa atg ttc aaa gga atc aat ttt gcc cct att tta aaa gaa cta tac    1152
Gln Met Phe Lys Gly Ile Asn Phe Ala Pro Ile Leu Lys Glu Leu Tyr
    370                 375                 380 aag cgc att gac gtt tct aaa ctt tct ttg caa tat gat tca aat gta    1200
Lys Arg Ile Asp Val Ser Lys Leu Ser Leu Gln Tyr Asp Ser Asn Val
385                 390                 395                 400 act caa tat acg aac gaa aca atg cgg tta gaa gat cct acc aat gga    1248
Thr Gln Tyr Thr Asn Glu Thr Met Arg Leu Glu Asp Pro Thr Asn Gly
                405                 410                 415 caa tca agc att att aca caa gtt cac tta caa aag acg atg cct aaa    1296
Gln Ser Ser Ile Ile Thr Gln Val His Leu Gln Lys Thr Met Pro Lys
            420                 425                 430 ttt ttg aac cct ggt gat gtt gtc gtt tgt gaa aca ggc tct ttt caa    1344
Phe Leu Asn Pro Gly Asp Val Val Val Cys Glu Thr Gly Ser Phe Gln
        435                 440                 445 ttc tct gtt cgt gat ttc gcg ttt cct tcg caa tta aaa tat ata tcg    1392
Phe Ser Val Arg Asp Phe Ala Phe Pro Ser Gln Leu Lys Tyr Ile Ser
    450                 455                 460 caa gga ttt ttc ctt tcc att ggc atg gcc ctt cct gcc gcc cta ggt    1440
Gln Gly Phe Phe Leu Ser Ile Gly Met Ala Leu Pro Ala Ala Leu Gly
465                 470                 475                 480 gtt gga att gcc atg caa gac cac tca aac gct cac atc aat ggt ggc    1488
Val Gly Ile Ala Met Gln Asp His Ser Asn Ala His Ile Asn Gly Gly
                485                 490                 495 aac gta aaa gag gac tat aag cca aga tta att ttg ttt gaa ggt gac    1536
Asn Val Lys Glu Asp Tyr Lys Pro Arg Leu Ile Leu Phe Glu Gly Asp
            500                 505                 510 ggt gca gca cag atg aca atc caa gaa ctg agc acc att ctg aag tgc    1584
Gly Ala Ala Gln Met Thr Ile Gln Glu Leu Ser Thr Ile Leu Lys Cys
        515                 520                 525 aat att cca cta gaa gtt atc att tgg aac aat aac ggc tac act att    1632
Asn Ile Pro Leu Glu Val Ile Ile Trp Asn Asn Asn Gly Tyr Thr Ile
    530                 535                 540 gaa aga gcc atc atg ggc cct acc agg tcg tat aac gac gtt atg tct    1680
Glu Arg Ala Ile Met Gly Pro Thr Arg Ser Tyr Asn Asp Val Met Ser
545                 550                 555                 560 tgg aaa tgg acc aaa cta ttt gaa gca ttc gga gac ttc gac gga aag    1728
Trp Lys Trp Thr Lys Leu Phe Glu Ala Phe Gly Asp Phe Asp Gly Lys
                565                 570                 575 tat act aat agc act ctc att caa tgt ccc tct aaa tta gca ctg aaa    1776
Tyr Thr Asn Ser Thr Leu Ile Gln Cys Pro Ser Lys Leu Ala Leu Lys
            580                 585                 590 ttg gag gag ctt aag aat tca aac aaa aga agc ggg ata gaa ctt tta    1824
Leu Glu Glu Leu Lys Asn Ser Asn Lys Arg Ser Gly Ile Glu Leu Leu
        595                 600                 605 gaa gtc aaa tta ggc gaa ttg gat ttc ccc gaa cag cta aag tgc atg    1872
```

-continued

```
Glu Val Lys Leu Gly Glu Leu Asp Phe Pro Glu Gln Leu Lys Cys Met
610                 615                 620 gtt gaa gca gcg gca ctt aaa aga aat aaa aaa tag                    1908
Val Glu Ala Ala Ala Leu Lys Arg Asn Lys Lys
625                 630                 635

<210> SEQ ID NO 6
<211> LENGTH: 635
<212> TYPE: PRT
<213> ORGANISM: Saccharomyces cerevisiae

<400> SEQUENCE: 6

Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
                20                  25                  30

Lys Arg Leu Leu Ser Ile Asp Thr Lys Ser Val Phe Gly Val Pro Gly
            35                  40                  45

Asp Phe Asn Leu Ser Leu Leu Glu Tyr Leu Tyr Ser Pro Ser Val Glu
        50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125

Lys Ser Ile Asp Ser Arg Ser Ser Asn Phe Ser Asp Arg Asn Leu His
130                 135                 140

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
                165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
        195                 200                 205

Asp Phe Ala Asp Met Ser Val Thr Cys Asp Asn Leu Val Asn Val Pro
210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
                245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
        275                 280                 285

Val Met Gly Lys Ser Val Ile Asp Glu Ser Asn Pro Thr Tyr Met Gly
290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
                325                 330                 335

Asn Gly His Tyr Thr Phe Thr Tyr Lys Pro Asn Ala Lys Ile Ile Gln
```

```
                340             345             350
 Phe His Pro Asn Tyr Ile Arg Leu Val Asp Thr Arg Gln Gly Asn Glu
             355                 360                 365

Gln Met Phe Lys Gly Ile Asn Phe Ala Pro Ile Leu Lys Glu Leu Tyr
     370                 375                 380

Lys Arg Ile Asp Val Ser Lys Leu Ser Leu Gln Tyr Asp Ser Asn Val
 385                 390                 395                 400

Thr Gln Tyr Thr Asn Glu Thr Met Arg Leu Glu Asp Pro Thr Asn Gly
                 405                 410                 415

Gln Ser Ser Ile Ile Thr Gln Val His Leu Gln Lys Thr Met Pro Lys
             420                 425                 430

Phe Leu Asn Pro Gly Asp Val Val Cys Glu Thr Gly Ser Phe Gln
             435                 440                 445

Phe Ser Val Arg Asp Phe Ala Phe Pro Ser Gln Leu Lys Tyr Ile Ser
     450                 455                 460

Gln Gly Phe Phe Leu Ser Ile Gly Met Ala Leu Pro Ala Ala Leu Gly
 465                 470                 475                 480

Val Gly Ile Ala Met Gln Asp His Ser Asn Ala His Ile Asn Gly Gly
                 485                 490                 495

Asn Val Lys Glu Asp Tyr Lys Pro Arg Leu Ile Leu Phe Glu Gly Asp
             500                 505                 510

Gly Ala Ala Gln Met Thr Ile Gln Glu Leu Ser Thr Ile Leu Lys Cys
         515                 520                 525

Asn Ile Pro Leu Glu Val Ile Ile Trp Asn Asn Asn Gly Tyr Thr Ile
         530                 535                 540

Glu Arg Ala Ile Met Gly Pro Thr Arg Ser Tyr Asn Asp Val Met Ser
 545                 550                 555                 560

Trp Lys Trp Thr Lys Leu Phe Glu Ala Phe Gly Asp Phe Asp Gly Lys
                 565                 570                 575

Tyr Thr Asn Ser Thr Leu Ile Gln Cys Pro Ser Lys Leu Ala Leu Lys
             580                 585                 590

Leu Glu Glu Leu Lys Asn Ser Asn Lys Arg Ser Gly Ile Glu Leu Leu
             595                 600                 605

Glu Val Lys Leu Gly Glu Leu Asp Phe Pro Glu Gln Leu Lys Cys Met
     610                 615                 620

Val Glu Ala Ala Ala Leu Lys Arg Asn Lys Lys
 625                 630                 635

<210> SEQ ID NO 7
<211> LENGTH: 1835
<212> TYPE: DNA
<213> ORGANISM: Saccharomyces cerevisiae
<220> FEATURE:
<221> NAME/KEY: CDS
<222> LOCATION: (133)..(1314)
<223> OTHER INFORMATION: GenBank Accession No. X78961

<400> SEQUENCE: 7
aagctttgaa aaaaaaaag catctgaaaa aaatggcact ataagagag ctagtggtaa      60 caactacatg ttttcgttag aataaatcac cctataaacg caaaatcagc tagaaccta   120 gcatactaaa ac atg ttg cag aga cat tcc ttg aag ttg ggg aaa ttc tcc   171
              Met Leu Gln Arg His Ser Leu Lys Leu Gly Lys Phe Ser
                1               5                  10 atc aga aca ctc gct act ggt gcc cca tta gat gca tcc aaa cta aaa   219
Ile Arg Thr Leu Ala Thr Gly Ala Pro Leu Asp Ala Ser Lys Leu Lys
    15                  20                  25
```

| | | |
|---|---|---|
| att act aga aac cca aat cca tcc aag cca aga cca aat gaa gaa tta<br>Ile Thr Arg Asn Pro Asn Pro Ser Lys Pro Arg Pro Asn Glu Glu Leu<br>30                  35                    40                   45 | 267 |
| gtg ttc ggc cag aca ttc acc gat cat atg ttg acc att cct tgg tca<br>Val Phe Gly Gln Thr Phe Thr Asp His Met Leu Thr Ile Pro Trp Ser<br>                  50                    55                   60 | 315 |
| gcc aaa gaa ggg tgg ggc act cca cac atc aag cct tac ggt aat ctt<br>Ala Lys Glu Gly Trp Gly Thr Pro His Ile Lys Pro Tyr Gly Asn Leu<br>                  65                    70                   75 | 363 |
| tct ctt gac cca tct gct tgt gta ttc cat tat gca ttt gaa tta ttt<br>Ser Leu Asp Pro Ser Ala Cys Val Phe His Tyr Ala Phe Glu Leu Phe<br>         80                    85                    90 | 411 |
| gaa ggt ttg aaa gcc tac aga act cct caa aat act atc acc atg ttc<br>Glu Gly Leu Lys Ala Tyr Arg Thr Pro Gln Asn Thr Ile Thr Met Phe<br>95                  100                  105 | 459 |
| cgt ccg gat aag aac atg gcc cgt atg aac aag tct gcc gct aga att<br>Arg Pro Asp Lys Asn Met Ala Arg Met Asn Lys Ser Ala Ala Arg Ile<br>110                   115                  120                 125 | 507 |
| tgt ttg cca act ttc gaa tct gaa gaa ttg atc aaa ctt acc ggg aaa<br>Cys Leu Pro Thr Phe Glu Ser Glu Glu Leu Ile Lys Leu Thr Gly Lys<br>                  130                  135                 140 | 555 |
| ttg atc gaa caa gat aaa cac ttg gtt cct caa ggt aat ggt tac tca<br>Leu Ile Glu Gln Asp Lys His Leu Val Pro Gln Gly Asn Gly Tyr Ser<br>                 145                  150                 155 | 603 |
| tta tac atc aga cca aca atg att ggt aca tcc aag ggt tta ggt gtt<br>Leu Tyr Ile Arg Pro Thr Met Ile Gly Thr Ser Lys Gly Leu Gly Val<br>                160                  165                 170 | 651 |
| ggc act ccc tcc gag gct ctt ctt tat gtt att act tct cca gtc ggt<br>Gly Thr Pro Ser Glu Ala Leu Leu Tyr Val Ile Thr Ser Pro Val Gly<br>     175                  180                  185 | 699 |
| cct tat tat aag act ggt ttc aaa gcc gta cgt ctt gaa gca aca gac<br>Pro Tyr Tyr Lys Thr Gly Phe Lys Ala Val Arg Leu Glu Ala Thr Asp<br>190                   195                  200                 205 | 747 |
| tat gct aca aga gct tgg cca ggt ggt gtt ggc gac aaa aaa ttg ggt<br>Tyr Ala Thr Arg Ala Trp Pro Gly Gly Val Gly Asp Lys Lys Leu Gly<br>          210                  215                 220 | 795 |
| gct aac tat gcc cca tgc atc tta cct caa cta caa gct gcc aaa aga<br>Ala Asn Tyr Ala Pro Cys Ile Leu Pro Gln Leu Gln Ala Ala Lys Arg<br>                 225                  230                 235 | 843 |
| ggg tac caa caa aat cta tgg ttg ttc ggc cca gaa aag aac atc act<br>Gly Tyr Gln Gln Asn Leu Trp Leu Phe Gly Pro Glu Lys Asn Ile Thr<br>          240                  245                 250 | 891 |
| gag gtt ggt act atg aac gtg ttc ttc gtt ttc ctc aac aaa gtc act<br>Glu Val Gly Thr Met Asn Val Phe Phe Val Phe Leu Asn Lys Val Thr<br>255                   260                  265 | 939 |
| ggc aag aag gaa ttg gtt acc gct cca tta gat ggt acc att tta gaa<br>Gly Lys Lys Glu Leu Val Thr Ala Pro Leu Asp Gly Thr Ile Leu Glu<br>270                   275                  280                 285 | 987 |
| ggt gtt acc aga gac tct gtt tta aca ttg gct cgt gac aaa cta gat<br>Gly Val Thr Arg Asp Ser Val Leu Thr Leu Ala Arg Asp Lys Leu Asp<br>                  290                  295                 300 | 1035 |
| cct caa gaa tgg gac atc aac gag cgt tat tac act att act gaa gtc<br>Pro Gln Glu Trp Asp Ile Asn Glu Arg Tyr Tyr Thr Ile Thr Glu Val<br>                 305                  310                 315 | 1083 |
| gcc act aga gca aaa caa ggt gaa cta tta gaa gcc ttc ggt tct ggt<br>Ala Thr Arg Ala Lys Gln Gly Glu Leu Leu Glu Ala Phe Gly Ser Gly<br>          320                  325                 330 | 1131 |
| act gct gct gtc gtt tca cct atc aag gaa att ggc tgg aac aac gaa<br>Thr Ala Ala Val Val Ser Pro Ile Lys Glu Ile Gly Trp Asn Asn Glu | 1179 |

-continued

```
                 335                340                345
gat att cat gtt cca cta ttg cct ggt gaa caa tgt ggt gca ttg acc    1227
Asp Ile His Val Pro Leu Leu Pro Gly Glu Gln Cys Gly Ala Leu Thr
350                 355                360                365 aag caa gtt gct caa tgg att gct gat atc caa tac ggt aga gtc aat    1275
Lys Gln Val Ala Gln Trp Ile Ala Asp Ile Gln Tyr Gly Arg Val Asn
                370                375                380 tat ggt aac tgg tca aaa act gtt gcc gac ttg aac taa tgataatgaa     1324
Tyr Gly Asn Trp Ser Lys Thr Val Ala Asp Leu Asn
                385                390 ggtacacatg cctggtcccc caaaaaaaaa aaacgtgaat tcctctcaga gatctgtttt   1384
ttacaattcc tgttgagttt atttattata agaaatattg gattactatt attattatag  1444
cttatgctaa gccattgtgc gcttcttacg ctttttgaaa ttgttgacct aacaacttgg   1504
cacattattg aatttcatag agactgcttg taatttagtt gccaaggtat ctcgctggac   1564
tttacatgta aaatgaatgc ggcaagatac ccaagagagt tgattatgcc aaaaaaaaaa   1624
aatctataag atatccctgg tattttctga agaataaatt ctagcgtagt tcagaagagg   1684
tgcaagtaca gtatgaataa tggtatgcct tccatcatcg tggcatacag gttcaggcat   1744
gaagagatga ttatgttccc tcaccggtcc ataatcctga tttaaacagt tcattagtat   1804
atgttcgagc caacacaaca acgagaagct t                                  1835
```

<210> SEQ ID NO 8
<211> LENGTH: 393
<212> TYPE: PRT
<213> ORGANISM: Saccharomyces cerevisiae

<400> SEQUENCE: 8

```
Met Leu Gln Arg His Ser Leu Lys Leu Gly Lys Phe Ser Ile Arg Thr
1               5                   10                  15

Leu Ala Thr Gly Ala Pro Leu Asp Ala Ser Lys Leu Lys Ile Thr Arg
                20                  25                  30

Asn Pro Asn Pro Ser Lys Pro Arg Pro Asn Glu Glu Leu Val Phe Gly
            35                  40                  45

Gln Thr Phe Thr Asp His Met Leu Thr Ile Pro Trp Ser Ala Lys Glu
        50                  55                  60

Gly Trp Gly Thr Pro His Ile Lys Pro Tyr Gly Asn Leu Ser Leu Asp
65                  70                  75                  80

Pro Ser Ala Cys Val Phe His Tyr Ala Phe Glu Leu Phe Glu Gly Leu
                85                  90                  95

Lys Ala Tyr Arg Thr Pro Gln Asn Thr Ile Thr Met Phe Arg Pro Asp
                100                 105                 110

Lys Asn Met Ala Arg Met Asn Lys Ser Ala Ala Arg Ile Cys Leu Pro
            115                 120                 125

Thr Phe Glu Ser Glu Glu Leu Ile Lys Leu Thr Gly Lys Leu Ile Glu
        130                 135                 140

Gln Asp Lys His Leu Val Pro Gln Gly Asn Gly Tyr Ser Leu Tyr Ile
145                 150                 155                 160

Arg Pro Thr Met Ile Gly Thr Ser Lys Gly Leu Gly Val Gly Thr Pro
                165                 170                 175

Ser Glu Ala Leu Leu Tyr Val Ile Thr Ser Pro Val Gly Pro Tyr Tyr
                180                 185                 190

Lys Thr Gly Phe Lys Ala Val Arg Leu Glu Ala Thr Asp Tyr Ala Thr
            195                 200                 205
```

```
Arg Ala Trp Pro Gly Gly Val Gly Asp Lys Lys Leu Gly Ala Asn Tyr
    210                 215                 220

Ala Pro Cys Ile Leu Pro Gln Leu Gln Ala Ala Lys Arg Gly Tyr Gln
225                 230                 235                 240

Gln Asn Leu Trp Leu Phe Gly Pro Glu Lys Asn Ile Thr Glu Val Gly
                245                 250                 255

Thr Met Asn Val Phe Phe Val Phe Leu Asn Lys Val Thr Gly Lys Lys
            260                 265                 270

Glu Leu Val Thr Ala Pro Leu Asp Gly Thr Ile Leu Glu Gly Val Thr
        275                 280                 285

Arg Asp Ser Val Leu Thr Leu Ala Arg Asp Lys Leu Asp Pro Gln Glu
290                 295                 300

Trp Asp Ile Asn Glu Arg Tyr Tyr Thr Ile Thr Glu Val Ala Thr Arg
305                 310                 315                 320

Ala Lys Gln Gly Glu Leu Leu Glu Ala Phe Gly Ser Gly Thr Ala Ala
                325                 330                 335

Val Val Ser Pro Ile Lys Glu Ile Gly Trp Asn Asn Glu Asp Ile His
            340                 345                 350

Val Pro Leu Leu Pro Gly Glu Gln Cys Gly Ala Leu Thr Lys Gln Val
        355                 360                 365

Ala Gln Trp Ile Ala Asp Ile Gln Tyr Gly Arg Val Asn Tyr Gly Asn
370                 375                 380

Trp Ser Lys Thr Val Ala Asp Leu Asn
385                 390
```

<210> SEQ ID NO 9
<211> LENGTH: 1131
<212> TYPE: DNA
<213> ORGANISM: Saccharomyces cerevisiae
<220> FEATURE:
<221> NAME/KEY: CDS
<222> LOCATION: (1)..(1131)
<223> OTHER INFORMATION: GenBank Accession No. NM_001181806

<400> SEQUENCE: 9

```
atg acc ttg gca ccc cta gac gcc tcc aaa gtt aag ata act acc aca      48
Met Thr Leu Ala Pro Leu Asp Ala Ser Lys Val Lys Ile Thr Thr Thr
1               5                   10                  15 caa cat gca tct aag cca aaa ccg aac agt gag tta gtg ttt ggc aag      96
Gln His Ala Ser Lys Pro Lys Pro Asn Ser Glu Leu Val Phe Gly Lys
                20                  25                  30 agc ttc acg gac cac atg tta act gcg gaa tgg aca gct gaa aaa ggg     144
Ser Phe Thr Asp His Met Leu Thr Ala Glu Trp Thr Ala Glu Lys Gly
            35                  40                  45 tgg ggt acc cca gag att aaa cct tat caa aat ctg tct tta gac cct     192
Trp Gly Thr Pro Glu Ile Lys Pro Tyr Gln Asn Leu Ser Leu Asp Pro
        50                  55                  60 tcc gcg gtg gtt ttc cat tat gct ttt gag cta ttc gaa ggg atg aag     240
Ser Ala Val Val Phe His Tyr Ala Phe Glu Leu Phe Glu Gly Met Lys
65                  70                  75                  80 gct tac aga acg gtg gac aac aaa att aca atg ttt cgt cca gat atg     288
Ala Tyr Arg Thr Val Asp Asn Lys Ile Thr Met Phe Arg Pro Asp Met
                85                  90                  95 aat atg aag cgc atg aat aag tct gct cag aga atc tgt ttg cca acg     336
Asn Met Lys Arg Met Asn Lys Ser Ala Gln Arg Ile Cys Leu Pro Thr
            100                 105                 110 ttc gac cca gaa gag ttg att acc cta att ggg aaa ctg atc cag caa     384
Phe Asp Pro Glu Glu Leu Ile Thr Leu Ile Gly Lys Leu Ile Gln Gln
        115                 120                 125
```

| | | | | | | | | | | | | | | |
|---|---|---|---|---|---|---|---|---|---|---|---|---|---|---|
| gat | aag | tgc | tta | gtt | cct | gaa | gga | aaa | ggt | tac | tct | tta | tat | atc | agg | 432 |
| Asp | Lys | Cys | Leu | Val | Pro | Glu | Gly | Lys | Gly | Tyr | Ser | Leu | Tyr | Ile | Arg |
| | 130 | | | | 135 | | | | | 140 | | | | |

```
gat aag tgc tta gtt cct gaa gga aaa ggt tac tct tta tat atc agg      432
Asp Lys Cys Leu Val Pro Glu Gly Lys Gly Tyr Ser Leu Tyr Ile Arg
    130                 135                 140 cct aca tta atc ggc act acg gcc ggt tta ggg gtt tcc acg cct gat      480
Pro Thr Leu Ile Gly Thr Thr Ala Gly Leu Gly Val Ser Thr Pro Asp
145                 150                 155                 160 aga gcc ttg cta tat gtc att tgc tgc cct gtg ggt cct tat tac aaa      528
Arg Ala Leu Leu Tyr Val Ile Cys Cys Pro Val Gly Pro Tyr Tyr Lys
                165                 170                 175 act gga ttt aag gcg gtc aga ctg gaa gcc act gat tat gcc aca aga      576
Thr Gly Phe Lys Ala Val Arg Leu Glu Ala Thr Asp Tyr Ala Thr Arg
            180                 185                 190 gct tgg cca gga ggc tgt ggt gac aag aaa cta ggt gca aac tac gcc      624
Ala Trp Pro Gly Gly Cys Gly Asp Lys Lys Leu Gly Ala Asn Tyr Ala
        195                 200                 205 ccc tgc gtc ctg cca caa ttg caa gct gct tca agg ggt tac caa caa      672
Pro Cys Val Leu Pro Gln Leu Gln Ala Ala Ser Arg Gly Tyr Gln Gln
    210                 215                 220 aat tta tgg cta ttt ggt cca aat aac aac att act gaa gtc ggc acc      720
Asn Leu Trp Leu Phe Gly Pro Asn Asn Asn Ile Thr Glu Val Gly Thr
225                 230                 235                 240 atg aat gct ttt ttc gtg ttt aaa gat agt aaa acg ggc aag aag gaa      768
Met Asn Ala Phe Phe Val Phe Lys Asp Ser Lys Thr Gly Lys Lys Glu
                245                 250                 255 cta gtt act gct cca cta gac ggt acc att ttg gaa ggt gtt act agg      816
Leu Val Thr Ala Pro Leu Asp Gly Thr Ile Leu Glu Gly Val Thr Arg
            260                 265                 270 gat tcc att tta aat ctt gct aaa gaa aga ctc gaa cca agt gaa tgg      864
Asp Ser Ile Leu Asn Leu Ala Lys Glu Arg Leu Glu Pro Ser Glu Trp
        275                 280                 285 acc att agt gaa cgc tac ttc act ata ggc gaa gtt act gag aga tcc      912
Thr Ile Ser Glu Arg Tyr Phe Thr Ile Gly Glu Val Thr Glu Arg Ser
    290                 295                 300 aag aac ggt gaa cta ctt gaa gcc ttt ggt tct ggt act gct gcg att      960
Lys Asn Gly Glu Leu Leu Glu Ala Phe Gly Ser Gly Thr Ala Ala Ile
305                 310                 315                 320 gtt tct ccc att aag gaa atc ggc tgg aaa ggc gaa caa att aat att     1008
Val Ser Pro Ile Lys Glu Ile Gly Trp Lys Gly Glu Gln Ile Asn Ile
                325                 330                 335 ccg ttg ttg ccc ggc gaa caa acc ggt cca ttg gcc aaa gaa gtt gca     1056
Pro Leu Leu Pro Gly Glu Gln Thr Gly Pro Leu Ala Lys Glu Val Ala
            340                 345                 350 caa tgg att aat gga atc caa tat ggc gag act gag cat ggc aat tgg     1104
Gln Trp Ile Asn Gly Ile Gln Tyr Gly Glu Thr Glu His Gly Asn Trp
        355                 360                 365 tca agg gtt gtt act gat ttg aac tga                                 1131
Ser Arg Val Val Thr Asp Leu Asn
    370                 375

<210> SEQ ID NO 10
<211> LENGTH: 376
<212> TYPE: PRT
<213> ORGANISM: Saccharomyces cerevisiae

<400> SEQUENCE: 10

Met Thr Leu Ala Pro Leu Asp Ala Ser Lys Val Lys Ile Thr Thr Thr
1               5                   10                  15

Gln His Ala Ser Lys Pro Lys Pro Asn Ser Glu Leu Val Phe Gly Lys
            20                  25                  30
```

Ser Phe Thr Asp His Met Leu Thr Ala Glu Trp Thr Ala Glu Lys Gly
                 35                  40                  45

Trp Gly Thr Pro Glu Ile Lys Pro Tyr Gln Asn Leu Ser Leu Asp Pro
     50                  55                  60

Ser Ala Val Val Phe His Tyr Ala Phe Glu Leu Phe Glu Gly Met Lys
 65                  70                  75                  80

Ala Tyr Arg Thr Val Asp Asn Lys Ile Thr Met Phe Arg Pro Asp Met
                 85                  90                  95

Asn Met Lys Arg Met Asn Lys Ser Ala Gln Arg Ile Cys Leu Pro Thr
                100                 105                 110

Phe Asp Pro Glu Glu Leu Ile Thr Leu Ile Gly Lys Leu Ile Gln Gln
            115                 120                 125

Asp Lys Cys Leu Val Pro Glu Gly Lys Gly Tyr Ser Leu Tyr Ile Arg
        130                 135                 140

Pro Thr Leu Ile Gly Thr Thr Ala Gly Leu Gly Val Ser Thr Pro Asp
145                 150                 155                 160

Arg Ala Leu Leu Tyr Val Ile Cys Cys Pro Val Gly Pro Tyr Tyr Lys
                165                 170                 175

Thr Gly Phe Lys Ala Val Arg Leu Glu Ala Thr Asp Tyr Ala Thr Arg
            180                 185                 190

Ala Trp Pro Gly Gly Cys Gly Asp Lys Lys Leu Gly Ala Asn Tyr Ala
        195                 200                 205

Pro Cys Val Leu Pro Gln Leu Gln Ala Ala Ser Arg Gly Tyr Gln Gln
    210                 215                 220

Asn Leu Trp Leu Phe Gly Pro Asn Asn Asn Ile Thr Glu Val Gly Thr
225                 230                 235                 240

Met Asn Ala Phe Phe Val Phe Lys Asp Ser Lys Thr Gly Lys Lys Glu
                245                 250                 255

Leu Val Thr Ala Pro Leu Asp Gly Thr Ile Leu Glu Gly Val Thr Arg
            260                 265                 270

Asp Ser Ile Leu Asn Leu Ala Lys Glu Arg Leu Glu Pro Ser Glu Trp
        275                 280                 285

Thr Ile Ser Glu Arg Tyr Phe Thr Ile Gly Glu Val Thr Glu Arg Ser
    290                 295                 300

Lys Asn Gly Glu Leu Leu Glu Ala Phe Gly Ser Gly Thr Ala Ala Ile
305                 310                 315                 320

Val Ser Pro Ile Lys Glu Ile Gly Trp Lys Gly Glu Gln Ile Asn Ile
                325                 330                 335

Pro Leu Leu Pro Gly Glu Gln Thr Gly Pro Leu Ala Lys Glu Val Ala
            340                 345                 350

Gln Trp Ile Asn Gly Ile Gln Tyr Gly Glu Thr Glu His Gly Asn Trp
        355                 360                 365

Ser Arg Val Val Thr Asp Leu Asn
    370                 375

<210> SEQ ID NO 11
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)
<223> OTHER INFORMATION: GenBank Accession No. NM_001181931

<400> SEQUENCE: 11 atg tct gaa att act ttg ggt aaa tat ttg ttc gaa aga tta aag caa         48

```
Met Ser Glu Ile Thr Leu Gly Lys Tyr Leu Phe Glu Arg Leu Lys Gln
1               5                   10                  15 gtc aac gtt aac acc gtt ttc ggt ttg cca ggt gac ttc aac ttg tcc         96
Val Asn Val Asn Thr Val Phe Gly Leu Pro Gly Asp Phe Asn Leu Ser
                20                  25                  30 ttg ttg gac aag atc tac gaa gtt gaa ggt atg aga tgg gct ggt aac         144
Leu Leu Asp Lys Ile Tyr Glu Val Glu Gly Met Arg Trp Ala Gly Asn
            35                  40                  45 gcc aac gaa ttg aac gct gct tac gcc gct gat ggt tac gct cgt atc         192
Ala Asn Glu Leu Asn Ala Ala Tyr Ala Ala Asp Gly Tyr Ala Arg Ile
        50                  55                  60 aag ggt atg tct tgt atc atc acc acc ttc ggt gtc ggt gaa ttg tct         240
Lys Gly Met Ser Cys Ile Ile Thr Thr Phe Gly Val Gly Glu Leu Ser
65                  70                  75                  80 gct ttg aac ggt att gcc ggt tct tac gct gaa cac gtc ggt gtt ttg         288
Ala Leu Asn Gly Ile Ala Gly Ser Tyr Ala Glu His Val Gly Val Leu
                85                  90                  95 cac gtt gtt ggt gtc cca tcc atc tct gct caa gct aag caa ttg ttg         336
His Val Val Gly Val Pro Ser Ile Ser Ala Gln Ala Lys Gln Leu Leu
                100                 105                 110 ttg cac cac acc ttg ggt aac ggt gac ttc act gtt ttc cac aga atg         384
Leu His His Thr Leu Gly Asn Gly Asp Phe Thr Val Phe His Arg Met
            115                 120                 125 tct gcc aac att tct gaa acc act gct atg atc act gac att gct acc         432
Ser Ala Asn Ile Ser Glu Thr Thr Ala Met Ile Thr Asp Ile Ala Thr
        130                 135                 140 gcc cca gct gaa att gac aga tgt atc aga acc act tac gtc acc caa         480
Ala Pro Ala Glu Ile Asp Arg Cys Ile Arg Thr Thr Tyr Val Thr Gln
145                 150                 155                 160 aga cca gtc tac tta ggt ttg cca gct aac ttg gtc gac ttg aac gtc         528
Arg Pro Val Tyr Leu Gly Leu Pro Ala Asn Leu Val Asp Leu Asn Val
                165                 170                 175 cca gct aag ttg ttg caa act cca att gac atg tct ttg aag cca aac         576
Pro Ala Lys Leu Leu Gln Thr Pro Ile Asp Met Ser Leu Lys Pro Asn
            180                 185                 190 gat gct gaa tcc gaa aag gaa gtc att gac acc atc ttg gct ttg gtc         624
Asp Ala Glu Ser Glu Lys Glu Val Ile Asp Thr Ile Leu Ala Leu Val
        195                 200                 205 aag gat gct aag aac cca gtt atc ttg gct gat gct tgt tgt tcc aga         672
Lys Asp Ala Lys Asn Pro Val Ile Leu Ala Asp Ala Cys Cys Ser Arg
210                 215                 220 cac gac gtc aag gct gaa act aag aag ttg att gac ttg act caa ttc         720
His Asp Val Lys Ala Glu Thr Lys Lys Leu Ile Asp Leu Thr Gln Phe
225                 230                 235                 240 cca gct ttc gtc acc cca atg ggt aag ggt tcc att gac gaa caa cac         768
Pro Ala Phe Val Thr Pro Met Gly Lys Gly Ser Ile Asp Glu Gln His
                245                 250                 255 cca aga tac ggt ggt gtt tac gtc ggt acc ttg tcc aag cca gaa gtt         816
Pro Arg Tyr Gly Gly Val Tyr Val Gly Thr Leu Ser Lys Pro Glu Val
            260                 265                 270 aag gaa gcc gtt gaa tct gct gac ttg att ttg tct gtc ggt gct ttg         864
Lys Glu Ala Val Glu Ser Ala Asp Leu Ile Leu Ser Val Gly Ala Leu
        275                 280                 285 ttg tct gat ttc aac acc ggt tct ttc tct tac tct tac aag acc aag         912
Leu Ser Asp Phe Asn Thr Gly Ser Phe Ser Tyr Ser Tyr Lys Thr Lys
        290                 295                 300 aac att gtc gaa ttc cac tcc gac cac atg aag atc aga aac gcc act         960
Asn Ile Val Glu Phe His Ser Asp His Met Lys Ile Arg Asn Ala Thr
305                 310                 315                 320
```

```
ttc cca ggt gtc caa atg aaa ttc gtt ttg caa aag ttg ttg acc act        1008
Phe Pro Gly Val Gln Met Lys Phe Val Leu Gln Lys Leu Leu Thr Thr
                325                 330                 335 att gct gac gcc gct aag ggt tac aag cca gtt gct gtc cca gct aga        1056
Ile Ala Asp Ala Ala Lys Gly Tyr Lys Pro Val Ala Val Pro Ala Arg
            340                 345                 350 act cca gct aac gct gct gtc cca gct tct acc cca ttg aag caa gaa        1104
Thr Pro Ala Asn Ala Ala Val Pro Ala Ser Thr Pro Leu Lys Gln Glu
        355                 360                 365 tgg atg tgg aac caa ttg ggt aac ttc ttg caa gaa ggt gat gtt gtc        1152
Trp Met Trp Asn Gln Leu Gly Asn Phe Leu Gln Glu Gly Asp Val Val
    370                 375                 380 att gct gaa acc ggt acc tcc gct ttc ggt atc aac caa acc act ttc        1200
Ile Ala Glu Thr Gly Thr Ser Ala Phe Gly Ile Asn Gln Thr Thr Phe
385                 390                 395                 400 cca aac aac acc tac ggt atc tct caa gtc tta tgg ggt tcc att ggt        1248
Pro Asn Asn Thr Tyr Gly Ile Ser Gln Val Leu Trp Gly Ser Ile Gly
                405                 410                 415 ttc acc act ggt gct acc ttg ggt gct gct ttc gct gct gaa gaa att        1296
Phe Thr Thr Gly Ala Thr Leu Gly Ala Ala Phe Ala Ala Glu Glu Ile
            420                 425                 430 gat cca aag aag aga gtt atc tta ttc att ggt gac ggt tct ttg caa        1344
Asp Pro Lys Lys Arg Val Ile Leu Phe Ile Gly Asp Gly Ser Leu Gln
        435                 440                 445 ttg act gtt caa gaa atc tcc acc atg atc aga tgg ggc ttg aag cca        1392
Leu Thr Val Gln Glu Ile Ser Thr Met Ile Arg Trp Gly Leu Lys Pro
    450                 455                 460 tac ttg ttc gtc ttg aac aac gat ggt tac acc att gaa aag ttg att        1440
Tyr Leu Phe Val Leu Asn Asn Asp Gly Tyr Thr Ile Glu Lys Leu Ile
465                 470                 475                 480 cac ggt cca aag gct caa tac aac gaa att caa ggt tgg gac cac cta        1488
His Gly Pro Lys Ala Gln Tyr Asn Glu Ile Gln Gly Trp Asp His Leu
                485                 490                 495 tcc ttg ttg cca act ttc ggt gct aag gac tat gaa acc cac aga gtc        1536
Ser Leu Leu Pro Thr Phe Gly Ala Lys Asp Tyr Glu Thr His Arg Val
            500                 505                 510 gct acc acc ggt gaa tgg gac aag ttg acc caa gac aag tct ttc aac        1584
Ala Thr Thr Gly Glu Trp Asp Lys Leu Thr Gln Asp Lys Ser Phe Asn
        515                 520                 525 gac aac tct aag atc aga atg att gaa atc atg ttg cca gtc ttc gat        1632
Asp Asn Ser Lys Ile Arg Met Ile Glu Ile Met Leu Pro Val Phe Asp
    530                 535                 540 gct cca caa aac ttg gtt gaa caa gct aag ttg act gct gct acc aac        1680
Ala Pro Gln Asn Leu Val Glu Gln Ala Lys Leu Thr Ala Ala Thr Asn
545                 550                 555                 560 gct aag caa taa                                                         1692
Ala Lys Gln <210> SEQ ID NO 12
<211> LENGTH: 563
<212> TYPE: PRT
<213> ORGANISM: Saccharomyces cerevisiae

<400> SEQUENCE: 12

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
                20                  25                  30

Leu Leu Asp Lys Ile Tyr Glu Val Glu Gly Met Arg Trp Ala Gly Asn
        35                  40                  45
```

```
Ala Asn Glu Leu Asn Ala Ala Tyr Ala Ala Asp Gly Tyr Ala Arg Ile
     50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                     85                  90                  95

His Val Gly Val Pro Ser Ile Ser Ala Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ala Met Ile Thr Asp Ile Ala Thr
            130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
                180                 185                 190

Asp Ala Glu Ser Glu Lys Glu Val Ile Asp Thr Ile Leu Ala Leu Val
            195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
                260                 265                 270

Lys Glu Ala Val Glu Ser Ala Asp Leu Ile Leu Ser Val Gly Ala Leu
            275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
        370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
            450                 455                 460
```

```
Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
            485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
            515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 13
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)
<223> OTHER INFORMATION: GenBank Accession No. NM_001182021

<400> SEQUENCE: 13 atg tct gaa ata acc tta ggt aaa tat tta ttt gaa aga ttg agc caa      48
Met Ser Glu Ile Thr Leu Gly Lys Tyr Leu Phe Glu Arg Leu Ser Gln
1               5                   10                  15 gtc aac tgt aac acc gtc ttc ggt ttg cca ggt gac ttt aac ttg tct      96
Val Asn Cys Asn Thr Val Phe Gly Leu Pro Gly Asp Phe Asn Leu Ser
                20                  25                  30 ctt ttg gat aag ctt tat gaa gtc aaa ggt atg aga tgg gct ggt aac     144
Leu Leu Asp Lys Leu Tyr Glu Val Lys Gly Met Arg Trp Ala Gly Asn
            35                  40                  45 gct aac gaa ttg aac gct gcc tat gct gct gat ggt tac gct cgt atc     192
Ala Asn Glu Leu Asn Ala Ala Tyr Ala Ala Asp Gly Tyr Ala Arg Ile
        50                  55                  60 aag ggt atg tcc tgt att att acc acc ttc ggt gtt ggt gaa ttg tct     240
Lys Gly Met Ser Cys Ile Ile Thr Thr Phe Gly Val Gly Glu Leu Ser
65                  70                  75                  80 gct ttg aat ggt att gcc ggt tct tac gct gaa cat gtc ggt gtt ttg     288
Ala Leu Asn Gly Ile Ala Gly Ser Tyr Ala Glu His Val Gly Val Leu
                85                  90                  95 cac gtt gtt ggt gtt cca tcc atc tct tct caa gct aag caa ttg ttg     336
His Val Val Gly Val Pro Ser Ile Ser Ser Gln Ala Lys Gln Leu Leu
                100                 105                 110 ttg cat cat acc ttg ggt aac ggt gac ttc act gtt ttc cac aga atg     384
Leu His His Thr Leu Gly Asn Gly Asp Phe Thr Val Phe His Arg Met
            115                 120                 125 tct gcc aac att tct gaa acc act gcc atg atc act gat att gct aac     432
Ser Ala Asn Ile Ser Glu Thr Thr Ala Met Ile Thr Asp Ile Ala Asn
        130                 135                 140 gct cca gct gaa att gac aga tgt atc aga acc acc tac act acc caa     480
Ala Pro Ala Glu Ile Asp Arg Cys Ile Arg Thr Thr Tyr Thr Thr Gln
145                 150                 155                 160 aga cca gtc tac ttg ggt ttg cca gct aac ttg gtt gac ttg aac gtc     528
Arg Pro Val Tyr Leu Gly Leu Pro Ala Asn Leu Val Asp Leu Asn Val
                165                 170                 175 cca gcc aag tta ttg gaa act cca att gac ttg tct ttg aag cca aac     576
Pro Ala Lys Leu Leu Glu Thr Pro Ile Asp Leu Ser Leu Lys Pro Asn
                180                 185                 190
```

```
gac gct gaa gct gaa gct gaa gtt gtt aga act gtt gtt gaa ttg atc     624
Asp Ala Glu Ala Glu Ala Glu Val Val Arg Thr Val Val Glu Leu Ile
        195                 200                 205 aag gat gct aag aac cca gtt atc ttg gct gat gct tgt gct tct aga     672
Lys Asp Ala Lys Asn Pro Val Ile Leu Ala Asp Ala Cys Ala Ser Arg
    210                 215                 220 cat gat gtc aag gct gaa act aag aag ttg atg gac ttg act caa ttc     720
His Asp Val Lys Ala Glu Thr Lys Lys Leu Met Asp Leu Thr Gln Phe
225                 230                 235                 240 cca gtt tac gtc acc cca atg ggt aag ggt gct att gac gaa caa cac     768
Pro Val Tyr Val Thr Pro Met Gly Lys Gly Ala Ile Asp Glu Gln His
                245                 250                 255 cca aga tac ggt ggt gtt tac gtt ggt acc ttg tct aga cca gaa gtt     816
Pro Arg Tyr Gly Gly Val Tyr Val Gly Thr Leu Ser Arg Pro Glu Val
            260                 265                 270 aag aag gct gta gaa tct gct gat ttg ata ttg tct atc ggt gct ttg     864
Lys Lys Ala Val Glu Ser Ala Asp Leu Ile Leu Ser Ile Gly Ala Leu
        275                 280                 285 ttg tct gat ttc aat acc ggt tct ttc tct tac tcc tac aag acc aaa     912
Leu Ser Asp Phe Asn Thr Gly Ser Phe Ser Tyr Ser Tyr Lys Thr Lys
    290                 295                 300 aat atc gtt gaa ttc cac tct gac cac atc aag atc aga aac gcc acc     960
Asn Ile Val Glu Phe His Ser Asp His Ile Lys Ile Arg Asn Ala Thr
305                 310                 315                 320 ttc cca ggt gtt caa atg aaa ttt gcc ttg caa aaa ttg ttg gat gct    1008
Phe Pro Gly Val Gln Met Lys Phe Ala Leu Gln Lys Leu Leu Asp Ala
                325                 330                 335 att cca gaa gtc gtc aag gac tac aaa cct gtt gct gtc cca gct aga    1056
Ile Pro Glu Val Val Lys Asp Tyr Lys Pro Val Ala Val Pro Ala Arg
            340                 345                 350 gtt cca att acc aag tct act cca gct aac act cca atg aag caa gaa    1104
Val Pro Ile Thr Lys Ser Thr Pro Ala Asn Thr Pro Met Lys Gln Glu
        355                 360                 365 tgg atg tgg aac cat ttg ggt aac ttc ttg aga gaa ggt gat att gtt    1152
Trp Met Trp Asn His Leu Gly Asn Phe Leu Arg Glu Gly Asp Ile Val
370                 375                 380 att gct gaa acc ggt act tcc gcc ttc ggt att aac caa act act ttc    1200
Ile Ala Glu Thr Gly Thr Ser Ala Phe Gly Ile Asn Gln Thr Thr Phe
385                 390                 395                 400 cca aca gat gta tac gct atc gtc caa gtc ttg tgg ggt tcc att ggt    1248
Pro Thr Asp Val Tyr Ala Ile Val Gln Val Leu Trp Gly Ser Ile Gly
                405                 410                 415 ttc aca gtc ggc gct cta ttg ggt gct act atg gcc gct gaa gaa ctt    1296
Phe Thr Val Gly Ala Leu Leu Gly Ala Thr Met Ala Ala Glu Glu Leu
            420                 425                 430 gat cca aag aag aga gtt att tta ttc att ggt gac ggt tct cta caa    1344
Asp Pro Lys Lys Arg Val Ile Leu Phe Ile Gly Asp Gly Ser Leu Gln
        435                 440                 445 ttg act gtt caa gaa atc tct acc atg att aga tgg ggt ttg aag cca    1392
Leu Thr Val Gln Glu Ile Ser Thr Met Ile Arg Trp Gly Leu Lys Pro
    450                 455                 460 tac att ttt gtc ttg aat aac aac ggt tac acc att gaa aaa ttg att    1440
Tyr Ile Phe Val Leu Asn Asn Asn Gly Tyr Thr Ile Glu Lys Leu Ile
465                 470                 475                 480 cac ggt cct cat gcc gaa tat aat gaa att caa ggt tgg gac cac ttg    1488
His Gly Pro His Ala Glu Tyr Asn Glu Ile Gln Gly Trp Asp His Leu
                485                 490                 495 gcc tta ttg cca act ttt ggt gct aga aac tac gaa acc cac aga gtt    1536
Ala Leu Leu Pro Thr Phe Gly Ala Arg Asn Tyr Glu Thr His Arg Val
```

-continued

```
                      500                     505                     510
gct acc act ggt gaa tgg gaa aag ttg act caa gac aag gac ttc caa       1584
Ala Thr Thr Gly Glu Trp Glu Lys Leu Thr Gln Asp Lys Asp Phe Gln
            515                     520                     525 gac aac tct aag att aga atg att gaa gtt atg ttg cca gtc ttt gat       1632
Asp Asn Ser Lys Ile Arg Met Ile Glu Val Met Leu Pro Val Phe Asp
        530                     535                     540 gct cca caa aac ttg gtt aaa caa gct caa ttg act gcc gct act aac       1680
Ala Pro Gln Asn Leu Val Lys Gln Ala Gln Leu Thr Ala Ala Thr Asn
545                     550                     555                 560 gct aaa caa taa                                                       1692
Ala Lys Gln
```

<210> SEQ ID NO 14
<211> LENGTH: 563
<212> TYPE: PRT
<213> ORGANISM: Saccharomyces cerevisiae

<400> SEQUENCE: 14

```
Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
            20                  25                  30

Leu Leu Asp Lys Leu Tyr Glu Val Lys Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
    130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
            180                 185                 190

Asp Ala Glu Ala Glu Ala Val Val Arg Thr Val Val Glu Leu Ile
        195                 200                 205

Lys Asp Ala Lys Asn Pro Val Ile Leu Ala Asp Ala Cys Ala Ser Arg
    210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
        275                 280                 285
```

```
Leu Ser Asp Phe Asn Thr Gly Ser Phe Ser Tyr Ser Tyr Lys Thr Lys
    290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
            340                 345                 350

Val Pro Ile Thr Lys Ser Thr Pro Ala Asn Thr Pro Met Lys Gln Glu
        355                 360                 365

Trp Met Trp Asn His Leu Gly Asn Phe Leu Arg Glu Gly Asp Ile Val
370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
                405                 410                 415

Phe Thr Val Gly Ala Leu Leu Gly Ala Thr Met Ala Ala Glu Glu Leu
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Ile Phe Val Leu Asn Asn Asn Gly Tyr Thr Ile Glu Lys Leu Ile
465                 470                 475                 480

His Gly Pro His Ala Glu Tyr Asn Glu Ile Gln Gly Trp Asp His Leu
                485                 490                 495

Ala Leu Leu Pro Thr Phe Gly Ala Arg Asn Tyr Glu Thr His Arg Val
            500                 505                 510

Ala Thr Thr Gly Glu Trp Glu Lys Leu Thr Gln Asp Lys Asp Phe Gln
        515                 520                 525

Asp Asn Ser Lys Ile Arg Met Ile Glu Val Met Leu Pro Val Phe Asp
    530                 535                 540

Ala Pro Gln Asn Leu Val Lys Gln Ala Gln Leu Thr Ala Ala Thr Asn
545                 550                 555                 560

Ala Lys Gln

<210> SEQ ID NO 15
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)
<223> OTHER INFORMATION: GenBank Accession No. NM_001181216

<400> SEQUENCE: 15 atg tct gaa att act ctt gga aaa tac tta ttt gaa aga ttg aag caa      48
Met Ser Glu Ile Thr Leu Gly Lys Tyr Leu Phe Glu Arg Leu Lys Gln
1               5                   10                  15 gtt aat gtt aac acc att ttt ggg cta cca ggc gac ttc aac ttg tcc      96
Val Asn Val Asn Thr Ile Phe Gly Leu Pro Gly Asp Phe Asn Leu Ser
            20                  25                  30 cta ttg gac aag att tac gag gta gat gga ttg aga tgg gct ggt aat     144
Leu Leu Asp Lys Ile Tyr Glu Val Asp Gly Leu Arg Trp Ala Gly Asn
        35                  40                  45 gca aat gag ctg aac gcc gcc tat gcc gcc gat ggt tac gca cgc atc     192
Ala Asn Glu Leu Asn Ala Ala Tyr Ala Ala Asp Gly Tyr Ala Arg Ile
```

```
            50                  55                  60
aag ggt tta tct gtg ctg gta act act ttt ggc gta ggt gaa tta tcc    240
Lys Gly Leu Ser Val Leu Val Thr Thr Phe Gly Val Gly Glu Leu Ser
 65                  70                  75                  80 gcc ttg aat ggt att gca gga tcg tat gca gaa cac gtc ggt gta ctg    288
Ala Leu Asn Gly Ile Ala Gly Ser Tyr Ala Glu His Val Gly Val Leu
                 85                  90                  95 cat gtt gtt ggt gtc ccc tct atc tcc gct cag gct aag caa ttg ttg    336
His Val Val Gly Val Pro Ser Ile Ser Ala Gln Ala Lys Gln Leu Leu
            100                 105                 110 ttg cat cat acc ttg ggt aac ggt gat ttt acc gtt ttt cac aga atg    384
Leu His His Thr Leu Gly Asn Gly Asp Phe Thr Val Phe His Arg Met
        115                 120                 125 tcc gcc aat atc tca gaa act aca tca atg att aca gac att gct aca    432
Ser Ala Asn Ile Ser Glu Thr Thr Ser Met Ile Thr Asp Ile Ala Thr
    130                 135                 140 gcc cct tca gaa atc gat agg ttg atc agg aca aca ttt ata aca caa    480
Ala Pro Ser Glu Ile Asp Arg Leu Ile Arg Thr Thr Phe Ile Thr Gln
145                 150                 155                 160 agg cct agc tac ttg ggg ttg cca gcg aat ttg gta gat cta aag gtt    528
Arg Pro Ser Tyr Leu Gly Leu Pro Ala Asn Leu Val Asp Leu Lys Val
                165                 170                 175 cct ggt tct ctt ttg gaa aaa ccg att gat cta tca tta aaa cct aac    576
Pro Gly Ser Leu Leu Glu Lys Pro Ile Asp Leu Ser Leu Lys Pro Asn
            180                 185                 190 gat ccc gaa gct gaa aag gaa gtt att gat acc gta cta gaa ttg atc    624
Asp Pro Glu Ala Glu Lys Glu Val Ile Asp Thr Val Leu Glu Leu Ile
        195                 200                 205 cag aat tcg aaa aac cct gtt ata cta tcg gat gcc tgt gct tct agg    672
Gln Asn Ser Lys Asn Pro Val Ile Leu Ser Asp Ala Cys Ala Ser Arg
    210                 215                 220 cac aac gtt aaa aaa gaa acc cag aag tta att gat ttg acg caa ttc    720
His Asn Val Lys Lys Glu Thr Gln Lys Leu Ile Asp Leu Thr Gln Phe
225                 230                 235                 240 cca gct ttt gtg aca cct cta ggt aaa ggg tca ata gat gaa cag cat    768
Pro Ala Phe Val Thr Pro Leu Gly Lys Gly Ser Ile Asp Glu Gln His
                245                 250                 255 ccc aga tat ggc ggt gtt tat gtg gga acg ctg tcc aaa caa gac gtg    816
Pro Arg Tyr Gly Gly Val Tyr Val Gly Thr Leu Ser Lys Gln Asp Val
            260                 265                 270 aaa cag gcc gtt gag tcg gct gat ttg atc ctt tcg gtc ggt gct ttg    864
Lys Gln Ala Val Glu Ser Ala Asp Leu Ile Leu Ser Val Gly Ala Leu
        275                 280                 285 ctc tct gat ttt aac aca ggt tcg ttt tcc tac tcc tac aag act aaa    912
Leu Ser Asp Phe Asn Thr Gly Ser Phe Ser Tyr Ser Tyr Lys Thr Lys
    290                 295                 300 aat gta gtg gag ttt cat tcc gat tac gta aag gtg aag aac gct acg    960
Asn Val Val Glu Phe His Ser Asp Tyr Val Lys Val Lys Asn Ala Thr
305                 310                 315                 320 ttc ctc ggt gta caa atg aaa ttt gca cta caa aac tta ctg aag gtt   1008
Phe Leu Gly Val Gln Met Lys Phe Ala Leu Gln Asn Leu Leu Lys Val
                325                 330                 335 att ccc gat gtt gtt aag ggc tac aag agc gtt ccc gta cca acc aaa   1056
Ile Pro Asp Val Val Lys Gly Tyr Lys Ser Val Pro Val Pro Thr Lys
            340                 345                 350 act ccc gca aac aaa ggt gta cct gct agc acg ccc ttg aaa caa gag   1104
Thr Pro Ala Asn Lys Gly Val Pro Ala Ser Thr Pro Leu Lys Gln Glu
        355                 360                 365 tgg ttg tgg aac gaa ttg tcc aaa ttc ttg caa gaa ggt gat gtt atc   1152
```

```
Trp Leu Trp Asn Glu Leu Ser Lys Phe Leu Gln Glu Gly Asp Val Ile
    370                 375                 380 att tcc gag acc ggc acg tct gcc ttc ggt atc aat caa act atc ttt    1200
Ile Ser Glu Thr Gly Thr Ser Ala Phe Gly Ile Asn Gln Thr Ile Phe
385                 390                 395                 400 cct aag gac gcc tac ggt atc tcg cag gtg ttg tgg ggg tcc atc ggt    1248
Pro Lys Asp Ala Tyr Gly Ile Ser Gln Val Leu Trp Gly Ser Ile Gly
                405                 410                 415 ttt aca aca gga gca act tta ggt gct gcc ttt gcc gct gag gag att    1296
Phe Thr Thr Gly Ala Thr Leu Gly Ala Ala Phe Ala Ala Glu Glu Ile
            420                 425                 430 gac ccc aac aag aga gtc atc tta ttc ata ggt gac ggg tct ttg cag    1344
Asp Pro Asn Lys Arg Val Ile Leu Phe Ile Gly Asp Gly Ser Leu Gln
        435                 440                 445 tta acc gtc caa gaa atc tcc acc atg atc aga tgg ggg tta aag ccg    1392
Leu Thr Val Gln Glu Ile Ser Thr Met Ile Arg Trp Gly Leu Lys Pro
    450                 455                 460 tat ctt ttt gtc ctt aac aac gac ggc tac act atc gaa aag ctg att    1440
Tyr Leu Phe Val Leu Asn Asn Asp Gly Tyr Thr Ile Glu Lys Leu Ile
465                 470                 475                 480 cat ggg cct cac gca gag tac aac gaa atc cag acc tgg gat cac ctc    1488
His Gly Pro His Ala Glu Tyr Asn Glu Ile Gln Thr Trp Asp His Leu
                485                 490                 495 gcc ctg ttg ccc gca ttt ggt gcg aaa aag tac gaa aat cac aag atc    1536
Ala Leu Leu Pro Ala Phe Gly Ala Lys Lys Tyr Glu Asn His Lys Ile
            500                 505                 510 gcc act acg ggt gag tgg gat gcc tta acc act gat tca gag ttc cag    1584
Ala Thr Thr Gly Glu Trp Asp Ala Leu Thr Thr Asp Ser Glu Phe Gln
        515                 520                 525 aaa aac tcg gtg atc aga cta att gaa ctg aaa ctg ccc gtc ttt gat    1632
Lys Asn Ser Val Ile Arg Leu Ile Glu Leu Lys Leu Pro Val Phe Asp
    530                 535                 540 gct ccg gaa agt ttg atc aaa caa gcg caa ttg act gcc gct aca aat    1680
Ala Pro Glu Ser Leu Ile Lys Gln Ala Gln Leu Thr Ala Ala Thr Asn
545                 550                 555                 560 gcc aaa caa taa                                                    1692
Ala Lys Gln <210> SEQ ID NO 16
<211> LENGTH: 563
<212> TYPE: PRT
<213> ORGANISM: Saccharomyces cerevisiae

<400> SEQUENCE: 16

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
                20                  25                  30

Leu Leu Asp Lys Ile Tyr Glu Val Asp Gly Leu Arg Trp Ala Gly Asn
            35                  40                  45

Ala Asn Glu Leu Asn Ala Ala Tyr Ala Ala Asp Gly Tyr Ala Arg Ile
        50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110
```

```
Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile Arg Leu Ile Glu Leu Lys Leu Pro Val Phe Asp
```

```
                530              535              540
           Ala Pro Glu Ser Leu Ile Lys Gln Ala Gln Leu Thr Ala Ala Thr Asn
           545              550              555              560

Ala Lys Gln

<210> SEQ ID NO 17
<211> LENGTH: 3169
<212> TYPE: DNA
<213> ORGANISM: Saccharomyces cerevisiae
<220> FEATURE:
<221> NAME/KEY: CDS
<222> LOCATION: (217)..(1923)
<223> OTHER INFORMATION: GenBank Accession No. D21880

<400> SEQUENCE: 17
gatattgtgt agaaaagagt aaaatataat aaaacgaaaa aaaaaaggtt tgaaagaaca      60
taactactaa aacgcaccgt cgtcattctg aagatgaatt ctagctatac acagagatat    120
gcactgccga agtgtatagc aatatcagat tatcttttcc atcggctcaa ccagctgaac    180
atacatacca tatttggact ctccggagaa tttagc atg ccg ttg ctg gat aaa    234
                                     Met Pro Leu Leu Asp Lys
                                      1               5 cta tac aac att ccg aac tta cga tgg gcc ggt aat tct aat gag tta    282
Leu Tyr Asn Ile Pro Asn Leu Arg Trp Ala Gly Asn Ser Asn Glu Leu
         10                  15                  20 aat gct gcc tac gca gca gat gga tac tca cga cta aaa ggc ttg gga    330
Asn Ala Ala Tyr Ala Ala Asp Gly Tyr Ser Arg Leu Lys Gly Leu Gly
             25                  30                  35 tgt ctc ata aca acc ttt ggt gta ggc gaa tta tcg gca atc aat ggc    378
Cys Leu Ile Thr Thr Phe Gly Val Gly Glu Leu Ser Ala Ile Asn Gly
 40                  45                  50 gtg gcc gga tct tac gct gaa cat gta gga ata ctt cac ata gtg ggt    426
Val Ala Gly Ser Tyr Ala Glu His Val Gly Ile Leu His Ile Val Gly
 55                  60                  65                  70 atg ccg cca aca agt gca caa acg aaa caa cta cta ctg cat cat act    474
Met Pro Pro Thr Ser Ala Gln Thr Lys Gln Leu Leu Leu His His Thr
                 75                  80                  85 ctg ggc aat ggt gat ttc acg gta ttt cat aga ata gcc agt gat gta    522
Leu Gly Asn Gly Asp Phe Thr Val Phe His Arg Ile Ala Ser Asp Val
             90                  95                 100 gca tgc tat aca aca ttg att att gac tct gaa tta tgt gcc gac gaa    570
Ala Cys Tyr Thr Thr Leu Ile Ile Asp Ser Glu Leu Cys Ala Asp Glu
        105                 110                 115 gtc gat aag tgc atc aaa aag gct tgg ata gaa cag agg cca gta tac    618
Val Asp Lys Cys Ile Lys Lys Ala Trp Ile Glu Gln Arg Pro Val Tyr
    120                 125                 130 atg ggc atg cct gtc aac cag gta aat ctc ccg att gaa tca gca agg    666
Met Gly Met Pro Val Asn Gln Val Asn Leu Pro Ile Glu Ser Ala Arg
135                 140                 145                 150 ctt aat aca cct ctg gat tta caa ttg cat aaa aac gac cca gac gta    714
Leu Asn Thr Pro Leu Asp Leu Gln Leu His Lys Asn Asp Pro Asp Val
                155                 160                 165 gag aaa gaa gtt att tct cga ata ttg agt ttt ata tac aaa agc cag    762
Glu Lys Glu Val Ile Ser Arg Ile Leu Ser Phe Ile Tyr Lys Ser Gln
            170                 175                 180 aat ccg gca atc atc gta gat gca tgt act agt cga cag aat tta atc    810
Asn Pro Ala Ile Ile Val Asp Ala Cys Thr Ser Arg Gln Asn Leu Ile
        185                 190                 195 gag gag act aaa gag ctt tgt aat agg ctt aaa ttt cca gtt ttt gtt    858
Glu Glu Thr Lys Glu Leu Cys Asn Arg Leu Lys Phe Pro Val Phe Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 200 |     |     |     |     | 205 |     |     |     |     | 210 |     |     |     |      |
| aca | cct | atg | ggt | aag | ggt | aca | gta | aac | gaa | aca | gac | ccg | caa | ttt | ggg | 906  |
| Thr | Pro | Met | Gly | Lys | Gly | Thr | Val | Asn | Glu | Thr | Asp | Pro | Gln | Phe | Gly |      |
| 215 |     |     |     | 220 |     |     |     |     | 225 |     |     |     |     | 230 |     |      |
| ggc | gta | ttc | acg | ggc | tcg | ata | tca | gcc | cca | gaa | gta | aga | gaa | gta | gtt | 954  |
| Gly | Val | Phe | Thr | Gly | Ser | Ile | Ser | Ala | Pro | Glu | Val | Arg | Glu | Val | Val |      |
|     |     |     |     | 235 |     |     |     |     | 240 |     |     |     |     | 245 |     |      |
| gat | ttt | gcc | gat | ttt | atc | atc | gtc | att | ggt | tgc | atg | ctc | tcc | gaa | ttc | 1002 |
| Asp | Phe | Ala | Asp | Phe | Ile | Ile | Val | Ile | Gly | Cys | Met | Leu | Ser | Glu | Phe |      |
|     |     |     | 250 |     |     |     |     | 255 |     |     |     |     | 260 |     |     |      |
| agc | acg | tca | act | ttc | cac | ttc | caa | tat | aaa | act | aag | aat | tgt | gcg | cta | 1050 |
| Ser | Thr | Ser | Thr | Phe | His | Phe | Gln | Tyr | Lys | Thr | Lys | Asn | Cys | Ala | Leu |      |
|     |     | 265 |     |     |     |     | 270 |     |     |     |     | 275 |     |     |     |      |
| cta | tat | tct | aca | tct | gtg | aaa | ttg | aaa | aat | gcc | aca | tat | cct | gac | ttg | 1098 |
| Leu | Tyr | Ser | Thr | Ser | Val | Lys | Leu | Lys | Asn | Ala | Thr | Tyr | Pro | Asp | Leu |      |
|     | 280 |     |     |     |     | 285 |     |     |     |     | 290 |     |     |     |     |      |
| agc | att | aaa | tta | cta | cta | cag | aaa | ata | tta | gca | aat | ctt | gat | gaa | tct | 1146 |
| Ser | Ile | Lys | Leu | Leu | Leu | Gln | Lys | Ile | Leu | Ala | Asn | Leu | Asp | Glu | Ser |      |
| 295 |     |     |     | 300 |     |     |     |     | 305 |     |     |     |     | 310 |     |      |
| aaa | ctg | tct | tac | caa | cca | agc | gaa | caa | ccc | agt | atg | atg | gtt | cca | aga | 1194 |
| Lys | Leu | Ser | Tyr | Gln | Pro | Ser | Glu | Gln | Pro | Ser | Met | Met | Val | Pro | Arg |      |
|     |     |     |     | 315 |     |     |     |     | 320 |     |     |     |     | 325 |     |      |
| cct | tac | cca | gca | gga | aat | gtc | ctc | ttg | aga | caa | gaa | tgg | gtc | tgg | aat | 1242 |
| Pro | Tyr | Pro | Ala | Gly | Asn | Val | Leu | Leu | Arg | Gln | Glu | Trp | Val | Trp | Asn |      |
|     |     |     | 330 |     |     |     |     | 335 |     |     |     |     | 340 |     |     |      |
| gaa | ata | tcc | cat | tgg | ttc | caa | cca | ggt | gac | ata | atc | ata | aca | gaa | act | 1290 |
| Glu | Ile | Ser | His | Trp | Phe | Gln | Pro | Gly | Asp | Ile | Ile | Ile | Thr | Glu | Thr |      |
|     |     | 345 |     |     |     |     | 350 |     |     |     |     | 355 |     |     |     |      |
| ggt | gct | tct | gca | ttt | gga | gtt | aac | cag | acc | aga | ttt | ccg | gta | aat | aca | 1338 |
| Gly | Ala | Ser | Ala | Phe | Gly | Val | Asn | Gln | Thr | Arg | Phe | Pro | Val | Asn | Thr |      |
|     | 360 |     |     |     |     | 365 |     |     |     |     | 370 |     |     |     |     |      |
| cta | ggt | att | tcg | caa | gct | ctt | tgg | gga | tct | gtc | gga | tat | aca | atg | ggg | 1386 |
| Leu | Gly | Ile | Ser | Gln | Ala | Leu | Trp | Gly | Ser | Val | Gly | Tyr | Thr | Met | Gly |      |
| 375 |     |     |     | 380 |     |     |     |     | 385 |     |     |     |     | 390 |     |      |
| gcg | tgt | ctt | ggg | gca | gaa | ttt | gct | gtt | caa | gag | ata | aac | aag | gat | aaa | 1434 |
| Ala | Cys | Leu | Gly | Ala | Glu | Phe | Ala | Val | Gln | Glu | Ile | Asn | Lys | Asp | Lys |      |
|     |     |     |     | 395 |     |     |     |     | 400 |     |     |     |     | 405 |     |      |
| ttc | ccc | gca | act | aaa | cat | aga | gtt | att | ctg | ttt | atg | ggt | gac | ggt | gct | 1482 |
| Phe | Pro | Ala | Thr | Lys | His | Arg | Val | Ile | Leu | Phe | Met | Gly | Asp | Gly | Ala |      |
|     |     |     | 410 |     |     |     |     | 415 |     |     |     |     | 420 |     |     |      |
| ttc | caa | ttg | aca | gtt | caa | gaa | tta | tcc | aca | att | gtt | aag | tgg | gga | ttg | 1530 |
| Phe | Gln | Leu | Thr | Val | Gln | Glu | Leu | Ser | Thr | Ile | Val | Lys | Trp | Gly | Leu |      |
|     |     | 425 |     |     |     |     | 430 |     |     |     |     | 435 |     |     |     |      |
| aca | cct | tat | att | ttt | gtg | atg | aat | aac | caa | ggt | tac | tct | gtg | gac | agg | 1578 |
| Thr | Pro | Tyr | Ile | Phe | Val | Met | Asn | Asn | Gln | Gly | Tyr | Ser | Val | Asp | Arg |      |
|     | 440 |     |     |     |     | 445 |     |     |     |     | 450 |     |     |     |     |      |
| ttt | ttg | cat | cac | agg | tca | gat | gct | agt | tat | tac | gat | atc | caa | cct | tgg | 1626 |
| Phe | Leu | His | His | Arg | Ser | Asp | Ala | Ser | Tyr | Tyr | Asp | Ile | Gln | Pro | Trp |      |
| 455 |     |     |     | 460 |     |     |     |     | 465 |     |     |     |     | 470 |     |      |
| aac | tac | ttg | gga | tta | ttg | cga | gta | ttt | ggt | tgc | acg | aac | tac | gaa | acg | 1674 |
| Asn | Tyr | Leu | Gly | Leu | Leu | Arg | Val | Phe | Gly | Cys | Thr | Asn | Tyr | Glu | Thr |      |
|     |     |     |     | 475 |     |     |     |     | 480 |     |     |     |     | 485 |     |      |
| aaa | aaa | att | att | act | gtt | gga | gaa | ttc | aga | tcc | atg | atc | agt | gac | cca | 1722 |
| Lys | Lys | Ile | Ile | Thr | Val | Gly | Glu | Phe | Arg | Ser | Met | Ile | Ser | Asp | Pro |      |
|     |     |     | 490 |     |     |     |     | 495 |     |     |     |     | 500 |     |     |      |
| aac | ttt | gcg | acc | aat | gac | aaa | att | cgg | atg | ata | gag | att | atg | cta | cca | 1770 |
| Asn | Phe | Ala | Thr | Asn | Asp | Lys | Ile | Arg | Met | Ile | Glu | Ile | Met | Leu | Pro |      |
|     |     | 505 |     |     |     |     | 510 |     |     |     |     | 515 |     |     |     |      |
| cca | agg | gat | gtt | cca | cag | gct | ctg | ctt | gac | agg | tgg | gtg | gta | gaa | aaa | 1818 |

```
Pro Arg Asp Val Pro Gln Ala Leu Leu Asp Arg Trp Val Val Glu Lys
    520                 525                 530 gaa cag agc aaa caa gtg caa gag gag aac gaa aat tct agc gca gta    1866
Glu Gln Ser Lys Gln Val Gln Glu Glu Asn Glu Asn Ser Ser Ala Val
535                 540                 545                 550 aat acg cca act cca gaa ttc caa cca ctt cta aaa aaa aat caa gtt    1914
Asn Thr Pro Thr Pro Glu Phe Gln Pro Leu Leu Lys Lys Asn Gln Val
                555                 560                 565 gga tac tga tctgatctct ccgccctact accagggacc ctcatgatta            1963
Gly Tyr ccgctcgaat gcgacgtttc ctgcctcata aaactggctt gaaaatattt attcgctgaa  2023
cagtagccta gcttataaaa atttcattta attaatgtaa tatgaaaact cacatgcctt  2083
ctgtttctaa aattgtcaca ggaagaaata acattaccat acgtgatctt attaaactct  2143
agtatcttgt ctaatacttc atttaaaaga agccttaacc ctgtagcctc atctatgtct  2203
gctacatatc gtgaggtacg aatatcgtaa gatgatacca cgcaactttg taatgatttt  2263 tttttttttca ttttttaaag aatgccttta catggtattt gaaaaaaata tctttataaa 2323 gtttgcgatc tcttctgttc tgaataattt ttagtaaaag aaatcaaaag aataagaaa   2383 tagtccgctt tgtccaatac aacagcttaa accgattatc tctaaaataa caagaagaaa  2443
tgtctatgaa tccgctttgt cttacgccgc cttgattttg gctgactctg aaatcgaaat  2503
ctcttctgaa aagttgttga ctttgactaa cgctgccaat gtcccagttg aaaatatctg  2563
ggctgatatt tttgctaagg ctttggacgg ccaaaacttg aaggacttat tggtcaactt  2623
cagcgtggtg ctgctgcccc agctggtgtc gctggtggtg tcgctggtgg tgaagccggt  2683
gaagccgaag tgaaaaggaa gaagaagaag ctaaagaaga tccgatgac gacatgggtt   2743 tcggtttatt tgattagaag tgccgcactg tttagaagaa attgcatatt ctacatttaa  2803
aattttttat aattttctat atagtcgctt ttaatacaat agacagtact ttcttttttgt 2863 tcaataccat ctttcgcatc tcttctatgc tatatataat gccacgttgt gctcgaagga  2923
aaagcctgca aacctgacta ctactaatac aataatgttc catcatatca agaaaactgc  2983
gctaacttgt aaaatactg tcaaccatat tctcacccag actataaagt taaggaaatg   3043
ataaattata agtgatggct tcccgtttat acattgtaca tatatatttt ttatgaaatt  3103
gaacagataa aaagaagga aaatacaaaa attgtggatg aaaaattctt tgatgaagtt   3163
tttaga                                                             3169
```

<210> SEQ ID NO 18
<211> LENGTH: 568
<212> TYPE: PRT
<213> ORGANISM: Saccharomyces cerevisiae

<400> SEQUENCE: 18

```
Met Pro Leu Leu Asp Lys Leu Tyr Asn Ile Pro Asn Leu Arg Trp Ala
1               5                   10                  15

Gly Asn Ser Asn Glu Leu Asn Ala Ala Tyr Ala Ala Asp Gly Tyr Ser
                20                  25                  30

Arg Leu Lys Gly Leu Gly Cys Leu Ile Thr Thr Phe Gly Val Gly Glu
            35                  40                  45

Leu Ser Ala Ile Asn Gly Val Ala Gly Ser Tyr Ala Glu His Val Gly
        50                  55                  60

Ile Leu His Ile Val Gly Met Pro Pro Thr Ser Ala Gln Thr Lys Gln
65                  70                  75                  80
```

```
Leu Leu Leu His His Thr Leu Gly Asn Gly Asp Phe Thr Val Phe His
                 85                  90                  95

Arg Ile Ala Ser Asp Val Ala Cys Tyr Thr Thr Leu Ile Ile Asp Ser
            100                 105                 110

Glu Leu Cys Ala Asp Glu Val Asp Lys Cys Ile Lys Lys Ala Trp Ile
        115                 120                 125

Glu Gln Arg Pro Val Tyr Met Gly Met Pro Val Asn Gln Val Asn Leu
    130                 135                 140

Pro Ile Glu Ser Ala Arg Leu Asn Thr Pro Leu Asp Leu Gln Leu His
145                 150                 155                 160

Lys Asn Asp Pro Asp Val Glu Lys Glu Val Ile Ser Arg Ile Leu Ser
                165                 170                 175

Phe Ile Tyr Lys Ser Gln Asn Pro Ala Ile Ile Val Asp Ala Cys Thr
            180                 185                 190

Ser Arg Gln Asn Leu Ile Glu Glu Thr Lys Glu Leu Cys Asn Arg Leu
        195                 200                 205

Lys Phe Pro Val Phe Val Thr Pro Met Gly Lys Gly Thr Val Asn Glu
    210                 215                 220

Thr Asp Pro Gln Phe Gly Gly Val Phe Thr Gly Ser Ile Ser Ala Pro
225                 230                 235                 240

Glu Val Arg Glu Val Val Asp Phe Ala Asp Phe Ile Ile Val Ile Gly
                245                 250                 255

Cys Met Leu Ser Glu Phe Ser Thr Ser Thr Phe His Phe Gln Tyr Lys
            260                 265                 270

Thr Lys Asn Cys Ala Leu Leu Tyr Ser Thr Ser Val Lys Leu Lys Asn
        275                 280                 285

Ala Thr Tyr Pro Asp Leu Ser Ile Lys Leu Leu Leu Gln Lys Ile Leu
    290                 295                 300

Ala Asn Leu Asp Glu Ser Lys Leu Ser Tyr Gln Pro Ser Glu Gln Pro
305                 310                 315                 320

Ser Met Met Val Pro Arg Pro Tyr Pro Ala Gly Asn Val Leu Leu Arg
                325                 330                 335

Gln Glu Trp Val Trp Asn Glu Ile Ser His Trp Phe Gln Pro Gly Asp
            340                 345                 350

Ile Ile Ile Thr Glu Thr Gly Ala Ser Ala Phe Gly Val Asn Gln Thr
        355                 360                 365

Arg Phe Pro Val Asn Thr Leu Gly Ile Ser Gln Ala Leu Trp Gly Ser
    370                 375                 380

Val Gly Tyr Thr Met Gly Ala Cys Leu Gly Ala Glu Phe Ala Val Gln
385                 390                 395                 400

Glu Ile Asn Lys Asp Lys Phe Pro Ala Thr Lys His Arg Val Ile Leu
                405                 410                 415

Phe Met Gly Asp Gly Ala Phe Gln Leu Thr Val Gln Glu Leu Ser Thr
            420                 425                 430

Ile Val Lys Trp Gly Leu Thr Pro Tyr Ile Phe Val Met Asn Asn Gln
        435                 440                 445

Gly Tyr Ser Val Asp Arg Phe Leu His His Arg Ser Asp Ala Ser Tyr
    450                 455                 460

Tyr Asp Ile Gln Pro Trp Asn Tyr Leu Gly Leu Leu Arg Val Phe Gly
465                 470                 475                 480

Cys Thr Asn Tyr Glu Thr Lys Lys Ile Ile Thr Val Gly Glu Phe Arg
                485                 490                 495

Ser Met Ile Ser Asp Pro Asn Phe Ala Thr Asn Asp Lys Ile Arg Met
```

```
                500             505             510
Ile Glu Ile Met Leu Pro Pro Arg Asp Val Pro Gln Ala Leu Leu Asp
            515                 520                 525

Arg Trp Val Val Glu Lys Glu Gln Ser Lys Gln Val Gln Glu Glu Asn
        530                 535                 540

Glu Asn Ser Ser Ala Val Asn Thr Pro Thr Pro Glu Phe Gln Pro Leu
545                 550                 555                 560

Leu Lys Lys Asn Gln Val Gly Tyr
                565

<210> SEQ ID NO 19
<211> LENGTH: 360
<212> TYPE: DNA
<213> ORGANISM: Saccharomyces cerevisiae
<220> FEATURE:
<221> NAME/KEY: CDS
<222> LOCATION: (1)..(360)
<223> OTHER INFORMATION: GenBank Accession No. V01291

<400> SEQUENCE: 19 atc ggt ggt gaa gtc ttc att gac ttc act aag gaa aag gac att gtc      48
Ile Gly Gly Glu Val Phe Ile Asp Phe Thr Lys Glu Lys Asp Ile Val
1               5                   10                  15 ggt gct gtt cta aag gcc act gac ggt ggt gct cac ggt gtc atc aac      96
Gly Ala Val Leu Lys Ala Thr Asp Gly Gly Ala His Gly Val Ile Asn
            20                  25                  30 gtt tcc gtt tcc gaa gcc gct att gaa gct tct acc aga tac gtt aga     144
Val Ser Val Ser Glu Ala Ala Ile Glu Ala Ser Thr Arg Tyr Val Arg
        35                  40                  45 gct aac ggt acc acc gtt ttg gtc ggt atg cca gct ggt gcc aag tgt     192
Ala Asn Gly Thr Thr Val Leu Val Gly Met Pro Ala Gly Ala Lys Cys
    50                  55                  60 tgt tct gat gtc ttc aac caa gtc gtc aag tcc atc tct att gtt ggt     240
Cys Ser Asp Val Phe Asn Gln Val Val Lys Ser Ile Ser Ile Val Gly
65                  70                  75                  80 tct tac gtc ggt aac aga gcc gac acc aga gaa gct ttg gac ttc ttc     288
Ser Tyr Val Gly Asn Arg Ala Asp Thr Arg Glu Ala Leu Asp Phe Phe
                85                  90                  95 gcc aga ggt ttg gtc aag tct cca atc aag gtt gtc ggc ttg tct acc     336
Ala Arg Gly Leu Val Lys Ser Pro Ile Lys Val Val Gly Leu Ser Thr
            100                 105                 110 ttg cca gaa att tac gaa aag atg                                     360
Leu Pro Glu Ile Tyr Glu Lys Met
        115                 120

<210> SEQ ID NO 20
<211> LENGTH: 120
<212> TYPE: PRT
<213> ORGANISM: Saccharomyces cerevisiae

<400> SEQUENCE: 20

Ile Gly Gly Glu Val Phe Ile Asp Phe Thr Lys Glu Lys Asp Ile Val
1               5                   10                  15

Gly Ala Val Leu Lys Ala Thr Asp Gly Gly Ala His Gly Val Ile Asn
            20                  25                  30

Val Ser Val Ser Glu Ala Ala Ile Glu Ala Ser Thr Arg Tyr Val Arg
        35                  40                  45

Ala Asn Gly Thr Thr Val Leu Val Gly Met Pro Ala Gly Ala Lys Cys
    50                  55                  60

Cys Ser Asp Val Phe Asn Gln Val Val Lys Ser Ile Ser Ile Val Gly
```

```
                 65                  70                  75                  80
Ser Tyr Val Gly Asn Arg Ala Asp Thr Arg Glu Ala Leu Asp Phe Phe
                             85                  90                  95

Ala Arg Gly Leu Val Lys Ser Pro Ile Lys Val Val Gly Leu Ser Thr
            100                 105                 110

Leu Pro Glu Ile Tyr Glu Lys Met
            115                 120

<210> SEQ ID NO 21
<211> LENGTH: 1047
<212> TYPE: DNA
<213> ORGANISM: Saccharomyces cerevisiae
<220> FEATURE:
<221> NAME/KEY: CDS
<222> LOCATION: (1)..(1047)
<223> OTHER INFORMATION: GenBank Accession No. NM_001182812

<400> SEQUENCE: 21 atg tct att cca gaa act caa aaa gcc att atc ttc tac gaa tcc aac      48
Met Ser Ile Pro Glu Thr Gln Lys Ala Ile Ile Phe Tyr Glu Ser Asn
1               5                  10                  15 ggc aag ttg gag cat aag gat atc cca gtt cca aag cca aag ccc aac      96
Gly Lys Leu Glu His Lys Asp Ile Pro Val Pro Lys Pro Lys Pro Asn
            20                  25                  30 gaa ttg tta atc aac gtc aag tac tct ggt gtc tgc cac acc gat ttg     144
Glu Leu Leu Ile Asn Val Lys Tyr Ser Gly Val Cys His Thr Asp Leu
        35                  40                  45 cac gct tgg cat ggt gac tgg cca ttg cca act aag tta cca tta gtt     192
His Ala Trp His Gly Asp Trp Pro Leu Pro Thr Lys Leu Pro Leu Val
    50                  55                  60 ggt ggt cac gaa ggt gcc ggt gtc gtt gtc ggc atg ggt gaa aac gtt     240
Gly Gly His Glu Gly Ala Gly Val Val Val Gly Met Gly Glu Asn Val
65                  70                  75                  80 aag ggc tgg aag atc ggt gac tac gcc ggt atc aaa tgg ttg aac ggt     288
Lys Gly Trp Lys Ile Gly Asp Tyr Ala Gly Ile Lys Trp Leu Asn Gly
                85                  90                  95 tct tgt atg gcc tgt gaa tac tgt gaa ttg ggt aac gaa tcc aac tgt     336
Ser Cys Met Ala Cys Glu Tyr Cys Glu Leu Gly Asn Glu Ser Asn Cys
            100                 105                 110 cct cac gct gac ttg tct ggt tac acc cac gac ggt tct ttc caa gaa     384
Pro His Ala Asp Leu Ser Gly Tyr Thr His Asp Gly Ser Phe Gln Glu
        115                 120                 125 tac gct acc gct gac gct gtt caa gcc gct cac att cct caa ggt act     432
Tyr Ala Thr Ala Asp Ala Val Gln Ala Ala His Ile Pro Gln Gly Thr
    130                 135                 140 gac ttg gct gaa gtc gcg cca atc ttg tgt gct ggt atc acc gta tac     480
Asp Leu Ala Glu Val Ala Pro Ile Leu Cys Ala Gly Ile Thr Val Tyr
145                 150                 155                 160 aag gct ttg aag tct gcc aac ttg aga gca ggc cac tgg gcg gcc att     528
Lys Ala Leu Lys Ser Ala Asn Leu Arg Ala Gly His Trp Ala Ala Ile
                165                 170                 175 tct ggt gct gct ggt ggt cta ggt tct ttg gct gtt caa tat gct aag     576
Ser Gly Ala Ala Gly Gly Leu Gly Ser Leu Ala Val Gln Tyr Ala Lys
            180                 185                 190 gcg atg ggt tac aga gtc tta ggt att gat ggt ggt cca gga aag gaa     624
Ala Met Gly Tyr Arg Val Leu Gly Ile Asp Gly Gly Pro Gly Lys Glu
        195                 200                 205 gaa ttg ttt acc tcg ctc ggt ggt gaa gta ttc atc gac ttc acc aaa     672
Glu Leu Phe Thr Ser Leu Gly Gly Glu Val Phe Ile Asp Phe Thr Lys
    210                 215                 220
```

```
gag aag gac att gtt agc gca gtc gtt aag gct acc aac ggc ggt gcc      720
Glu Lys Asp Ile Val Ser Ala Val Val Lys Ala Thr Asn Gly Gly Ala
225                 230                 235                 240 cac ggt atc atc aat gtt tcc gtt tcc gaa gcc gct atc gaa gct tct      768
His Gly Ile Ile Asn Val Ser Val Ser Glu Ala Ala Ile Glu Ala Ser
                245                 250                 255 acc aga tac tgt agg gcg aac ggt act gtt gtc ttg gtt ggt tta cca      816
Thr Arg Tyr Cys Arg Ala Asn Gly Thr Val Val Leu Val Gly Leu Pro
            260                 265                 270 gcc ggt gca aag tgc tcc tct gat gtc ttc aac cac gtt gtc aag tct      864
Ala Gly Ala Lys Cys Ser Ser Asp Val Phe Asn His Val Val Lys Ser
        275                 280                 285 atc tcc att gtc ggc tct tac gtg ggg aac aga gct gat acc aga gaa      912
Ile Ser Ile Val Gly Ser Tyr Val Gly Asn Arg Ala Asp Thr Arg Glu
    290                 295                 300 gcc tta gat ttc ttt gcc aga ggt cta gtc aag tct cca ata aag gta      960
Ala Leu Asp Phe Phe Ala Arg Gly Leu Val Lys Ser Pro Ile Lys Val
305                 310                 315                 320 gtt ggc tta tcc agt tta cca gaa att tac gaa aag atg gag aag ggc     1008
Val Gly Leu Ser Ser Leu Pro Glu Ile Tyr Glu Lys Met Glu Lys Gly
                325                 330                 335 caa att gct ggt aga tac gtt gtt gac act tct aaa taa                 1047
Gln Ile Ala Gly Arg Tyr Val Val Asp Thr Ser Lys
            340                 345
```

<210> SEQ ID NO 22
<211> LENGTH: 348
<212> TYPE: PRT
<213> ORGANISM: Saccharomyces cerevisiae

<400> SEQUENCE: 22

```
Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125

Tyr Ala Thr Ala Asp Ala Val Gln Ala Ala His Ile Pro Gln Gly Thr
    130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
        195                 200                 205
```

```
Glu Leu Phe Thr Ser Leu Gly Gly Glu Val Phe Ile Asp Phe Thr Lys
    210             215                 220
Glu Lys Asp Ile Val Ser Ala Val Val Lys Ala Thr Asn Gly Gly Ala
225                 230                 235                 240
His Gly Ile Ile Asn Val Ser Val Ser Glu Ala Ala Ile Glu Ala Ser
                245                 250                 255
Thr Arg Tyr Cys Arg Ala Asn Gly Thr Val Val Leu Val Gly Leu Pro
            260                 265                 270
Ala Gly Ala Lys Cys Ser Ser Asp Val Phe Asn His Val Lys Ser
        275                 280                 285
Ile Ser Ile Val Gly Ser Tyr Val Gly Asn Arg Ala Asp Thr Arg Glu
    290                 295                 300
Ala Leu Asp Phe Phe Ala Arg Gly Leu Val Lys Ser Pro Ile Lys Val
305                 310                 315                 320
Val Gly Leu Ser Ser Leu Pro Glu Ile Tyr Glu Lys Met Glu Lys Gly
                325                 330                 335
Gln Ile Ala Gly Arg Tyr Val Val Asp Thr Ser Lys
            340                 345

<210> SEQ ID NO 23
<211> LENGTH: 1128
<212> TYPE: DNA
<213> ORGANISM: Saccharomyces cerevisiae
<220> FEATURE:
<221> NAME/KEY: CDS
<222> LOCATION: (1)..(1128)
<223> OTHER INFORMATION: GenBank Accession No. NM_001182582

<400> SEQUENCE: 23 atg ttg aga acg tca aca ttg ttc acc agg cgt gtc caa cca agc cta     48
Met Leu Arg Thr Ser Thr Leu Phe Thr Arg Arg Val Gln Pro Ser Leu
1               5                   10                  15 ttt tct aga aac att ctt aga ttg caa tcc aca gct gca atc cct aag    96
Phe Ser Arg Asn Ile Leu Arg Leu Gln Ser Thr Ala Ala Ile Pro Lys
            20                  25                  30 act caa aaa ggt gtc atc ttt tat gag aat aag ggg aag ctg cat tac   144
Thr Gln Lys Gly Val Ile Phe Tyr Glu Asn Lys Gly Lys Leu His Tyr
        35                  40                  45 aaa gat atc cct gtc ccc gag cct aag cca aat gaa att tta atc aac   192
Lys Asp Ile Pro Val Pro Glu Pro Lys Pro Asn Glu Ile Leu Ile Asn
    50                  55                  60 gtt aaa tat tct ggt gta tgt cac acc gat tta cat gct tgg cac ggc   240
Val Lys Tyr Ser Gly Val Cys His Thr Asp Leu His Ala Trp His Gly
65                  70                  75                  80 gat tgg cca tta cct gtt aaa cta cca tta gta ggt ggt cat gaa ggt   288
Asp Trp Pro Leu Pro Val Lys Leu Pro Leu Val Gly Gly His Glu Gly
                85                  90                  95 gct ggt gta gtt gtc aaa cta ggt tcc aat gtc aag ggc tgg aaa gtc   336
Ala Gly Val Val Val Lys Leu Gly Ser Asn Val Lys Gly Trp Lys Val
            100                 105                 110 ggt gat tta gca ggt atc aaa tgg ctg aac ggt tct tgt atg aca tgc   384
Gly Asp Leu Ala Gly Ile Lys Trp Leu Asn Gly Ser Cys Met Thr Cys
        115                 120                 125 gaa ttc tgt gaa tca ggt cat gaa tca aat tgt cca gat gct gat tta   432
Glu Phe Cys Glu Ser Gly His Glu Ser Asn Cys Pro Asp Ala Asp Leu
    130                 135                 140 tct ggt tac act cat gat ggt tct ttc caa caa ttt gcg acc gct gat   480
Ser Gly Tyr Thr His Asp Gly Ser Phe Gln Gln Phe Ala Thr Ala Asp
145                 150                 155                 160
```

| | | |
|---|---|---|
| gct att caa gcc gcc aaa att caa cag ggt acc gac ttg gcc gaa gta<br>Ala Ile Gln Ala Ala Lys Ile Gln Gln Gly Thr Asp Leu Ala Glu Val<br>165　　　　　　　　　170　　　　　　　　　175 | | 528 |
| gcc cca ata tta tgt gct ggt gtt act gta tat aaa gca cta aaa gag<br>Ala Pro Ile Leu Cys Ala Gly Val Thr Val Tyr Lys Ala Leu Lys Glu<br>　　180　　　　　　　　　185　　　　　　　　　190 | | 576 |
| gca gac ttg aaa gct ggt gac tgg gtt gcc atc tct ggt gct gca ggt<br>Ala Asp Leu Lys Ala Gly Asp Trp Val Ala Ile Ser Gly Ala Ala Gly<br>　　　195　　　　　　　　　200　　　　　　　　　205 | | 624 |
| ggc ttg ggt tcc ttg gcc gtt caa tat gca act gcg atg ggt tac aga<br>Gly Leu Gly Ser Leu Ala Val Gln Tyr Ala Thr Ala Met Gly Tyr Arg<br>210　　　　　　　　　215　　　　　　　　　220 | | 672 |
| gtt cta ggt att gat gca ggt gag gaa aag gaa aaa ctt ttc aag aaa<br>Val Leu Gly Ile Asp Ala Gly Glu Glu Lys Glu Lys Leu Phe Lys Lys<br>225　　　　　　　　　230　　　　　　　　　235　　　　　　　　　240 | | 720 |
| ttg ggg ggt gaa gta ttc atc gac ttt act aaa aca aag aat atg gtt<br>Leu Gly Gly Glu Val Phe Ile Asp Phe Thr Lys Thr Lys Asn Met Val<br>　　　　　　　　　245　　　　　　　　　250　　　　　　　　　255 | | 768 |
| tct gac att caa gaa gct acc aaa ggt ggc cct cat ggt gtc att aac<br>Ser Asp Ile Gln Glu Ala Thr Lys Gly Gly Pro His Gly Val Ile Asn<br>　　260　　　　　　　　　265　　　　　　　　　270 | | 816 |
| gtt tcc gtt tct gaa gcc gct att tct cta tct acg gaa tat gtt aga<br>Val Ser Val Ser Glu Ala Ala Ile Ser Leu Ser Thr Glu Tyr Val Arg<br>　　　275　　　　　　　　　280　　　　　　　　　285 | | 864 |
| cca tgt ggt acc gtc gtt ttg gtt ggt ttg ccc gct aac gcc tac gtt<br>Pro Cys Gly Thr Val Val Leu Val Gly Leu Pro Ala Asn Ala Tyr Val<br>290　　　　　　　　　295　　　　　　　　　300 | | 912 |
| aaa tca gag gta ttc tct cat gtg gtg aag tcc atc aat atc aag ggt<br>Lys Ser Glu Val Phe Ser His Val Val Lys Ser Ile Asn Ile Lys Gly<br>305　　　　　　　　　310　　　　　　　　　315　　　　　　　　　320 | | 960 |
| tct tat gtt ggt aac aga gct gat acg aga gaa gcc tta gac ttc ttt<br>Ser Tyr Val Gly Asn Arg Ala Asp Thr Arg Glu Ala Leu Asp Phe Phe<br>　　　　　　　　　325　　　　　　　　　330　　　　　　　　　335 | | 1008 |
| agc aga ggt ttg atc aaa tca cca atc aaa att gtt gga tta tct gaa<br>Ser Arg Gly Leu Ile Lys Ser Pro Ile Lys Ile Val Gly Leu Ser Glu<br>　　340　　　　　　　　　345　　　　　　　　　350 | | 1056 |
| tta cca aag gtt tat gac ttg atg gaa aag ggc aag att ttg ggt aga<br>Leu Pro Lys Val Tyr Asp Leu Met Glu Lys Gly Lys Ile Leu Gly Arg<br>　　　355　　　　　　　　　360　　　　　　　　　365 | | 1104 |
| tac gtc gtc gat act agt aaa taa<br>Tyr Val Val Asp Thr Ser Lys<br>370　　　　　　　　　375 | | 1128 |

<210> SEQ ID NO 24
<211> LENGTH: 375
<212> TYPE: PRT
<213> ORGANISM: Saccharomyces cerevisiae

<400> SEQUENCE: 24

Met Leu Arg Thr Ser Thr Leu Phe Thr Arg Arg Val Gln Pro Ser Leu
1               5                   10                  15

Phe Ser Arg Asn Ile Leu Arg Leu Gln Ser Thr Ala Ala Ile Pro Lys
            20                  25                  30

Thr Gln Lys Gly Val Ile Phe Tyr Glu Asn Lys Gly Lys Leu His Tyr
        35                  40                  45

Lys Asp Ile Pro Val Pro Glu Pro Lys Pro Asn Glu Ile Leu Ile Asn
    50                  55                  60

Val Lys Tyr Ser Gly Val Cys His Thr Asp Leu His Ala Trp His Gly
65                  70                  75                  80

-continued

```
Asp Trp Pro Leu Pro Val Lys Leu Pro Leu Val Gly Gly His Glu Gly
            85                  90                  95
Ala Gly Val Val Val Lys Leu Gly Ser Asn Val Lys Gly Trp Lys Val
        100                 105                 110
Gly Asp Leu Ala Gly Ile Lys Trp Leu Asn Gly Ser Cys Met Thr Cys
    115                 120                 125
Glu Phe Cys Glu Ser Gly His Glu Ser Asn Cys Pro Asp Ala Asp Leu
130                 135                 140
Ser Gly Tyr Thr His Asp Gly Ser Phe Gln Gln Phe Ala Thr Ala Asp
145                 150                 155                 160
Ala Ile Gln Ala Ala Lys Ile Gln Gln Gly Thr Asp Leu Ala Glu Val
                165                 170                 175
Ala Pro Ile Leu Cys Ala Gly Val Thr Val Tyr Lys Ala Leu Lys Glu
            180                 185                 190
Ala Asp Leu Lys Ala Gly Asp Trp Val Ala Ile Ser Gly Ala Ala Gly
        195                 200                 205
Gly Leu Gly Ser Leu Ala Val Gln Tyr Ala Thr Ala Met Gly Tyr Arg
    210                 215                 220
Val Leu Gly Ile Asp Ala Gly Glu Glu Lys Glu Lys Leu Phe Lys Lys
225                 230                 235                 240
Leu Gly Gly Glu Val Phe Ile Asp Phe Thr Lys Thr Lys Asn Met Val
                245                 250                 255
Ser Asp Ile Gln Glu Ala Thr Lys Gly Gly Pro His Gly Val Ile Asn
            260                 265                 270
Val Ser Val Ser Glu Ala Ala Ile Ser Leu Ser Thr Glu Tyr Val Arg
        275                 280                 285
Pro Cys Gly Thr Val Val Leu Val Gly Leu Pro Ala Asn Ala Tyr Val
    290                 295                 300
Lys Ser Glu Val Phe Ser His Val Val Lys Ser Ile Asn Ile Lys Gly
305                 310                 315                 320
Ser Tyr Val Gly Asn Arg Ala Asp Thr Arg Glu Ala Leu Asp Phe Phe
                325                 330                 335
Ser Arg Gly Leu Ile Lys Ser Pro Ile Lys Ile Val Gly Leu Ser Glu
            340                 345                 350
Leu Pro Lys Val Tyr Asp Leu Met Glu Lys Gly Lys Ile Leu Gly Arg
        355                 360                 365
Tyr Val Val Asp Thr Ser Lys
    370                 375
```

<210> SEQ ID NO 25
<211> LENGTH: 2160
<212> TYPE: DNA
<213> ORGANISM: Saccharomyces cerevisiae
<220> FEATURE:
<221> NAME/KEY: CDS
<222> LOCATION: (442)..(1590)
<223> OTHER INFORMATION: GenBank Accession No. X05992

<400> SEQUENCE: 25

```
ggccttcaat gagcttccaa tttattttct ccaaggaggc cattttttgt agtgtgatgt      60
tgacatggtt ataactgtta gcagtgtttg tgatgatggc tgtagtatca ccgcagtgga     120
ttagctatga aaaaaaaaaa aagaactag  ttttagttc gcgcatcacg aggtacgtgt     180
ttaatatgtc agatgcttgg gatcacgtat gccgttaact ctacaaagca attgatattt     240
tgctgcctca aatatctcac actgctagga tatattcttt tatcaaacag aaaaaaaggg     300
```

```
cagcgtacca acatgtataa aagggttatt agcatttctg gtttattaaa gactggagtc      360
aaacgttttt cttctgtcta ttgcaaaaca accatcaaca acaagtttac atttgcaaca      420
actaatagtc aaataagaaa a atg tct tcc gtt act ggg ttt tac att cca        471
                        Met Ser Ser Val Thr Gly Phe Tyr Ile Pro
                         1           5                      10 cca atc tct ttc ttt ggt gaa ggt gct tta gaa gaa acc gct gat tac        519
Pro Ile Ser Phe Phe Gly Glu Gly Ala Leu Glu Glu Thr Ala Asp Tyr
             15                  20                  25 atc aaa aac aag gat tac aaa aag gct ttg atc gtt act gat cct ggt        567
Ile Lys Asn Lys Asp Tyr Lys Lys Ala Leu Ile Val Thr Asp Pro Gly
             30                  35                  40 att gca gct att ggt ctc tcc ggt aga gtc caa aag atg ttg gaa gaa        615
Ile Ala Ala Ile Gly Leu Ser Gly Arg Val Gln Lys Met Leu Glu Glu
         45                  50                  55 cgt ggc tta aac gtt gct atc tat gac aaa act caa cca aac cca aat        663
Arg Gly Leu Asn Val Ala Ile Tyr Asp Lys Thr Gln Pro Asn Pro Asn
 60                  65                  70 att gcc aat gtc aca gct ggt ttg aag gtt ttg aag gaa gaa aac tct        711
Ile Ala Asn Val Thr Ala Gly Leu Lys Val Leu Lys Glu Glu Asn Ser
 75                  80                  85                  90 gaa att gtc gtt tcc att ggt ggt ggt tct gct cac gac aat gct aag        759
Glu Ile Val Val Ser Ile Gly Gly Gly Ser Ala His Asp Asn Ala Lys
                 95                 100                 105 gcc att gct tta ttg gct act aac ggt ggg gaa att gga gat tat gaa        807
Ala Ile Ala Leu Leu Ala Thr Asn Gly Gly Glu Ile Gly Asp Tyr Glu
            110                 115                 120 ggt gtc aac caa tct aag aag gct gct tta ccg cta ttt gcc atc aac        855
Gly Val Asn Gln Ser Lys Lys Ala Ala Leu Pro Leu Phe Ala Ile Asn
        125                 130                 135 act act gct ggt act gct tcc gag atg acc aga ttc act att atc tct        903
Thr Thr Ala Gly Thr Ala Ser Glu Met Thr Arg Phe Thr Ile Ile Ser
    140                 145                 150 aat gaa gaa aag aaa atc aag atg gcc atc att gac aac aac gtc act        951
Asn Glu Glu Lys Lys Ile Lys Met Ala Ile Ile Asp Asn Asn Val Thr
155                 160                 165                 170 cca gct gtt gct gtc aac gac cca tct acc atg ttt ggt ttg cca cct        999
Pro Ala Val Ala Val Asn Asp Pro Ser Thr Met Phe Gly Leu Pro Pro
                175                 180                 185 gct ttg act gct gct act ggt cta gat gct ttg act cac tgt atc gaa       1047
Ala Leu Thr Ala Ala Thr Gly Leu Asp Ala Leu Thr His Cys Ile Glu
            190                 195                 200 gct tac gtt tcc acc gcc tct aac cca atc acc gat gct tgt gct ttg       1095
Ala Tyr Val Ser Thr Ala Ser Asn Pro Ile Thr Asp Ala Cys Ala Leu
        205                 210                 215 aag ggt att gat ttg atc aat gaa agc ttg gtc gcc gca tac aaa gac       1143
Lys Gly Ile Asp Leu Ile Asn Glu Ser Leu Val Ala Ala Tyr Lys Asp
    220                 225                 230 ggt aaa gac aag aag gcc aga act gat atg tgt tac gca gaa tac ttg       1191
Gly Lys Asp Lys Lys Ala Arg Thr Asp Met Cys Tyr Ala Glu Tyr Leu
235                 240                 245                 250 gca ggt atg gct ttc aac aat gct tct cta ggt tat gtt cat gcc ctt       1239
Ala Gly Met Ala Phe Asn Asn Ala Ser Leu Gly Tyr Val His Ala Leu
                255                 260                 265 gct cat caa ctt ggt ggt ttc tac cac ttg cct cat ggt gtt tgt aac       1287
Ala His Gln Leu Gly Gly Phe Tyr His Leu Pro His Gly Val Cys Asn
            270                 275                 280 gct gtc ttg ttg cct cat gtt caa gag gcc aac atg caa tgt cca aag       1335
Ala Val Leu Leu Pro His Val Gln Glu Ala Asn Met Gln Cys Pro Lys
        285                 290                 295
```

-continued

```
gcc aag aag aga tta ggt gaa att gcc ttg cat tgc ggt gct tct caa      1383
Ala Lys Lys Arg Leu Gly Glu Ile Ala Leu His Cys Gly Ala Ser Gln
    300                 305                 310 gaa gat cca gaa gaa acc atc aag gct ttg cac gtt tta aac aga acc      1431
Glu Asp Pro Glu Glu Thr Ile Lys Ala Leu His Val Leu Asn Arg Thr
315                 320                 325                 330 atg aac att cca aga aac ttg aaa gac tta ggt gtt aaa acc gaa gat      1479
Met Asn Ile Pro Arg Asn Leu Lys Asp Leu Gly Val Lys Thr Glu Asp
                335                 340                 345 ttt gac att ttg gct gaa cac gcc atg cat gat gcc tgc cat ttg act      1527
Phe Asp Ile Leu Ala Glu His Ala Met His Asp Ala Cys His Leu Thr
            350                 355                 360 aac cca gtt caa ttc acc aaa gaa caa gtg gtt gcc att atc aag aaa      1575
Asn Pro Val Gln Phe Thr Lys Glu Gln Val Val Ala Ile Ile Lys Lys
        365                 370                 375 gcc tat gaa tat taa aaaaatcgaa cgaactcata acgtcaatt atgcgtgtgc      1630
Ala Tyr Glu Tyr
    380 cttatttatt tagttgtgcg tacagtataa tgcacttatt tatttaccaa tcaaatgatt   1690 tttttaactt ttcacgatct atataattac gttaatttcg agtatataac aatgaaatat   1750 atatcttacg ttgtcttgaa tggaaaaaag aagaattgaa gctctattaa tgagaccgag   1810 accggtacgt ttgttgaaaa tagtttggat ttaattgctg atatactgtt ggctttgaag   1870 catttaagat tgaaaaatag tcatgtaaaa gtcatgcttt aatatggtgg gcttcatgtt   1930 ggatgcaaga aataaaatga aattcgaagg cctttcgcaa ttaaacaagg catcgtcaac   1990 cagacaatgt cgaaaatttt gagtcaatct aaatcaatcc accgccacac tgaattatgc   2050 caatgatatt gtcttccttt ttttggtttg atatctctaa tattcaacct gttataagca   2110 acgtcaatcc gattactttc gactgtcatt cacatgcgca tattttttt              2160

<210> SEQ ID NO 26
<211> LENGTH: 382
<212> TYPE: PRT
<213> ORGANISM: Saccharomyces cerevisiae

<400> SEQUENCE: 26

Met Ser Ser Val Thr Gly Phe Tyr Ile Pro Pro Ile Ser Phe Phe Gly
1               5                   10                  15

Glu Gly Ala Leu Glu Glu Thr Ala Asp Tyr Ile Lys Asn Lys Asp Tyr
                20                  25                  30

Lys Lys Ala Leu Ile Val Thr Asp Pro Gly Ile Ala Ala Ile Gly Leu
            35                  40                  45

Ser Gly Arg Val Gln Lys Met Leu Glu Glu Arg Gly Leu Asn Val Ala
        50                  55                  60

Ile Tyr Asp Lys Thr Gln Pro Asn Pro Asn Ile Ala Asn Val Thr Ala
65                  70                  75                  80

Gly Leu Lys Val Leu Lys Glu Glu Asn Ser Glu Ile Val Val Ser Ile
                85                  90                  95

Gly Gly Gly Ser Ala His Asp Asn Ala Lys Ala Ile Ala Leu Leu Ala
            100                 105                 110

Thr Asn Gly Gly Glu Ile Gly Asp Tyr Glu Gly Val Asn Gln Ser Lys
        115                 120                 125

Lys Ala Ala Leu Pro Leu Phe Ala Ile Asn Thr Thr Ala Gly Thr Ala
    130                 135                 140

Ser Glu Met Thr Arg Phe Thr Ile Ile Ser Asn Glu Glu Lys Lys Ile
```

```
                        145                 150                 155                 160
Lys Met Ala Ile Ile Asp Asn Asn Val Thr Pro Ala Val Ala Val Asn
                    165                 170                 175

Asp Pro Ser Thr Met Phe Gly Leu Pro Pro Ala Leu Thr Ala Ala Thr
                180                 185                 190

Gly Leu Asp Ala Leu Thr His Cys Ile Glu Ala Tyr Val Ser Thr Ala
            195                 200                 205

Ser Asn Pro Ile Thr Asp Ala Cys Ala Leu Lys Gly Ile Asp Leu Ile
        210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
            260                 265                 270

Phe Tyr His Leu Pro His Gly Val Cys Asn Ala Val Leu Leu Pro His
        275                 280                 285

Val Gln Glu Ala Asn Met Gln Cys Pro Lys Ala Lys Lys Arg Leu Gly
    290                 295                 300

Glu Ile Ala Leu His Cys Gly Ala Ser Gln Glu Asp Pro Glu Glu Thr
305                 310                 315                 320

Ile Lys Ala Leu His Val Leu Asn Arg Thr Met Asn Ile Pro Arg Asn
                325                 330                 335

Leu Lys Asp Leu Gly Val Lys Thr Glu Asp Phe Asp Ile Leu Ala Glu
            340                 345                 350

His Ala Met His Asp Ala Cys His Leu Thr Asn Pro Val Gln Phe Thr
        355                 360                 365

Lys Glu Gln Val Val Ala Ile Ile Lys Lys Ala Tyr Glu Tyr
    370                 375                 380

<210> SEQ ID NO 27
<211> LENGTH: 1056
<212> TYPE: DNA
<213> ORGANISM: Saccharomyces cerevisiae
<220> FEATURE:
<221> NAME/KEY: CDS
<222> LOCATION: (1)..(1056)
<223> OTHER INFORMATION: GenBank Accession No. NM_001178493

<400> SEQUENCE: 27 atg cct tcg caa gtc att cct gaa aaa caa aag gct att gtc ttt tat    48
Met Pro Ser Gln Val Ile Pro Glu Lys Gln Lys Ala Ile Val Phe Tyr
1               5                  10                  15 gag aca gat gga aaa ttg gaa tat aaa gac gtc aca gtt ccg gaa cct    96
Glu Thr Asp Gly Lys Leu Glu Tyr Lys Asp Val Thr Val Pro Glu Pro
            20                  25                  30 aag cct aac gaa att tta gtc cac gtt aaa tat tct ggt gtt tgt cat   144
Lys Pro Asn Glu Ile Leu Val His Val Lys Tyr Ser Gly Val Cys His
        35                  40                  45 agt gac ttg cac gcg tgg cac ggt gat tgg cca ttt caa ttg aaa ttt   192
Ser Asp Leu His Ala Trp His Gly Asp Trp Pro Phe Gln Leu Lys Phe
    50                  55                  60 cca tta atc ggt ggt cac gaa ggt gct ggt gtt gtt aag ttg gga       240
Pro Leu Ile Gly Gly His Glu Gly Ala Gly Val Val Val Lys Leu Gly
65                  70                  75                  80 tct aac gtt aag ggc tgg aaa gtc ggt gat ttt gca ggt ata aaa tgg   288
Ser Asn Val Lys Gly Trp Lys Val Gly Asp Phe Ala Gly Ile Lys Trp
                85                  90                  95
```

```
ttg aat ggg act tgc atg tcc tgt gaa tat tgt gaa gta ggt aat gaa      336
Leu Asn Gly Thr Cys Met Ser Cys Glu Tyr Cys Glu Val Gly Asn Glu
            100                 105                 110 tct caa tgt cct tat ttg gat ggt act ggc ttc aca cat gat ggt act      384
Ser Gln Cys Pro Tyr Leu Asp Gly Thr Gly Phe Thr His Asp Gly Thr
        115                 120                 125 ttt caa gaa tac gca act gcc gat gcc gtt caa gct gcc cat att cca      432
Phe Gln Glu Tyr Ala Thr Ala Asp Ala Val Gln Ala Ala His Ile Pro
130                 135                 140 cca aac gtc aat ctt gct gaa gtt gcc cca atc ttg tgt gca ggt atc      480
Pro Asn Val Asn Leu Ala Glu Val Ala Pro Ile Leu Cys Ala Gly Ile
145                 150                 155                 160 act gtt tat aag gcg ttg aaa aga gcc aat gtg ata cca ggc caa tgg      528
Thr Val Tyr Lys Ala Leu Lys Arg Ala Asn Val Ile Pro Gly Gln Trp
                165                 170                 175 gtc act ata tcc ggt gca tgc ggt ggc ttg ggt tct ctg gca atc caa      576
Val Thr Ile Ser Gly Ala Cys Gly Gly Leu Gly Ser Leu Ala Ile Gln
            180                 185                 190 tac gcc ctt gct atg ggt tac agg gtc att ggt atc gat ggt ggt aat      624
Tyr Ala Leu Ala Met Gly Tyr Arg Val Ile Gly Ile Asp Gly Gly Asn
        195                 200                 205 gcc aag cga aag tta ttt gaa caa tta ggc gga gaa ata ttc atc gat      672
Ala Lys Arg Lys Leu Phe Glu Gln Leu Gly Gly Glu Ile Phe Ile Asp
210                 215                 220 ttc acg gaa gaa aaa gac att gtt ggt gct ata ata aag gcc act aat      720
Phe Thr Glu Glu Lys Asp Ile Val Gly Ala Ile Ile Lys Ala Thr Asn
225                 230                 235                 240 ggc ggt tct cat gga gtt att aat gtg tct gtt tct gaa gca gct atc      768
Gly Gly Ser His Gly Val Ile Asn Val Ser Val Ser Glu Ala Ala Ile
                245                 250                 255 gag gct tct acg agg tat tgt agg ccc aat ggt act gtc gtc ctg gtt      816
Glu Ala Ser Thr Arg Tyr Cys Arg Pro Asn Gly Thr Val Val Leu Val
            260                 265                 270 ggt atg cca gct cat gct tac tgc aat tcc gat gtt ttc aat caa gtt      864
Gly Met Pro Ala His Ala Tyr Cys Asn Ser Asp Val Phe Asn Gln Val
        275                 280                 285 gta aaa tca atc tcc atc gtt gga tct tgt gtt gga aat aga gct gat      912
Val Lys Ser Ile Ser Ile Val Gly Ser Cys Val Gly Asn Arg Ala Asp
290                 295                 300 aca agg gag gct tta gat ttc ttc gcc aga ggt ttg atc aaa tct ccg      960
Thr Arg Glu Ala Leu Asp Phe Phe Ala Arg Gly Leu Ile Lys Ser Pro
305                 310                 315                 320 atc cac tta gct ggc cta tcg gat gtt cct gaa att ttt gca aag atg     1008
Ile His Leu Ala Gly Leu Ser Asp Val Pro Glu Ile Phe Ala Lys Met
                325                 330                 335 gag aag ggt gaa att gtt ggt aga tat gtt gtt gag act tct aaa tga     1056
Glu Lys Gly Glu Ile Val Gly Arg Tyr Val Val Glu Thr Ser Lys
            340                 345                 350

<210> SEQ ID NO 28
<211> LENGTH: 351
<212> TYPE: PRT
<213> ORGANISM: Saccharomyces cerevisiae

<400> SEQUENCE: 28

Met Pro Ser Gln Val Ile Pro Glu Lys Gln Lys Ala Ile Val Phe Tyr
1               5                   10                  15

Glu Thr Asp Gly Lys Leu Glu Tyr Lys Asp Val Thr Val Pro Glu Pro
            20                  25                  30
```

```
Lys Pro Asn Glu Ile Leu Val His Val Lys Tyr Ser Gly Val Cys His
             35                  40                  45

Ser Asp Leu His Ala Trp His Gly Asp Trp Pro Phe Gln Leu Lys Phe
 50                  55                  60

Pro Leu Ile Gly Gly His Glu Gly Ala Gly Val Val Lys Leu Gly
 65                  70                  75                  80

Ser Asn Val Lys Gly Trp Lys Val Gly Asp Phe Ala Gly Ile Lys Trp
                 85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
            340                 345                 350

<210> SEQ ID NO 29
<211> LENGTH: 1083
<212> TYPE: DNA
<213> ORGANISM: Saccharomyces cerevisiae
<220> FEATURE:
<221> NAME/KEY: CDS
<222> LOCATION: (1)..(1083)
<223> OTHER INFORMATION: GenBank Accession No. NM_001182831

<400> SEQUENCE: 29 atg tct tat cct gag aaa ttt gaa ggt atc gct att caa tca cac gaa      48
Met Ser Tyr Pro Glu Lys Phe Glu Gly Ile Ala Ile Gln Ser His Glu
 1               5                  10                  15 gat tgg aaa aac cca aag aag aca aag tat gac cca aaa cca ttt tac      96
Asp Trp Lys Asn Pro Lys Lys Thr Lys Tyr Asp Pro Lys Pro Phe Tyr
                20                  25                  30
```

```
gat cat gac att gac att aag atc gaa gca tgt ggt gtc tgc ggt agt    144
Asp His Asp Ile Asp Ile Lys Ile Glu Ala Cys Gly Val Cys Gly Ser
        35                  40                  45 gat att cat tgt gca gct ggt cat tgg ggc aat atg aag atg ccg cta    192
Asp Ile His Cys Ala Ala Gly His Trp Gly Asn Met Lys Met Pro Leu
 50                  55                  60 gtc gtt ggt cat gaa atc gtt ggt aaa gtt gtc aag cta ggg ccc aag    240
Val Val Gly His Glu Ile Val Gly Lys Val Lys Leu Gly Pro Lys
 65                  70                  75                  80 tca aac agt ggg ttg aaa gtc ggt caa cgt gtt ggt gta ggt gct caa    288
Ser Asn Ser Gly Leu Lys Val Gly Gln Arg Val Gly Val Gly Ala Gln
                 85                  90                  95 gtc ttt tca tgc ttg gaa tgt gac cgt tgt aag aat gat aat gaa cca    336
Val Phe Ser Cys Leu Glu Cys Asp Arg Cys Lys Asn Asp Asn Glu Pro
            100                 105                 110 tac tgc acc aag ttt gtt acc aca tac agt cag cct tat gaa gac ggc    384
Tyr Cys Thr Lys Phe Val Thr Thr Tyr Ser Gln Pro Tyr Glu Asp Gly
        115                 120                 125 tat gtg tcg cag ggt ggc tat gca aac tac gtc aga gtt cat gaa cat    432
Tyr Val Ser Gln Gly Gly Tyr Ala Asn Tyr Val Arg Val His Glu His
130                 135                 140 ttt gtg gtg cct atc cca gag aat att cca tca cat ttg gct gct cca    480
Phe Val Val Pro Ile Pro Glu Asn Ile Pro Ser His Leu Ala Ala Pro
145                 150                 155                 160 cta tta tgt ggt ggt ttg act gtg tac tct cca ttg gtt cgt aac ggt    528
Leu Leu Cys Gly Gly Leu Thr Val Tyr Ser Pro Leu Val Arg Asn Gly
            165                 170                 175 tgc ggt cca ggt aaa aaa gtt ggt ata gtt ggt ctt ggt ggt atc ggc    576
Cys Gly Pro Gly Lys Lys Val Gly Ile Val Gly Leu Gly Gly Ile Gly
        180                 185                 190 agt atg ggt aca ttg att tcc aaa gcc atg ggg gca gag acg tat gtt    624
Ser Met Gly Thr Leu Ile Ser Lys Ala Met Gly Ala Glu Thr Tyr Val
            195                 200                 205 att tct cgt tct tcg aga aaa aga gaa gat gca atg aag atg ggc gcc    672
Ile Ser Arg Ser Ser Arg Lys Arg Glu Asp Ala Met Lys Met Gly Ala
210                 215                 220 gat cac tac att gct aca tta gaa gaa ggt gat tgg ggt gaa aag tac    720
Asp His Tyr Ile Ala Thr Leu Glu Glu Gly Asp Trp Gly Glu Lys Tyr
225                 230                 235                 240 ttt gac acc ttc gac ctg att gta gtc tgt gct tcc tcc ctt acc gac    768
Phe Asp Thr Phe Asp Leu Ile Val Val Cys Ala Ser Ser Leu Thr Asp
                245                 250                 255 att gac ttc aac att atg cca aag gct atg aag gtt ggt ggt aga att    816
Ile Asp Phe Asn Ile Met Pro Lys Ala Met Lys Val Gly Gly Arg Ile
            260                 265                 270 gtc tca atc tct ata cca gaa caa cac gaa atg tta tcg cta aag cca    864
Val Ser Ile Ser Ile Pro Glu Gln His Glu Met Leu Ser Leu Lys Pro
        275                 280                 285 tat ggc tta aag gct gtc tcc att tct tac agt gct tta ggt tcc atc    912
Tyr Gly Leu Lys Ala Val Ser Ile Ser Tyr Ser Ala Leu Gly Ser Ile
290                 295                 300 aaa gaa ttg aac caa ctc ttg aaa tta gtc tct gaa aaa gat atc aaa    960
Lys Glu Leu Asn Gln Leu Leu Lys Leu Val Ser Glu Lys Asp Ile Lys
305                 310                 315                 320 att tgg gtg gaa aca tta cct gtt ggt gaa gcc ggc gtc cat gaa gcc   1008
Ile Trp Val Glu Thr Leu Pro Val Gly Glu Ala Gly Val His Glu Ala
                325                 330                 335 ttc gaa agg atg gaa aag ggt gac gtt aga tat aga ttt acc tta gtc   1056
Phe Glu Arg Met Glu Lys Gly Asp Val Arg Tyr Arg Phe Thr Leu Val
```

```
                     340          345          350
ggc tac gac aaa gaa ttt tca gac tag                          1083
Gly Tyr Asp Lys Glu Phe Ser Asp
        355                 360

<210> SEQ ID NO 30
<211> LENGTH: 360
<212> TYPE: PRT
<213> ORGANISM: Saccharomyces cerevisiae

<400> SEQUENCE: 30

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350
```

Gly Tyr Asp Lys Glu Phe Ser Asp
            355                 360

<210> SEQ ID NO 31
<211> LENGTH: 1161
<212> TYPE: DNA
<213> ORGANISM: Saccharomyces cerevisiae
<220> FEATURE:
<221> NAME/KEY: CDS
<222> LOCATION: (1)..(1161)
<223> OTHER INFORMATION: GenBank Accession No. NM_001180228

<400> SEQUENCE: 31

```
atg tcc gct gct act gtt ggt aaa cct att aag tgc att gct gct gtt       48
Met Ser Ala Ala Thr Val Gly Lys Pro Ile Lys Cys Ile Ala Ala Val
1               5                   10                  15 gcg tat gat gcg aag aaa cca tta agt gtt gaa gaa atc acg gta gac       96
Ala Tyr Asp Ala Lys Lys Pro Leu Ser Val Glu Glu Ile Thr Val Asp
                20                  25                  30 gcc cca aaa gcg cac gaa gta cgt atc aaa att gaa tat act gct gta      144
Ala Pro Lys Ala His Glu Val Arg Ile Lys Ile Glu Tyr Thr Ala Val
            35                  40                  45 tgc cac act gat gcg tac act tta tca ggc tct gat cca gaa gga ctt      192
Cys His Thr Asp Ala Tyr Thr Leu Ser Gly Ser Asp Pro Glu Gly Leu
        50                  55                  60 ttc cct tgc gtt ctg ggc cac gaa gga gcc ggt atc gta gaa tct gta      240
Phe Pro Cys Val Leu Gly His Glu Gly Ala Gly Ile Val Glu Ser Val
65                  70                  75                  80 ggc gat gat gtc ata aca gtt aag cct ggt gat cat gtt att gct ttg      288
Gly Asp Asp Val Ile Thr Val Lys Pro Gly Asp His Val Ile Ala Leu
                85                  90                  95 tac act gct gag tgt ggc aaa tgt aag ttc tgt act tcc ggt aaa acc      336
Tyr Thr Ala Glu Cys Gly Lys Cys Lys Phe Cys Thr Ser Gly Lys Thr
                100                 105                 110 aac tta tgt ggt gct gtt aga gct act caa ggg aaa ggt gta atg cct      384
Asn Leu Cys Gly Ala Val Arg Ala Thr Gln Gly Lys Gly Val Met Pro
            115                 120                 125 gat ggg acc aca aga ttt cat aat gcg aaa ggt gaa gat ata tac cat      432
Asp Gly Thr Thr Arg Phe His Asn Ala Lys Gly Glu Asp Ile Tyr His
        130                 135                 140 ttc atg ggt tgc tct act ttt tcc gaa tat act gtg gtg gca gat gtc      480
Phe Met Gly Cys Ser Thr Phe Ser Glu Tyr Thr Val Val Ala Asp Val
145                 150                 155                 160 tct gtg gtt gcc atc gat cca aaa gct ccc ttg gat gct gcc tgt tta      528
Ser Val Val Ala Ile Asp Pro Lys Ala Pro Leu Asp Ala Ala Cys Leu
                165                 170                 175 ctg ggt tgt ggt gtt act act ggt ttt ggg gcg gct ctt aag aca gct      576
Leu Gly Cys Gly Val Thr Thr Gly Phe Gly Ala Ala Leu Lys Thr Ala
                180                 185                 190 aat gtg caa aaa ggc gat acc gtt gca gta ttt ggc tgc ggg act gta      624
Asn Val Gln Lys Gly Asp Thr Val Ala Val Phe Gly Cys Gly Thr Val
            195                 200                 205 gga ctc tcc gtt atc caa ggt gca aag tta agg ggc gct tcc aag atc      672
Gly Leu Ser Val Ile Gln Gly Ala Lys Leu Arg Gly Ala Ser Lys Ile
        210                 215                 220 att gcc att gac att aac aat aag aaa aaa caa tat tgt tct caa ttt      720
Ile Ala Ile Asp Ile Asn Asn Lys Lys Lys Gln Tyr Cys Ser Gln Phe
225                 230                 235                 240 ggt gcc acg gat ttt gtt aat ccc aag gaa gat ttg gcc aaa gat caa      768
Gly Ala Thr Asp Phe Val Asn Pro Lys Glu Asp Leu Ala Lys Asp Gln
                245                 250                 255
```

```
act atc gtt gaa aag tta att gaa atg act gat ggg ggt ctg gat ttt      816
Thr Ile Val Glu Lys Leu Ile Glu Met Thr Asp Gly Gly Leu Asp Phe
        260                 265                 270 act ttt gac tgt act ggt aat acc aaa att atg aga gat gct ttg gaa      864
Thr Phe Asp Cys Thr Gly Asn Thr Lys Ile Met Arg Asp Ala Leu Glu
    275                 280                 285 gcc tgt cat aaa ggt tgg ggt caa tct att atc att ggt gtg gct gcc      912
Ala Cys His Lys Gly Trp Gly Gln Ser Ile Ile Ile Gly Val Ala Ala
290                 295                 300 gct ggt gaa gaa att tct aca agg ccg ttc cag ctg gtc act ggt aga      960
Ala Gly Glu Glu Ile Ser Thr Arg Pro Phe Gln Leu Val Thr Gly Arg
305                 310                 315                 320 gtg tgg aaa ggc tct gct ttt ggt ggc atc aaa ggt aga tct gaa atg     1008
Val Trp Lys Gly Ser Ala Phe Gly Gly Ile Lys Gly Arg Ser Glu Met
                325                 330                 335 ggc ggt tta att aaa gac tat caa aaa ggt gcc tta aaa gtc gaa gaa     1056
Gly Gly Leu Ile Lys Asp Tyr Gln Lys Gly Ala Leu Lys Val Glu Glu
            340                 345                 350 ttt atc act cac agg aga cca ttc aaa gaa atc aat caa gcc ttt gaa     1104
Phe Ile Thr His Arg Arg Pro Phe Lys Glu Ile Asn Gln Ala Phe Glu
        355                 360                 365 gat ttg cat aac ggt gat tgc tta aga acc gtc ttg aag tct gat gaa     1152
Asp Leu His Asn Gly Asp Cys Leu Arg Thr Val Leu Lys Ser Asp Glu
    370                 375                 380 ata aaa tag                                                         1161
Ile Lys
385

<210> SEQ ID NO 32
<211> LENGTH: 386
<212> TYPE: PRT
<213> ORGANISM: Saccharomyces cerevisiae

<400> SEQUENCE: 32

Met Ser Ala Ala Thr Val Gly Lys Pro Ile Lys Cys Ile Ala Ala Val
1               5                   10                  15

Ala Tyr Asp Ala Lys Lys Pro Leu Ser Val Glu Glu Ile Thr Val Asp
            20                  25                  30

Ala Pro Lys Ala His Glu Val Arg Ile Lys Ile Glu Tyr Thr Ala Val
        35                  40                  45

Cys His Thr Asp Ala Tyr Thr Leu Ser Gly Ser Asp Pro Glu Gly Leu
    50                  55                  60

Phe Pro Cys Val Leu Gly His Glu Gly Ala Gly Ile Val Glu Ser Val
65                  70                  75                  80

Gly Asp Asp Val Ile Thr Val Lys Pro Gly Asp His Val Ile Ala Leu
                85                  90                  95

Tyr Thr Ala Glu Cys Gly Lys Cys Lys Phe Cys Thr Ser Gly Lys Thr
            100                 105                 110

Asn Leu Cys Gly Ala Val Arg Ala Thr Gln Gly Lys Gly Val Met Pro
        115                 120                 125

Asp Gly Thr Thr Arg Phe His Asn Ala Lys Gly Glu Asp Ile Tyr His
    130                 135                 140

Phe Met Gly Cys Ser Thr Phe Ser Glu Tyr Thr Val Val Ala Asp Val
145                 150                 155                 160

Ser Val Val Ala Ile Asp Pro Lys Ala Pro Leu Asp Ala Ala Cys Leu
                165                 170                 175

Leu Gly Cys Gly Val Thr Thr Gly Phe Gly Ala Ala Leu Lys Thr Ala
```

```
                    180                 185                 190
Asn Val Gln Lys Gly Asp Thr Val Ala Val Phe Gly Cys Gly Thr Val
                195                 200                 205
Gly Leu Ser Val Ile Gln Gly Ala Lys Leu Arg Gly Ala Ser Lys Ile
            210                 215                 220
Ile Ala Ile Asp Ile Asn Asn Lys Lys Gln Tyr Cys Ser Gln Phe
225                 230                 235                 240
Gly Ala Thr Asp Phe Val Asn Pro Lys Glu Asp Leu Ala Lys Asp Gln
                245                 250                 255
Thr Ile Val Glu Lys Leu Ile Glu Met Thr Asp Gly Gly Leu Asp Phe
            260                 265                 270
Thr Phe Asp Cys Thr Gly Asn Thr Lys Ile Met Arg Asp Ala Leu Glu
        275                 280                 285
Ala Cys His Lys Gly Trp Gly Gln Ser Ile Ile Ile Gly Val Ala Ala
        290                 295                 300
Ala Gly Glu Glu Ile Ser Thr Arg Pro Phe Gln Leu Val Thr Gly Arg
305                 310                 315                 320
Val Trp Lys Gly Ser Ala Phe Gly Gly Ile Lys Gly Arg Ser Glu Met
                325                 330                 335
Gly Gly Leu Ile Lys Asp Tyr Gln Lys Gly Ala Leu Lys Val Glu Glu
            340                 345                 350
Phe Ile Thr His Arg Arg Pro Phe Lys Glu Ile Asn Gln Ala Phe Glu
        355                 360                 365
Asp Leu His Asn Gly Asp Cys Leu Arg Thr Val Leu Lys Ser Asp Glu
        370                 375                 380
Ile Lys
385

<210> SEQ ID NO 33
<211> LENGTH: 1092
<212> TYPE: DNA
<213> ORGANISM: Saccharomyces cerevisiae
<220> FEATURE:
<221> NAME/KEY: CDS
<222> LOCATION: (1)..(1092)
<223> OTHER INFORMATION: GenBank Accession No. NM_001178814

<400> SEQUENCE: 33 atg att ggg tcc gcg tcc gac tca tct agc aag tta gga cgc ctc cga      48
Met Ile Gly Ser Ala Ser Asp Ser Ser Ser Lys Leu Gly Arg Leu Arg
1               5                   10                  15 ttt ctt tct gaa act gcc gct att aaa gta ccg tta atc cta gga         96
Phe Leu Ser Glu Thr Ala Ala Ile Lys Val Ser Pro Leu Ile Leu Gly
            20                  25                  30 gaa gtc tca tac gat gga gca cgt tcg gat ttt ctc aaa tca atg aac    144
Glu Val Ser Tyr Asp Gly Ala Arg Ser Asp Phe Leu Lys Ser Met Asn
        35                  40                  45 aag aat cga gct ttt gaa ttg ctt gat act ttt tac gag gca ggt gga   192
Lys Asn Arg Ala Phe Glu Leu Leu Asp Thr Phe Tyr Glu Ala Gly Gly
    50                  55                  60 aat ttc att gat gcc gca aac aac tgc caa aac gag caa tca gaa gaa   240
Asn Phe Ile Asp Ala Ala Asn Asn Cys Gln Asn Glu Gln Ser Glu Glu
65                  70                  75                  80 tgg att ggt gaa tgg ata cag tcc aga agg tta cgt gat caa att gtc   288
Trp Ile Gly Glu Trp Ile Gln Ser Arg Arg Leu Arg Asp Gln Ile Val
                85                  90                  95 att gca acc aag ttt ata aaa agc gat aaa aag tat aaa gca ggt gaa   336
Ile Ala Thr Lys Phe Ile Lys Ser Asp Lys Lys Tyr Lys Ala Gly Glu
```

```
agt aac act gcc aac tac tgt ggt aat cac aag cgt agt tta cat gtg      384
Ser Asn Thr Ala Asn Tyr Cys Gly Asn His Lys Arg Ser Leu His Val
            115                 120                 125 agt gtg agg gat tct ctc cgc aaa ttg caa act gat tgg att gat ata      432
Ser Val Arg Asp Ser Leu Arg Lys Leu Gln Thr Asp Trp Ile Asp Ile
130                 135                 140 ctt tac gtt cac tgg tgg gat tat atg agt tca atc gaa gaa ttt atg      480
Leu Tyr Val His Trp Trp Asp Tyr Met Ser Ser Ile Glu Glu Phe Met
145                 150                 155                 160 gat agt ttg cat att ctg gtc cag cag ggc aag gtc ctc tat ttg ggt      528
Asp Ser Leu His Ile Leu Val Gln Gln Gly Lys Val Leu Tyr Leu Gly
                165                 170                 175 gta tct gat aca cct gct tgg gtt gtt tct gcg gca aac tac tac gct      576
Val Ser Asp Thr Pro Ala Trp Val Val Ser Ala Ala Asn Tyr Tyr Ala
            180                 185                 190 aca tct tat ggt aaa act ccc ttt agt atc tac caa ggt aaa tgg aac      624
Thr Ser Tyr Gly Lys Thr Pro Phe Ser Ile Tyr Gln Gly Lys Trp Asn
        195                 200                 205 gtg ttg aac aga gat ttt gag cgt gat att att cca atg gct agg cat      672
Val Leu Asn Arg Asp Phe Glu Arg Asp Ile Ile Pro Met Ala Arg His
210                 215                 220 ttc ggt atg gcc ctc gcc cca tgg gat gtc atg gga ggt gga aga ttt      720
Phe Gly Met Ala Leu Ala Pro Trp Asp Val Met Gly Gly Gly Arg Phe
225                 230                 235                 240 cag agt aaa aaa gca atg gag gaa cgg agg aag aat gga gag ggt att      768
Gln Ser Lys Lys Ala Met Glu Glu Arg Arg Lys Asn Gly Glu Gly Ile
                245                 250                 255 cgt tct ttc gtt ggc gcc tcc gaa caa aca gat gca gaa atc aag att      816
Arg Ser Phe Val Gly Ala Ser Glu Gln Thr Asp Ala Glu Ile Lys Ile
            260                 265                 270 agt gaa gca ttg gcc aag att gct gag gaa cat ggc act gag tct gtt      864
Ser Glu Ala Leu Ala Lys Ile Ala Glu Glu His Gly Thr Glu Ser Val
        275                 280                 285 act gct att gct att gcc tat gtt cgc tct aag gcg aaa aat ttt ttt      912
Thr Ala Ile Ala Ile Ala Tyr Val Arg Ser Lys Ala Lys Asn Phe Phe
290                 295                 300 ccg tcg gtt gaa gga gga aaa att gag gat ctc aaa gag aac att aag      960
Pro Ser Val Glu Gly Gly Lys Ile Glu Asp Leu Lys Glu Asn Ile Lys
305                 310                 315                 320 gct ctc agt atc gat cta acg cca gac aat ata aaa tac tta gaa agt     1008
Ala Leu Ser Ile Asp Leu Thr Pro Asp Asn Ile Lys Tyr Leu Glu Ser
                325                 330                 335 ata gtt cct ttt gac atc gga ttt cct aat aat ttt atc gtg tta aat     1056
Ile Val Pro Phe Asp Ile Gly Phe Pro Asn Asn Phe Ile Val Leu Asn
            340                 345                 350 tcc ttg act caa aaa tat ggt acg aat aat gtt tag                     1092
Ser Leu Thr Gln Lys Tyr Gly Thr Asn Asn Val
        355                 360

<210> SEQ ID NO 34
<211> LENGTH: 363
<212> TYPE: PRT
<213> ORGANISM: Saccharomyces cerevisiae

<400> SEQUENCE: 34

Met Ile Gly Ser Ala Ser Asp Ser Ser Lys Leu Gly Arg Leu Arg
1               5                   10                  15

Phe Leu Ser Glu Thr Ala Ala Ile Lys Val Ser Pro Leu Ile Leu Gly
                20                  25                  30
```

```
Glu Val Ser Tyr Asp Gly Ala Arg Ser Asp Phe Leu Lys Ser Met Asn
         35                  40                  45

Lys Asn Arg Ala Phe Glu Leu Leu Asp Thr Phe Tyr Glu Ala Gly Gly
     50                  55                  60

Asn Phe Ile Asp Ala Ala Asn Cys Gln Asn Glu Gln Ser Glu Glu
65                   70                  75                  80

Trp Ile Gly Glu Trp Ile Gln Ser Arg Arg Leu Arg Asp Gln Ile Val
                 85                  90                  95

Ile Ala Thr Lys Phe Ile Lys Ser Asp Lys Lys Tyr Lys Ala Gly Glu
             100                 105                 110

Ser Asn Thr Ala Asn Tyr Cys Gly Asn His Lys Arg Ser Leu His Val
         115                 120                 125

Ser Val Arg Asp Ser Leu Arg Lys Leu Gln Thr Asp Trp Ile Asp Ile
    130                 135                 140

Leu Tyr Val His Trp Trp Asp Tyr Met Ser Ser Ile Glu Glu Phe Met
145                 150                 155                 160

Asp Ser Leu His Ile Leu Val Gln Gln Gly Lys Val Leu Tyr Leu Gly
                165                 170                 175

Val Ser Asp Thr Pro Ala Trp Val Val Ser Ala Ala Asn Tyr Tyr Ala
            180                 185                 190

Thr Ser Tyr Gly Lys Thr Pro Phe Ser Ile Tyr Gln Gly Lys Trp Asn
        195                 200                 205

Val Leu Asn Arg Asp Phe Glu Arg Asp Ile Ile Pro Met Ala Arg His
    210                 215                 220

Phe Gly Met Ala Leu Ala Pro Trp Asp Val Met Gly Gly Gly Arg Phe
225                 230                 235                 240

Gln Ser Lys Lys Ala Met Glu Glu Arg Lys Asn Gly Glu Gly Ile
                245                 250                 255

Arg Ser Phe Val Gly Ala Ser Glu Gln Thr Asp Ala Glu Ile Lys Ile
            260                 265                 270

Ser Glu Ala Leu Ala Lys Ile Ala Glu Glu His Gly Thr Glu Ser Val
        275                 280                 285

Thr Ala Ile Ala Ile Ala Tyr Val Arg Ser Lys Ala Lys Asn Phe Phe
    290                 295                 300

Pro Ser Val Glu Gly Gly Lys Ile Glu Asp Leu Lys Glu Asn Ile Lys
305                 310                 315                 320

Ala Leu Ser Ile Asp Leu Thr Pro Asp Asn Ile Lys Tyr Leu Glu Ser
                325                 330                 335

Ile Val Pro Phe Asp Ile Gly Phe Pro Asn Asn Phe Ile Val Leu Asn
            340                 345                 350

Ser Leu Thr Gln Lys Tyr Gly Thr Asn Asn Val
        355                 360
```

<210> SEQ ID NO 35
<211> LENGTH: 990
<212> TYPE: DNA
<213> ORGANISM: Saccharomyces cerevisiae
<220> FEATURE:
<221> NAME/KEY: CDS
<222> LOCATION: (1)..(990)
<223> OTHER INFORMATION: GenBank Accession No. NM_001180303

<400> SEQUENCE: 35

```
atg ggc tct atg aat aag gaa cag gct ttt gaa ctt ctt gat gct ttt    48
Met Gly Ser Met Asn Lys Glu Gln Ala Phe Glu Leu Leu Asp Ala Phe
1               5                   10                  15
```

```
tat gaa gca gga ggt aat tgc att gat act gca aac agt tac caa aat     96
Tyr Glu Ala Gly Gly Asn Cys Ile Asp Thr Ala Asn Ser Tyr Gln Asn
         20                  25                  30 gaa gag tca gag att tgg ata ggt gaa tgg atg aaa tca aga aag ttg    144
Glu Glu Ser Glu Ile Trp Ile Gly Glu Trp Met Lys Ser Arg Lys Leu
 35                  40                  45 cgt gac caa att gta att gcc acc aag ttt acc gga gat tat aag aag    192
Arg Asp Gln Ile Val Ile Ala Thr Lys Phe Thr Gly Asp Tyr Lys Lys
         50                  55                  60 tat gaa gta ggt ggc ggt aaa agt gcc aac tat tgt ggt aat cac aag    240
Tyr Glu Val Gly Gly Gly Lys Ser Ala Asn Tyr Cys Gly Asn His Lys
 65                  70                  75                  80 cat agt tta cat gtg agt gtg agg gat tct ctc cgc aaa ttg caa act    288
His Ser Leu His Val Ser Val Arg Asp Ser Leu Arg Lys Leu Gln Thr
                 85                  90                  95 gat tgg att gat ata ctt tac gtt cac tgg tgg gat tat atg agt tca    336
Asp Trp Ile Asp Ile Leu Tyr Val His Trp Trp Asp Tyr Met Ser Ser
            100                 105                 110 atc gaa gaa gtt atg gat agt ttg cat att tta gtt cag cag ggc aaa    384
Ile Glu Glu Val Met Asp Ser Leu His Ile Leu Val Gln Gln Gly Lys
            115                 120                 125 gtc ctc tat ttg ggt gtg tct gat aca cct gct tgg gtt gtt tct gcg    432
Val Leu Tyr Leu Gly Val Ser Asp Thr Pro Ala Trp Val Val Ser Ala
130                 135                 140 gca aac tac tac gcc aca tct cat ggg aaa act cct ttt agt atc tat    480
Ala Asn Tyr Tyr Ala Thr Ser His Gly Lys Thr Pro Phe Ser Ile Tyr
145                 150                 155                 160 caa ggt aaa tgg aat gtg ttg aac agg gac ttt gag cgc gat atc att    528
Gln Gly Lys Trp Asn Val Leu Asn Arg Asp Phe Glu Arg Asp Ile Ile
                165                 170                 175 cca atg gcc aga cat ttt ggt atg gct cta gcc cca tgg gat gtt atg    576
Pro Met Ala Arg His Phe Gly Met Ala Leu Ala Pro Trp Asp Val Met
            180                 185                 190 gga ggt gga aga ttt cag agt aaa aaa gca atg gag gaa cgg aag aag    624
Gly Gly Gly Arg Phe Gln Ser Lys Lys Ala Met Glu Glu Arg Lys Lys
            195                 200                 205 aat gga gag ggt ctg cgt act gtt tcg ggt act tct aaa cag acg gat    672
Asn Gly Glu Gly Leu Arg Thr Val Ser Gly Thr Ser Lys Gln Thr Asp
210                 215                 220 aaa gag gtt aag atc agt gaa gca ttg gcc aag gtt gct gag gaa cat    720
Lys Glu Val Lys Ile Ser Glu Ala Leu Ala Lys Val Ala Glu Glu His
225                 230                 235                 240 ggc act gag tct gtt act gct att gct att gcc tat gtt cgc tct aag    768
Gly Thr Glu Ser Val Thr Ala Ile Ala Ile Ala Tyr Val Arg Ser Lys
                245                 250                 255 gcg aaa aat gtt ttc cca ttg gtt ggt gga agg aaa att gaa cac ctc    816
Ala Lys Asn Val Phe Pro Leu Val Gly Gly Arg Lys Ile Glu His Leu
            260                 265                 270 aaa cag aac att gag gct tta agt atc aaa ctg aca cca gaa cag ata    864
Lys Gln Asn Ile Glu Ala Leu Ser Ile Lys Leu Thr Pro Glu Gln Ile
            275                 280                 285 gaa tac tta gaa agt att att cct ttt gat gtt ggt ttt cct act aat    912
Glu Tyr Leu Glu Ser Ile Ile Pro Phe Asp Val Gly Phe Pro Thr Asn
            290                 295                 300 ttt atc ggt gat gat ccg gct gtt acc aag aag gct tca ctt ctc acg    960
Phe Ile Gly Asp Asp Pro Ala Val Thr Lys Lys Ala Ser Leu Leu Thr
305                 310                 315                 320 gca atg tct gcg cag att tcc ttc gat taa                            990
Ala Met Ser Ala Gln Ile Ser Phe Asp
```

325

<210> SEQ ID NO 36
<211> LENGTH: 329
<212> TYPE: PRT
<213> ORGANISM: Saccharomyces cerevisiae

<400> SEQUENCE: 36

Met Gly Ser Met Asn Lys Glu Gln Ala Phe Glu Leu Leu Asp Ala Phe
1               5                   10                  15

Tyr Glu Ala Gly Gly Asn Cys Ile Asp Thr Ala Asn Ser Tyr Gln Asn
            20                  25                  30

Glu Glu Ser Glu Ile Trp Ile Gly Glu Trp Met Lys Ser Arg Lys Leu
        35                  40                  45

Arg Asp Gln Ile Val Ile Ala Thr Lys Phe Thr Gly Asp Tyr Lys Lys
50                  55                  60

Tyr Glu Val Gly Gly Gly Lys Ser Ala Asn Tyr Cys Gly Asn His Lys
65                  70                  75                  80

His Ser Leu His Val Ser Val Arg Asp Ser Leu Arg Lys Leu Gln Thr
                85                  90                  95

Asp Trp Ile Asp Ile Leu Tyr Val His Trp Trp Asp Tyr Met Ser Ser
            100                 105                 110

Ile Glu Glu Val Met Asp Ser Leu His Ile Leu Val Gln Gln Gly Lys
        115                 120                 125

Val Leu Tyr Leu Gly Val Ser Asp Thr Pro Ala Trp Val Val Ser Ala
130                 135                 140

Ala Asn Tyr Tyr Ala Thr Ser His Gly Lys Thr Pro Phe Ser Ile Tyr
145                 150                 155                 160

Gln Gly Lys Trp Asn Val Leu Asn Arg Asp Phe Glu Arg Asp Ile Ile
                165                 170                 175

Pro Met Ala Arg His Phe Gly Met Ala Leu Ala Pro Trp Asp Val Met
            180                 185                 190

Gly Gly Gly Arg Phe Gln Ser Lys Lys Ala Met Glu Glu Arg Lys Lys
        195                 200                 205

Asn Gly Glu Gly Leu Arg Thr Val Ser Gly Thr Ser Lys Gln Thr Asp
210                 215                 220

Lys Glu Val Lys Ile Ser Glu Ala Leu Ala Lys Val Ala Glu His
225                 230                 235                 240

Gly Thr Glu Ser Val Thr Ala Ile Ala Ile Ala Tyr Val Arg Ser Lys
                245                 250                 255

Ala Lys Asn Val Phe Pro Leu Val Gly Gly Arg Lys Ile Glu His Leu
            260                 265                 270

Lys Gln Asn Ile Glu Ala Leu Ser Ile Lys Leu Thr Pro Glu Gln Ile
        275                 280                 285

Glu Tyr Leu Glu Ser Ile Ile Pro Phe Asp Val Gly Phe Pro Thr Asn
290                 295                 300

Phe Ile Gly Asp Asp Pro Ala Val Thr Lys Lys Ala Ser Leu Leu Thr
305                 310                 315                 320

Ala Met Ser Ala Gln Ile Ser Phe Asp
                325

<210> SEQ ID NO 37
<211> LENGTH: 639
<212> TYPE: DNA
<213> ORGANISM: Saccharomyces cerevisiae
<220> FEATURE:

```
<221> NAME/KEY: CDS
<222> LOCATION: (1)..(639)
<223> OTHER INFORMATION: GenBank Accession No. NM_001179911

<400> SEQUENCE: 37 atg gct gat tta ttt gct cct gct cct gaa cca tct aca gag tta gga       48
Met Ala Asp Leu Phe Ala Pro Ala Pro Glu Pro Ser Thr Glu Leu Gly
1               5                   10                  15 cgt ctc aga gtt ctt tct aaa agt gct ggt att aga gtt tcc cct ctc       96
Arg Leu Arg Val Leu Ser Lys Ser Ala Gly Ile Arg Val Ser Pro Leu
                20                  25                  30 att ttg gga gga atg tca att ggc gac gct tgg tct gaa atc cta gga      144
Ile Leu Gly Gly Met Ser Ile Gly Asp Ala Trp Ser Glu Ile Leu Gly
            35                  40                  45 tca atg agc aag gag cga gct ttt gag ttg ctc gat gct ttt tat gag      192
Ser Met Ser Lys Glu Arg Ala Phe Glu Leu Leu Asp Ala Phe Tyr Glu
50                  55                  60 gca ggt gga aat ttc att gat act gca aat aat tat caa aac gaa cag      240
Ala Gly Gly Asn Phe Ile Asp Thr Ala Asn Asn Tyr Gln Asn Glu Gln
65                  70                  75                  80 tca gaa gct tgg atc ggt gaa tgg atg gtt tca aga aaa tta cgc gac      288
Ser Glu Ala Trp Ile Gly Glu Trp Met Val Ser Arg Lys Leu Arg Asp
                85                  90                  95 cag att gta atc gcc acc aag ttt acc act gac tat aag aaa tac gac      336
Gln Ile Val Ile Ala Thr Lys Phe Thr Thr Asp Tyr Lys Lys Tyr Asp
            100                 105                 110 gtt ggt ggt ggt aaa agc gca aac tac tgt ggc aat cac aag cgt agt      384
Val Gly Gly Gly Lys Ser Ala Asn Tyr Cys Gly Asn His Lys Arg Ser
        115                 120                 125 ttg cat gtg agt gtg agg gat tct ctc cgc aaa ttg caa act gat tgg      432
Leu His Val Ser Val Arg Asp Ser Leu Arg Lys Leu Gln Thr Asp Trp
130                 135                 140 att gat ata ctt tac gtt cac tgg tgg gat tat atg agt tct atc gaa      480
Ile Asp Ile Leu Tyr Val His Trp Trp Asp Tyr Met Ser Ser Ile Glu
145                 150                 155                 160 gaa gtt atg gat agt tta cac att cta gtg cag cag gca agg tcc tct      528
Glu Val Met Asp Ser Leu His Ile Leu Val Gln Gln Ala Arg Ser Ser
                165                 170                 175 att tgg gtg tgt ctg ata cgc ctg cct ggg ttg ttt ctg cgg caa att      576
Ile Trp Val Cys Leu Ile Arg Leu Pro Gly Leu Phe Leu Arg Gln Ile
            180                 185                 190 act acg cta aat ctc atg gta aaa ccc ctt tta gca tct atc aag gta      624
Thr Thr Leu Asn Leu Met Val Lys Pro Leu Leu Ala Ser Ile Lys Val
        195                 200                 205 aat gga acc tgt tga                                                  639
Asn Gly Thr Cys
    210

<210> SEQ ID NO 38
<211> LENGTH: 212
<212> TYPE: PRT
<213> ORGANISM: Saccharomyces cerevisiae

<400> SEQUENCE: 38

Met Ala Asp Leu Phe Ala Pro Ala Pro Glu Pro Ser Thr Glu Leu Gly
1               5                   10                  15

Arg Leu Arg Val Leu Ser Lys Ser Ala Gly Ile Arg Val Ser Pro Leu
                20                  25                  30

Ile Leu Gly Gly Met Ser Ile Gly Asp Ala Trp Ser Glu Ile Leu Gly
            35                  40                  45
```

```
Ser Met Ser Lys Glu Arg Ala Phe Glu Leu Leu Asp Ala Phe Tyr Glu
    50                  55                  60

Ala Gly Gly Asn Phe Ile Asp Thr Ala Asn Asn Tyr Gln Asn Glu Gln
65                  70                  75                  80

Ser Glu Ala Trp Ile Gly Glu Trp Met Val Ser Arg Lys Leu Arg Asp
                85                  90                  95

Gln Ile Val Ile Ala Thr Lys Phe Thr Thr Asp Tyr Lys Lys Tyr Asp
                100                 105                 110

Val Gly Gly Gly Lys Ser Ala Asn Tyr Cys Gly Asn His Lys Arg Ser
                115                 120                 125

Leu His Val Ser Val Arg Asp Ser Leu Arg Lys Leu Gln Thr Asp Trp
130                 135                 140

Ile Asp Ile Leu Tyr Val His Trp Trp Asp Tyr Met Ser Ser Ile Glu
145                 150                 155                 160

Glu Val Met Asp Ser Leu His Ile Leu Val Gln Gln Ala Arg Ser Ser
                165                 170                 175

Ile Trp Val Cys Leu Ile Arg Leu Pro Gly Leu Phe Leu Arg Gln Ile
                180                 185                 190

Thr Thr Leu Asn Leu Met Val Lys Pro Leu Leu Ala Ser Ile Lys Val
                195                 200                 205

Asn Gly Thr Cys
            210

<210> SEQ ID NO 39
<211> LENGTH: 867
<212> TYPE: DNA
<213> ORGANISM: Saccharomyces cerevisiae
<220> FEATURE:
<221> NAME/KEY: CDS
<222> LOCATION: (1)..(867)
<223> OTHER INFORMATION: GenBank Accession No. NM_001181813

<400> SEQUENCE: 39 atg gca tca aga aaa ctg cgt gac cag att gta att gcc act aaa ttt      48
Met Ala Ser Arg Lys Leu Arg Asp Gln Ile Val Ile Ala Thr Lys Phe
1               5                   10                  15 acc acg gat tat aag ggg tat gat gta ggc aag ggg aag agt gcc aat      96
Thr Thr Asp Tyr Lys Gly Tyr Asp Val Gly Lys Gly Lys Ser Ala Asn
                20                  25                  30 ttc tgt ggg aat cac aag cgc agt ttg cat gta agt gtg aga gat tcc     144
Phe Cys Gly Asn His Lys Arg Ser Leu His Val Ser Val Arg Asp Ser
            35                  40                  45 ctt cgt aag ttg caa act gat tgg att gat att ctt tac gtt cac tgg     192
Leu Arg Lys Leu Gln Thr Asp Trp Ile Asp Ile Leu Tyr Val His Trp
50                  55                  60 tgg gat tat atg agc tcc att gag gaa gtt atg gat agt ttg cac att     240
Trp Asp Tyr Met Ser Ser Ile Glu Glu Val Met Asp Ser Leu His Ile
65                  70                  75                  80 ctt gtg cag cag ggc aaa gta ctc tat cta ggt gtg tct gat act cct     288
Leu Val Gln Gln Gly Lys Val Leu Tyr Leu Gly Val Ser Asp Thr Pro
                85                  90                  95 gcc tgg gtt gtt tct gca gca aat tac tac gcc aca tct cat ggt aaa     336
Ala Trp Val Val Ser Ala Ala Asn Tyr Tyr Ala Thr Ser His Gly Lys
                100                 105                 110 act ccc ttt agt atc tat caa ggt aaa tgg aat gta ttg aac agg gac     384
Thr Pro Phe Ser Ile Tyr Gln Gly Lys Trp Asn Val Leu Asn Arg Asp
            115                 120                 125 ttt gaa cgt gat atc att cca atg gct agg cat ttt ggt atg gct ctt     432
Phe Glu Arg Asp Ile Ile Pro Met Ala Arg His Phe Gly Met Ala Leu
```

```
                130             135                 140
gct cca tgg gat gtt atg gga ggc ggg aga ttt cag agt aaa aag gca    480
Ala Pro Trp Asp Val Met Gly Gly Gly Arg Phe Gln Ser Lys Lys Ala
145             150                 155                 160 gtg gaa gag cgg aag aag aaa gga gaa ggc ttg cgt acc ttt ttt ggt    528
Val Glu Glu Arg Lys Lys Lys Gly Glu Gly Leu Arg Thr Phe Phe Gly
                165                 170                 175 act tcg gaa cag acg gat atg gag gtt aaa atc agc gaa gca ttg tta    576
Thr Ser Glu Gln Thr Asp Met Glu Val Lys Ile Ser Glu Ala Leu Leu
            180                 185                 190 aaa gtt gcg gaa gaa cat ggc act gag tct gtc act gct att gcc ata    624
Lys Val Ala Glu Glu His Gly Thr Glu Ser Val Thr Ala Ile Ala Ile
        195                 200                 205 gct tat gtt cgg tct aaa gcg aaa cat gtt ttc cca tta gtg gga gga    672
Ala Tyr Val Arg Ser Lys Ala Lys His Val Phe Pro Leu Val Gly Gly
    210                 215                 220 aga aag atc gaa cat ctc aaa cag aac att gag gct ttg agc att aaa    720
Arg Lys Ile Glu His Leu Lys Gln Asn Ile Glu Ala Leu Ser Ile Lys
225                 230                 235                 240 tta aca cca gaa caa ata aag tac tta gaa agt att gtt cct ttt gat    768
Leu Thr Pro Glu Gln Ile Lys Tyr Leu Glu Ser Ile Val Pro Phe Asp
                245                 250                 255 gtc gga ttt ccc act aat ttt att gga gat gac cca gct gtt acc aag    816
Val Gly Phe Pro Thr Asn Phe Ile Gly Asp Asp Pro Ala Val Thr Lys
            260                 265                 270 aaa cct tca ttt ctc acc gaa atg tct gcc aag att agc ttc gaa gat    864
Lys Pro Ser Phe Leu Thr Glu Met Ser Ala Lys Ile Ser Phe Glu Asp
        275                 280                 285 tag                                                                867

<210> SEQ ID NO 40
<211> LENGTH: 288
<212> TYPE: PRT
<213> ORGANISM: Saccharomyces cerevisiae

<400> SEQUENCE: 40

Met Ala Ser Arg Lys Leu Arg Asp Gln Ile Val Ile Ala Thr Lys Phe
1               5                   10                  15

Thr Thr Asp Tyr Lys Gly Tyr Asp Val Gly Lys Gly Lys Ser Ala Asn
                20                  25                  30

Phe Cys Gly Asn His Lys Arg Ser Leu His Val Ser Val Arg Asp Ser
            35                  40                  45

Leu Arg Lys Leu Gln Thr Asp Trp Ile Asp Ile Leu Tyr Val His Trp
        50                  55                  60

Trp Asp Tyr Met Ser Ser Ile Glu Glu Val Met Asp Ser Leu His Ile
65                  70                  75                  80

Leu Val Gln Gln Gly Lys Val Leu Tyr Leu Gly Val Ser Asp Thr Pro
                85                  90                  95

Ala Trp Val Val Ser Ala Ala Asn Tyr Tyr Ala Thr Ser His Gly Lys
            100                 105                 110

Thr Pro Phe Ser Ile Tyr Gln Gly Lys Trp Asn Val Leu Asn Arg Asp
        115                 120                 125

Phe Glu Arg Asp Ile Ile Pro Met Ala Arg His Phe Gly Met Ala Leu
    130                 135                 140

Ala Pro Trp Asp Val Met Gly Gly Gly Arg Phe Gln Ser Lys Lys Ala
145                 150                 155                 160

Val Glu Glu Arg Lys Lys Lys Gly Glu Gly Leu Arg Thr Phe Phe Gly
```

```
                    165                 170                 175
Thr Ser Glu Gln Thr Asp Met Glu Val Lys Ile Ser Glu Ala Leu Leu
            180                 185                 190

Lys Val Ala Glu Glu His Gly Thr Glu Ser Val Thr Ala Ile Ala Ile
                195                 200                 205

Ala Tyr Val Arg Ser Lys Ala Lys His Val Phe Pro Leu Val Gly Gly
            210                 215                 220

Arg Lys Ile Glu His Leu Lys Gln Asn Ile Glu Ala Leu Ser Ile Lys
225                 230                 235                 240

Leu Thr Pro Glu Gln Ile Lys Tyr Leu Glu Ser Ile Val Pro Phe Asp
                245                 250                 255

Val Gly Phe Pro Thr Asn Phe Ile Gly Asp Asp Pro Ala Val Thr Lys
            260                 265                 270

Lys Pro Ser Phe Leu Thr Glu Met Ser Ala Lys Ile Ser Phe Glu Asp
            275                 280                 285

<210> SEQ ID NO 41
<211> LENGTH: 1131
<212> TYPE: DNA
<213> ORGANISM: Saccharomyces cerevisiae
<220> FEATURE:
<221> NAME/KEY: CDS
<222> LOCATION: (1)..(1131)
<223> OTHER INFORMATION: GenBank Accession No. NM_001183169

<400> SEQUENCE: 41 atg act gac ttg ttt aaa cct cta cct gaa cca cct acc gaa ttg gga      48
Met Thr Asp Leu Phe Lys Pro Leu Pro Glu Pro Pro Thr Glu Leu Gly
1               5                   10                  15 cgt ctc agg gtt ctt tct aaa act gcc ggc ata agg gtt tca ccg cta      96
Arg Leu Arg Val Leu Ser Lys Thr Ala Gly Ile Arg Val Ser Pro Leu
                20                  25                  30 att ctg gga gga gct tca atc ggc gac gca tgg tca ggc ttt atg ggc     144
Ile Leu Gly Gly Ala Ser Ile Gly Asp Ala Trp Ser Gly Phe Met Gly
            35                  40                  45 tct atg aat aag gaa cag gcc ttt gaa ctt ctt gat gct ttt tat gaa     192
Ser Met Asn Lys Glu Gln Ala Phe Glu Leu Leu Asp Ala Phe Tyr Glu
        50                  55                  60 gct gga ggt aat tgt att gat act gca aac agt tac caa aat gaa gag     240
Ala Gly Gly Asn Cys Ile Asp Thr Ala Asn Ser Tyr Gln Asn Glu Glu
65                  70                  75                  80 tca gag att tgg ata ggt gaa tgg atg gca tca aga aaa ctg cgt gac     288
Ser Glu Ile Trp Ile Gly Glu Trp Met Ala Ser Arg Lys Leu Arg Asp
                85                  90                  95 cag att gta att gcc acc aag ttt acc gga gat tat aag aag tat gaa     336
Gln Ile Val Ile Ala Thr Lys Phe Thr Gly Asp Tyr Lys Lys Tyr Glu
                100                 105                 110 gta ggt ggt ggt aaa agt gcc aac tac tgt ggt aat cac aag cgt agt     384
Val Gly Gly Gly Lys Ser Ala Asn Tyr Cys Gly Asn His Lys Arg Ser
            115                 120                 125 tta cat gtg agt gtg agg gat tct ctc cgc aaa ttg caa act gat tgg     432
Leu His Val Ser Val Arg Asp Ser Leu Arg Lys Leu Gln Thr Asp Trp
        130                 135                 140 att gat ata ctt tac att cac tgg tgg gat tat atg agt tca atc gaa     480
Ile Asp Ile Leu Tyr Ile His Trp Trp Asp Tyr Met Ser Ser Ile Glu
145                 150                 155                 160 gaa gtt atg gat agt ttg cat att tta gtt cag cag ggc aag gtc cta     528
Glu Val Met Asp Ser Leu His Ile Leu Val Gln Gln Gly Lys Val Leu
                165                 170                 175
```

| | | |
|---|---|---|
| tat tta gga gta tct gat aca cct gct tgg gtt gtt tct gcg gca aat<br>Tyr Leu Gly Val Ser Asp Thr Pro Ala Trp Val Val Ser Ala Ala Asn<br>180 185 190 | | 576 |
| tac tac gct aca tct cat ggt aaa act cct ttt agc gtc tat caa ggt<br>Tyr Tyr Ala Thr Ser His Gly Lys Thr Pro Phe Ser Val Tyr Gln Gly<br>195 200 205 | | 624 |
| aaa tgg aat gta ttg aac agg gac ttt gag cgt gat att att cca atg<br>Lys Trp Asn Val Leu Asn Arg Asp Phe Glu Arg Asp Ile Ile Pro Met<br>210 215 220 | | 672 |
| gct agg cat ttt ggt atg gct cta gcc cca tgg gat gtc atg gga ggt<br>Ala Arg His Phe Gly Met Ala Leu Ala Pro Trp Asp Val Met Gly Gly<br>225 230 235 240 | | 720 |
| gga aga ttt cag agt aaa aaa gca atg gaa gaa cgg aag aag aat gga<br>Gly Arg Phe Gln Ser Lys Lys Ala Met Glu Glu Arg Lys Lys Asn Gly<br>245 250 255 | | 768 |
| gag ggt ctg cgt act ttt gtg ggt ggc ccc gaa caa aca gaa ttg gag<br>Glu Gly Leu Arg Thr Phe Val Gly Gly Pro Glu Gln Thr Glu Leu Glu<br>260 265 270 | | 816 |
| gtt aaa atc agc gaa gca ttg act aaa att gct gag gaa cat gga aca<br>Val Lys Ile Ser Glu Ala Leu Thr Lys Ile Ala Glu Glu His Gly Thr<br>275 280 285 | | 864 |
| gag tct gtt act gct atc gct att gcc tat gtt cgc tct aaa gcg aaa<br>Glu Ser Val Thr Ala Ile Ala Ile Ala Tyr Val Arg Ser Lys Ala Lys<br>290 295 300 | | 912 |
| aat gtt ttc cca ttg att gga gga agg aaa att gaa cat ctc aag cag<br>Asn Val Phe Pro Leu Ile Gly Gly Arg Lys Ile Glu His Leu Lys Gln<br>305 310 315 320 | | 960 |
| aac att gag gct ttg agt att aaa tta aca ccg gaa caa ata gaa tac<br>Asn Ile Glu Ala Leu Ser Ile Lys Leu Thr Pro Glu Gln Ile Glu Tyr<br>325 330 335 | | 1008 |
| ctg gaa agt att gtt cct ttt gat gtt ggc ttt ccc aaa agt tta ata<br>Leu Glu Ser Ile Val Pro Phe Asp Val Gly Phe Pro Lys Ser Leu Ile<br>340 345 350 | | 1056 |
| gga gat gac cca gcg gta acc aag aag ctt tca ccc ctc aca tcg atg<br>Gly Asp Asp Pro Ala Val Thr Lys Lys Leu Ser Pro Leu Thr Ser Met<br>355 360 365 | | 1104 |
| tct gcc agg ata gct ttt gac aat tag<br>Ser Ala Arg Ile Ala Phe Asp Asn<br>370 375 | | 1131 |

<210> SEQ ID NO 42
<211> LENGTH: 376
<212> TYPE: PRT
<213> ORGANISM: Saccharomyces cerevisiae

<400> SEQUENCE: 42

Met Thr Asp Leu Phe Lys Pro Leu Pro Glu Pro Pro Thr Glu Leu Gly
1               5                   10                  15

Arg Leu Arg Val Leu Ser Lys Thr Ala Gly Ile Arg Val Ser Pro Leu
            20                  25                  30

Ile Leu Gly Gly Ala Ser Ile Gly Asp Ala Trp Ser Gly Phe Met Gly
        35                  40                  45

Ser Met Asn Lys Glu Gln Ala Phe Glu Leu Leu Asp Ala Phe Tyr Glu
    50                  55                  60

Ala Gly Gly Asn Cys Ile Asp Thr Ala Asn Ser Tyr Gln Asn Glu Glu
65                  70                  75                  80

Ser Glu Ile Trp Ile Gly Glu Trp Met Ala Ser Arg Lys Leu Arg Asp
                85                  90                  95

Gln Ile Val Ile Ala Thr Lys Phe Thr Gly Asp Tyr Lys Lys Tyr Glu

```
                100                 105                 110
Val Gly Gly Gly Lys Ser Ala Asn Tyr Cys Gly Asn His Lys Arg Ser
            115                 120                 125

Leu His Val Ser Val Arg Asp Ser Leu Arg Lys Leu Gln Thr Asp Trp
130                 135                 140

Ile Asp Ile Leu Tyr Ile His Trp Trp Asp Tyr Met Ser Ser Ile Glu
145                 150                 155                 160

Glu Val Met Asp Ser Leu His Ile Leu Val Gln Gln Gly Lys Val Leu
                165                 170                 175

Tyr Leu Gly Val Ser Asp Thr Pro Ala Trp Val Val Ser Ala Ala Asn
            180                 185                 190

Tyr Tyr Ala Thr Ser His Gly Lys Thr Pro Phe Ser Val Tyr Gln Gly
        195                 200                 205

Lys Trp Asn Val Leu Asn Arg Asp Phe Glu Arg Asp Ile Ile Pro Met
    210                 215                 220

Ala Arg His Phe Gly Met Ala Leu Ala Pro Trp Asp Val Met Gly Gly
225                 230                 235                 240

Gly Arg Phe Gln Ser Lys Lys Ala Met Glu Glu Arg Lys Lys Asn Gly
                245                 250                 255

Glu Gly Leu Arg Thr Phe Val Gly Gly Pro Glu Gln Thr Glu Leu Glu
            260                 265                 270

Val Lys Ile Ser Glu Ala Leu Thr Lys Ile Ala Glu Glu His Gly Thr
        275                 280                 285

Glu Ser Val Thr Ala Ile Ala Ile Ala Tyr Val Arg Ser Lys Ala Lys
    290                 295                 300

Asn Val Phe Pro Leu Ile Gly Gly Arg Lys Ile Glu His Leu Lys Gln
305                 310                 315                 320

Asn Ile Glu Ala Leu Ser Ile Lys Leu Thr Pro Glu Gln Ile Glu Tyr
                325                 330                 335

Leu Glu Ser Ile Val Pro Phe Asp Val Gly Phe Pro Lys Ser Leu Ile
            340                 345                 350

Gly Asp Asp Pro Ala Val Thr Lys Lys Leu Ser Pro Leu Thr Ser Met
        355                 360                 365

Ser Ala Arg Ile Ala Phe Asp Asn
    370                 375

<210> SEQ ID NO 43
<211> LENGTH: 432
<212> TYPE: DNA
<213> ORGANISM: Saccharomyces cerevisiae
<220> FEATURE:
<221> NAME/KEY: CDS
<222> LOCATION: (1)..(432)
<223> OTHER INFORMATION: GenBank Accession No. NM_001183418

<400> SEQUENCE: 43 atg gct agg cat ttc ggt atg gcc ctc gcc cca tgg gat gtc atg gga    48
Met Ala Arg His Phe Gly Met Ala Leu Ala Pro Trp Asp Val Met Gly
1               5                   10                  15 ggt gga aga ttt cag agt aaa aaa gca atg gag gaa cgg agg aag aat    96
Gly Gly Arg Phe Gln Ser Lys Lys Ala Met Glu Glu Arg Arg Lys Asn
            20                  25                  30 gga gag tgt att cgt tct ttc gtt ggc gcc tcc gaa caa aca gat gca    144
Gly Glu Cys Ile Arg Ser Phe Val Gly Ala Ser Glu Gln Thr Asp Ala
        35                  40                  45 gaa atc aag att agt gaa gca tta gcc aag gtt gct gag gaa cat ggc    192
Glu Ile Lys Ile Ser Glu Ala Leu Ala Lys Val Ala Glu Glu His Gly
```

```
act gag tct gtt act gct att gct att gcc tat gtt cgc tct aag gcg        240
Thr Glu Ser Val Thr Ala Ile Ala Ile Ala Tyr Val Arg Ser Lys Ala
 65                  70                  75                  80 aaa aat gtt ttt ccg tcg gtt gaa gga gga aaa att gag gat ctc aaa        288
Lys Asn Val Phe Pro Ser Val Glu Gly Gly Lys Ile Glu Asp Leu Lys
                 85                  90                  95 gag aac att aag gct ctc agt atc gat cta acg ccg gac aat ata aaa        336
Glu Asn Ile Lys Ala Leu Ser Ile Asp Leu Thr Pro Asp Asn Ile Lys
            100                 105                 110 tac ttg gaa aat gta gtt cct ttt gac atc gga ttt cct aac act ttt        384
Tyr Leu Glu Asn Val Val Pro Phe Asp Ile Gly Phe Pro Asn Thr Phe
        115                 120                 125 atc gtg tta aat tcc ttg act caa aaa tat ggt acg aat aat gtt tag        432
Ile Val Leu Asn Ser Leu Thr Gln Lys Tyr Gly Thr Asn Asn Val
    130                 135                 140

<210> SEQ ID NO 44
<211> LENGTH: 143
<212> TYPE: PRT
<213> ORGANISM: Saccharomyces cerevisiae

<400> SEQUENCE: 44

Met Ala Arg His Phe Gly Met Ala Leu Ala Pro Trp Asp Val Met Gly
1               5                   10                  15

Gly Gly Arg Phe Gln Ser Lys Lys Ala Met Glu Glu Arg Arg Lys Asn
            20                  25                  30

Gly Glu Cys Ile Arg Ser Phe Val Gly Ala Ser Glu Gln Thr Asp Ala
        35                  40                  45

Glu Ile Lys Ile Ser Glu Ala Leu Ala Lys Val Ala Glu Glu His Gly
    50                  55                  60

Thr Glu Ser Val Thr Ala Ile Ala Ile Ala Tyr Val Arg Ser Lys Ala
65                  70                  75                  80

Lys Asn Val Phe Pro Ser Val Glu Gly Gly Lys Ile Glu Asp Leu Lys
                85                  90                  95

Glu Asn Ile Lys Ala Leu Ser Ile Asp Leu Thr Pro Asp Asn Ile Lys
            100                 105                 110

Tyr Leu Glu Asn Val Val Pro Phe Asp Ile Gly Phe Pro Asn Thr Phe
        115                 120                 125

Ile Val Leu Asn Ser Leu Thr Gln Lys Tyr Gly Thr Asn Asn Val
    130                 135                 140

<210> SEQ ID NO 45
<211> LENGTH: 459
<212> TYPE: DNA
<213> ORGANISM: Saccharomyces cerevisiae
<220> FEATURE:
<221> NAME/KEY: CDS
<222> LOCATION: (1)..(459)
<223> OTHER INFORMATION: GenBank Accession No. NM_001179910

<400> SEQUENCE: 45 atg gct agg cat ttc ggt atg gcc ctc gcc cca tgg gat gtc atg gga        48
Met Ala Arg His Phe Gly Met Ala Leu Ala Pro Trp Asp Val Met Gly
1               5                   10                  15 ggt gga aga ttt cag agt aaa aaa gca atg gag gaa cgg agg aag aat        96
Gly Gly Arg Phe Gln Ser Lys Lys Ala Met Glu Glu Arg Arg Lys Asn
            20                  25                  30 gga gag ggt att cgt tct ttc gtt ggc gcc tct gaa caa aca gat gca       144
Gly Glu Gly Ile Arg Ser Phe Val Gly Ala Ser Glu Gln Thr Asp Ala
```

```
                    35                  40                  45
gaa atc aag att agt gaa gca ttg gcc aag gtt gct gag gaa cat ggc       192
Glu Ile Lys Ile Ser Glu Ala Leu Ala Lys Val Ala Glu Glu His Gly
 50                  55                  60 act gaa tct gtt act gct att gct att gcc tat gtt cgc tct aag gcg      240
Thr Glu Ser Val Thr Ala Ile Ala Ile Ala Tyr Val Arg Ser Lys Ala
 65                  70                  75                  80 aaa aat gtt ttt cca ttg gtt gga gga agg aaa att gaa cac ctc aaa      288
Lys Asn Val Phe Pro Leu Val Gly Gly Arg Lys Ile Glu His Leu Lys
                     85                  90                  95 cag aac att gag gct ttg agc att aaa tta aca cca gaa caa ata aag      336
Gln Asn Ile Glu Ala Leu Ser Ile Lys Leu Thr Pro Glu Gln Ile Lys
                 100                 105                 110 tac tta gaa agt att att cct ttt gat gtt ggt ttt cct act aat ttt      384
Tyr Leu Glu Ser Ile Ile Pro Phe Asp Val Gly Phe Pro Thr Asn Phe
             115                 120                 125 atc ggt gat gat ccg gct gtt acc aag aag gct tca ctt ctc acg gca      432
Ile Gly Asp Asp Pro Ala Val Thr Lys Lys Ala Ser Leu Leu Thr Ala
130                 135                 140 atg tct gcg cag att tcc ttc gat taa                                  459
Met Ser Ala Gln Ile Ser Phe Asp
145                 150
```

<210> SEQ ID NO 46
<211> LENGTH: 152
<212> TYPE: PRT
<213> ORGANISM: Saccharomyces cerevisiae

<400> SEQUENCE: 46

```
Met Ala Arg His Phe Gly Met Ala Leu Ala Pro Trp Asp Val Met Gly
  1               5                  10                  15

Gly Gly Arg Phe Gln Ser Lys Lys Ala Met Glu Glu Arg Arg Lys Asn
                 20                  25                  30

Gly Glu Gly Ile Arg Ser Phe Val Gly Ala Ser Glu Gln Thr Asp Ala
             35                  40                  45

Glu Ile Lys Ile Ser Glu Ala Leu Ala Lys Val Ala Glu Glu His Gly
 50                  55                  60

Thr Glu Ser Val Thr Ala Ile Ala Ile Ala Tyr Val Arg Ser Lys Ala
 65                  70                  75                  80

Lys Asn Val Phe Pro Leu Val Gly Gly Arg Lys Ile Glu His Leu Lys
                 85                  90                  95

Gln Asn Ile Glu Ala Leu Ser Ile Lys Leu Thr Pro Glu Gln Ile Lys
            100                 105                 110

Tyr Leu Glu Ser Ile Ile Pro Phe Asp Val Gly Phe Pro Thr Asn Phe
        115                 120                 125

Ile Gly Asp Asp Pro Ala Val Thr Lys Lys Ala Ser Leu Leu Thr Ala
    130                 135                 140

Met Ser Ala Gln Ile Ser Phe Asp
145                 150
```

<210> SEQ ID NO 47
<211> LENGTH: 1029
<212> TYPE: DNA
<213> ORGANISM: Saccharomyces cerevisiae
<220> FEATURE:
<221> NAME/KEY: CDS
<222> LOCATION: (1)..(1029)
<223> OTHER INFORMATION: GenBank Accession No. NM_001183902

<400> SEQUENCE: 47

```
atg gtt tta gtt aag cag gta aga ctc ggt aac tca ggt ctt aag ata    48
Met Val Leu Val Lys Gln Val Arg Leu Gly Asn Ser Gly Leu Lys Ile
1               5                   10                  15 tca ccg ata gtg ata gga tgt atg tca tac ggg tcc aag aaa tgg gcg    96
Ser Pro Ile Val Ile Gly Cys Met Ser Tyr Gly Ser Lys Lys Trp Ala
                20                  25                  30 gac tgg gtc ata gag gac aag acc caa att ttc aag att atg aag cat   144
Asp Trp Val Ile Glu Asp Lys Thr Gln Ile Phe Lys Ile Met Lys His
            35                  40                  45 tgt tac gat aaa ggt ctt cgt act ttt gac aca gca gat ttt tat tct   192
Cys Tyr Asp Lys Gly Leu Arg Thr Phe Asp Thr Ala Asp Phe Tyr Ser
        50                  55                  60 aat ggt ttg agt gaa aga ata att aag gag ttt ctg gag tac tac agt   240
Asn Gly Leu Ser Glu Arg Ile Ile Lys Glu Phe Leu Glu Tyr Tyr Ser
65                  70                  75                  80 ata aag aga gaa acg gtg gtg att atg acc aaa att tac ttc cca gtt   288
Ile Lys Arg Glu Thr Val Val Ile Met Thr Lys Ile Tyr Phe Pro Val
                85                  90                  95 gat gaa acg ctt gat ttg cat cat aac ttc act tta aat gaa ttt gaa   336
Asp Glu Thr Leu Asp Leu His His Asn Phe Thr Leu Asn Glu Phe Glu
            100                 105                 110 gaa ttg gac ttg tcc aac cag cgg ggt tta tcc aga aag cat ata att   384
Glu Leu Asp Leu Ser Asn Gln Arg Gly Leu Ser Arg Lys His Ile Ile
        115                 120                 125 gct ggt gtc gag aac tct gtg aaa aga ctg ggc aca tat ata gac ctt   432
Ala Gly Val Glu Asn Ser Val Lys Arg Leu Gly Thr Tyr Ile Asp Leu
130                 135                 140 tta caa att cac aga tta gat cat gaa acg cca atg aaa gag atc atg   480
Leu Gln Ile His Arg Leu Asp His Glu Thr Pro Met Lys Glu Ile Met
145                 150                 155                 160 aag gca ttg aat gat gtt gtt gaa gcg ggc cac gtt aga tac att ggg   528
Lys Ala Leu Asn Asp Val Val Glu Ala Gly His Val Arg Tyr Ile Gly
                165                 170                 175 gct tcg agt atg ttg gca act gaa ttt gca gaa ctg cag ttc aca gcc   576
Ala Ser Ser Met Leu Ala Thr Glu Phe Ala Glu Leu Gln Phe Thr Ala
            180                 185                 190 gat aaa tat ggc tgg ttt cag ttc att tct tcg cag tct tac tac aat   624
Asp Lys Tyr Gly Trp Phe Gln Phe Ile Ser Ser Gln Ser Tyr Tyr Asn
        195                 200                 205 ttg ctc tat cgt gaa gat gaa cgc gaa ttg att cct ttt gcc aaa aga   672
Leu Leu Tyr Arg Glu Asp Glu Arg Glu Leu Ile Pro Phe Ala Lys Arg
210                 215                 220 cac aat att ggt tta ctt cca tgg tct cct aac gca cga ggc atg ttg   720
His Asn Ile Gly Leu Leu Pro Trp Ser Pro Asn Ala Arg Gly Met Leu
225                 230                 235                 240 act cgt cct ctg aac caa agc acg gac agg att aag agt gat cca act   768
Thr Arg Pro Leu Asn Gln Ser Thr Asp Arg Ile Lys Ser Asp Pro Thr
                245                 250                 255 ttc aag tcg tta cat ttg gat aat ctc gaa gaa gaa caa aag gaa att   816
Phe Lys Ser Leu His Leu Asp Asn Leu Glu Glu Glu Gln Lys Glu Ile
            260                 265                 270 ata aat cgt gtg gaa aag gtg tcg aag gac aaa aaa gtc tcg atg gct   864
Ile Asn Arg Val Glu Lys Val Ser Lys Asp Lys Lys Val Ser Met Ala
        275                 280                 285 atg ctc tcc att gca tgg gtt ttg cat aaa gga tgt cac cct att gtg   912
Met Leu Ser Ile Ala Trp Val Leu His Lys Gly Cys His Pro Ile Val
290                 295                 300 gga ttg aac act aca gca aga gta gac gaa gcg att gcc gca cta caa   960
Gly Leu Asn Thr Thr Ala Arg Val Asp Glu Ala Ile Ala Ala Leu Gln
```

```
                    305                 310                 315                 320
gta act cta aca gaa gaa gag ata aag tac ctc gag gag ccc tac aaa              1008
Val Thr Leu Thr Glu Glu Glu Ile Lys Tyr Leu Glu Glu Pro Tyr Lys
                    325                 330                 335 ccc cag agg caa aga tgt taa                                                  1029
Pro Gln Arg Gln Arg Cys
                    340

<210> SEQ ID NO 48
<211> LENGTH: 342
<212> TYPE: PRT
<213> ORGANISM: Saccharomyces cerevisiae

<400> SEQUENCE: 48

Met Val Leu Val Lys Gln Val Arg Leu Gly Asn Ser Gly Leu Lys Ile
1               5                   10                  15

Ser Pro Ile Val Ile Gly Cys Met Ser Tyr Gly Ser Lys Lys Trp Ala
                20                  25                  30

Asp Trp Val Ile Glu Asp Lys Thr Gln Ile Phe Lys Ile Met Lys His
            35                  40                  45

Cys Tyr Asp Lys Gly Leu Arg Thr Phe Asp Thr Ala Asp Phe Tyr Ser
        50                  55                  60

Asn Gly Leu Ser Glu Arg Ile Ile Lys Glu Phe Leu Glu Tyr Tyr Ser
65                  70                  75                  80

Ile Lys Arg Glu Thr Val Val Ile Met Thr Lys Ile Tyr Phe Pro Val
                85                  90                  95

Asp Glu Thr Leu Asp Leu His His Asn Phe Thr Leu Asn Glu Phe Glu
            100                 105                 110

Glu Leu Asp Leu Ser Asn Gln Arg Gly Leu Ser Arg Lys His Ile Ile
        115                 120                 125

Ala Gly Val Glu Asn Ser Val Lys Arg Leu Gly Thr Tyr Ile Asp Leu
    130                 135                 140

Leu Gln Ile His Arg Leu Asp His Glu Thr Pro Met Lys Glu Ile Met
145                 150                 155                 160

Lys Ala Leu Asn Asp Val Val Glu Ala Gly His Val Arg Tyr Ile Gly
                165                 170                 175

Ala Ser Ser Met Leu Ala Thr Glu Phe Ala Glu Leu Gln Phe Thr Ala
            180                 185                 190

Asp Lys Tyr Gly Trp Phe Gln Phe Ile Ser Ser Gln Ser Tyr Tyr Asn
        195                 200                 205

Leu Leu Tyr Arg Glu Asp Glu Arg Glu Leu Ile Pro Phe Ala Lys Arg
    210                 215                 220

His Asn Ile Gly Leu Leu Pro Trp Ser Pro Asn Ala Arg Gly Met Leu
225                 230                 235                 240

Thr Arg Pro Leu Asn Gln Ser Thr Asp Arg Ile Lys Ser Asp Pro Thr
                245                 250                 255

Phe Lys Ser Leu His Leu Asp Asn Leu Glu Glu Glu Gln Lys Glu Ile
            260                 265                 270

Ile Asn Arg Val Glu Lys Val Ser Lys Asp Lys Val Ser Met Ala
        275                 280                 285

Met Leu Ser Ile Ala Trp Val Leu His Lys Gly Cys His Pro Ile Val
    290                 295                 300

Gly Leu Asn Thr Thr Ala Arg Val Asp Glu Ala Ile Ala Ala Leu Gln
305                 310                 315                 320

Val Thr Leu Thr Glu Glu Glu Ile Lys Tyr Leu Glu Glu Pro Tyr Lys
```

```
                    325                 330                 335
Pro Gln Arg Gln Arg Cys
                340

<210> SEQ ID NO 49
<211> LENGTH: 4536
<212> TYPE: DNA
<213> ORGANISM: Saccharomyces cerevisiae
<220> FEATURE:
<221> NAME/KEY: CDS
<222> LOCATION: (1)..(4536)
<223> OTHER INFORMATION: GenBank Accession No. NM_001183872

<400> SEQUENCE: 49 atg tct tcg act gac gaa cat att gag aaa gac att tcg tcg aga tcg      48
Met Ser Ser Thr Asp Glu His Ile Glu Lys Asp Ile Ser Ser Arg Ser
1               5                   10                  15 aac cat gac gat gat tat gct aat tcg gta caa tcc tac gct gcc tcc      96
Asn His Asp Asp Asp Tyr Ala Asn Ser Val Gln Ser Tyr Ala Ala Ser
            20                  25                  30 gaa ggc caa gtt gat aat gag gat ttg gca gcc act tct cag cta tcc     144
Glu Gly Gln Val Asp Asn Glu Asp Leu Ala Ala Thr Ser Gln Leu Ser
        35                  40                  45 cgt cac ctt tca aac att ctt tcc aat gaa gaa ggt att gaa agg ttg     192
Arg His Leu Ser Asn Ile Leu Ser Asn Glu Glu Gly Ile Glu Arg Leu
    50                  55                  60 gag tct atg gcg aga gtc att tca cat aag aca aag aag gaa atg gac     240
Glu Ser Met Ala Arg Val Ile Ser His Lys Thr Lys Lys Glu Met Asp
65                  70                  75                  80 tct ttt gaa att aat gac tta gat ttt gat ttg cgc tca cta tta cat     288
Ser Phe Glu Ile Asn Asp Leu Asp Phe Asp Leu Arg Ser Leu Leu His
                85                  90                  95 tat ttg agg tct cgt caa ttg gaa cag gga att gaa cct ggt gat tct     336
Tyr Leu Arg Ser Arg Gln Leu Glu Gln Gly Ile Glu Pro Gly Asp Ser
            100                 105                 110 ggt att gcc ttt aaa aac cta aca gca gtc ggt gtt gat gcc tct gct     384
Gly Ile Ala Phe Lys Asn Leu Thr Ala Val Gly Val Asp Ala Ser Ala
        115                 120                 125 gca tat ggg cct agt gtt gaa gag atg ttt aga aat att gct agt ata     432
Ala Tyr Gly Pro Ser Val Glu Glu Met Phe Arg Asn Ile Ala Ser Ile
    130                 135                 140 ccg gca cat ctc ata agt aaa ttt acc aag aaa tct gat gtc cca tta     480
Pro Ala His Leu Ile Ser Lys Phe Thr Lys Lys Ser Asp Val Pro Leu
145                 150                 155                 160 agg aat att att caa aat tgt acg ggt gtc gtt gaa tct ggt gaa atg     528
Arg Asn Ile Ile Gln Asn Cys Thr Gly Val Val Glu Ser Gly Glu Met
                165                 170                 175 tta ttt gtc gtc ggt agg cca ggt gca ggt tgc tcc act ttc cta aag     576
Leu Phe Val Val Gly Arg Pro Gly Ala Gly Cys Ser Thr Phe Leu Lys
            180                 185                 190 tgt cta tct ggt gaa act tca gaa tta gtt gat gta caa ggt gaa ttc     624
Cys Leu Ser Gly Glu Thr Ser Glu Leu Val Asp Val Gln Gly Glu Phe
        195                 200                 205 tcc tat gat ggt ctg gac caa agc gaa atg atg tct aag tat aaa ggt     672
Ser Tyr Asp Gly Leu Asp Gln Ser Glu Met Met Ser Lys Tyr Lys Gly
    210                 215                 220 tac gtt att tac tgt ccc gag ctt gat ttc cat ttc cca aaa att act     720
Tyr Val Ile Tyr Cys Pro Glu Leu Asp Phe His Phe Pro Lys Ile Thr
225                 230                 235                 240 gtg aag gaa aca atc gat ttt gcc cta aaa tgt aag act cct cgt gtt     768
Val Lys Glu Thr Ile Asp Phe Ala Leu Lys Cys Lys Thr Pro Arg Val
```

|  |  |  |  |  |  |  |  |  |  |  |  |  |  |  |  |
|---|---|---|---|---|---|---|---|---|---|---|---|---|---|---|---|
|  |  | 245 |  |  |  |  | 250 |  |  |  |  | 255 |  |  |  |
| aga | att | gac | aaa | atg | acg | aga | aag | caa | tac | gtt | gat | aac | atc | aga | gat |
| Arg | Ile | Asp | Lys | Met | Thr | Arg | Lys | Gln | Tyr | Val | Asp | Asn | Ile | Arg | Asp |
|  |  | 260 |  |  |  |  | 265 |  |  |  |  | 270 |  |  |  |

816 atg tgg tgt acc gtt ttt ggt tta aga cac aca tat gcc acc aaa gtc        864
Met Trp Cys Thr Val Phe Gly Leu Arg His Thr Tyr Ala Thr Lys Val
            275                 280                 285 ggt aac gat ttc gta aga ggt gtt tct ggt ggt gaa cgt aag cgt gtt        912
Gly Asn Asp Phe Val Arg Gly Val Ser Gly Gly Glu Arg Lys Arg Val
        290                 295                 300 tcc ttg gtt gaa gct cag gca atg aat gcc tcc atc tac tct tgg gat        960
Ser Leu Val Glu Ala Gln Ala Met Asn Ala Ser Ile Tyr Ser Trp Asp
305                 310                 315                 320 aac gcc aca aga ggt ttg gat gcc tct act gct tta gag ttt gcc caa       1008
Asn Ala Thr Arg Gly Leu Asp Ala Ser Thr Ala Leu Glu Phe Ala Gln
                325                 330                 335 gcc att aga acg gct aca aat atg gta aac aac tct gct att gtt gct       1056
Ala Ile Arg Thr Ala Thr Asn Met Val Asn Asn Ser Ala Ile Val Ala
            340                 345                 350 att tac caa gct ggt gaa aat att tat gaa tta ttt gat aaa act act       1104
Ile Tyr Gln Ala Gly Glu Asn Ile Tyr Glu Leu Phe Asp Lys Thr Thr
        355                 360                 365 gtt cta tat aac ggt aga cag att tac ttc ggt cct gct gat aaa gct       1152
Val Leu Tyr Asn Gly Arg Gln Ile Tyr Phe Gly Pro Ala Asp Lys Ala
370                 375                 380 gtt gga tat ttc caa aga atg ggt tgg gtt aaa cca aac aga atg acc       1200
Val Gly Tyr Phe Gln Arg Met Gly Trp Val Lys Pro Asn Arg Met Thr
                385                 390                 395                 400 tct gcg gaa ttt tta aca tcc gtc acg gtc gat ttt gaa aat agg aca       1248
Ser Ala Glu Phe Leu Thr Ser Val Thr Val Asp Phe Glu Asn Arg Thr
            405                 410                 415 ttg gat att aaa cct ggc tat gaa gat aaa gtt cca aaa tct agt tca       1296
Leu Asp Ile Lys Pro Gly Tyr Glu Asp Lys Val Pro Lys Ser Ser Ser
        420                 425                 430 gag ttt gag gaa tac tgg ttg aac tct gag gat tat cag gaa ctt tta       1344
Glu Phe Glu Glu Tyr Trp Leu Asn Ser Glu Asp Tyr Gln Glu Leu Leu
                435                 440                 445 aga act tat gat gat tat caa agt aga cac cct gtt aat gaa acg aga       1392
Arg Thr Tyr Asp Asp Tyr Gln Ser Arg His Pro Val Asn Glu Thr Arg
450                 455                 460 gat aga ctg gat gtg gcc aag aag caa aga ctg caa caa ggc caa aga       1440
Asp Arg Leu Asp Val Ala Lys Lys Gln Arg Leu Gln Gln Gly Gln Arg
465                 470                 475                 480 gaa aat tct caa tat gtt gtc aat tat tgg aca caa gtt tat tat tgt       1488
Glu Asn Ser Gln Tyr Val Val Asn Tyr Trp Thr Gln Val Tyr Tyr Cys
            485                 490                 495 atg att cgt ggt ttt caa agg gtt aag ggt gat tca acg tat act aag       1536
Met Ile Arg Gly Phe Gln Arg Val Lys Gly Asp Ser Thr Tyr Thr Lys
        500                 505                 510 gtc tac tta agt tct ttt ttg atc aaa gct ttg att atc ggt tct atg       1584
Val Tyr Leu Ser Ser Phe Leu Ile Lys Ala Leu Ile Ile Gly Ser Met
                515                 520                 525 ttc cac aaa att gat gac aaa agt caa tcc acc acg gca ggt gct tat       1632
Phe His Lys Ile Asp Asp Lys Ser Gln Ser Thr Thr Ala Gly Ala Tyr
530                 535                 540 tct cgt ggt ggt atg tta ttc tat gtt tta ttg ttc gct tct gtt act       1680
Ser Arg Gly Gly Met Leu Phe Tyr Val Leu Leu Phe Ala Ser Val Thr
545                 550                 555                 560 tcc ttg gcc gaa att ggt aac tct ttt tct agt aga cct gtt att gtc       1728

```
                Ser Leu Ala Glu Ile Gly Asn Ser Phe Ser Ser Arg Pro Val Ile Val
                                    565                 570                 575 aaa cac aaa tca tat tcc atg tac cat ttg tct gcg gaa tcg tta caa        1776
Lys His Lys Ser Tyr Ser Met Tyr His Leu Ser Ala Glu Ser Leu Gln
            580                 585                 590 gag att atc act gag ttc cct act aaa ttt gtc gct att gtg ata cta        1824
Glu Ile Ile Thr Glu Phe Pro Thr Lys Phe Val Ala Ile Val Ile Leu
                595                 600                 605 tgt ttg att act tac tgg att cca ttt atg aaa tat gaa gct ggt gct        1872
Cys Leu Ile Thr Tyr Trp Ile Pro Phe Met Lys Tyr Glu Ala Gly Ala
            610                 615                 620 ttc ttc cag tat att tta tat cta ctg act gtg caa caa tgt act tct        1920
Phe Phe Gln Tyr Ile Leu Tyr Leu Leu Thr Val Gln Gln Cys Thr Ser
625                 630                 635                 640 ttc att ttc aag ttt gtt gct act atg agt aaa tct ggt gtg gat gcc        1968
Phe Ile Phe Lys Phe Val Ala Thr Met Ser Lys Ser Gly Val Asp Ala
                645                 650                 655 cat gcc gtc ggt ggt tta tgg gtc ctg atg ctt tgt gtt tat gct ggt        2016
His Ala Val Gly Gly Leu Trp Val Leu Met Leu Cys Val Tyr Ala Gly
            660                 665                 670 ttt gtc ttg cca att ggt gaa atg cat cat tgg att aga tgg ctt cat        2064
Phe Val Leu Pro Ile Gly Glu Met His His Trp Ile Arg Trp Leu His
                675                 680                 685 ttc att aat cct tta act tat gct ttt gaa agt tta gtt tcc act gaa        2112
Phe Ile Asn Pro Leu Thr Tyr Ala Phe Glu Ser Leu Val Ser Thr Glu
        690                 695                 700 ttt cac cac agg gaa atg ttg tgt agc gcc tta gtc cca tct ggt cct        2160
Phe His His Arg Glu Met Leu Cys Ser Ala Leu Val Pro Ser Gly Pro
705                 710                 715                 720 ggt tat gaa ggt att tct att gct aac caa gtc tgt gat gct gct ggt        2208
Gly Tyr Glu Gly Ile Ser Ile Ala Asn Gln Val Cys Asp Ala Ala Gly
                725                 730                 735 gcg gtt aag ggt aac ttg tat gtt agc ggt gac tct tac atc tta cac        2256
Ala Val Lys Gly Asn Leu Tyr Val Ser Gly Asp Ser Tyr Ile Leu His
            740                 745                 750 caa tat cat ttc gca tat aag cat gct tgg aga aat tgg ggt gtg aac        2304
Gln Tyr His Phe Ala Tyr Lys His Ala Trp Arg Asn Trp Gly Val Asn
                755                 760                 765 att gtg tgg act ttt ggt tat att gtg ttc aat gtc atc tta tca gaa        2352
Ile Val Trp Thr Phe Gly Tyr Ile Val Phe Asn Val Ile Leu Ser Glu
        770                 775                 780 tat ttg aaa cct gtt gag gga gga ggt gac ttg ctg tta tat aag aga        2400
Tyr Leu Lys Pro Val Glu Gly Gly Gly Asp Leu Leu Leu Tyr Lys Arg
785                 790                 795                 800 ggt cat atg ccg gag tta ggt acc gaa aat gca gat gca aga acc gct        2448
Gly His Met Pro Glu Leu Gly Thr Glu Asn Ala Asp Ala Arg Thr Ala
                805                 810                 815 tcc aga gag gaa atg atg gag gct ctg aat ggt cca aat gtc gat tta        2496
Ser Arg Glu Glu Met Met Glu Ala Leu Asn Gly Pro Asn Val Asp Leu
            820                 825                 830 gaa aag gtc att gca gaa aag gac gtt ttc acc tgg aac cat ctg gac        2544
Glu Lys Val Ile Ala Glu Lys Asp Val Phe Thr Trp Asn His Leu Asp
                835                 840                 845 tac acc att cca tac gac gga gct aca aga aaa tta tta tcg gat gtc        2592
Tyr Thr Ile Pro Tyr Asp Gly Ala Thr Arg Lys Leu Leu Ser Asp Val
        850                 855                 860 ttt ggt tac gtt aag cct ggt aag atg acc gcc ttg atg ggt gaa tcc        2640
Phe Gly Tyr Val Lys Pro Gly Lys Met Thr Ala Leu Met Gly Glu Ser
865                 870                 875                 880
```

```
ggt gct ggt aaa act acc ttg tta aat gtt tta gca caa aga atc aat    2688
Gly Ala Gly Lys Thr Thr Leu Leu Asn Val Leu Ala Gln Arg Ile Asn
                885                 890                 895 atg ggt gtc atc act ggt gat atg tta gtc aat gcc aag ccc ttg cct    2736
Met Gly Val Ile Thr Gly Asp Met Leu Val Asn Ala Lys Pro Leu Pro
        900                 905                 910 gct tct ttc aac aga tca tgt ggt tat gtt gcg caa gcc gat aat cat    2784
Ala Ser Phe Asn Arg Ser Cys Gly Tyr Val Ala Gln Ala Asp Asn His
            915                 920                 925 atg gcc gaa tta tct gtt agg gaa tcc ctg aga ttt gca gcc gag tta    2832
Met Ala Glu Leu Ser Val Arg Glu Ser Leu Arg Phe Ala Ala Glu Leu
        930                 935                 940 aga cag caa agt tcc gtt ccg tta gag gag aaa tat gaa tat gtt gaa    2880
Arg Gln Gln Ser Ser Val Pro Leu Glu Glu Lys Tyr Glu Tyr Val Glu
945                 950                 955                 960 aaa att atc aca ttg cta ggt atg caa aat tac gct gaa gcc tta gtt    2928
Lys Ile Ile Thr Leu Leu Gly Met Gln Asn Tyr Ala Glu Ala Leu Val
                965                 970                 975 ggt aag act ggt aga ggt ttg aac gtt gaa cag aga aag aag tta tct    2976
Gly Lys Thr Gly Arg Gly Leu Asn Val Glu Gln Arg Lys Lys Leu Ser
            980                 985                 990 att ggt gtt gaa ctg gtt gct aaa cca tca tta tta ttg ttt ttg gat    3024
Ile Gly Val Glu Leu Val Ala Lys Pro Ser Leu Leu Leu Phe Leu Asp
        995                 1000                1005 gag cct acc tct ggt ctg gac tct cag tct gct tgg tca att gtt        3069
Glu Pro Thr Ser Gly Leu Asp Ser Gln Ser Ala Trp Ser Ile Val
    1010                1015                1020 caa ttc atg aga gcc tta gct gat tct ggt caa tcc att ttg tgt        3114
Gln Phe Met Arg Ala Leu Ala Asp Ser Gly Gln Ser Ile Leu Cys
    1025                1030                1035 acg att cat caa ccc tct gct acc ttg ttt gaa cag ttt gac aga        3159
Thr Ile His Gln Pro Ser Ala Thr Leu Phe Glu Gln Phe Asp Arg
    1040                1045                1050 ttg ttg ttg tta aag aaa ggt ggt aag atg gtt tac ttt ggt gac        3204
Leu Leu Leu Leu Lys Lys Gly Gly Lys Met Val Tyr Phe Gly Asp
    1055                1060                1065 att ggt cca aat tct gaa act ttg ttg aag tat ttt gaa cgt caa        3249
Ile Gly Pro Asn Ser Glu Thr Leu Leu Lys Tyr Phe Glu Arg Gln
    1070                1075                1080 tct ggt atg aag tgt ggt gtt tct gaa aat cca gct gaa tat att        3294
Ser Gly Met Lys Cys Gly Val Ser Glu Asn Pro Ala Glu Tyr Ile
    1085                1090                1095 ttg aat tgt att ggt gcc ggt gcc act gct agt gtt aac tct gat        3339
Leu Asn Cys Ile Gly Ala Gly Ala Thr Ala Ser Val Asn Ser Asp
    1100                1105                1110 tgg cac gac tta tgg ctt gct tcc cca gaa tgt gcc gct gca agg        3384
Trp His Asp Leu Trp Leu Ala Ser Pro Glu Cys Ala Ala Ala Arg
    1115                1120                1125 gct gaa gtt gaa gaa tta cat cgt act tta cct ggt aga gca gtt        3429
Ala Glu Val Glu Glu Leu His Arg Thr Leu Pro Gly Arg Ala Val
    1130                1135                1140 aat gat gat cct gag tta gct aca aga ttt gct gcc agt tac atg        3474
Asn Asp Asp Pro Glu Leu Ala Thr Arg Phe Ala Ala Ser Tyr Met
    1145                1150                1155 act caa atc aaa tgt gtt tta cgt aga aca gct ctt caa ttt tgg        3519
Thr Gln Ile Lys Cys Val Leu Arg Arg Thr Ala Leu Gln Phe Trp
    1160                1165                1170 aga tcg cct gtc tat atc agg gcc aaa ttc ttt gaa tgt gtc gca        3564
Arg Ser Pro Val Tyr Ile Arg Ala Lys Phe Phe Glu Cys Val Ala
    1175                1180                1185
```

| | | | | | | | | | | | |
|---|---|---|---|---|---|---|---|---|---|---|---|
| tgt | gct | ttg | ttc | gtc | ggt | tta | tca | tat | gtt | ggt | gta | aat | cac | tct | 3609 |
| Cys | Ala | Leu | Phe | Val | Gly | Leu | Ser | Tyr | Val | Gly | Val | Asn | His | Ser | |
| | 1190 | | | | 1195 | | | | | 1200 | | | | | |

```
tgt gct ttg ttc gtc ggt tta tca tat gtt ggt gta aat cac tct       3609
Cys Ala Leu Phe Val Gly Leu Ser Tyr Val Gly Val Asn His Ser
    1190            1195                1200 gtt ggt ggt gcc att gag gcc ttt tcg tct att ttc atg cta tta       3654
Val Gly Gly Ala Ile Glu Ala Phe Ser Ser Ile Phe Met Leu Leu
    1205            1210                1215 ttg att gct ctg gct atg atc aat caa ctg cac gtc ttc gct tat       3699
Leu Ile Ala Leu Ala Met Ile Asn Gln Leu His Val Phe Ala Tyr
    1220            1225                1230 gat agt agg gaa tta tat gag gtt aga gaa gcc gct tct aac act       3744
Asp Ser Arg Glu Leu Tyr Glu Val Arg Glu Ala Ala Ser Asn Thr
    1235            1240                1245 ttc cat tgg agt gtc ttg tta tgt cat gct gct gtt gaa aac           3789
Phe His Trp Ser Val Leu Leu Cys His Ala Ala Val Glu Asn
    1250            1255                1260 ttt tgg tcc aca ctt tgt cag ttt atg tgt ttc att tgc tac tac       3834
Phe Trp Ser Thr Leu Cys Gln Phe Met Cys Phe Ile Cys Tyr Tyr
    1265            1270                1275 tgg cca gct caa ttc agt gga cgt gca tct cat gca ggt ttc ttc       3879
Trp Pro Ala Gln Phe Ser Gly Arg Ala Ser His Ala Gly Phe Phe
    1280            1285                1290 ttc ttc ttc tat gtt tta att ttc cca tta tat ttt gtc aca tat       3924
Phe Phe Phe Tyr Val Leu Ile Phe Pro Leu Tyr Phe Val Thr Tyr
    1295            1300                1305 ggt cta tgg atc ctg tac atg tct cct gat gtt ccc tca gct tct       3969
Gly Leu Trp Ile Leu Tyr Met Ser Pro Asp Val Pro Ser Ala Ser
    1310            1315                1320 atg att aat tcc aat ttg ttt gct gct atg tta ctg ttc tgt ggt       4014
Met Ile Asn Ser Asn Leu Phe Ala Ala Met Leu Leu Phe Cys Gly
    1325            1330                1335 att tta caa cca aga gag aaa atg cct gcc ttc tgg aga aga ttg       4059
Ile Leu Gln Pro Arg Glu Lys Met Pro Ala Phe Trp Arg Arg Leu
    1340            1345                1350 atg tat aat gta tca cca ttt acc tac gtg gtt caa gct ttg gtt       4104
Met Tyr Asn Val Ser Pro Phe Thr Tyr Val Val Gln Ala Leu Val
    1355            1360                1365 aca cca tta gtt cac aat aaa aag gtc gtt tgt aat cct cat gaa       4149
Thr Pro Leu Val His Asn Lys Lys Val Val Cys Asn Pro His Glu
    1370            1375                1380 tac aac atc atg gac cca cca agc gga aaa act tgt ggt gag ttt       4194
Tyr Asn Ile Met Asp Pro Pro Ser Gly Lys Thr Cys Gly Glu Phe
    1385            1390                1395 tta tct acc tat atg gac aat aat acc ggt tat ttg gta aat cca       4239
Leu Ser Thr Tyr Met Asp Asn Asn Thr Gly Tyr Leu Val Asn Pro
    1400            1405                1410 act gcc acc gaa aac tgt caa tat tgc cca tac act gtt caa gat       4284
Thr Ala Thr Glu Asn Cys Gln Tyr Cys Pro Tyr Thr Val Gln Asp
    1415            1420                1425 caa gtt gtg gct aaa tac aat gtc aaa tgg gat cac aga tgg aga       4329
Gln Val Val Ala Lys Tyr Asn Val Lys Trp Asp His Arg Trp Arg
    1430            1435                1440 aac ttt ggt ttc atg tgg gct tat att tgc ttc aat att gcc gct       4374
Asn Phe Gly Phe Met Trp Ala Tyr Ile Cys Phe Asn Ile Ala Ala
    1445            1450                1455 atg ttg att tgt tac tat gtt gta aga gtt aag gtg tgg tct ttg       4419
Met Leu Ile Cys Tyr Tyr Val Val Arg Val Lys Val Trp Ser Leu
    1460            1465                1470 aag tct gtt ttg aat ttc aag aaa tgg ttt aat ggg cca aga aag       4464
Lys Ser Val Leu Asn Phe Lys Lys Trp Phe Asn Gly Pro Arg Lys
```

```
                    1475                1480               1485
gaa aga cat gaa aaa gat acc aac att ttc caa aca gtt cca ggt        4509
Glu Arg His Glu Lys Asp Thr Asn Ile Phe Gln Thr Val Pro Gly
    1490                1495               1500 gac gaa aat aaa atc acg aag aaa taa                                4536
Asp Glu Asn Lys Ile Thr Lys Lys
    1505                1510
```

<210> SEQ ID NO 50
<211> LENGTH: 1511
<212> TYPE: PRT
<213> ORGANISM: Saccharomyces cerevisiae

<400> SEQUENCE: 50

```
Met Ser Ser Thr Asp Glu His Ile Glu Lys Asp Ile Ser Ser Arg Ser
1               5                   10                  15

Asn His Asp Asp Asp Tyr Ala Asn Ser Val Gln Ser Tyr Ala Ala Ser
            20                  25                  30

Glu Gly Gln Val Asp Asn Glu Asp Leu Ala Ala Thr Ser Gln Leu Ser
        35                  40                  45

Arg His Leu Ser Asn Ile Leu Ser Asn Glu Glu Gly Ile Glu Arg Leu
    50                  55                  60

Glu Ser Met Ala Arg Val Ile Ser His Lys Thr Lys Lys Glu Met Asp
65                  70                  75                  80

Ser Phe Glu Ile Asn Asp Leu Asp Phe Asp Leu Arg Ser Leu Leu His
                85                  90                  95

Tyr Leu Arg Ser Arg Gln Leu Glu Gln Gly Ile Glu Pro Gly Asp Ser
            100                 105                 110

Gly Ile Ala Phe Lys Asn Leu Thr Ala Val Gly Val Asp Ala Ser Ala
        115                 120                 125

Ala Tyr Gly Pro Ser Val Glu Glu Met Phe Arg Asn Ile Ala Ser Ile
    130                 135                 140

Pro Ala His Leu Ile Ser Lys Phe Thr Lys Ser Asp Val Pro Leu
145                 150                 155                 160

Arg Asn Ile Ile Gln Asn Cys Thr Gly Val Val Glu Ser Gly Glu Met
                165                 170                 175

Leu Phe Val Val Gly Arg Pro Gly Ala Gly Cys Ser Thr Phe Leu Lys
            180                 185                 190

Cys Leu Ser Gly Glu Thr Ser Glu Leu Val Asp Val Gln Gly Glu Phe
        195                 200                 205

Ser Tyr Asp Gly Leu Asp Gln Ser Glu Met Met Ser Lys Tyr Lys Gly
    210                 215                 220

Tyr Val Ile Tyr Cys Pro Glu Leu Asp Phe His Phe Pro Lys Ile Thr
225                 230                 235                 240

Val Lys Glu Thr Ile Asp Phe Ala Leu Lys Cys Lys Thr Pro Arg Val
                245                 250                 255

Arg Ile Asp Lys Met Thr Arg Lys Gln Tyr Val Asp Asn Ile Arg Asp
            260                 265                 270

Met Trp Cys Thr Val Phe Gly Leu Arg His Thr Tyr Ala Thr Lys Val
        275                 280                 285

Gly Asn Asp Phe Val Arg Gly Val Ser Gly Glu Arg Lys Arg Val
    290                 295                 300

Ser Leu Val Glu Ala Gln Ala Met Asn Ala Ser Ile Tyr Ser Trp Asp
305                 310                 315                 320

Asn Ala Thr Arg Gly Leu Asp Ala Ser Thr Ala Leu Glu Phe Ala Gln
```

-continued

```
                325                 330                 335
Ala Ile Arg Thr Ala Thr Asn Met Val Asn Asn Ser Ala Ile Val Ala
                340                 345                 350
Ile Tyr Gln Ala Gly Glu Asn Ile Tyr Glu Leu Phe Asp Lys Thr Thr
                355                 360                 365
Val Leu Tyr Asn Gly Arg Gln Ile Tyr Phe Gly Pro Ala Asp Lys Ala
                370                 375                 380
Val Gly Tyr Phe Gln Arg Met Gly Trp Val Lys Pro Asn Arg Met Thr
385                 390                 395                 400
Ser Ala Glu Phe Leu Thr Ser Val Thr Val Asp Phe Glu Asn Arg Thr
                405                 410                 415
Leu Asp Ile Lys Pro Gly Tyr Glu Asp Lys Val Pro Lys Ser Ser Ser
                420                 425                 430
Glu Phe Glu Glu Tyr Trp Leu Asn Ser Glu Asp Tyr Gln Glu Leu Leu
                435                 440                 445
Arg Thr Tyr Asp Asp Tyr Gln Ser Arg His Pro Val Asn Glu Thr Arg
                450                 455                 460
Asp Arg Leu Asp Val Ala Lys Lys Gln Arg Leu Gln Gln Gly Gln Arg
465                 470                 475                 480
Glu Asn Ser Gln Tyr Val Val Asn Tyr Trp Thr Gln Val Tyr Tyr Cys
                485                 490                 495
Met Ile Arg Gly Phe Gln Arg Val Lys Gly Asp Ser Thr Tyr Thr Lys
                500                 505                 510
Val Tyr Leu Ser Ser Phe Leu Ile Lys Ala Leu Ile Ile Gly Ser Met
                515                 520                 525
Phe His Lys Ile Asp Asp Lys Ser Gln Ser Thr Thr Ala Gly Ala Tyr
                530                 535                 540
Ser Arg Gly Gly Met Leu Phe Tyr Val Leu Leu Phe Ala Ser Val Thr
545                 550                 555                 560
Ser Leu Ala Glu Ile Gly Asn Ser Phe Ser Ser Arg Pro Val Ile Val
                565                 570                 575
Lys His Lys Ser Tyr Ser Met Tyr His Leu Ser Ala Glu Ser Leu Gln
                580                 585                 590
Glu Ile Ile Thr Glu Phe Pro Thr Lys Phe Val Ala Ile Val Ile Leu
                595                 600                 605
Cys Leu Ile Thr Tyr Trp Ile Pro Phe Met Lys Tyr Glu Ala Gly Ala
                610                 615                 620
Phe Phe Gln Tyr Ile Leu Tyr Leu Leu Thr Val Gln Gln Cys Thr Ser
625                 630                 635                 640
Phe Ile Phe Lys Phe Val Ala Thr Met Ser Lys Ser Gly Val Asp Ala
                645                 650                 655
His Ala Val Gly Gly Leu Trp Val Leu Met Leu Cys Val Tyr Ala Gly
                660                 665                 670
Phe Val Leu Pro Ile Gly Glu Met His His Trp Ile Arg Trp Leu His
                675                 680                 685
Phe Ile Asn Pro Leu Thr Tyr Ala Phe Glu Ser Leu Val Ser Thr Glu
                690                 695                 700
Phe His His Arg Glu Met Leu Cys Ser Ala Leu Val Pro Ser Gly Pro
705                 710                 715                 720
Gly Tyr Glu Gly Ile Ser Ile Ala Asn Gln Val Cys Asp Ala Ala Gly
                725                 730                 735
Ala Val Lys Gly Asn Leu Tyr Val Ser Gly Asp Ser Tyr Ile Leu His
                740                 745                 750
```

```
Gln Tyr His Phe Ala Tyr Lys His Ala Trp Arg Asn Trp Gly Val Asn
        755                 760                 765

Ile Val Trp Thr Phe Gly Tyr Ile Val Phe Asn Val Ile Leu Ser Glu
        770                 775                 780

Tyr Leu Lys Pro Val Glu Gly Gly Asp Leu Leu Leu Tyr Lys Arg
785                 790                 795                 800

Gly His Met Pro Glu Leu Gly Thr Glu Asn Ala Asp Ala Arg Thr Ala
                805                 810                 815

Ser Arg Glu Glu Met Met Glu Ala Leu Asn Gly Pro Asn Val Asp Leu
                820                 825                 830

Glu Lys Val Ile Ala Glu Lys Asp Val Phe Thr Trp Asn His Leu Asp
                835                 840                 845

Tyr Thr Ile Pro Tyr Asp Gly Ala Thr Arg Lys Leu Leu Ser Asp Val
        850                 855                 860

Phe Gly Tyr Val Lys Pro Gly Lys Met Thr Ala Leu Met Gly Glu Ser
865                 870                 875                 880

Gly Ala Gly Lys Thr Thr Leu Leu Asn Val Leu Ala Gln Arg Ile Asn
                885                 890                 895

Met Gly Val Ile Thr Gly Asp Met Leu Val Asn Ala Lys Pro Leu Pro
                900                 905                 910

Ala Ser Phe Asn Arg Ser Cys Gly Tyr Val Ala Gln Ala Asp Asn His
                915                 920                 925

Met Ala Glu Leu Ser Val Arg Glu Ser Leu Arg Phe Ala Ala Glu Leu
        930                 935                 940

Arg Gln Gln Ser Ser Val Pro Leu Glu Glu Lys Tyr Glu Tyr Val Glu
945                 950                 955                 960

Lys Ile Ile Thr Leu Leu Gly Met Gln Asn Tyr Ala Glu Ala Leu Val
                965                 970                 975

Gly Lys Thr Gly Arg Gly Leu Asn Val Glu Gln Arg Lys Lys Leu Ser
                980                 985                 990

Ile Gly Val Glu Leu Val Ala Lys Pro Ser Leu Leu Phe Leu Asp
        995                 1000                1005

Glu Pro Thr Ser Gly Leu Asp Ser Gln Ser Ala Trp Ser Ile Val
    1010                1015                1020

Gln Phe Met Arg Ala Leu Ala Asp Ser Gly Gln Ser Ile Leu Cys
    1025                1030                1035

Thr Ile His Gln Pro Ser Ala Thr Leu Phe Glu Gln Phe Asp Arg
    1040                1045                1050

Leu Leu Leu Leu Lys Lys Gly Gly Lys Met Val Tyr Phe Gly Asp
    1055                1060                1065

Ile Gly Pro Asn Ser Glu Thr Leu Leu Lys Tyr Phe Glu Arg Gln
    1070                1075                1080

Ser Gly Met Lys Cys Gly Val Ser Glu Asn Pro Ala Glu Tyr Ile
    1085                1090                1095

Leu Asn Cys Ile Gly Ala Gly Ala Thr Ala Ser Val Asn Ser Asp
    1100                1105                1110

Trp His Asp Leu Trp Leu Ala Ser Pro Glu Cys Ala Ala Ala Arg
    1115                1120                1125

Ala Glu Val Glu Glu Leu His Arg Thr Leu Pro Gly Arg Ala Val
    1130                1135                1140

Asn Asp Asp Pro Glu Leu Ala Thr Arg Phe Ala Ala Ser Tyr Met
    1145                1150                1155
```

-continued

```
Thr Gln Ile Lys Cys Val Leu Arg Arg Thr Ala Leu Gln Phe Trp
    1160                1165                1170
Arg Ser Pro Val Tyr Ile Arg Ala Lys Phe Phe Glu Cys Val Ala
    1175                1180                1185
Cys Ala Leu Phe Val Gly Leu Ser Tyr Val Gly Val Asn His Ser
    1190                1195                1200
Val Gly Gly Ala Ile Glu Ala Phe Ser Ser Ile Phe Met Leu Leu
    1205                1210                1215
Leu Ile Ala Leu Ala Met Ile Asn Gln Leu His Val Phe Ala Tyr
    1220                1225                1230
Asp Ser Arg Glu Leu Tyr Glu Val Arg Glu Ala Ala Ser Asn Thr
    1235                1240                1245
Phe His Trp Ser Val Leu Leu Cys His Ala Ala Val Glu Asn
    1250                1255                1260
Phe Trp Ser Thr Leu Cys Gln Phe Met Cys Phe Ile Cys Tyr Tyr
    1265                1270                1275
Trp Pro Ala Gln Phe Ser Gly Arg Ala Ser His Ala Gly Phe Phe
    1280                1285                1290
Phe Phe Phe Tyr Val Leu Ile Phe Pro Leu Tyr Phe Val Thr Tyr
    1295                1300                1305
Gly Leu Trp Ile Leu Tyr Met Ser Pro Asp Val Pro Ser Ala Ser
    1310                1315                1320
Met Ile Asn Ser Asn Leu Phe Ala Ala Met Leu Leu Phe Cys Gly
    1325                1330                1335
Ile Leu Gln Pro Arg Glu Lys Met Pro Ala Phe Trp Arg Arg Leu
    1340                1345                1350
Met Tyr Asn Val Ser Pro Phe Thr Tyr Val Val Gln Ala Leu Val
    1355                1360                1365
Thr Pro Leu Val His Asn Lys Lys Val Val Cys Asn Pro His Glu
    1370                1375                1380
Tyr Asn Ile Met Asp Pro Pro Ser Gly Lys Thr Cys Gly Glu Phe
    1385                1390                1395
Leu Ser Thr Tyr Met Asp Asn Asn Thr Gly Tyr Leu Val Asn Pro
    1400                1405                1410
Thr Ala Thr Glu Asn Cys Gln Tyr Cys Pro Tyr Thr Val Gln Asp
    1415                1420                1425
Gln Val Val Ala Lys Tyr Asn Val Lys Trp Asp His Arg Trp Arg
    1430                1435                1440
Asn Phe Gly Phe Met Trp Ala Tyr Ile Cys Phe Asn Ile Ala Ala
    1445                1450                1455
Met Leu Ile Cys Tyr Tyr Val Arg Val Lys Val Trp Ser Leu
    1460                1465                1470
Lys Ser Val Leu Asn Phe Lys Lys Trp Phe Asn Gly Pro Arg Lys
    1475                1480                1485
Glu Arg His Glu Lys Asp Thr Asn Ile Phe Gln Thr Val Pro Gly
    1490                1495                1500
Asp Glu Asn Lys Ile Thr Lys Lys
    1505                1510

<210> SEQ ID NO 51
<211> LENGTH: 1521
<212> TYPE: DNA
<213> ORGANISM: Saccharomyces cerevisiae
<220> FEATURE:
<221> NAME/KEY: CDS
```

<222> LOCATION: (1)..(1521)
<223> OTHER INFORMATION: GenBank Accession No. NM_001182674

<400> SEQUENCE: 51

```
atg cct acc ttg tat act gat atc gaa atc cca caa ttg aaa atc tct      48
Met Pro Thr Leu Tyr Thr Asp Ile Glu Ile Pro Gln Leu Lys Ile Ser
1               5                   10                  15 tta aag caa ccg cta ggg ttg ttt atc aac aat gag ttt tgt cca tca      96
Leu Lys Gln Pro Leu Gly Leu Phe Ile Asn Asn Glu Phe Cys Pro Ser
            20                  25                  30 tca gat gga aag acc atc gaa act gtg aac cca gct act ggc gaa ccg     144
Ser Asp Gly Lys Thr Ile Glu Thr Val Asn Pro Ala Thr Gly Glu Pro
        35                  40                  45 ata aca tcc ttc caa gca gct aac gaa aag gat gta gac aaa gct gtg     192
Ile Thr Ser Phe Gln Ala Ala Asn Glu Lys Asp Val Asp Lys Ala Val
    50                  55                  60 aaa gct gcc agg gct gct ttt gat aac gtt tgg tcg aag aca tct tct     240
Lys Ala Ala Arg Ala Ala Phe Asp Asn Val Trp Ser Lys Thr Ser Ser
65                  70                  75                  80 gag caa cgt ggt att tat ctt tca aac tta tta aaa ctt att gag gag     288
Glu Gln Arg Gly Ile Tyr Leu Ser Asn Leu Leu Lys Leu Ile Glu Glu
                85                  90                  95 gag caa gac aca ctt gcc gca tta gag act tta gac gct gga aag cct     336
Glu Gln Asp Thr Leu Ala Ala Leu Glu Thr Leu Asp Ala Gly Lys Pro
            100                 105                 110 tac cat tca aat gcc aaa ggt gat ttg gca caa att tta cag ctt acc     384
Tyr His Ser Asn Ala Lys Gly Asp Leu Ala Gln Ile Leu Gln Leu Thr
        115                 120                 125 aga tat ttt gct ggg tcc gct gat aag ttt gac aaa ggt gca acc ata     432
Arg Tyr Phe Ala Gly Ser Ala Asp Lys Phe Asp Lys Gly Ala Thr Ile
    130                 135                 140 cca ttg act ttt aac aag ttt gca tat act cta aaa gtt cct ttt ggc     480
Pro Leu Thr Phe Asn Lys Phe Ala Tyr Thr Leu Lys Val Pro Phe Gly
145                 150                 155                 160 gtt gtt gct caa atc gtt cca tgg aat tat cct cta gct atg gct tgt     528
Val Val Ala Gln Ile Val Pro Trp Asn Tyr Pro Leu Ala Met Ala Cys
                165                 170                 175 tgg aaa ttg caa ggt gcc tta gca gcc ggt aac acg gtt atc atc aaa     576
Trp Lys Leu Gln Gly Ala Leu Ala Ala Gly Asn Thr Val Ile Ile Lys
            180                 185                 190 cct gct gag aat acc tct cta tct cta ctt tat ttt gct act tta att     624
Pro Ala Glu Asn Thr Ser Leu Ser Leu Leu Tyr Phe Ala Thr Leu Ile
        195                 200                 205 aaa aaa gca ggt ttt cca cct ggt gtt gtc aat atc gtt cct ggt tat     672
Lys Lys Ala Gly Phe Pro Pro Gly Val Val Asn Ile Val Pro Gly Tyr
    210                 215                 220 gga tca ctt gta ggc caa gcc cta gca tct cac atg gat atc gac aaa     720
Gly Ser Leu Val Gly Gln Ala Leu Ala Ser His Met Asp Ile Asp Lys
225                 230                 235                 240 ata tct ttt acg gga agc acc aag gtc ggt gga ttt gtg ttg gaa gct     768
Ile Ser Phe Thr Gly Ser Thr Lys Val Gly Gly Phe Val Leu Glu Ala
                245                 250                 255 tcc ggc caa tcg aac ctt aaa gac gtt aca cta gaa tgc ggt ggt aag     816
Ser Gly Gln Ser Asn Leu Lys Asp Val Thr Leu Glu Cys Gly Gly Lys
            260                 265                 270 tct cct gct ctc gta ttt gaa gat gca gac ctt gat aag gct atc gat     864
Ser Pro Ala Leu Val Phe Glu Asp Ala Asp Leu Asp Lys Ala Ile Asp
        275                 280                 285 tgg ata gca gct ggc att ttc tac aat tca gga cag aat tgt acc gca     912
Trp Ile Ala Ala Gly Ile Phe Tyr Asn Ser Gly Gln Asn Cys Thr Ala
```

```
              290                 295                 300
aac tca aga gtt tat gtt caa agt tcg atc tac gac aag ttt gtt gaa      960
Asn Ser Arg Val Tyr Val Gln Ser Ser Ile Tyr Asp Lys Phe Val Glu
305                 310                 315                 320 aag ttt aaa gaa act gca aag aag gag tgg gat gtt gca gga aaa ttt     1008
Lys Phe Lys Glu Thr Ala Lys Lys Glu Trp Asp Val Ala Gly Lys Phe
                325                 330                 335 gat ccg ttt gat gag aaa tgc atc gtt ggt cca gtt ata tca agt aca     1056
Asp Pro Phe Asp Glu Lys Cys Ile Val Gly Pro Val Ile Ser Ser Thr
            340                 345                 350 cag tat gac cgc atc aaa agt tac ata gaa cgt ggt aaa agg gag gaa     1104
Gln Tyr Asp Arg Ile Lys Ser Tyr Ile Glu Arg Gly Lys Arg Glu Glu
        355                 360                 365 aag ttg gac atg ttc cag acc tct gaa ttt cct att ggt gga gct aaa     1152
Lys Leu Asp Met Phe Gln Thr Ser Glu Phe Pro Ile Gly Gly Ala Lys
370                 375                 380 ggc tac ttc att ccc cca acc atc ttc act gat gtc ccg caa aca tcg     1200
Gly Tyr Phe Ile Pro Pro Thr Ile Phe Thr Asp Val Pro Gln Thr Ser
385                 390                 395                 400 aaa ctg tta cag gat gag ata ttt ggc ccg gtt gtg gtt gtt agc aag     1248
Lys Leu Leu Gln Asp Glu Ile Phe Gly Pro Val Val Val Val Ser Lys
                405                 410                 415 ttc aca aat tat gat gac gct ctg aag ctg gct aat gat act tgc tac     1296
Phe Thr Asn Tyr Asp Asp Ala Leu Lys Leu Ala Asn Asp Thr Cys Tyr
            420                 425                 430 ggg ctc gcc tct gcg gtc ttc aca aaa gat gtc aag aaa gcg cac atg     1344
Gly Leu Ala Ser Ala Val Phe Thr Lys Asp Val Lys Lys Ala His Met
        435                 440                 445 ttt gct cgc gat att aaa gca gga act gtt tgg atc aac tca tct aac     1392
Phe Ala Arg Asp Ile Lys Ala Gly Thr Val Trp Ile Asn Ser Ser Asn
450                 455                 460 gat gaa gat gtt acc gtt cct ttt ggc ggg ttt aaa atg agt ggt att     1440
Asp Glu Asp Val Thr Val Pro Phe Gly Gly Phe Lys Met Ser Gly Ile
465                 470                 475                 480 ggt aga gaa ctg ggg caa agt ggt gtt gat acc tat ctt caa aca aaa     1488
Gly Arg Glu Leu Gly Gln Ser Gly Val Asp Thr Tyr Leu Gln Thr Lys
                485                 490                 495 gca gtt cac ata aat ctc tct ttg gac aac taa                         1521
Ala Val His Ile Asn Leu Ser Leu Asp Asn
            500                 505

<210> SEQ ID NO 52
<211> LENGTH: 506
<212> TYPE: PRT
<213> ORGANISM: Saccharomyces cerevisiae

<400> SEQUENCE: 52

Met Pro Thr Leu Tyr Thr Asp Ile Glu Ile Pro Gln Leu Lys Ile Ser
1               5                   10                  15

Leu Lys Gln Pro Leu Gly Leu Phe Ile Asn Asn Glu Phe Cys Pro Ser
                20                  25                  30

Ser Asp Gly Lys Thr Ile Glu Thr Val Asn Pro Ala Thr Gly Glu Pro
            35                  40                  45

Ile Thr Ser Phe Gln Ala Ala Asn Glu Lys Asp Val Asp Lys Ala Val
        50                  55                  60

Lys Ala Ala Arg Ala Ala Phe Asp Asn Val Trp Ser Lys Thr Ser Ser
65                  70                  75                  80

Glu Gln Arg Gly Ile Tyr Leu Ser Asn Leu Leu Lys Leu Ile Glu Glu
                85                  90                  95
```

```
Glu Gln Asp Thr Leu Ala Ala Leu Glu Thr Leu Asp Ala Gly Lys Pro
            100                 105                 110

Tyr His Ser Asn Ala Lys Gly Asp Leu Ala Gln Ile Leu Gln Leu Thr
            115                 120                 125

Arg Tyr Phe Ala Gly Ser Ala Asp Lys Phe Asp Lys Gly Ala Thr Ile
            130                 135                 140

Pro Leu Thr Phe Asn Lys Phe Ala Tyr Thr Leu Lys Val Pro Phe Gly
145                 150                 155                 160

Val Val Ala Gln Ile Val Pro Trp Asn Tyr Pro Leu Ala Met Ala Cys
                165                 170                 175

Trp Lys Leu Gln Gly Ala Leu Ala Ala Gly Asn Thr Val Ile Ile Lys
            180                 185                 190

Pro Ala Glu Asn Thr Ser Leu Ser Leu Leu Tyr Phe Ala Thr Leu Ile
            195                 200                 205

Lys Lys Ala Gly Phe Pro Pro Gly Val Val Asn Ile Val Pro Gly Tyr
210                 215                 220

Gly Ser Leu Val Gly Gln Ala Leu Ala Ser His Met Asp Ile Asp Lys
225                 230                 235                 240

Ile Ser Phe Thr Gly Ser Thr Lys Val Gly Gly Phe Val Leu Glu Ala
                245                 250                 255

Ser Gly Gln Ser Asn Leu Lys Asp Val Thr Leu Glu Cys Gly Gly Lys
            260                 265                 270

Ser Pro Ala Leu Val Phe Glu Asp Ala Asp Leu Asp Lys Ala Ile Asp
            275                 280                 285

Trp Ile Ala Ala Gly Ile Phe Tyr Asn Ser Gly Gln Asn Cys Thr Ala
290                 295                 300

Asn Ser Arg Val Tyr Val Gln Ser Ser Ile Tyr Asp Lys Phe Val Glu
305                 310                 315                 320

Lys Phe Lys Glu Thr Ala Lys Lys Glu Trp Asp Val Ala Gly Lys Phe
                325                 330                 335

Asp Pro Phe Asp Glu Lys Cys Ile Val Gly Pro Val Ile Ser Ser Thr
            340                 345                 350

Gln Tyr Asp Arg Ile Lys Ser Tyr Ile Glu Arg Gly Lys Arg Glu Glu
            355                 360                 365

Lys Leu Asp Met Phe Gln Thr Ser Glu Phe Pro Ile Gly Gly Ala Lys
370                 375                 380

Gly Tyr Phe Ile Pro Pro Thr Ile Phe Thr Asp Val Pro Gln Thr Ser
385                 390                 395                 400

Lys Leu Leu Gln Asp Glu Ile Phe Gly Pro Val Val Val Val Ser Lys
                405                 410                 415

Phe Thr Asn Tyr Asp Asp Ala Leu Lys Leu Ala Asn Asp Thr Cys Tyr
            420                 425                 430

Gly Leu Ala Ser Ala Val Phe Thr Lys Asp Val Lys Lys Ala His Met
            435                 440                 445

Phe Ala Arg Asp Ile Lys Ala Gly Thr Val Trp Ile Asn Ser Ser Asn
450                 455                 460

Asp Glu Asp Val Thr Val Pro Phe Gly Gly Phe Lys Met Ser Gly Ile
465                 470                 475                 480

Gly Arg Glu Leu Gly Gln Ser Gly Val Asp Thr Tyr Leu Gln Thr Lys
                485                 490                 495

Ala Val His Ile Asn Leu Ser Leu Asp Asn
            500                 505
```

<210> SEQ ID NO 53
<211> LENGTH: 1521
<212> TYPE: DNA
<213> ORGANISM: Saccharomyces cerevisiae
<220> FEATURE:
<221> NAME/KEY: CDS
<222> LOCATION: (1)..(1521)
<223> OTHER INFORMATION: GenBank Accession No. NM_001182673

<400> SEQUENCE: 53

| | | | | | | | | | | | | | | | | |
|---|---|---|---|---|---|---|---|---|---|---|---|---|---|---|---|---|
| atg | cct | acc | ttg | tat | act | gat | atc | gaa | atc | cca | caa | ttg | aaa | atc | tct | 48 |
| Met | Pro | Thr | Leu | Tyr | Thr | Asp | Ile | Glu | Ile | Pro | Gln | Leu | Lys | Ile | Ser | |
| 1 | | | | 5 | | | | | 10 | | | | | 15 | | |

| tta | aag | caa | ccg | cta | ggg | ttg | ttt | atc | aac | aat | gag | ttt | tgt | cca | tca | 96 |
|---|---|---|---|---|---|---|---|---|---|---|---|---|---|---|---|---|
| Leu | Lys | Gln | Pro | Leu | Gly | Leu | Phe | Ile | Asn | Asn | Glu | Phe | Cys | Pro | Ser | |
| | | | 20 | | | | | 25 | | | | | 30 | | | |

| tca | gat | gga | aag | acc | atc | gaa | act | gtg | aac | cca | gct | act | ggc | gaa | ccg | 144 |
|---|---|---|---|---|---|---|---|---|---|---|---|---|---|---|---|---|
| Ser | Asp | Gly | Lys | Thr | Ile | Glu | Thr | Val | Asn | Pro | Ala | Thr | Gly | Glu | Pro | |
| | | 35 | | | | | 40 | | | | | 45 | | | | |

| ata | aca | tcc | ttc | caa | gca | gct | aac | gaa | aag | gat | gta | gac | aaa | gct | gtg | 192 |
|---|---|---|---|---|---|---|---|---|---|---|---|---|---|---|---|---|
| Ile | Thr | Ser | Phe | Gln | Ala | Ala | Asn | Glu | Lys | Asp | Val | Asp | Lys | Ala | Val | |
| 50 | | | | | 55 | | | | | 60 | | | | | | |

| aaa | gct | gcc | agg | gct | gct | ttt | gat | aac | gtt | tgg | tcg | aag | aca | tct | tct | 240 |
|---|---|---|---|---|---|---|---|---|---|---|---|---|---|---|---|---|
| Lys | Ala | Ala | Arg | Ala | Ala | Phe | Asp | Asn | Val | Trp | Ser | Lys | Thr | Ser | Ser | |
| 65 | | | | | 70 | | | | | 75 | | | | | 80 | |

| gag | caa | cgt | ggt | att | tat | ctt | tca | aac | tta | tta | aaa | ctt | att | gag | gag | 288 |
|---|---|---|---|---|---|---|---|---|---|---|---|---|---|---|---|---|
| Glu | Gln | Arg | Gly | Ile | Tyr | Leu | Ser | Asn | Leu | Leu | Lys | Leu | Ile | Glu | Glu | |
| | | | | 85 | | | | | 90 | | | | | 95 | | |

| gag | caa | gac | aca | ctt | gcc | gca | tta | gag | act | tta | gac | gct | ggt | aag | cct | 336 |
|---|---|---|---|---|---|---|---|---|---|---|---|---|---|---|---|---|
| Glu | Gln | Asp | Thr | Leu | Ala | Ala | Leu | Glu | Thr | Leu | Asp | Ala | Gly | Lys | Pro | |
| | | | 100 | | | | | 105 | | | | | 110 | | | |

| ttc | cat | tcc | aat | gct | aaa | caa | gac | tta | gcc | cag | att | ata | gaa | ctt | aca | 384 |
|---|---|---|---|---|---|---|---|---|---|---|---|---|---|---|---|---|
| Phe | His | Ser | Asn | Ala | Lys | Gln | Asp | Leu | Ala | Gln | Ile | Ile | Glu | Leu | Thr | |
| | | 115 | | | | | 120 | | | | | 125 | | | | |

| aga | tac | tat | gcg | ggg | gcg | gtc | gac | aag | ttc | aat | atg | ggt | gaa | acc | att | 432 |
|---|---|---|---|---|---|---|---|---|---|---|---|---|---|---|---|---|
| Arg | Tyr | Tyr | Ala | Gly | Ala | Val | Asp | Lys | Phe | Asn | Met | Gly | Glu | Thr | Ile | |
| | 130 | | | | | 135 | | | | | 140 | | | | | |

| cca | ttg | act | ttt | aac | aag | ttt | gca | tat | act | cta | aaa | gtt | cct | ttt | ggc | 480 |
|---|---|---|---|---|---|---|---|---|---|---|---|---|---|---|---|---|
| Pro | Leu | Thr | Phe | Asn | Lys | Phe | Ala | Tyr | Thr | Leu | Lys | Val | Pro | Phe | Gly | |
| 145 | | | | | 150 | | | | | 155 | | | | | 160 | |

| gtt | gtt | gct | caa | atc | gtt | cca | tgg | aat | tat | cct | cta | gct | atg | gct | tgt | 528 |
|---|---|---|---|---|---|---|---|---|---|---|---|---|---|---|---|---|
| Val | Val | Ala | Gln | Ile | Val | Pro | Trp | Asn | Tyr | Pro | Leu | Ala | Met | Ala | Cys | |
| | | | | 165 | | | | | 170 | | | | | 175 | | |

| aga | aaa | atg | caa | ggt | gcc | tta | gcg | gcc | ggt | aac | acg | gtt | atc | atc | aaa | 576 |
|---|---|---|---|---|---|---|---|---|---|---|---|---|---|---|---|---|
| Arg | Lys | Met | Gln | Gly | Ala | Leu | Ala | Ala | Gly | Asn | Thr | Val | Ile | Ile | Lys | |
| | | | 180 | | | | | 185 | | | | | 190 | | | |

| cct | gct | gaa | aat | acc | tct | cta | tct | cta | ctt | tat | ttt | gct | act | tta | att | 624 |
|---|---|---|---|---|---|---|---|---|---|---|---|---|---|---|---|---|
| Pro | Ala | Glu | Asn | Thr | Ser | Leu | Ser | Leu | Leu | Tyr | Phe | Ala | Thr | Leu | Ile | |
| | | 195 | | | | | 200 | | | | | 205 | | | | |

| aaa | aaa | gca | ggt | ttt | cca | cct | ggt | gtt | gtc | aat | gtc | att | cct | ggt | tat | 672 |
|---|---|---|---|---|---|---|---|---|---|---|---|---|---|---|---|---|
| Lys | Lys | Ala | Gly | Phe | Pro | Pro | Gly | Val | Val | Asn | Val | Ile | Pro | Gly | Tyr | |
| | 210 | | | | | 215 | | | | | 220 | | | | | |

| ggt | tcc | gtt | gtg | ggg | aaa | gct | tta | gga | acc | cac | atg | gat | atc | gac | aaa | 720 |
|---|---|---|---|---|---|---|---|---|---|---|---|---|---|---|---|---|
| Gly | Ser | Val | Val | Gly | Lys | Ala | Leu | Gly | Thr | His | Met | Asp | Ile | Asp | Lys | |
| 225 | | | | | 230 | | | | | 235 | | | | | 240 | |

| ata | tct | ttt | acg | gga | agt | act | aag | gtt | ggc | ggc | tca | gta | ttg | gaa | gct | 768 |
|---|---|---|---|---|---|---|---|---|---|---|---|---|---|---|---|---|
| Ile | Ser | Phe | Thr | Gly | Ser | Thr | Lys | Val | Gly | Gly | Ser | Val | Leu | Glu | Ala | |
| | | | | 245 | | | | | 250 | | | | | 255 | | |

| tcc | ggc | caa | tcg | aac | ctt | aag | gat | atc | aca | cta | gaa | tgc | ggt | ggt | aag | 816 |
|---|---|---|---|---|---|---|---|---|---|---|---|---|---|---|---|---|
| Ser | Gly | Gln | Ser | Asn | Leu | Lys | Asp | Ile | Thr | Leu | Glu | Cys | Gly | Gly | Lys | |
| | | | 260 | | | | | 265 | | | | | 270 | | | |

| | | | | | | | | | | | | | | | | |
|---|---|---|---|---|---|---|---|---|---|---|---|---|---|---|---|---|
| tct | cct | gct | ctt | gta | ttt | gaa | gat | gca | gac | ctt | gat | aag | gct | ata | gaa | 864 |
| Ser | Pro | Ala | Leu | Val | Phe | Glu | Asp | Ala | Asp | Leu | Asp | Lys | Ala | Ile | Glu | |
| | | | 275 | | | | 280 | | | | | 285 | | | | |
| tgg | gta | gca | aat | ggt | att | ttt | ttt | aat | tcg | gga | cag | atc | tgc | act | gca | 912 |
| Trp | Val | Ala | Asn | Gly | Ile | Phe | Phe | Asn | Ser | Gly | Gln | Ile | Cys | Thr | Ala | |
| | 290 | | | | | 295 | | | | | 300 | | | | | |
| aac | tca | aga | gtt | tat | gtt | caa | agt | tcg | atc | tac | gac | aag | ttt | gtt | gaa | 960 |
| Asn | Ser | Arg | Val | Tyr | Val | Gln | Ser | Ser | Ile | Tyr | Asp | Lys | Phe | Val | Glu | |
| 305 | | | | | 310 | | | | | 315 | | | | | 320 | |
| aag | ttt | aaa | gaa | act | gca | aag | aag | gag | tgg | gat | gtt | gca | gga | aaa | ttt | 1008 |
| Lys | Phe | Lys | Glu | Thr | Ala | Lys | Lys | Glu | Trp | Asp | Val | Ala | Gly | Lys | Phe | |
| | | | | 325 | | | | | 330 | | | | | 335 | | |
| gat | ccg | ttt | gat | gag | aaa | tgc | atc | gtt | ggt | cca | gtt | ata | tca | agt | aca | 1056 |
| Asp | Pro | Phe | Asp | Glu | Lys | Cys | Ile | Val | Gly | Pro | Val | Ile | Ser | Ser | Thr | |
| | | 340 | | | | | 345 | | | | | 350 | | | | |
| cag | tat | gac | cgc | atc | aaa | agt | tac | ata | gaa | cgt | ggt | aaa | aag | gag | gaa | 1104 |
| Gln | Tyr | Asp | Arg | Ile | Lys | Ser | Tyr | Ile | Glu | Arg | Gly | Lys | Lys | Glu | Glu | |
| | 355 | | | | | 360 | | | | | 365 | | | | | |
| aag | ttg | gac | atg | ttc | cag | acc | tct | gaa | ttt | cct | att | ggt | gga | gct | aaa | 1152 |
| Lys | Leu | Asp | Met | Phe | Gln | Thr | Ser | Glu | Phe | Pro | Ile | Gly | Gly | Ala | Lys | |
| 370 | | | | | 375 | | | | | 380 | | | | | | |
| ggc | tac | ttc | att | ccc | cca | acc | atc | ttc | act | gat | gta | cca | gaa | aca | tct | 1200 |
| Gly | Tyr | Phe | Ile | Pro | Pro | Thr | Ile | Phe | Thr | Asp | Val | Pro | Glu | Thr | Ser | |
| 385 | | | | | 390 | | | | | 395 | | | | | 400 | |
| aag | ttg | ctg | cgt | gat | gaa | ata | ttt | ggc | ccg | gtt | gtg | gtt | gtt | agc | aag | 1248 |
| Lys | Leu | Leu | Arg | Asp | Glu | Ile | Phe | Gly | Pro | Val | Val | Val | Val | Ser | Lys | |
| | | | | 405 | | | | | 410 | | | | | 415 | | |
| ttc | aca | aat | tat | gat | gac | gct | ctg | aag | ctg | gct | aat | gat | act | tgc | tac | 1296 |
| Phe | Thr | Asn | Tyr | Asp | Asp | Ala | Leu | Lys | Leu | Ala | Asn | Asp | Thr | Cys | Tyr | |
| | | | 420 | | | | | 425 | | | | | 430 | | | |
| ggg | ctc | gcc | tct | gcg | gtc | ttc | acc | aaa | gat | gtc | aag | aaa | gcg | cac | atg | 1344 |
| Gly | Leu | Ala | Ser | Ala | Val | Phe | Thr | Lys | Asp | Val | Lys | Lys | Ala | His | Met | |
| | | 435 | | | | | 440 | | | | | 445 | | | | |
| ttt | gct | cgc | gat | att | aaa | gca | gga | act | gtt | tgg | atc | aat | caa | acc | aat | 1392 |
| Phe | Ala | Arg | Asp | Ile | Lys | Ala | Gly | Thr | Val | Trp | Ile | Asn | Gln | Thr | Asn | |
| | 450 | | | | | 455 | | | | | 460 | | | | | |
| caa | gaa | gaa | gct | aaa | gtt | cct | ttt | ggc | gga | ttt | aag | atg | agt | ggt | att | 1440 |
| Gln | Glu | Glu | Ala | Lys | Val | Pro | Phe | Gly | Gly | Phe | Lys | Met | Ser | Gly | Ile | |
| 465 | | | | | 470 | | | | | 475 | | | | | 480 | |
| ggt | aga | gaa | tca | ggc | gac | acc | ggc | gtt | gat | aac | tat | tta | caa | ata | aaa | 1488 |
| Gly | Arg | Glu | Ser | Gly | Asp | Thr | Gly | Val | Asp | Asn | Tyr | Leu | Gln | Ile | Lys | |
| | | | | 485 | | | | | 490 | | | | | 495 | | |
| tca | gtc | cat | gtg | gat | ctt | tca | ttg | gat | aaa | taa | | | | | | 1521 |
| Ser | Val | His | Val | Asp | Leu | Ser | Leu | Asp | Lys | | | | | | | |
| | | | 500 | | | | | 505 | | | | | | | | |

<210> SEQ ID NO 54
<211> LENGTH: 506
<212> TYPE: PRT
<213> ORGANISM: Saccharomyces cerevisiae

<400> SEQUENCE: 54

Met Pro Thr Leu Tyr Thr Asp Ile Glu Ile Pro Gln Leu Lys Ile Ser
1               5                   10                  15

Leu Lys Gln Pro Leu Gly Leu Phe Ile Asn Asn Glu Phe Cys Pro Ser
                20                  25                  30

Ser Asp Gly Lys Thr Ile Glu Thr Val Asn Pro Ala Thr Gly Glu Pro
            35                  40                  45

Ile Thr Ser Phe Gln Ala Ala Asn Glu Lys Asp Val Asp Lys Ala Val

```
                50                  55                  60
Lys Ala Arg Ala Ala Phe Asp Asn Val Trp Ser Lys Thr Ser Ser
 65                  70                  75                  80
Glu Gln Arg Gly Ile Tyr Leu Ser Asn Leu Leu Lys Leu Ile Glu Glu
                 85                  90                  95
Glu Gln Asp Thr Leu Ala Ala Leu Glu Thr Leu Asp Ala Gly Lys Pro
                100                 105                 110
Phe His Ser Asn Ala Lys Gln Asp Leu Ala Gln Ile Ile Glu Leu Thr
                115                 120                 125
Arg Tyr Tyr Ala Gly Ala Val Asp Lys Phe Asn Met Gly Glu Thr Ile
                130                 135                 140
Pro Leu Thr Phe Asn Lys Phe Ala Tyr Thr Leu Lys Val Pro Phe Gly
145                 150                 155                 160
Val Val Ala Gln Ile Val Pro Trp Asn Tyr Pro Leu Ala Met Ala Cys
                165                 170                 175
Arg Lys Met Gln Gly Ala Leu Ala Ala Gly Asn Thr Val Ile Ile Lys
                180                 185                 190
Pro Ala Glu Asn Thr Ser Leu Ser Leu Leu Tyr Phe Ala Thr Leu Ile
                195                 200                 205
Lys Lys Ala Gly Phe Pro Pro Gly Val Val Asn Val Ile Pro Gly Tyr
210                 215                 220
Gly Ser Val Val Gly Lys Ala Leu Gly Thr His Met Asp Ile Asp Lys
225                 230                 235                 240
Ile Ser Phe Thr Gly Ser Thr Lys Val Gly Gly Ser Val Leu Glu Ala
                245                 250                 255
Ser Gly Gln Ser Asn Leu Lys Asp Ile Thr Leu Glu Cys Gly Gly Lys
                260                 265                 270
Ser Pro Ala Leu Val Phe Glu Asp Ala Asp Leu Asp Lys Ala Ile Glu
                275                 280                 285
Trp Val Ala Asn Gly Ile Phe Phe Asn Ser Gly Gln Ile Cys Thr Ala
                290                 295                 300
Asn Ser Arg Val Tyr Val Gln Ser Ser Ile Tyr Asp Lys Phe Val Glu
305                 310                 315                 320
Lys Phe Lys Glu Thr Ala Lys Lys Glu Trp Asp Val Ala Gly Lys Phe
                325                 330                 335
Asp Pro Phe Asp Glu Lys Cys Ile Val Gly Pro Val Ile Ser Ser Thr
                340                 345                 350
Gln Tyr Asp Arg Ile Lys Ser Tyr Ile Glu Arg Gly Lys Lys Glu Glu
                355                 360                 365
Lys Leu Asp Met Phe Gln Thr Ser Glu Phe Pro Ile Gly Gly Ala Lys
                370                 375                 380
Gly Tyr Phe Ile Pro Pro Thr Ile Phe Thr Asp Val Pro Glu Thr Ser
385                 390                 395                 400
Lys Leu Leu Arg Asp Glu Ile Phe Gly Pro Val Val Val Val Ser Lys
                405                 410                 415
Phe Thr Asn Tyr Asp Asp Ala Leu Lys Leu Ala Asn Asp Thr Cys Tyr
                420                 425                 430
Gly Leu Ala Ser Ala Val Phe Thr Lys Asp Val Lys Lys Ala His Met
                435                 440                 445
Phe Ala Arg Asp Ile Lys Ala Gly Thr Val Trp Ile Asn Gln Thr Asn
                450                 455                 460
Gln Glu Glu Ala Lys Val Pro Phe Gly Gly Phe Lys Met Ser Gly Ile
465                 470                 475                 480
```

```
Gly Arg Glu Ser Gly Asp Thr Gly Val Asp Asn Tyr Leu Gln Ile Lys
                485                 490                 495

Ser Val His Val Asp Leu Ser Leu Asp Lys
            500                 505

<210> SEQ ID NO 55
<211> LENGTH: 1560
<212> TYPE: DNA
<213> ORGANISM: Saccharomyces cerevisiae
<220> FEATURE:
<221> NAME/KEY: CDS
<222> LOCATION: (1)..(1560)
<223> OTHER INFORMATION: GenBank Accession No. NM_001183794

<400> SEQUENCE: 55 atg ttc agt aga tct acg ctc tgc tta aag acg tct gca tcc tcc att        48
Met Phe Ser Arg Ser Thr Leu Cys Leu Lys Thr Ser Ala Ser Ser Ile
1               5                   10                  15 ggg aga ctt caa ttg aga tat ttc tca cac ctt cct atg aca gtg cct        96
Gly Arg Leu Gln Leu Arg Tyr Phe Ser His Leu Pro Met Thr Val Pro
            20                  25                  30 atc aag ctg ccc aat ggg ttg gaa tat gag caa cca acg ggg ttg ttc        144
Ile Lys Leu Pro Asn Gly Leu Glu Tyr Glu Gln Pro Thr Gly Leu Phe
        35                  40                  45 atc aac aac aag ttt gtt cct tct aaa cag aac aag acc ttc gaa gtc        192
Ile Asn Asn Lys Phe Val Pro Ser Lys Gln Asn Lys Thr Phe Glu Val
    50                  55                  60 att aac cct tcc acg gaa gaa gaa ata tgt cat att tat gaa ggt aga        240
Ile Asn Pro Ser Thr Glu Glu Glu Ile Cys His Ile Tyr Glu Gly Arg
65                  70                  75                  80 gag gac gat gtg gaa gag gcc gtg cag gcc gcc gac cgt gcc ttc tct        288
Glu Asp Asp Val Glu Glu Ala Val Gln Ala Ala Asp Arg Ala Phe Ser
                85                  90                  95 aat ggg tct tgg aac ggt atc gac cct att gac agg ggt aag gct ttg        336
Asn Gly Ser Trp Asn Gly Ile Asp Pro Ile Asp Arg Gly Lys Ala Leu
            100                 105                 110 tac agg tta gcc gaa tta att gaa cag gac aag gat gtc att gct tcc        384
Tyr Arg Leu Ala Glu Leu Ile Glu Gln Asp Lys Asp Val Ile Ala Ser
        115                 120                 125 atc gag act ttg gat aac ggt aaa gct atc tct tcc tcg aga gga gat        432
Ile Glu Thr Leu Asp Asn Gly Lys Ala Ile Ser Ser Ser Arg Gly Asp
    130                 135                 140 gtt gat tta gtc atc aac tat ttg aaa tct tct gct ggc ttt gct gat        480
Val Asp Leu Val Ile Asn Tyr Leu Lys Ser Ser Ala Gly Phe Ala Asp
145                 150                 155                 160 aaa att gat ggt aga atg att gat act ggt aga acc cat ttt tct tac        528
Lys Ile Asp Gly Arg Met Ile Asp Thr Gly Arg Thr His Phe Ser Tyr
                165                 170                 175 act aag aga cag cct ttg ggt gtt tgt ggg cag att att cct tgg aat        576
Thr Lys Arg Gln Pro Leu Gly Val Cys Gly Gln Ile Ile Pro Trp Asn
            180                 185                 190 ttc cca ctg ttg atg tgg gcc tgg aag att gcc cct gct ttg gtc acc        624
Phe Pro Leu Leu Met Trp Ala Trp Lys Ile Ala Pro Ala Leu Val Thr
        195                 200                 205 ggt aac acc gtc gtg ttg aag act gcc gaa tcc acc cca ttg tcc gct        672
Gly Asn Thr Val Val Leu Lys Thr Ala Glu Ser Thr Pro Leu Ser Ala
    210                 215                 220 ttg tat gtg tct aaa tac atc cca cag gcg ggt att cca cct ggt gtg        720
Leu Tyr Val Ser Lys Tyr Ile Pro Gln Ala Gly Ile Pro Pro Gly Val
225                 230                 235                 240
```

```
atc aac att gta tcc ggg ttt ggt aag att gtg ggt gag gcc att aca        768
Ile Asn Ile Val Ser Gly Phe Gly Lys Ile Val Gly Glu Ala Ile Thr
            245                 250                 255 aac cat cca aaa atc aaa aag gtt gcc ttc aca ggg tcc acg gct acg        816
Asn His Pro Lys Ile Lys Lys Val Ala Phe Thr Gly Ser Thr Ala Thr
        260                 265                 270 ggt aga cac att tac cag tcc gca gcc gca ggc ttg aaa aaa gtg act        864
Gly Arg His Ile Tyr Gln Ser Ala Ala Ala Gly Leu Lys Lys Val Thr
        275                 280                 285 ttg gag ctg ggt ggt aaa tca cca aac att gtc ttc gcg gac gcc gag        912
Leu Glu Leu Gly Gly Lys Ser Pro Asn Ile Val Phe Ala Asp Ala Glu
        290                 295                 300 ttg aaa aaa gcc gtg caa aac att atc ctt ggt atc tac tac aat tct        960
Leu Lys Lys Ala Val Gln Asn Ile Ile Leu Gly Ile Tyr Tyr Asn Ser
305                 310                 315                 320 ggt gag gtc tgt tgt gcg ggt tca agg gtg tat gtt gaa gaa tct att       1008
Gly Glu Val Cys Cys Ala Gly Ser Arg Val Tyr Val Glu Glu Ser Ile
                325                 330                 335 tac gac aaa ttc att gaa gag ttc aaa gcc gct tct gaa tcc atc aag       1056
Tyr Asp Lys Phe Ile Glu Glu Phe Lys Ala Ala Ser Glu Ser Ile Lys
            340                 345                 350 gtg ggc gac cca ttc gat gaa tct act ttc caa ggt gca caa acc tct       1104
Val Gly Asp Pro Phe Asp Glu Ser Thr Phe Gln Gly Ala Gln Thr Ser
        355                 360                 365 caa atg caa cta aac aaa atc ttg aaa tac gtt gac att ggt aag aat       1152
Gln Met Gln Leu Asn Lys Ile Leu Lys Tyr Val Asp Ile Gly Lys Asn
        370                 375                 380 gaa ggt gct act ttg att acc ggt ggt gaa aga tta ggt agc aag ggt       1200
Glu Gly Ala Thr Leu Ile Thr Gly Gly Glu Arg Leu Gly Ser Lys Gly
385                 390                 395                 400 tac ttc att aag cca act gtc ttt ggt gac gtt aag gaa gac atg aga       1248
Tyr Phe Ile Lys Pro Thr Val Phe Gly Asp Val Lys Glu Asp Met Arg
                405                 410                 415 att gtc aaa gag gaa atc ttt ggc cct gtt gtc act gta acc aaa ttc       1296
Ile Val Lys Glu Glu Ile Phe Gly Pro Val Val Thr Val Thr Lys Phe
            420                 425                 430 aaa tct gcc gac gaa gtc att aac atg gcg aac gat tct gaa tac ggg       1344
Lys Ser Ala Asp Glu Val Ile Asn Met Ala Asn Asp Ser Glu Tyr Gly
        435                 440                 445 ttg gct gct ggt att cac acc tct aat att aat acc gcc tta aaa gtg       1392
Leu Ala Ala Gly Ile His Thr Ser Asn Ile Asn Thr Ala Leu Lys Val
        450                 455                 460 gct gat aga gtt aat gcg ggt acg gtc tgg ata aac act tat aac gat       1440
Ala Asp Arg Val Asn Ala Gly Thr Val Trp Ile Asn Thr Tyr Asn Asp
465                 470                 475                 480 ttc cac cac gca gtt cct ttc ggt ggg ttc aat gca tct ggt ttg ggc       1488
Phe His His Ala Val Pro Phe Gly Gly Phe Asn Ala Ser Gly Leu Gly
                485                 490                 495 agg gaa atg tct gtt gat gct tta caa aac tac ttg caa gtt aaa gcg       1536
Arg Glu Met Ser Val Asp Ala Leu Gln Asn Tyr Leu Gln Val Lys Ala
            500                 505                 510 gtc cgt gcc aaa ttg gac gag taa                                       1560
Val Arg Ala Lys Leu Asp Glu
        515

<210> SEQ ID NO 56
<211> LENGTH: 519
<212> TYPE: PRT
<213> ORGANISM: Saccharomyces cerevisiae

<400> SEQUENCE: 56
```

```
Met Phe Ser Arg Ser Thr Leu Cys Leu Lys Thr Ser Ala Ser Ser Ile
1               5                   10                  15

Gly Arg Leu Gln Leu Arg Tyr Phe Ser His Leu Pro Met Thr Val Pro
            20                  25                  30

Ile Lys Leu Pro Asn Gly Leu Glu Tyr Glu Gln Pro Thr Gly Leu Phe
            35                  40                  45

Ile Asn Asn Lys Phe Val Pro Ser Lys Gln Asn Lys Thr Phe Glu Val
50                      55                  60

Ile Asn Pro Ser Thr Glu Glu Ile Cys His Ile Tyr Glu Gly Arg
65                  70              75                  80

Glu Asp Asp Val Glu Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
            100                 105                 110

Tyr Arg Leu Ala Glu Leu Ile Glu Gln Asp Lys Asp Val Ile Ala Ser
            115                 120                 125

Ile Glu Thr Leu Asp Asn Gly Lys Ala Ile Ser Ser Ser Arg Gly Asp
            130                 135                 140

Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
                165                 170                 175

Thr Lys Arg Gln Pro Leu Gly Val Cys Gly Gln Ile Ile Pro Trp Asn
            180                 185                 190

Phe Pro Leu Leu Met Trp Ala Trp Lys Ile Ala Pro Ala Leu Val Thr
            195                 200                 205

Gly Asn Thr Val Val Leu Lys Thr Ala Glu Ser Thr Pro Leu Ser Ala
            210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
                245                 250                 255

Asn His Pro Lys Ile Lys Lys Val Ala Phe Thr Gly Ser Thr Ala Thr
            260                 265                 270

Gly Arg His Ile Tyr Gln Ser Ala Ala Ala Gly Leu Lys Lys Val Thr
            275                 280                 285

Leu Glu Leu Gly Gly Lys Ser Pro Asn Ile Val Phe Ala Asp Ala Glu
            290                 295                 300

Leu Lys Lys Ala Val Gln Asn Ile Ile Leu Gly Ile Tyr Tyr Asn Ser
305                 310                 315                 320

Gly Glu Val Cys Cys Ala Gly Ser Arg Val Tyr Val Glu Glu Ser Ile
                325                 330                 335

Tyr Asp Lys Phe Ile Glu Glu Phe Lys Ala Ala Ser Glu Ser Ile Lys
            340                 345                 350

Val Gly Asp Pro Phe Asp Glu Ser Thr Phe Gln Gly Ala Gln Thr Ser
            355                 360                 365

Gln Met Gln Leu Asn Lys Ile Leu Lys Tyr Val Asp Ile Gly Lys Asn
            370                 375                 380

Glu Gly Ala Thr Leu Ile Thr Gly Gly Glu Arg Leu Gly Ser Lys Gly
385                 390                 395                 400

Tyr Phe Ile Lys Pro Thr Val Phe Gly Asp Val Lys Glu Asp Met Arg
                405                 410                 415
```

```
Ile Val Lys Glu Glu Ile Phe Gly Pro Val Val Thr Val Thr Lys Phe
                420                 425                 430

Lys Ser Ala Asp Glu Val Ile Asn Met Ala Asn Asp Ser Glu Tyr Gly
            435                 440                 445

Leu Ala Ala Gly Ile His Thr Ser Asn Ile Thr Ala Leu Lys Val
        450                 455                 460

Ala Asp Arg Val Asn Ala Gly Thr Val Trp Ile Asn Thr Tyr Asn Asp
465                 470                 475                 480

Phe His His Ala Val Pro Phe Gly Gly Phe Asn Ala Ser Gly Leu Gly
                485                 490                 495

Arg Glu Met Ser Val Asp Ala Leu Gln Asn Tyr Leu Gln Val Lys Ala
            500                 505                 510

Val Arg Ala Lys Leu Asp Glu
        515

<210> SEQ ID NO 57
<211> LENGTH: 1563
<212> TYPE: DNA
<213> ORGANISM: Saccharomyces cerevisiae
<220> FEATURE:
<221> NAME/KEY: CDS
<222> LOCATION: (1)..(1563)
<223> OTHER INFORMATION: GenBank Accession No. NM_001178964

<400> SEQUENCE: 57 atg ctt tct cgc aca aga gct gca gct ccg aat tcc aga ata ttc act    48
Met Leu Ser Arg Thr Arg Ala Ala Ala Pro Asn Ser Arg Ile Phe Thr
1               5                   10                  15 aga agc ttg tta cgt ctt tat tct caa gca cca tta cgc gtt cca att    96
Arg Ser Leu Leu Arg Leu Tyr Ser Gln Ala Pro Leu Arg Val Pro Ile
            20                  25                  30 act ctt cca aat ggt ttc acc tac gaa cag cca aca ggg tta ttc atc   144
Thr Leu Pro Asn Gly Phe Thr Tyr Glu Gln Pro Thr Gly Leu Phe Ile
        35                  40                  45 aat ggt gaa ttt gtt gcc tcg aag caa aag aaa acg ttt gac gtg atc   192
Asn Gly Glu Phe Val Ala Ser Lys Gln Lys Lys Thr Phe Asp Val Ile
50                  55                  60 aat cca tct aac gaa gaa aag ata aca act gta tac aag gct atg gaa   240
Asn Pro Ser Asn Glu Glu Lys Ile Thr Thr Val Tyr Lys Ala Met Glu
65                  70                  75                  80 gat gat gtt gat gaa gcc gtt gca gcg gct aaa aaa gct ttt gaa acg   288
Asp Asp Val Asp Glu Ala Val Ala Ala Ala Lys Lys Ala Phe Glu Thr
                85                  90                  95 aag tgg tct att gta gag ccg gag gtt cgc gct aaa gct tta ttc aat   336
Lys Trp Ser Ile Val Glu Pro Glu Val Arg Ala Lys Ala Leu Phe Asn
            100                 105                 110 ctc gct gac ttg gtt gag aaa cac caa gaa aca ctg gct gcc att gag   384
Leu Ala Asp Leu Val Glu Lys His Gln Glu Thr Leu Ala Ala Ile Glu
        115                 120                 125 tca atg gat aat ggt aag tca ttg ttt tgt gcg cgc ggt gac gtc gct   432
Ser Met Asp Asn Gly Lys Ser Leu Phe Cys Ala Arg Gly Asp Val Ala
    130                 135                 140 tta gta tct aaa tac ttg cgt tct tgc ggt ggt tgg gca gat aaa atc   480
Leu Val Ser Lys Tyr Leu Arg Ser Cys Gly Gly Trp Ala Asp Lys Ile
145                 150                 155                 160 tac ggt aac gtt att gac aca ggt aaa aac cat ttt acc tac tca att   528
Tyr Gly Asn Val Ile Asp Thr Gly Lys Asn His Phe Thr Tyr Ser Ile
                165                 170                 175 aag gaa cca tta ggc gtt tgc ggc caa ata atc cct tgg aac ttc cct   576
Lys Glu Pro Leu Gly Val Cys Gly Gln Ile Ile Pro Trp Asn Phe Pro
```

```
                180              185              190
tta ttg atg tgg tca tgg aaa att ggg cct gct ctg gct aca ggt aac    624
Leu Leu Met Trp Ser Trp Lys Ile Gly Pro Ala Leu Ala Thr Gly Asn
        195              200              205 acc gtc gta ttg aaa ccc gct gaa aca aca cct tta tct gcc ctt ttc    672
Thr Val Val Leu Lys Pro Ala Glu Thr Thr Pro Leu Ser Ala Leu Phe
210              215              220 gct tcc cag ttg tgt cag gaa gca ggc ata ccc gct ggt gta gtc aat    720
Ala Ser Gln Leu Cys Gln Glu Ala Gly Ile Pro Ala Gly Val Val Asn
225              230              235              240 atc ctt ccg ggt tcc ggt aga gtt gtt gga gaa aga ttg agt gca cac    768
Ile Leu Pro Gly Ser Gly Arg Val Val Gly Glu Arg Leu Ser Ala His
            245              250              255 cca gac gtg aag aag att gct ttt aca ggc tct act gcc acc ggc cgc    816
Pro Asp Val Lys Lys Ile Ala Phe Thr Gly Ser Thr Ala Thr Gly Arg
        260              265              270 cat att atg aag gtc gct gcc gat act gtc aag aaa gtc act ttg gag    864
His Ile Met Lys Val Ala Ala Asp Thr Val Lys Lys Val Thr Leu Glu
    275              280              285 ctg gga ggt aaa tca cca aat att gtg ttt gct gac gct gat cta gat    912
Leu Gly Gly Lys Ser Pro Asn Ile Val Phe Ala Asp Ala Asp Leu Asp
290              295              300 aaa gcc gtc aag aac att gcc ttc ggt att ttt tac aac tct ggt gaa    960
Lys Ala Val Lys Asn Ile Ala Phe Gly Ile Phe Tyr Asn Ser Gly Glu
305              310              315              320 gtt tgc tgc gct ggt tcc aga ata tac att caa gat aca gta tac gag   1008
Val Cys Cys Ala Gly Ser Arg Ile Tyr Ile Gln Asp Thr Val Tyr Glu
            325              330              335 gag gtg ttg caa aaa cta aag gat tac acc gag tca cta aag gtc ggt   1056
Glu Val Leu Gln Lys Leu Lys Asp Tyr Thr Glu Ser Leu Lys Val Gly
        340              345              350 gac cca ttt gat gag gaa gtt ttc caa ggt gct caa aca tct gac aaa   1104
Asp Pro Phe Asp Glu Glu Val Phe Gln Gly Ala Gln Thr Ser Asp Lys
    355              360              365 cag ctg cat aaa att tta gac tat gtc gat gta gca aaa tca gag ggg   1152
Gln Leu His Lys Ile Leu Asp Tyr Val Asp Val Ala Lys Ser Glu Gly
370              375              380 gct cgt ctt gtg act gga ggg gcc aga cat ggc agt aaa ggt tat ttt   1200
Ala Arg Leu Val Thr Gly Gly Ala Arg His Gly Ser Lys Gly Tyr Phe
385              390              395              400 gtc aag cca aca gtg ttt gct gat gtc aaa gaa gat atg aga att gtt   1248
Val Lys Pro Thr Val Phe Ala Asp Val Lys Glu Asp Met Arg Ile Val
            405              410              415 aag gag gaa gtg ttt ggt ccc att gta act gta tcc aag ttt tct act   1296
Lys Glu Glu Val Phe Gly Pro Ile Val Thr Val Ser Lys Phe Ser Thr
        420              425              430 gtt gat gaa gtg att gct atg gca aat gat tct caa tat ggg tta gcc   1344
Val Asp Glu Val Ile Ala Met Ala Asn Asp Ser Gln Tyr Gly Leu Ala
    435              440              445 gca ggt att cac act aac gat att aac aag gct gtt gat gtg tcc aaa   1392
Ala Gly Ile His Thr Asn Asp Ile Asn Lys Ala Val Asp Val Ser Lys
450              455              460 aga gtg aaa gct ggt act gtt tgg ata aat acc tat aac aac ttc cac   1440
Arg Val Lys Ala Gly Thr Val Trp Ile Asn Thr Tyr Asn Asn Phe His
465              470              475              480 caa aat gtt cct ttc ggt ggc ttc ggc cag tca ggt att ggc cgt gaa   1488
Gln Asn Val Pro Phe Gly Gly Phe Gly Gln Ser Gly Ile Gly Arg Glu
            485              490              495 atg ggt gag gct gct tta agt aac tac act caa aca aaa tct gtc aga   1536
```

Met Gly Glu Ala Ala Leu Ser Asn Tyr Thr Gln Thr Lys Ser Val Arg
                500                 505                 510 att gcc att gac aag cca att cgt tga                                      1563
Ile Ala Ile Asp Lys Pro Ile Arg
            515                 520

<210> SEQ ID NO 58
<211> LENGTH: 520
<212> TYPE: PRT
<213> ORGANISM: Saccharomyces cerevisiae

<400> SEQUENCE: 58

Met Leu Ser Arg Thr Arg Ala Ala Pro Asn Ser Arg Ile Phe Thr
1               5                   10                  15

Arg Ser Leu Leu Arg Leu Tyr Ser Gln Ala Pro Leu Arg Val Pro Ile
                20                  25                  30

Thr Leu Pro Asn Gly Phe Thr Tyr Glu Gln Pro Thr Gly Leu Phe Ile
            35                  40                  45

Asn Gly Glu Phe Val Ala Ser Lys Gln Lys Thr Phe Asp Val Ile
50                  55                  60

Asn Pro Ser Asn Glu Glu Lys Ile Thr Thr Val Tyr Lys Ala Met Glu
65                  70                  75                  80

Asp Asp Val Asp Glu Ala Val Ala Ala Lys Lys Ala Phe Glu Thr
                85                  90                  95

Lys Trp Ser Ile Val Glu Pro Glu Val Arg Ala Lys Ala Leu Phe Asn
                100                 105                 110

Leu Ala Asp Leu Val Glu Lys His Gln Glu Thr Leu Ala Ala Ile Glu
            115                 120                 125

Ser Met Asp Asn Gly Lys Ser Leu Phe Cys Ala Arg Gly Asp Val Ala
            130                 135                 140

Leu Val Ser Lys Tyr Leu Arg Ser Cys Gly Gly Trp Ala Asp Lys Ile
145                 150                 155                 160

Tyr Gly Asn Val Ile Asp Thr Gly Lys Asn His Phe Thr Tyr Ser Ile
                165                 170                 175

Lys Glu Pro Leu Gly Val Cys Gly Gln Ile Ile Pro Trp Asn Phe Pro
            180                 185                 190

Leu Leu Met Trp Ser Trp Lys Ile Gly Pro Ala Leu Ala Thr Gly Asn
            195                 200                 205

Thr Val Val Leu Lys Pro Ala Glu Thr Thr Pro Leu Ser Ala Leu Phe
210                 215                 220

Ala Ser Gln Leu Cys Gln Glu Ala Gly Ile Pro Ala Gly Val Val Asn
225                 230                 235                 240

Ile Leu Pro Gly Ser Gly Arg Val Val Gly Glu Arg Leu Ser Ala His
                245                 250                 255

Pro Asp Val Lys Lys Ile Ala Phe Thr Gly Ser Thr Ala Thr Gly Arg
            260                 265                 270

His Ile Met Lys Val Ala Ala Asp Thr Val Lys Lys Val Thr Leu Glu
            275                 280                 285

Leu Gly Gly Lys Ser Pro Asn Ile Val Phe Ala Asp Ala Asp Leu Asp
            290                 295                 300

Lys Ala Val Lys Asn Ile Ala Phe Gly Ile Phe Tyr Asn Ser Gly Glu
305                 310                 315                 320

Val Cys Cys Ala Gly Ser Arg Ile Tyr Ile Gln Asp Thr Val Tyr Glu
                325                 330                 335

Glu Val Leu Gln Lys Leu Lys Asp Tyr Thr Glu Ser Leu Lys Val Gly

```
                      340                 345                 350
Asp Pro Phe Asp Glu Val Phe Gln Gly Ala Gln Thr Ser Asp Lys
        355                 360                 365

Gln Leu His Lys Ile Leu Asp Tyr Val Asp Val Ala Lys Ser Glu Gly
    370                 375                 380

Ala Arg Leu Val Thr Gly Gly Ala Arg His Gly Ser Lys Gly Tyr Phe
385                 390                 395                 400

Val Lys Pro Thr Val Phe Ala Asp Val Lys Glu Asp Met Arg Ile Val
                405                 410                 415

Lys Glu Glu Val Phe Gly Pro Ile Val Thr Val Ser Lys Phe Ser Thr
            420                 425                 430

Val Asp Glu Val Ile Ala Met Ala Asn Asp Ser Gln Tyr Gly Leu Ala
        435                 440                 445

Ala Gly Ile His Thr Asn Asp Ile Asn Lys Ala Val Asp Val Ser Lys
    450                 455                 460

Arg Val Lys Ala Gly Thr Val Trp Ile Asn Thr Tyr Asn Asn Phe His
465                 470                 475                 480

Gln Asn Val Pro Phe Gly Gly Phe Gly Gln Ser Gly Ile Gly Arg Glu
                485                 490                 495

Met Gly Glu Ala Ala Leu Ser Asn Tyr Thr Gln Thr Lys Ser Val Arg
            500                 505                 510

Ile Ala Ile Asp Lys Pro Ile Arg
        515                 520

<210> SEQ ID NO 59
<211> LENGTH: 1503
<212> TYPE: DNA
<213> ORGANISM: Saccharomyces cerevisiae
<220> FEATURE:
<221> NAME/KEY: CDS
<222> LOCATION: (1)..(1503)
<223> OTHER INFORMATION: GenBank Accession No. NM_001183875

<400> SEQUENCE: 59 atg act aag cta cac ttt gac act gct gaa cca gtc aag atc aca ctt     48
Met Thr Lys Leu His Phe Asp Thr Ala Glu Pro Val Lys Ile Thr Leu
1               5                   10                  15 cca aat ggt ttg aca tac gag caa cca acc ggt cta ttc att aac aac     96
Pro Asn Gly Leu Thr Tyr Glu Gln Pro Thr Gly Leu Phe Ile Asn Asn
            20                  25                  30 aag ttt atg aaa gct caa gac ggt aag acc tat ccc gtc gaa gat cct    144
Lys Phe Met Lys Ala Gln Asp Gly Lys Thr Tyr Pro Val Glu Asp Pro
        35                  40                  45 tcc act gaa aac acc gtt tgt gag gtc tct tct gcc act gaa gat        192
Ser Thr Glu Asn Thr Val Cys Glu Val Ser Ser Ala Thr Glu Asp
    50                  55                  60 gtt gaa tat gct atc gaa tgt gcc gac cgt gct ttc cac gac act gaa    240
Val Glu Tyr Ala Ile Glu Cys Ala Asp Arg Ala Phe His Asp Thr Glu
65                  70                  75                  80 tgg gct acc caa gac cca aga gaa aga ggc cgt cta cta agt aag ttg    288
Trp Ala Thr Gln Asp Pro Arg Glu Arg Gly Arg Leu Leu Ser Lys Leu
                85                  90                  95 gct gac gaa ttg gaa agc caa att gac ttg gtt tct tcc att gaa gct    336
Ala Asp Glu Leu Glu Ser Gln Ile Asp Leu Val Ser Ser Ile Glu Ala
            100                 105                 110 ttg gac aat ggt aaa act ttg gcc tta gcc cgt ggg gat gtt acc att    384
Leu Asp Asn Gly Lys Thr Leu Ala Leu Ala Arg Gly Asp Val Thr Ile
        115                 120                 125
```

```
gca atc aac tgt cta aga gat gct gct gcc tat gcc gac aaa gtc aac      432
Ala Ile Asn Cys Leu Arg Asp Ala Ala Ala Tyr Ala Asp Lys Val Asn
130             135                 140 ggt aga aca atc aac acc ggt gac ggc tac atg aac ttc acc acc tta      480
Gly Arg Thr Ile Asn Thr Gly Asp Gly Tyr Met Asn Phe Thr Thr Leu
145             150                 155                 160 gag cca atc ggt gtc tgt ggt caa att att cca tgg aac ttt cca ata      528
Glu Pro Ile Gly Val Cys Gly Gln Ile Ile Pro Trp Asn Phe Pro Ile
                165                 170                 175 atg atg ttg gct tgg aag atc gcc cca gca ttg gcc atg ggt aac gtc      576
Met Met Leu Ala Trp Lys Ile Ala Pro Ala Leu Ala Met Gly Asn Val
            180                 185                 190 tgt atc ttg aaa ccc gct gct gtc aca cct tta aat gcc cta tac ttt      624
Cys Ile Leu Lys Pro Ala Ala Val Thr Pro Leu Asn Ala Leu Tyr Phe
        195                 200                 205 gct tct tta tgt aag aag gtt ggt att cca gct ggt gtc gtc aac atc      672
Ala Ser Leu Cys Lys Lys Val Gly Ile Pro Ala Gly Val Val Asn Ile
    210                 215                 220 gtt cca ggt cct ggt aga act gtt ggt gct gct ttg acc aac gac cca      720
Val Pro Gly Pro Gly Arg Thr Val Gly Ala Ala Leu Thr Asn Asp Pro
225                 230                 235                 240 aga atc aga aag ctg gct ttt acc ggt tct aca gaa gtc ggt aag agt      768
Arg Ile Arg Lys Leu Ala Phe Thr Gly Ser Thr Glu Val Gly Lys Ser
                245                 250                 255 gtt gct gtc gac tct tct gaa tct aac ttg aag aaa atc act ttg gaa      816
Val Ala Val Asp Ser Ser Glu Ser Asn Leu Lys Lys Ile Thr Leu Glu
            260                 265                 270 cta ggt ggt aag tcc gcc cat ttg gtc ttt gac gat gct aac att aag      864
Leu Gly Gly Lys Ser Ala His Leu Val Phe Asp Asp Ala Asn Ile Lys
        275                 280                 285 aag act tta cca aat cta gta aac ggt att ttc aag aac gct ggt caa      912
Lys Thr Leu Pro Asn Leu Val Asn Gly Ile Phe Lys Asn Ala Gly Gln
    290                 295                 300 att tgt tcc tct ggt tct aga att tac gtt caa gaa ggt att tac gac      960
Ile Cys Ser Ser Gly Ser Arg Ile Tyr Val Gln Glu Gly Ile Tyr Asp
305                 310                 315                 320 gaa cta ttg gct gct ttc aag gct tac ttg gaa acc gaa atc aaa gtt     1008
Glu Leu Leu Ala Ala Phe Lys Ala Tyr Leu Glu Thr Glu Ile Lys Val
                325                 330                 335 ggt aat cca ttt gac aag gct aac ttc caa ggt gct atc act aac cgt     1056
Gly Asn Pro Phe Asp Lys Ala Asn Phe Gln Gly Ala Ile Thr Asn Arg
            340                 345                 350 caa caa ttc gac aca att atg aac tac atc gat atc ggt aag aaa gaa     1104
Gln Gln Phe Asp Thr Ile Met Asn Tyr Ile Asp Ile Gly Lys Lys Glu
        355                 360                 365 ggc gcc aag atc tta act ggt ggc gaa aaa gtt ggt gac aag ggt tac     1152
Gly Ala Lys Ile Leu Thr Gly Gly Glu Lys Val Gly Asp Lys Gly Tyr
    370                 375                 380 ttc atc aga cca acc gtt ttc tac gat gtt aat gaa gac atg aga att     1200
Phe Ile Arg Pro Thr Val Phe Tyr Asp Val Asn Glu Asp Met Arg Ile
385                 390                 395                 400 gtt aag gaa gaa att ttt gga cca gtt gtc act gtc gca aag ttc aag     1248
Val Lys Glu Glu Ile Phe Gly Pro Val Val Thr Val Ala Lys Phe Lys
                405                 410                 415 act tta gaa gaa ggt gtc gaa atg gct aac agc tct gaa ttc ggt cta     1296
Thr Leu Glu Glu Gly Val Glu Met Ala Asn Ser Ser Glu Phe Gly Leu
            420                 425                 430 ggt tct ggt atc gaa aca gaa tct ttg agc aca ggt ttg aag gtg gcc     1344
Gly Ser Gly Ile Glu Thr Glu Ser Leu Ser Thr Gly Leu Lys Val Ala
        435                 440                 445
```

```
aag atg ttg aag gcc ggt acc gtc tgg atc aac aca tac aac gat ttt    1392
Lys Met Leu Lys Ala Gly Thr Val Trp Ile Asn Thr Tyr Asn Asp Phe
    450                 455                 460 gac tcc aga gtt cca ttc ggt ggt gtt aag caa tct ggt tac ggt aga    1440
Asp Ser Arg Val Pro Phe Gly Gly Val Lys Gln Ser Gly Tyr Gly Arg
465                 470                 475                 480 gaa atg ggt gaa gaa gtc tac cat gca tac act gaa gta aaa gct gtc    1488
Glu Met Gly Glu Glu Val Tyr His Ala Tyr Thr Glu Val Lys Ala Val
                485                 490                 495 aga att aag ttg taa                                                 1503
Arg Ile Lys Leu
            500

<210> SEQ ID NO 60
<211> LENGTH: 500
<212> TYPE: PRT
<213> ORGANISM: Saccharomyces cerevisiae

<400> SEQUENCE: 60

Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140

Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285
```

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
        500

<210> SEQ ID NO 61
<211> LENGTH: 4519
<212> TYPE: DNA
<213> ORGANISM: Artificial sequence
<220> FEATURE:
<223> OTHER INFORMATION: pLA54

<400> SEQUENCE: 61
caccttggct aactcgttgt atcatcactg gataacttcg tataatgtat gctatacgaa    60
gttatcgaac agagaaacta atccacatt aattgagagt tctatctatt agaaaatgca   120
aactccaact aaatgggaaa acagataacc tcttttattt tttttaatg tttgatattc    180 gagtcttttt cttttgttag gtttatattc atcatttcaa tgaataaaag aagcttctta   240
ttttggttgc aaagaatgaa aaaaaggat ttttcatac ttctaaagct tcaattataa    300 ccaaaatt tataaatgaa gagaaaaat ctagtagtat caagttaaac ttagaaaaac    360
tcatcgagca tcaaatgaaa ctgcaattta ttcatatcag gattatcaat accatatttt   420 tgaaaagcc gtttctgtaa tgaaggagaa aactcaccga ggcagttcca taggatggca   480
agatcctggt atcggtctgc gattccgact cgtccaacat caatacaacc tattaatttc   540
ccctcgtcaa aaataaggtt atcaagtgag aaatcaccat gagtgacgac tgaatccggt   600
gagaatggca aaagcttatg catttctttc cagacttgtt caacaggcca gccattacgc   660
tcgtcatcaa aatcactcgc atcaaccaaa ccgttattca ttcgtgattg cgcctgagcg   720
agacgaaata cgcgatcgct gttaaaagga caattacaaa caggaatcga atgcaaccgg   780
cgcaggaaca ctgccagcgc atcaacaata ttttcacctg aatcaggata ttcttctaat   840

```
acctggaatg ctgttttgcc ggggatcgca gtggtgagta accatgcatc atcaggagta     900
cggataaaat gcttgatggt cggaagaggc ataaattccg tcagccagtt tagtctgacc     960
atctcatctg taacatcatt ggcaacgcta cctttgccat gtttcagaaa caactctggc    1020
gcatcgggct tcccatacaa tcgatagatt gtcgcacctg attgcccgac attatcgcga    1080
gcccatttat acccatataa atcagcatcc atgttggaat ttaatcgcgg cctcgaaacg    1140
tgagtctttt ccttacccat ctcgagtttt aatgttactt ctcttgcagt tagggaacta    1200
taatgtaact caaaataaga ttaaacaaac taaaataaaa agaagttata cagaaaaacc    1260
catataaacc agtactaatc cataataata atacacaaaa aaactatcaa ataaaaccag    1320
aaaacagatt gaatagaaaa attttttcga tctccttta tattcaaaat tcgatatatg    1380
aaaaagggaa ctctcagaaa atcaccaaat caatttaatt agatttttct tttccttcta    1440
gcgttggaaa gaaaaatttt tctttttttt tttagaaatg aaaaattttt gccgtaggaa    1500
tcaccgtata aaccctgtat aaacgctact ctgttcacct gtgtaggcta tgattgaccc    1560
agtgttcatt gttattgcga gagagcggga gaaagaacc gatacaagag atccatgctg    1620
gtatagttgt ctgtccaaca cttttgatgaa cttgtaggac gatgatgtgt atttagacga    1680
gtacgtgtgt gactattaag tagttatgat agagaggttt gtacggtgtg ttctgtgtaa    1740
ttcgattgag aaaatggtta tgaatcccta gataacttcg tataatgtat gctatacgaa    1800
gttatctgaa cattagaata cgtaatccgc aatgcgggga tcctctagag tcgacctgca    1860
ggcatgcaag cttggcgtaa tcatggtcat agctgtttcc tgtgtgaaat tgttatccgc    1920
tcacaattcc acacaacata cgagccggaa gcataaagtg taaagcctgg ggtgcctaat    1980
gagtgagcta actcacatta attgcgttgc gctcactgcc cgctttccag tcgggaaacc    2040
tgtcgtgcca gctgcattaa tgaatcggcc aacgcgcggg gagaggcggt ttgcgtattg    2100
ggcgctcttc cgcttcctcg ctcactgact cgctgcgctc ggtcgttcgg ctgcggcgag    2160
cggtatcagc tcactcaaag gcggtaatac ggttatccac agaatcaggg gataacgcag    2220
gaaagaacat gtgagcaaaa ggccagcaaa aggccaggaa ccgtaaaaag gccgcgttgc    2280
tggcgttttt ccataggctc cgcccccctg acgagcatca caaaaatcga cgctcaagtc    2340
agaggtggcg aaacccgaca ggactataaa gataccaggc gtttccccct ggaagctccc    2400
tcgtgcgctc tcctgttccg accctgccgc ttaccggata cctgtccgcc tttctccctt    2460
cgggaagcgt ggcgctttct catagctcac gctgtaggta tctcagttcg gtgtaggtcg    2520
ttcgctccaa gctgggctgt gtgcacgaac cccccgttca gcccgaccgc tgcgccttat    2580
ccggtaacta tcgtcttgag tccaacccgg taagacacga cttatcgcca ctggcagcag    2640
ccactggtaa caggattagc agagcgaggt atgtaggcgg tgctacagag ttcttgaagt    2700
ggtggcctaa ctacggctac actagaagga cagtatttgg tatctgcgct ctgctgaagc    2760
cagttacctt cggaaaaaga gttggtagct cttgatccgg caaacaaacc accgctggta    2820
gcggtggttt ttttgtttgc aagcagcaga ttacgcgcag aaaaaaagga tctcaagaag    2880
atcctttgat cttttctacg ggtctgacgc tcagtggaa cgaaaactca cgttaaggga    2940
ttttggtcat gagattatca aaaaggatct tcacctagat ccttttaaat taaaaatgaa    3000
gttttaaatc aatctaaagt atatatgagt aaacttggtc tgacagttac caatgcttaa    3060
tcagtgaggc acctatctca gcgatctgtc tatttcgttc atccatagtt gcctgactcc    3120
ccgtcgtgta gataactacg atacgggagg gcttaccatc tggccccagt gctgcaatga    3180
```

-continued

| | |
|---|---|
| taccgcgaga cccacgctca ccggctccag atttatcagc aataaaccag ccagccggaa | 3240 |
| gggcccgagcg cagaagtggt cctgcaactt tatccgcctc catccagtct attaattgtt | 3300 |
| gccgggaagc tagagtaagt agttcgccag ttaatagttt gcgcaacgtt gttgccattg | 3360 |
| ctacaggcat cgtggtgtca cgctcgtcgt ttggtatggc ttcattcagc tccggttccc | 3420 |
| aacgatcaag gcgagttaca tgatccccca tgttgtgcaa aaaagcggtt agctccttcg | 3480 |
| gtcctccgat cgttgtcaga agtaagttgg ccgcagtgtt atcactcatg gttatggcag | 3540 |
| cactgcataa ttctcttact gtcatgccat ccgtaagatg cttttctgtg actggtgagt | 3600 |
| actcaaccaa gtcattctga gaatagtgta tgcggcgacc gagttgctct tgcccggcgt | 3660 |
| caatacggga taataccgcg ccacatagca gaactttaaa agtgctcatc attggaaaac | 3720 |
| gttcttcggg gcgaaaactc tcaaggatct taccgctgtt gagatccagt tcgatgtaac | 3780 |
| ccactcgtgc acccaactga tcttcagcat cttttacttt caccagcgtt tctgggtgag | 3840 |
| caaaaacagg aaggcaaaat gccgcaaaaa agggaataag ggcgacacgg aaatgttgaa | 3900 |
| tactcatact cttcctttttt caatattatt gaagcattta tcagggttat tgtctcatga | 3960 |
| gcggatacat atttgaatgt atttagaaaa ataaacaaat aggggttccg cgcacatttc | 4020 |
| cccgaaaagt gccacctgac gtctaagaaa ccattattat catgacatta acctataaaa | 4080 |
| ataggcgtat cacgaggccc tttcgtctcg cgcgtttcgg tgatgacggt gaaaacctct | 4140 |
| gacacatgca gctcccggag acggtcacag cttgtctgta gcggatgcc gggagcagac | 4200 |
| aagcccgtca gggcgcgtca gcgggtgttg gcgggtgtcg ggctggctt aactatgcgg | 4260 |
| catcagagca gattgtactg agagtgcacc atatgcggtg tgaaataccg cacagatgcg | 4320 |
| taaggagaaa ataccgcatc aggcgccatt cgccattcag gctgcgcaac tgttgggaag | 4380 |
| ggcgatcggt gcgggcctct tcgctattac gccagctggc gaaagggga tgtgctgcaa | 4440 |
| ggcgattaag ttgggtaacg ccagggtttt cccagtcacg acgttgtaaa acgacggcca | 4500 |
| gtgaattcga gctcggtac | 4519 |

<210> SEQ ID NO 62
<211> LENGTH: 80
<212> TYPE: DNA
<213> ORGANISM: Artificial sequence
<220> FEATURE:
<223> OTHER INFORMATION: BK505

<400> SEQUENCE: 62

| | |
|---|---|
| ttccggtttc tttgaaattt ttttgattcg gtaatctccg agcagaagga gcattgcgga | 60 |
| ttacgtattc taatgttcag | 80 |

<210> SEQ ID NO 63
<211> LENGTH: 81
<212> TYPE: DNA
<213> ORGANISM: Artificial sequence
<220> FEATURE:
<223> OTHER INFORMATION: BK506

<400> SEQUENCE: 63

| | |
|---|---|
| gggtaataac tgatataatt aaattgaagc tctaatttgt gagtttagta caccttggct | 60 |
| aactcgttgt atcatcactg g | 81 |

<210> SEQ ID NO 64
<211> LENGTH: 38
<212> TYPE: DNA
<213> ORGANISM: Artificial sequence

<220> FEATURE:
<223> OTHER INFORMATION: LA468

<400> SEQUENCE: 64
gcctcgagtt ttaatgttac ttctcttgca gttaggga            38

<210> SEQ ID NO 65
<211> LENGTH: 31
<212> TYPE: DNA
<213> ORGANISM: Artificial sequence
<220> FEATURE:
<223> OTHER INFORMATION: LA492

<400> SEQUENCE: 65
gctaaattcg agtgaaacac aggaagacca g                   31

<210> SEQ ID NO 66
<211> LENGTH: 23
<212> TYPE: DNA
<213> ORGANISM: Artificial sequence
<220> FEATURE:
<223> OTHER INFORMATION: AK109-1

<400> SEQUENCE: 66
agtcacatca agatcgttta tgg                            23

<210> SEQ ID NO 67
<211> LENGTH: 23
<212> TYPE: DNA
<213> ORGANISM: Artificial sequence
<220> FEATURE:
<223> OTHER INFORMATION: AK109-2

<400> SEQUENCE: 67
gcacggaata tgggactact tcg                            23

<210> SEQ ID NO 68
<211> LENGTH: 23
<212> TYPE: DNA
<213> ORGANISM: Artificial sequence
<220> FEATURE:
<223> OTHER INFORMATION: AK109-3

<400> SEQUENCE: 68
actccacttc aagtaagagt ttg                            23

<210> SEQ ID NO 69
<211> LENGTH: 24
<212> TYPE: DNA
<213> ORGANISM: Artificial sequence
<220> FEATURE:
<223> OTHER INFORMATION: oBP452

<400> SEQUENCE: 69
ttctcgacgt gggccttttt cttg                           24

<210> SEQ ID NO 70
<211> LENGTH: 49
<212> TYPE: DNA
<213> ORGANISM: Artificial sequence
<220> FEATURE:
<223> OTHER INFORMATION: oBP453

<400> SEQUENCE: 70
tgcagcttta aataatcggt gtcactactt tgccttcgtt tatcttgcc   49

```
<210> SEQ ID NO 71
<211> LENGTH: 49
<212> TYPE: DNA
<213> ORGANISM: Artificial sequence
<220> FEATURE:
<223> OTHER INFORMATION: oBP454

<400> SEQUENCE: 71
gagcaggcaa gataaacgaa ggcaaagtag tgacaccgat tatttaaag            49

<210> SEQ ID NO 72
<211> LENGTH: 49
<212> TYPE: DNA
<213> ORGANISM: Artificial sequence
<220> FEATURE:
<223> OTHER INFORMATION: oBP455

<400> SEQUENCE: 72
tatggaccct gaaaccacag ccacattgta accaccacga cggttgttg            49

<210> SEQ ID NO 73
<211> LENGTH: 49
<212> TYPE: DNA
<213> ORGANISM: Artificial sequence
<220> FEATURE:
<223> OTHER INFORMATION: oBP456

<400> SEQUENCE: 73
tttagcaaca accgtcgtgg tggttacaat gtggctgtgg tttcagggt            49

<210> SEQ ID NO 74
<211> LENGTH: 49
<212> TYPE: DNA
<213> ORGANISM: Artificial sequence
<220> FEATURE:
<223> OTHER INFORMATION: oBP457

<400> SEQUENCE: 74
ccagaaaccc tatacctgtg tggacgtaag gccatgaagc ttttctttt            49

<210> SEQ ID NO 75
<211> LENGTH: 49
<212> TYPE: DNA
<213> ORGANISM: Artificial sequence
<220> FEATURE:
<223> OTHER INFORMATION: oBP458

<400> SEQUENCE: 75
attggaaaga aaaagcttca tggccttacg tccacacagg tatagggtt            49

<210> SEQ ID NO 76
<211> LENGTH: 22
<212> TYPE: DNA
<213> ORGANISM: Artificial sequence
<220> FEATURE:
<223> OTHER INFORMATION: oBP459

<400> SEQUENCE: 76
cataagaaca cctttggtgg ag                                         22

<210> SEQ ID NO 77
<211> LENGTH: 22
<212> TYPE: DNA
<213> ORGANISM: Artificial sequence
<220> FEATURE:
<223> OTHER INFORMATION: BP460
```

-continued

<400> SEQUENCE: 77
aggattatca ttcataagtt tc						22

<210> SEQ ID NO 78
<211> LENGTH: 20
<212> TYPE: DNA
<213> ORGANISM: Artificial sequence
<220> FEATURE:
<223> OTHER INFORMATION: LA135

<400> SEQUENCE: 78
cttggcagca acaggactag						20

<210> SEQ ID NO 79
<211> LENGTH: 23
<212> TYPE: DNA
<213> ORGANISM: Artificial sequence
<220> FEATURE:
<223> OTHER INFORMATION: BP461

<400> SEQUENCE: 79
ttcttggagc tgggacatgt ttg					23

<210> SEQ ID NO 80
<211> LENGTH: 22
<212> TYPE: DNA
<213> ORGANISM: Artificial sequence
<220> FEATURE:
<223> OTHER INFORMATION: LA92

<400> SEQUENCE: 80
gagaagatgc ggccagcaaa ac					22

<210> SEQ ID NO 81
<211> LENGTH: 4242
<212> TYPE: DNA
<213> ORGANISM: Artificial sequence
<220> FEATURE:
<223> OTHER INFORMATION: pLA59

<400> SEQUENCE: 81
aaacgccagc aacgcggcct ttttacggtt cctggccttt tgctggcctt ttgctcacat			60 gttctttcct gcgttatccc ctgattctgt ggataaccgt attaccgcct ttgagtgagc			120 tgataccgct cgccgcagcc gaacgaccga gcgcagcgag tcagtgagcg aggaagcgga			180 agagcgccca atacgcaaac cgcctctccc cgcgcgttgg ccgattcatt aatgcagctg			240 gcacgacagg tttcccgact ggaaagcggg cagtgagcgc aacgcaatta atgtgagtta			300 gctcactcat taggcacccc aggctttaca ctttatgctt ccggctcgta tgttgtgtgg			360 aattgtgagc ggataacaat ttcacacagg aaacagctat gaccatgatt acgccaagct			420 tgcatgcctg caggtcgact ctagaggatc cgcaatgcgg atccgcattg cggattacgt			480 attctaatgt tcagtaccgt tcgtataatg tatgctatac gaagttatgc agattgtact			540 gagagtgcac cataccacct tttcaattca tcattttttt tttattcttt tttttgattt			600 cggtttcctt gaaatttttt tgattcggta atctccgaac agaaggaaga acgaaggaag			660 gagcacagac ttagattggt atatatacgc atatgtagtg ttgaagaaac atgaaattgc			720 ccagtattct taacccaact gcacagaaca aaaacctgca ggaaacgaag ataaatcatg			780 tcgaaagcta catataagga acgtgctgct actcatccta gtcctgttgc tgccaagcta			840

| | |
|---|---|
| tttaatatca tgcacgaaaa gcaaacaaac ttgtgtgctt cattggatgt tcgtaccacc | 900 |
| aaggaattac tggagttagt tgaagcatta ggtcccaaaa tttgtttact aaaaacacat | 960 |
| gtggatatct tgactgattt ttccatggag ggcacagtta agccgctaaa ggcattatcc | 1020 |
| gccaagtaca atttttact cttcgaagac agaaaatttg ctgacattgg taatacagtc | 1080 |
| aaattgcagt actctgcggg tgtatacaga atagcagaat gggcagacat tacgaatgca | 1140 |
| cacggtgtgg tgggcccagg tattgttagc ggtttgaagc aggcggcaga agaagtaaca | 1200 |
| aaggaaccta gaggcctttt gatgttagca gaattgtcat gcaagggctc cctatctact | 1260 |
| ggagaatata ctaagggtac tgttgacatt gcgaagagcg acaaagattt tgttatcggc | 1320 |
| tttattgctc aaagagacat gggtggaaga gatgaaggtt acgattggtt gattatgaca | 1380 |
| cccggtgtgg gtttagatga caagggagac gcattgggtc aacagtatag aaccgtggat | 1440 |
| gatgtggtct ctacaggatc tgacattatt attgttggaa gaggactatt tgcaagggga | 1500 |
| agggatgcta aggtagaggg tgaacgttac agaaaagcag gctgggaagc atatttgaga | 1560 |
| agatgcggcc agcaaaacta aaaaactgta ttataagtaa atgcatgtat actaaactca | 1620 |
| caaattagag cttcaattta attatatcag ttattaccct atgcggtgtg aaataccgca | 1680 |
| cagatgcgta aggagaaaat accgcatcag gaaattgtaa acgttaatat tttgttaaaa | 1740 |
| ttcgcgttaa attttgtta aatcagctca tttttaacc aataggccga atcggcaaa | 1800 |
| atcccttata aatcaaaaga atagaccgag atagggttga gtgttgttcc agtttggaac | 1860 |
| aagagtccac tattaaagaa cgtggactcc aacgtcaaag ggcgaaaaac cgtctatcag | 1920 |
| ggcgatggcc cactacgtga accatcaccc taatcaagat aacttcgtat aatgtatgct | 1980 |
| atacgaacgg taccagtgat gatacaacga gttagccaag gtgaattcac tggccgtcgt | 2040 |
| tttacaacgt cgtgactggg aaaaccctgg cgttacccaa cttaatcgcc ttgcagcaca | 2100 |
| tcccccttc gccagctggc gtaatagcga agaggcccgc accgatcgcc cttcccaaca | 2160 |
| gttgcgcagc ctgaatggcg aatggcgcct gatgcggtat tttctcctta cgcatctgtg | 2220 |
| cggtatttca caccgcatat ggtgcactct cagtacaatc tgctctgatg ccgcatagtt | 2280 |
| aagccagccc cgacacccgc caacacccgc tgacgcgccc tgacgggctt gtctgctccc | 2340 |
| ggcatccgct tacagacaag ctgtgaccgt ctccgggagc tgcatgtgtc agaggttttc | 2400 |
| accgtcatca ccgaaacgcg cgagacgaaa gggcctcgtg atacgcctat ttttataggt | 2460 |
| taatgtcatg ataataatgg tttcttagac gtcaggtggc acttttcggg gaaatgtgcg | 2520 |
| cggaacccct atttgtttat ttttctaaat acattcaaat atgtatccgc tcatgagaca | 2580 |
| ataaccctga taaatgcttc aataatattg aaaaaggaag agtatgagta ttcaacattt | 2640 |
| ccgtgtcgcc cttattccct ttttgcggc attttgcctt cctgttttg ctcacccaga | 2700 |
| aacgctggtg aaagtaaaag atgctgaaga tcagttgggt gcacgagtgg gttacatcga | 2760 |
| actggatctc aacagcggta agatccttga gagttttcgc cccgaagaac gttttccaat | 2820 |
| gatgagcact tttaaagttc tgctatgtgg cgcggtatta tcccgtattg acgccgggca | 2880 |
| agagcaactc ggtcgccgca tacactattc tcagaatgac ttggttgagt actcaccagt | 2940 |
| cacagaaaag catcttacgg atggcatgac agtaagagaa ttatgcagtg ctgccataac | 3000 |
| catgagtgat aacactgcgg ccaacttact tctgacaacg atcggaggac cgaaggagct | 3060 |
| aaccgctttt ttgcacaaca tgggggatca tgtaactcgc cttgatcgtt gggaaccgga | 3120 |
| gctgaatgaa gccataccaa acgacgagcg tgacaccacg atgcctgtag caatggcaac | 3180 |
| aacgttgcgc aaactattaa ctggcgaact acttactcta gcttcccggc aacaattaat | 3240 |

```
agactggatg gaggcggata aagttgcagg accacttctg cgctcggccc ttccggctgg    3300
ctggtttatt gctgataaat ctggagccgg tgagcgtggg tctcgcggta tcattgcagc    3360
actggggcca gatggtaagc cctcccgtat cgtagttatc tacacgacgg ggagtcaggc    3420
aactatggat gaacgaaata gacagatcgc tgagataggt gcctcactga ttaagcattg    3480
gtaactgtca gaccaagttt actcatatat actttagatt gatttaaaac ttcatttta    3540 atttaaaagg atctaggtga agatcctttt tgataatctc atgaccaaaa tcccttaacg    3600
tgagttttcg ttccactgag cgtcagaccc cgtagaaaag atcaaggat cttcttgaga    3660 tcctttttt ctgcgcgtaa tctgctgctt gcaaacaaaa aaaccaccgc taccagcggt    3720
ggtttgtttg ccggatcaag agctaccaac tcttttccg aaggtaactg gcttcagcag    3780
agcgcagata ccaaatactg tccttctagt gtagccgtag ttaggccacc acttcaagaa    3840
ctctgtagca ccgcctacat acctcgctct gctaatcctg ttaccagtgg ctgctgccag    3900
tggcgataag tcgtgtctta ccgggttgga ctcaagacga tagttaccgg ataaggcgca    3960
gcggtcgggc tgaacggggg gttcgtgcac acagcccagc ttggagcgaa cgacctacac    4020
cgaactgaga tacctacagc gtgagctatg agaaagcgcc acgcttcccg aagggagaaa    4080
ggcggacagg tatccggtaa gcggcagggt cggaacagga gagcgcacga gggagcttcc    4140
agggggaaac gcctggtatc tttatagtcc tgtcgggttt cgccacctct gacttgagcg    4200
tcgatttttg tgatgctcgt caggggggcg gagcctatgg aa                      4242

<210> SEQ ID NO 82
<211> LENGTH: 80
<212> TYPE: DNA
<213> ORGANISM: Artificial sequence
<220> FEATURE:
<223> OTHER INFORMATION: LA678

<400> SEQUENCE: 82
caacgttaac accgttttcg gtttgccagg tgacttcaac ttgtccttgt gcattgcgga    60
ttacgtattc taatgttcag                                                80

<210> SEQ ID NO 83
<211> LENGTH: 81
<212> TYPE: DNA
<213> ORGANISM: Artificial sequence
<220> FEATURE:
<223> OTHER INFORMATION: LA679

<400> SEQUENCE: 83
gtggagcatc gaagactggc aacatgattt caatcattct gatcttagag caccttggct    60
aactcgttgt atcatcactg g                                              81

<210> SEQ ID NO 84
<211> LENGTH: 23
<212> TYPE: DNA
<213> ORGANISM: Artificial sequence
<220> FEATURE:
<223> OTHER INFORMATION: LA337

<400> SEQUENCE: 84
ctcatttgaa tcagcttatg gtg                                            23

<210> SEQ ID NO 85
<211> LENGTH: 24
<212> TYPE: DNA
```

```
<213> ORGANISM: Artificial sequence
<220> FEATURE:
<223> OTHER INFORMATION: LA692

<400> SEQUENCE: 85
ggaagtcatt gacaccatct tggc                                            24

<210> SEQ ID NO 86
<211> LENGTH: 24
<212> TYPE: DNA
<213> ORGANISM: Artificial sequence
<220> FEATURE:
<223> OTHER INFORMATION: LA693

<400> SEQUENCE: 86
agaagctggg acagcagcgt tagc                                            24

<210> SEQ ID NO 87
<211> LENGTH: 7523
<212> TYPE: DNA
<213> ORGANISM: Artificial sequence
<220> FEATURE:
<223> OTHER INFORMATION: pLA34

<400> SEQUENCE: 87
ccagcttttg ttcccttag tgagggttaa ttgcgcgctt ggcgtaatca tggtcatagc       60
tgtttcctgt gtgaaattgt tatccgctca caattccaca acataggagcc cggaagca     120 taaagtgtaa agcctggggt gcctaatgag tgaggtaact cacattaatt gcgttgcgct    180
cactgcccgc tttccagtcg ggaaacctgt cgtgccagct gcattaatga atcggccaac    240
gcgcggggag aggcggtttg cgtattgggc gctcttccgc ttcctcgctc actgactcgc    300
tgcgctcggt cgttcggctg cggcgagcgg tatcagctca ctcaaaggcg gtaatacggt    360
tatccacaga atcaggggat aacgcaggaa agaacatgtg agcaaaaggc cagcaaaagg    420
ccaggaaccg taaaaaggcc gcgttgctgg cgttttttcca taggctccgc ccccctgacg    480
agcatcacaa aaatcgacgc tcaagtcaga ggtggcgaaa cccgacagga ctataaagat    540
accaggcgtt tcccctgga agctccctcg tgcgctctcc tgttccgacc ctgccgctta    600
ccggatacct gtccgccttt ctcccttcgg gaagcgtggc gctttctcat agctcacgct    660
gtaggtatct cagttcggtg taggtcgttc gctccaagct gggctgtgtg cacgaacccc    720
ccgttcagcc cgaccgctgc gccttatccg gtaactatcg tcttgagtcc aacccggtaa    780
gacacgactt atcgccactg gcagcagcca ctggtaacag gattagcaga gcgaggtatg    840
taggcggtgc tacagagttc ttgaagtggt ggcctaacta cggctacact agaaggacag    900
tatttggtat ctgcgctctg ctgaagccag ttaccttcgg aaaaagagtt ggtagctctt    960
gatccggcaa acaaaccacc gctggtagcg gtggtttttt tgtttgcaag cagcagatta   1020
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactcccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
```

```
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
tgtgcaaaaa agcggttagc tccttcggtc ctccgatcgt tgtcagaagt aagttggccg   1680
cagtgttatc actcatggtt atggcagcac tgcataattc tcttactgtc atgccatccg   1740
taagatgctt ttctgtgact ggtgagtact caaccaagtc attctgagaa tagtgtatgc   1800
ggcgaccgag ttgctcttgc ccggcgtcaa tacgggataa taccgcgcca catagcagaa   1860
ctttaaaagt gctcatcatt ggaaaacgtt cttcggggcg aaaactctca aggatcttac   1920
cgctgttgag atccagttcg atgtaaccca ctcgtgcacc caactgatct tcagcatctt   1980
ttactttcac cagcgtttct gggtgagcaa aaacaggaag gcaaaatgcc gcaaaaaagg   2040
gaataagggc gacacggaaa tgttgaatac tcatactctt ccttttttcaa tattattgaa   2100
gcatttatca gggttattgt ctcatgagcg gatacatatt tgaatgtatt tagaaaaata   2160
aacaaatagg ggttccgcgc acatttcccc gaaaagtgcc acctgaacga agcatctgtg   2220
cttcattttg tagaacaaaa atgcaacgcg agagcgctaa ttttttcaaac aaagaatctg   2280
agctgcattt ttacagaaca gaaatgcaac gcgaaagcgc tattttacca acgaagaatc   2340
tgtgcttcat ttttgtaaaa caaaaatgca acgcgagagc gctaattttt caaacaaaga   2400
atctgagctg catttttaca gaacagaaat gcaacgcgag agcgctattt taccaacaaa   2460
gaatctatac ttcttttttg ttctacaaaa atgcatcccg agagcgctat ttttctaaca   2520
aagcatctta gattactttt tttctccttt gtgcgctcta taatgcagtc tcttgataac   2580
ttttttgcact gtaggtccgt taaggttaga agaaggctac tttggtgtct attttctctt   2640
ccataaaaaa agcctgactc cacttcccgc gtttactgat tactagcgaa gctgcgggtg   2700
cattttttca agataaaggc atccccgatt atattctata ccgatgtgga ttgcgcatac   2760
tttgtgaaca gaaagtgata gcgttgatga ttcttcattg gtcagaaaat tatgaacggt   2820
ttcttctatt ttgtctctat atactacgta taggaaatgt ttacattttc gtattgtttt   2880
cgattcactc tatgaatagt tcttactaca attttttttgt ctaaagagta atactagaga   2940
taaacataaa aaatgtagag gtcgagttta gatgcaagtt caaggagcga aggtggatg   3000
ggtaggttat atagggatat agcacagaga tatatagcaa agagatactt ttgagcaatg   3060
tttgtggaag cggtattcgc aatattttag tagctcgtta cagtccggtg cgttttttggt   3120
tttttgaaag tgcgtcttca gagcgctttt ggttttcaaa agcgctctga agttcctata   3180
ctttctagag aataggaact tcggaatagg aacttcaaag cgtttccgaa aacgagcgct   3240
tccgaaaatg caacgcgagc tgcgcacata cagctcactg ttcacgtcgc acctatatct   3300
gcgtgttgcc tgtatatata tatacatgag aagaacggca tagtgcgtgt ttatgcttaa   3360
atgcgtactt atatgcgtct atttatgtag gatgaaaggt agtctagtac tcctgtgat   3420
attatcccat tccatgcggg gtatcgtatg cttccttcag cactacccct tagctgttct   3480
atatgctgcc actcctcaat tggattagtc tcatccttca atgctatcat ttccttttgat   3540
attggatcat ctaagaaacc attattatca tgacattaac ctataaaaat aggcgtatca   3600
cgaggccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaattcccgt tttaagagct tggtgagcgc taggagtcac   3840
```

```
tgccaggtat cgtttgaaca cggcattagt cagggaagtc ataacacagt cctttcccgc   3900
aattttcttt ttctattact cttggcctcc tctagtacac tctatatttt tttatgcctc   3960
ggtaatgatt ttcattttt ttttttcccct agcggatgac tcttttttt tcttagcgat   4020 tggcattatc acataatgaa ttatacatta tataaagtaa tgtgatttct tcgaagaata   4080
tactaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agcccacctcg cccaatggta   4740 ccaacgatgt tccctccacc aaaggtgttc ttatgtagtg acaccgatta tttaaagctg   4800
cagcatacga tatatataca tgtgtatata tgtataccta tgaatgtcag taagtatgta   4860
tacgaacagt atgatactga agatgacaag gtaatgcatc attctatacg tgtcattctg   4920
aacgaggcgc gctttccttt tttcttttg cttttctt ttttttctct tgaactcgac   4980
ggatctatgc ggtgtgaaat accgcacaga tgcgtaagga gaaataccg catcaggaaa   5040 ttgtaaacgt taatatttg ttaaaattcg cgttaaattt ttgttaaatc agctcatttt   5100
ttaaccaata ggccgaaatc ggcaaaatcc cttataaatc aaaagaatag accgagatag   5160
ggttgagtgt tgttccagtt tggaacaaga gtccactatt aaagaacgtg gactccaacg   5220
tcaaagggcg aaaaaccgtc tatcagggcg atggcccact acgtgaacca tcaccctaat   5280 caagttttt ggggtcgagg tgccgtaaag cactaaatcg gaaccctaaa gggagccccc   5340
gatttagagc ttgacgggga aagccggcga acgtggcgag aaaggaaggg aagaaagcga   5400
aaggagcggg cgctagggcg ctggcaagtg tagcggtcac gctgcgcgta accaccacac   5460
ccgccgcgct taatgcgccg ctacagggcg cgtcgcgcca ttcgccattc aggctgcgca   5520
actgttggga agggcgatcg gtgcgggcct cttcgctatt acgccagctg gcgaaagggg   5580
gatgtgctgc aaggcgatta agttgggtaa cgccagggtt ttcccagtca cgacgttgta   5640
aaacgacggc cagtgagcgc gcgtaatacg actcactata gggcgaattg ggtaccgggc   5700
cccccctcga ggtattagaa gccgccgagc gggcgacagc cctccgacgg aagactctcc   5760
tccgtgcgtc ctcgtcttca ccggtcgcgt tcctgaaacg cagatgtgcc tcgcgccgca   5820
ctgctccgaa caataaagat tctacaatac tagcttttat ggttatgaag aggaaaaatt   5880
ggcagtaacc tggccccaca aaccttcaaa ttaacgaatc aaattaacaa ccataggatg   5940
ataatgcgat tagtttttta gccttatttc tggggtaatt aatcagcgaa gcgatgattt   6000
ttgatctatt aacagatata taaatggaaa agctgcataa ccactttaac taatactttc   6060
aacattttca gtttgtatta cttcttattc aaatgtcata aaagtatcaa caaaaaattg   6120
ttaatatacc tctatacttt aacgtcaagg agaaaaatgt ccaatttact gcccgtacac   6180
caaaatttgc ctgcattacc ggtcgatgca acgagtgatg aggttcgcaa gaacctgatg   6240
```

```
gacatgttca gggatcgcca ggcgttttct gagcatacct ggaaaatgct tctgtccgtt    6300
tgccggtcgt gggcggcatg gtgcaagttg aataaccgga aatggtttcc cgcagaacct    6360
gaagatgttc gcgattatct tctatatctt caggcgcgcg gtctggcagt aaaaactatc    6420
cagcaacatt tgggccagct aaacatgctt catcgtcggt ccgggctgcc acgaccaagt    6480
gacagcaatg ctgtttcact ggttatgcgg cggatccgaa agaaaacgt tgatgccggt    6540 gaacgtgcaa aacaggctct agcgttcgaa cgcactgatt tcgaccaggt tcgttcactc    6600
atggaaaata gcgatcgctg ccaggatata cgtaatctgg catttctggg gattgcttat    6660
aacaccctgt tacgtatagc cgaaattgcc aggatcaggg ttaaagatat ctcacgtact    6720
gacggtggga gaatgttaat ccatattggc agaacgaaaa cgctggttag caccgcaggt    6780
gtagagaagg cacttagcct gggggtaact aaactggtcg agcgatggat ttccgtctct    6840
ggtgtagctg atgatccgaa taactacctg ttttgccggg tcagaaaaaa tggtgttgcc    6900
gcgccatctg ccaccagcca gctatcaact cgcgccctgg aagggatttt tgaagcaact    6960
catcgattga tttacggcgc taaggatgac tctggtcaga gatacctggc ctggtctgga    7020
cacagtgccc gtgtcggagc cgcgcgagat atggcccgcg ctggagtttc aataccggag    7080
atcatgcaag ctggtggctg gaccaatgta atatattgtca tgaactatat ccgtaacctg    7140
gatagtgaaa cagggggcaat ggtgcgcctg ctggaagatg gcgattagga gtaagcgaat    7200
ttcttatgat ttatgatttt tattattaaa taagttataa aaaaaataag tgtatacaaa    7260
ttttaaagtg actcttaggt tttaaaacga aaattcttat tcttgagtaa ctctttcctg    7320
taggtcaggt tgcttttctca ggtatagcat gaggtcgctc ttattgacca cacctctacc    7380
ggcatgccga gcaaatgcct gcaaatcgct ccccatttca cccaattgta gatatgctaa    7440
ctccagcaat gagttgatga atctcggtgt gtattttatg tcctcagagg acaacacctg    7500
tggtccgcca ccgcggtgga gct                                              7523

<210> SEQ ID NO 88
<211> LENGTH: 96
<212> TYPE: DNA
<213> ORGANISM: Artificial sequence
<220> FEATURE:
<223> OTHER INFORMATION: LA722

<400> SEQUENCE: 88
tgccaattat ttacctaaac atctataacc ttcaaaagta aaaaaataca caaacgttga    60
atcatcacct tggctaactc gttgtatcat cactgg                                96

<210> SEQ ID NO 89
<211> LENGTH: 80
<212> TYPE: DNA
<213> ORGANISM: Artificial sequence
<220> FEATURE:
<223> OTHER INFORMATION: LA733

<400> SEQUENCE: 89
cataatcaat ctcaaagaga acaacacaat acaataacaa gaagaacaaa gcattgcgga    60
ttacgtattc taatgttcag                                                  80

<210> SEQ ID NO 90
<211> LENGTH: 30
<212> TYPE: DNA
<213> ORGANISM: Artificial sequence
<220> FEATURE:
```

<223> OTHER INFORMATION: LA453

<400> SEQUENCE: 90
caccgaagaa gaatgcaaaa atttcagctc                                    30

<210> SEQ ID NO 91
<211> LENGTH: 25
<212> TYPE: DNA
<213> ORGANISM: Artificial sequence
<220> FEATURE:
<223> OTHER INFORMATION: LA694

<400> SEQUENCE: 91
gctgaagttg ttagaactgt tgttg                                         25

<210> SEQ ID NO 92
<211> LENGTH: 21
<212> TYPE: DNA
<213> ORGANISM: Artificial sequence
<220> FEATURE:
<223> OTHER INFORMATION: LA695

<400> SEQUENCE: 92
tgttagctgg agtagacttg g                                             21

<210> SEQ ID NO 93
<211> LENGTH: 22
<212> TYPE: DNA
<213> ORGANISM: Artificial sequence
<220> FEATURE:
<223> OTHER INFORMATION: oBP594

<400> SEQUENCE: 93
agctgtctcg tgttgtgggt tt                                            22

<210> SEQ ID NO 94
<211> LENGTH: 49
<212> TYPE: DNA
<213> ORGANISM: Artificial sequence
<220> FEATURE:
<223> OTHER INFORMATION: oBP595

<400> SEQUENCE: 94
cttaataata gaacaatatc atcctttacg ggcatcttat agtgtcgtt               49

<210> SEQ ID NO 95
<211> LENGTH: 49
<212> TYPE: DNA
<213> ORGANISM: Artificial sequence
<220> FEATURE:
<223> OTHER INFORMATION: oBP596

<400> SEQUENCE: 95
gcgccaacga cactataaga tgcccgtaaa ggatgatatt gttctatta               49

<210> SEQ ID NO 96
<211> LENGTH: 49
<212> TYPE: DNA
<213> ORGANISM: Artificial sequence
<220> FEATURE:
<223> OTHER INFORMATION: oBP597

<400> SEQUENCE: 96
tatggaccct gaaccacag ccacattgca acgacgacaa tgccaaacc                49

```
<210> SEQ ID NO 97
<211> LENGTH: 49
<212> TYPE: DNA
<213> ORGANISM: Artificial sequence
<220> FEATURE:
<223> OTHER INFORMATION: oBP598

<400> SEQUENCE: 97
tccttggttt ggcattgtcg tcgttgcaat gtggctgtgg tttcagggt            49

<210> SEQ ID NO 98
<211> LENGTH: 49
<212> TYPE: DNA
<213> ORGANISM: Artificial sequence
<220> FEATURE:
<223> OTHER INFORMATION: oBP599

<400> SEQUENCE: 98
atcctctcgc ggagtccctg ttcagtaaag gccatgaagc ttttctttt            49

<210> SEQ ID NO 99
<211> LENGTH: 49
<212> TYPE: DNA
<213> ORGANISM: Artificial sequence
<220> FEATURE:
<223> OTHER INFORMATION: oBP600

<400> SEQUENCE: 99
attggaaaga aaaagcttca tggcctttac tgaacaggga ctccgcgag             49

<210> SEQ ID NO 100
<211> LENGTH: 22
<212> TYPE: DNA
<213> ORGANISM: Artificial sequence
<220> FEATURE:
<223> OTHER INFORMATION: oBP601

<400> SEQUENCE: 100
tcataccaca atcttagacc at                                         22

<210> SEQ ID NO 101
<211> LENGTH: 21
<212> TYPE: DNA
<213> ORGANISM: Artificial sequence
<220> FEATURE:
<223> OTHER INFORMATION: oBP602

<400> SEQUENCE: 101
tgttcaaacc cctaaccaac c                                          21

<210> SEQ ID NO 102
<211> LENGTH: 22
<212> TYPE: DNA
<213> ORGANISM: Artificial sequence
<220> FEATURE:
<223> OTHER INFORMATION: oBP603

<400> SEQUENCE: 102
tgttcccaca atctattacc ta                                         22

<210> SEQ ID NO 103
<211> LENGTH: 31
<212> TYPE: DNA
<213> ORGANISM: Artificial sequence
<220> FEATURE:
<223> OTHER INFORMATION: LA811
```

```
<400> SEQUENCE: 103
aacgaagcat ctgtgcttca ttttgtagaa c                              31

<210> SEQ ID NO 104
<211> LENGTH: 59
<212> TYPE: DNA
<213> ORGANISM: Artificial sequence
<220> FEATURE:
<223> OTHER INFORMATION: LA817

<400> SEQUENCE: 104
cgatccactt gtatatttgg atgaattttt gaggaattct gaaccagtcc taaaacgag    59

<210> SEQ ID NO 105
<211> LENGTH: 31
<212> TYPE: DNA
<213> ORGANISM: Artificial sequence
<220> FEATURE:
<223> OTHER INFORMATION: LA812

<400> SEQUENCE: 105
aacaaagata tgctattgaa gtgcaagatg g                              31

<210> SEQ ID NO 106
<211> LENGTH: 33
<212> TYPE: DNA
<213> ORGANISM: Artificial sequence
<220> FEATURE:
<223> OTHER INFORMATION: LA818

<400> SEQUENCE: 106
ctcaaaaatt catccaaata tacaagtgga tcg                            33

<210> SEQ ID NO 107
<211> LENGTH: 90
<212> TYPE: DNA
<213> ORGANISM: Artificial sequence
<220> FEATURE:
<223> OTHER INFORMATION: LA512

<400> SEQUENCE: 107 gtatttggt agattcaatt ctctttccct ttccttttcc ttcgctcccc ttccttatca    60
gcattgcgga ttacgtattc taatgttcag                                   90

<210> SEQ ID NO 108
<211> LENGTH: 90
<212> TYPE: DNA
<213> ORGANISM: Artificial sequence
<220> FEATURE:
<223> OTHER INFORMATION: LA513

<400> SEQUENCE: 108
ttggttgggg gaaaagagg caacaggaaa gatcagaggg ggaggggggg ggagagtgtc    60
accttggcta actcgttgta tcatcactgg                                   90

<210> SEQ ID NO 109
<211> LENGTH: 29
<212> TYPE: DNA
<213> ORGANISM: Artificial sequence
<220> FEATURE:
<223> OTHER INFORMATION: LA516

<400> SEQUENCE: 109
ctcgaaacaa taagacgacg atggctctg                                 29
```

<210> SEQ ID NO 110
<211> LENGTH: 30
<212> TYPE: DNA
<213> ORGANISM: Artificial sequence
<220> FEATURE:
<223> OTHER INFORMATION: LA514

<400> SEQUENCE: 110
cactatctgg tgcaaacttg gcaccggaag                              30

<210> SEQ ID NO 111
<211> LENGTH: 29
<212> TYPE: DNA
<213> ORGANISM: Artificial sequence
<220> FEATURE:
<223> OTHER INFORMATION: LA515

<400> SEQUENCE: 111
tgtttgtagc cactcgtgaa cttctctgc                              29

<210> SEQ ID NO 112
<211> LENGTH: 6903
<212> TYPE: DNA
<213> ORGANISM: Artificial sequence
<220> FEATURE:
<223> OTHER INFORMATION: pLA71

<400> SEQUENCE: 112

| | |
|---|---|
| aaacgccagc aacgcggcct ttttacggtt cctggccttt tgctggcctt ttgctcacat | 60 |
| gttctttcct gcgttatccc ctgattctgt ggataaccgt attaccgcct ttgagtgagc | 120 |
| tgataccgct cgccgcagcc gaacgaccga gcgcagcgag tcagtgagcg aggaagcgga | 180 |
| agagcgccca atacgcaaac cgcctctccc cgcgcgttgg ccgattcatt aatgcagctg | 240 |
| gcacgacagg tttcccgact ggaaagcggg cagtgagcgc aacgcaatta atgtgagtta | 300 |
| gctcactcat taggcacccc aggctttaca ctttatgctt ccggctcgta tgttgtgtgg | 360 |
| aattgtgagc ggataacaat ttcacacagg aaacagctat gaccatgatt acgccaagct | 420 |
| tgcatgcgat ctgaaatgaa taacaatact gacagtagat ctgaaatgaa taacaatact | 480 |
| gacagtacta ataattgcc tacttggctt cacatacgtt gcatacgtcg atatagataa | 540 |
| taatgataat gacagcagga ttatcgtaat acgtaatagt tgaaaatctc aaaaatgtgt | 600 |
| gggtcattac gtaaataatg ataggaatgg gattcttcta tttttccttt tccattcta | 660 |
| gcagccgtcg ggaaaacgtg gcatcctctc tttcgggctc aattggagtc acgctgccgt | 720 |
| gagcatcctc tctttccata tctaacaact gagcacgtaa ccaatggaaa agcatgagct | 780 |
| tagcgttgct ccaaaaaagt attggatggt taataccatt tgtctgttct cttctgactt | 840 |
| tgactcctca aaaaaaaaaa atctacaatc aacagatcgc ttcaattacg ccctcacaaa | 900 |
| aacttttttc cttcttcttc gcccacgtta aattttatcc ctcatgttgt ctaacggatt | 960 |
| tctgcacttg atttattata aaaagacaaa gacataatac ttctctatca atttcagtta | 1020 |
| ttgttcttcc ttgcgttatt cttctgttct tcttttttctt ttgtcatata taaccataac | 1080 |
| caagtaatac atattcaaat ctagagctga ggatgttgac aaaagcaaca aaagaacaaa | 1140 |
| aatcccttgt gaaaaacaga ggggcggagc ttgttgttga ttgcttagtg gagcaaggtg | 1200 |
| tcacacatgt atttggcatt ccaggtgcaa aaattgatgc ggtatttgac gctttacaag | 1260 |
| ataaggacc tgaaattatc gttgcccggc acgaacaaaa cgcagcattc atggcccaag | 1320 |

```
cagtcggccg tttaactgga aaaccgggag tcgtgttagt cacatcagga ccgggtgcct    1380
ctaacttggc aacaggcctg ctgacagcga cactgaagg agaccctgtc gttgcgcttg    1440
ctggaaacgt gatccgtgca gatcgtttaa aacggacaca tcaatctttg gataatgcgg    1500
cgctattcca gccgattaca aaatacagtg tagaagttca agatgtaaaa aatataccgg    1560
aagctgttac aaatgcattt aggatagcgt cagcagggca ggctggggcc gcttttgtga    1620
gctttccgca agatgttgtg aatgaagtca aaatacgaa aaacgtgcgt gctgttgcag    1680
cgccaaaact cggtcctgca gcagatgatg caatcagtgc ggcccatagca aaaatccaaa    1740 cagcaaaact tcctgtcgtt ttggtcggca tgaaaggcgg aagaccggaa gcaattaaag    1800
cggttcgcaa gcttttgaaa aaggttcagc ttccatttgt tgaaacatat caagctgccg    1860
gtaccctttc tagagattta gaggatcaat attttggccg tatcggtttg ttccgcaacc    1920
agcctggcga tttactgcta gagcaggcag atgttgttct gacgatcggc tatgacccga    1980
ttgaatatga tccgaaattc tggaatatca atggagaccg gacaattatc catttagacg    2040
agattatcgc tgacattgat catgcttacc agcctgatct tgaattgatc ggtgacattc    2100
cgtccacgat caatcatatc gaacacgatg ctgtgaaagt ggaatttgca gagcgtgagc    2160
agaaaatcct ttctgattta aaacaatata tgcatgaagg tgagcaggtg cctgcagatt    2220
ggaaatcaga cagagcgcac cctcttgaaa tcgttaaaga gttgcgtaat gcagtcgatg    2280
atcatgttac agtaacttgc gatatcggtt cgcacgccat ttggatgtca cgttatttcc    2340
gcagctacga gccgttaaca ttaatgatca gtaacggtat gcaaacactc ggcgttgcgc    2400
ttccttgggc aatcggcgct tcattggtga accgggaga aaaagtggtt tctgtctctg    2460
gtgacggcgg tttcttattc tcagcaatgg aattagagac agcagttcga ctaaaagcac    2520
caattgtaca cattgtatgg aacgacagca catatgacat ggttgcattc cagcaattga    2580
aaaaatataa ccgtacatct gcggtcgatt tcggaaatat cgatatcgtg aaatatgcgg    2640
aaagcttcgg agcaactggc ttgcgcgtag aatcaccaga ccagctggca gatgttctgc    2700
gtcaaggcat gaacgctgaa ggtcctgtca tcatcgatgt cccggttgac tacagtgata    2760
acattaattt agcaagtgac aagcttccga aagaattcgg ggaactcatg aaaacgaaag    2820
ctctctagtt aattaatcat gtaattagtt atgtcacgct tacattcacg ccctccccc    2880 acatccgctc taaccgaaaa ggaaggagtt agacaacctg aagtctaggt ccctatttat    2940 tttttatag ttatgttagt attaagaacg ttatttatat ttcaaatttt tctttttttt    3000
ctgtacagac gcgtgtacgc atgtaacatt atactgaaaa ccttgcttga aaggttttg    3060 ggacgctcga aggctttaat ttaggttttg gacgctcga aggctttaat ttggatccgc    3120
attgcggatt acgtattcta atgttcagta ccgttcgtat aatgtatgct atacgaagtt    3180
atgcagattg tactgagagt gcaccatacc acagcttttc aattcaattc atcattttt    3240 ttttattctt tttttgatt tcggtttctt tgaaattttt ttgattcggt aatctccgaa    3300
cagaaggaag aacgaaggaa ggagcacaga cttagattgg tatatatacg catatgtagt    3360
gttgaagaaa catgaaattg cccagtattc ttaacccaac tgcacagaac aaaaacctgc    3420
aggaaacgaa gataaatcat gtcgaaagct acatataagg aacgtgctgc tactcatcct    3480
agtcctgttg ctgccaagct atttaatatc atgcacgaaa agcaaacaaa cttgtgtgct    3540
tcattggatg ttcgtaccac caaggaatta ctggagttag ttgaagcatt aggtcccaaa    3600
atttgtttac taaaaacaca tgtggatatc ttgactgatt tttccatgga gggcacagtt    3660
aagccgctaa aggcattatc cgccaagtac aatttttac tcttcgaaga cagaaaattt    3720
```

| | |
|---|---|
| gctgacattg gtaatacagt caaattgcag tactctgcgg gtgtatacag aatagcagaa | 3780 |
| tgggcagaca ttacgaatgc acacggtgtg gtgggcccag gtattgttag cggttttgaag | 3840 |
| caggcggcag aagaagtaac aaaggaacct agaggccttt tgatgttagc agaattgtca | 3900 |
| tgcaagggct ccctatctac tggagaatat actaagggta ctgttgacat tgcgaagagc | 3960 |
| gacaaagatt ttgttatcgg ctttattgct caaagagaca tgggtggaag agatgaaggt | 4020 |
| tacgattggt tgattatgac acccggtgtg ggtttagatg acaagggaga cgcattgggt | 4080 |
| caacagtata gaaccgtgga tgatgtggtc tctacaggat ctgacattat tattgttgga | 4140 |
| agaggactat ttgcaaaggg aagggatgct aaggtagagg gtgaacgtta cagaaaagca | 4200 |
| ggctgggaag catatttgag aagatgcggc cagcaaaact aaaaaactgt attataagta | 4260 |
| aatgcatgta tactaaactc acaaattaga gcttcaattt aattatatca gttattaccc | 4320 |
| tatgcggtgt gaaataccgc acagatgcgt aaggagaaaa taccgcatca ggaaattgta | 4380 |
| aacgttaata ttttgttaaa attcgcgtta aattttttgtt aaatcagctc attttttaac | 4440 |
| caataggccg aaatcggcaa aatcccttat aaatcaaaag aatagaccga datagggttg | 4500 |
| agtgttgttc cagtttggaa caagagtcca ctattaaaga acgtggactc caacgtcaaa | 4560 |
| gggcgaaaaa ccgtctatca gggcgatggc ccactacgtg aaccatcacc ctaatcaaga | 4620 |
| taacttcgta taatgtatgc tatacgaacg gtaccagtga tgatcaacg agttagccaa | 4680 |
| ggtgaattca ctggccgtcg ttttacaacg tcgtgactgg gaaaaccctg gcgttaccca | 4740 |
| acttaatcgc cttgcagcac atccccctt cgccagctgg cgtaatagcg aagaggcccg | 4800 |
| caccgatcgc ccttcccaac agttgcgcag cctgaatggc gaatggcgcc tgatgcggta | 4860 |
| ttttctcctt acgcatctgt gcggtatttc acaccgcata tggtgcactc tcagtacaat | 4920 |
| ctgctctgat gccgcatagt taagccagcc ccgacacccg ccaacacccg ctgacgcgcc | 4980 |
| ctgacgggct tgtctgctcc cggcatccgc ttacagacaa gctgtgaccg tctccgggag | 5040 |
| ctgcatgtgt cagaggtttt caccgtcatc accgaaacgc gcgagacgaa agggcctcgt | 5100 |
| gatacgccta tttttatagg ttaatgtcat gataataatg gtttcttaga cgtcaggtgg | 5160 |
| cacttttcgg ggaaatgtgc gcggaacccc tatttgttta ttttttctaaa tacattcaaa | 5220 |
| tatgtatccg ctcatgagac aataaccctg ataaatgctt caataatatt gaaaaaggaa | 5280 |
| gagtatgagt attcaacatt tccgtgtcgc ccttattccc ttttttgcgg cattttgcct | 5340 |
| tcctgttttt gctcacccag aaacgctggt gaaagtaaaa gatgctgaag atcagttggg | 5400 |
| tgcacgagtg ggttacatcg aactggatct caacagcggt aagatccttg agagttttcg | 5460 |
| ccccgaagaa cgttttccaa tgatgagcac ttttaaagtt ctgctatgtg gcgcggtatt | 5520 |
| atcccgtatt gacgccgggc aagagcaact cggtcgccgc atacactatt ctcagaatga | 5580 |
| cttggttgag tactcaccag tcacagaaaa gcatcttacg gatggcatga cagtaagaga | 5640 |
| attatgcagt gctgccataa ccatgagtga taacactgcg ccaacttac ttctgacaac | 5700 |
| gatcggagga ccgaaggagc taaccgcttt tttgcacaac atgggggatc atgtaactcg | 5760 |
| ccttgatcgt tgggaaccgg agctgaatga agccatacca aacgacgagc gtgacaccac | 5820 |
| gatgcctgta gcaatggcaa caacgttgcg caaactatta actggcgaac tacttactct | 5880 |
| agcttcccgg caacaattaa tagactggat ggaggcggat aaagttgcag gaccacttct | 5940 |
| gcgctcggcc cttccggctg gctggtttat tgctgataaa tctggagccg gtgagcgtgg | 6000 |
| gtctcgcggt atcattgcag cactggggcc agatggtaag ccctcccgta tcgtagttat | 6060 |

```
ctacacgacg gggagtcagg caactatgga tgaacgaaat agacagatcg ctgagatagg    6120
tgcctcactg attaagcatt ggtaactgtc agaccaagtt tactcatata tactttagat    6180
tgatttaaaa cttcattttt aatttaaaag gatctaggtg aagatccttt ttgataatct    6240
catgaccaaa atcccttaac gtgagttttc gttccactga gcgtcagacc ccgtagaaaa    6300
gatcaaagga tcttcttgag atcctttttt tctgcgcgta atctgctgct tgcaaacaaa    6360
aaaaccaccg ctaccagcgg tggtttgttt gccggatcaa gagctaccaa ctcttttttcc   6420 gaaggtaact ggcttcagca gagcgcagat accaaatact gtccttctag tgtagccgta    6480
gttaggccac cacttcaaga actctgtagc accgcctaca tacctcgctc tgctaatcct    6540
gttaccagtg gctgctgcca gtggcgataa gtcgtgtctt accgggttgg actcaagacg    6600
atagttaccg gataaggcgc agcggtcggg ctgaacgggg ggttcgtgca cacagcccag    6660
cttggagcga acgacctaca ccgaactgag atacctacag cgtgagctat gagaaagcgc    6720
cacgcttccc gaagggagaa aggcggacag gtatccggta agcggcaggg tcggaacagg    6780
agagcgcacg agggagcttc caggggggaaa cgcctggtat ctttatagtc ctgtcgggtt    6840
tcgccacctc tgacttgagc gtcgattttt gtgatgctcg tcaggggggc ggagcctatg    6900
gaa                                                                 6903

<210> SEQ ID NO 113
<211> LENGTH: 96
<212> TYPE: DNA
<213> ORGANISM: Artificial sequence
<220> FEATURE:
<223> OTHER INFORMATION: LA829

<400> SEQUENCE: 113
ccaaatttac aatatctcct gaattcttgg cttggaatat gggcagtaca gcttgtgtga    60
tattgcacct tggctaactc gttgtatcat cactgg                              96

<210> SEQ ID NO 114
<211> LENGTH: 90
<212> TYPE: DNA
<213> ORGANISM: Artificial sequence
<220> FEATURE:
<223> OTHER INFORMATION: LA834

<400> SEQUENCE: 114
atgtcccaag gtagaaaagc tgcagaaaga ttggctaaga agactgtcct cattacaggt    60
gatctgaaat gaataacaat actgacagta                                    90

<210> SEQ ID NO 115
<211> LENGTH: 29
<212> TYPE: DNA
<213> ORGANISM: Artificial sequence
<220> FEATURE:
<223> OTHER INFORMATION: N1257

<400> SEQUENCE: 115
gatgatgcta tttggtgcag agggtgatg                                     29

<210> SEQ ID NO 116
<211> LENGTH: 29
<212> TYPE: DNA
<213> ORGANISM: Artificial sequence
<220> FEATURE:
<223> OTHER INFORMATION: LA830

<400> SEQUENCE: 116
```

<210> SEQ ID NO 117
<211> LENGTH: 6369
<212> TYPE: DNA
<213> ORGANISM: Artificial Sequence
<220> FEATURE:
<223> OTHER INFORMATION: Plasmid pHR59::FBA1p-BAT1-CYC1t

<400> SEQUENCE: 117

```
aaacgccagc aacgcggcct ttttacggtt cctggccttt tgctggcctt ttgctcacat    60
gttctttcct gcgttatccc ctgattctgt ggataaccgt attaccgcct ttgagtgagc   120
tgataccgct cgccgcagcc gaacgaccga gcgcagcgag tcagtgagcg aggaagcgga   180
agagcgccca atacgcaaac cgcctctccc cgcgcgttgg ccgattcatt aatgcagctg   240
gcacgacagg tttcccgact ggaaagcggg cagtgagcgc aacgcaatta atgtgagtta   300
gctcactcat taggcacccc aggctttaca ctttatgctt ccggctcgta tgttgtgtgg   360
aattgtgagc ggataacaat ttcacacagg aaacagctat gaccatgatt acgccaagct   420
tgcatgcgat ctgaaatgaa taacaatact gacagtagat ctgaaatgaa taacaatact   480
gacagtacta ataattgcc tacttggctt cacatacgtt gcatacgtcg atatagataa   540
taatgataat gacagcagga ttatcgtaat acgtaatagt tgaaaatctc aaaaatgtgt   600
gggtcattac gtaaataatg ataggaatgg gattcttcta ttttttcctt tccattcta   660
gcagccgtcg ggaaaacgtg gcatcctctc tttcgggctc aattggagtc acgctgccgt   720
gagcatcctc tctttccata tctaacaact gagcacgtaa ccaatggaaa agcatgagct   780
tagcgttgct ccaaaaaagt attggatggt taataccatt tgtctgttct cttctgactt   840
tgactcctca aaaaaaaaa atctacaatc aacagatcgc ttcaattacg ccctcacaaa   900
aacttttttc cttcttcttc gcccacgtta aattttatcc ctcatgttgt ctaacggatt   960
tctgcacttg atttattata aaaagacaaa gacataatac ttctctatca atttcagtta  1020
ttgttcttcc ttgcgttatt cttctgttct tcttttttctt ttgtcatata taaccataac  1080
caagtaatac atattcaaat ctagagctga ggatgttgca gagacattcc ttgaagttgg  1140
ggaaattctc catcagaaca ctcgctactg gtgccccatt agatgcatcc aaactaaaaa  1200
ttactagaaa cccaaatcca tccaagccaa gaccaaatga agaattagtg ttcggccaga  1260
cattcaccga tcatatgttg accattcctt ggtcagccaa agaagggtgg ggcactccac  1320
acatcaagcc ttacgtaat cttttctcttg acccatctgc ttgtgtattc cattatgcat  1380
ttgaattatt tgaaggtttg aaagcctaca gaactcctca aaatactatc accatgttcc  1440
gtccggataa gaacatggcc cgtatgaaca agtctgccgc tagaatttgt ttgccaactt  1500
tcgaatctga agaattgatc aaacttaccg ggaaattgat cgaacaagat aaacacttgg  1560
ttcctcaagg taatggttac tcattataca tcagaccaac aatgattggt acatccaagg  1620
gtttaggtgt tggcactccc tccgaggctc ttctttatgt tattacttct ccagtcggtc  1680
cttattataa gactggtttc aaagccgtac gtcttgaagc aacagactat gctacaagag  1740
cttggccagg tggtgttggc gacaaaaaat gggtgctaa ctatgcccca tgcatcttac  1800
ctcaactaca agctgccaaa agagggtacc aacaaatct atggttgttc ggcccagaaa  1860
agaacatcac tgaggttggt actatgaacg tgttcttcgt tttcctcaac aaagtcactg  1920
gcaagaagga attggttacc gctccattag atggtaccat tttagaaggt gttaccagag  1980
```

```
actctgtttt aacattggct cgtgacaaac tagatcctca agaatgggac atcaacgagc    2040
gttattacac tattactgaa gtcgccacta gagcaaaaca aggtgaacta ttagaagcct    2100
tcggttctgg tactgctgct gtcgtttcac ctatcaagga aattggctgg aacaacgaag    2160
atattcatgt tccactattg cctggtgaac aatgtggtgc attgaccaag caagttgctc    2220
aatggattgc tgatatccaa tacggtagag tcaattatgg taactggtca aaaactgttg    2280
ccgacttgaa ctaattaatt aatcatgtaa ttagttatgt cacgcttaca ttcacgccct    2340
cccccacat ccgctctaac cgaaaaggaa ggagttagac aacctgaagt ctaggtccct     2400
atttatttt ttatagttat gttagtatta agaacgttat ttatatttca aattttctt     2460
ttttttctgt acagacgcgt gtacgcatgt aacattatac tgaaaacctt gcttgagaag    2520
gttttgggac gctcgaaggc tttaatttag gttttgggac gctcgaaggc tttaatttgg    2580
atccgcattg cggattacgt attctaatgt tcagtaccgt tcgtataatg tatgctatac    2640
gaagttatgc agattgtact gagagtgcac cataccacag cttttcaatt caattcatca    2700
tttttttttt attcttttt ttgatttcgg tttctttgaa atttttttga ttcggtaatc     2760
tccgaacaga aggaagaacg aaggaaggag cacagactta gattggtata tatacgcata    2820
tgtagtgttg aagaaacatg aaattgccca gtattcttaa cccaactgca cagaacaaaa    2880
acctgcagga aacgaagata aatcatgtcg aaagctacat ataaggaacg tgctgctact    2940
catcctagtc ctgttgctgc caagctattt aatatcatgc acgaaaagca acaaacttg     3000
tgtgcttcat tggatgttcg taccaccaag gaattactgg agttagttga agcattaggt    3060
cccaaaattt gttactaaa aacacatgtg gatatcttga ctgattttc catggagggc      3120
acagttaagc cgctaaaggc attatccgcc aagtacaatt ttttactctt cgaagacaga    3180
aaatttgctg acattggtaa tacagtcaaa ttgcagtact ctgcgggtgt atacagaata    3240
gcagaatggg cagacattac gaatgcacac ggtgtggtgg gcccaggtat tgttagcggt    3300
ttgaagcagg cggcagaaga agtaacaaag gaacctagag gccttttgat gttagcagaa    3360
ttgtcatgca agggctccct atctactgga gaatatacta agggtactgt tgacattgcg    3420
aagagcgaca aagattttgt tatcggcttt attgctcaaa gagacatggg tggaagagat    3480
gaaggttacg attggttgat tatgacaccc ggtgtgggtt tagatgacaa gggagacgca    3540
ttgggtcaac agtatagaac cgtggatgat gtggtctcta caggatctga cattattatt    3600
gttggaagag gactatttgc aaagggaagg gatgctaagg tagagggtga acgttacaga    3660
aaagcaggct gggaagcata tttgagaaga tgccggccagc aaaactaaaa aactgtatta   3720
taagtaaatg catgtatact aaactcacaa attagagctt caatttaatt atatcagtta    3780
ttaccctatg cggtgtgaaa taccgcacag atgcgtaagg agaaaatacc gcatcaggaa    3840
attgtaaacg ttaatatttt gttaaaattc gcgttaaatt tttgttaaat cagctcattt    3900
tttaaccaat aggccgaaat cggcaaaatc ccttataaat caaagaata gaccgagata     3960
gggttgagtg ttgttccagt ttggaacaag agtccactat taaagaacgt ggactccaac    4020
gtcaaagggc gaaaaaccgt ctatcagggc gatggcccac tacgtgaacc atcacgctaa    4080
tcaagataac ttcgtataat gtatgctata cgaacggtac cagtgatgat acaacgagtt    4140
agccaaggtg aattcactgg ccgtcgtttt acaacgtcgt gactgggaaa accctggcgt    4200
tacccaactt aatcgccttg cagcacatcc ccctttcgcc agctggcgta atagcgaaga    4260
ggcccgcacc gatcgccctt cccaacagtt gcgcagcctg aatggcgaat ggcgcctgat    4320
gcggtatttt ctccttacgc atctgtgcgg tatttcacac cgcatatggt gcactctcag    4380
```

```
tacaatctgc tctgatgccg catagttaag ccagccccga cacccgccaa cacccgctga   4440
cgcgccctga cgggcttgtc tgctcccggc atccgcttac agacaagctg tgaccgtctc   4500
cgggagctgc atgtgtcaga ggttttcacc gtcatcaccg aaacgcgcga gacgaaaggg   4560
cctcgtgata cgcctatttt tataggttaa tgtcatgata ataatggttt cttagacgtc   4620
aggtggcact tttcggggaa atgtgcgcgg aaccccctatt tgtttatttt tctaaataca   4680
ttcaaatatg tatccgctca tgagacaata accctgataa atgcttcaat aatattgaaa   4740
aaggaagagt atgagtattc aacatttccg tgtcgccctt attccctttt ttgcggcatt   4800
ttgccttcct gtttttgctc acccagaaac gctggtgaaa gtaaaagatg ctgaagatca   4860
gttgggtgca cgagtgggtt acatcgaact ggatctcaac agcggtaaga tccttgagag   4920
ttttcgcccc gaagaacgtt ttccaatgat gagcactttt aaagttctgc tatgtggcgc   4980
ggtattatcc cgtattgacg ccgggcaaga gcaactcggt cgccgcatac actattctca   5040
gaatgacttg gttgagtact caccagtcac agaaaagcat cttacggatg gcatgacagt   5100
aagagaatta tgcagtgctg ccataaccat gagtgataac actgcggcca acttacttct   5160
gacaacgatc ggaggaccga aggagctaac cgcttttttg cacaacatgg gggatcatgt   5220
aactcgcctt gatcgttggg aaccggagct gaatgaagcc ataccaaacg acgagcgtga   5280
caccacgatg cctgtagcaa tggcaacaac gttgcgcaaa ctattaactg gcgaactact   5340
tactctagct tcccggcaac aattaataga ctggatggag gcggataaag ttgcaggacc   5400
acttctgcgc tcggcccttc cggctggctg gtttattgct gataaatctg gagccggtga   5460
gcgtgggtct cgcggtatca ttgcagcact ggggccagat ggtaagccct cccgtatcgt   5520
agttatctac acgacgggga gtcaggcaac tatggatgaa cgaaatagac agatcgctga   5580
gataggtgcc tcactgatta agcattggta actgtcagac caagtttact catatatact   5640
ttagattgat ttaaaacttc attttttaatt taaaaggatc taggtgaaga tcctttttga   5700
taatctcatg accaaaatcc cttaacgtga gttttcgttc cactgagcgt cagacccgt    5760 agaaaagatc aaaggatctt cttgagatcc tttttttctg cgcgtaatct gctgcttgca   5820
aacaaaaaaa ccaccgctac cagcggtggt ttgtttgccg gatcaagagc taccaactct   5880
ttttccgaag gtaactggct tcagcagagc gcagatacca aatactgtcc ttctagtgta   5940
gccgtagtta ggccaccact tcaagaactc tgtagcaccg cctacatacc tcgctctgct   6000
aatcctgtta ccagtggctg ctgccagtgg cgataagtcg tgtcttaccg ggttggactc   6060
aagacgatag ttaccggata aggcgcagcg gtcgggctga acggggggtt cgtgcacaca   6120
gcccagcttg gagcgaacga cctacaccga actgagatac ctacagcgtg agctatgaga   6180
aagcgccacg cttcccgaag ggagaaaggc ggacaggtat ccggtaagcg gcagggtcgg   6240
aacaggagag cgcacgaggg agcttccagg gggaaacgcc tggtatcttt atagtcctgt   6300
cgggtttcgc cacctctgac ttgagcgtcg attttgtga tgctcgtcag gggggcggag   6360
cctatggaa                                                           6369
```

<210> SEQ ID NO 118
<211> LENGTH: 6318
<212> TYPE: DNA
<213> ORGANISM: Artificial Sequence
<220> FEATURE:
<223> OTHER INFORMATION: Plasmid pLA59::FBA1p-BAT2-CYC1t

<400> SEQUENCE: 118

```
aaacgccagc aacgcggcct ttttacggtt cctggccttt tgctggcctt ttgctcacat      60
gttctttcct gcgttatccc ctgattctgt ggataaccgt attaccgcct ttgagtgagc     120
tgataccgct cgccgcagcc gaacgaccga gcgcagcgag tcagtgagcg aggaagcgga     180
agagcgccca atacgcaaac cgcctctccc gcgcgttgg ccgattcatt aatgcagctg      240
gcacgacagg tttcccgact ggaaagcggg cagtgagcgc aacgcaatta atgtgagtta     300
gctcactcat taggcacccc aggctttaca ctttatgctt ccggctcgta tgttgtgtgg     360
aattgtgagc ggataacaat ttcacacagg aaacagctat gaccatgatt acgccaagct     420
tgcatgcgat ctgaaatgaa taacaatact gacagtagat ctgaaatgaa taacaatact     480
gacagtacta ataattgcc tacttggctt cacatacgtt gcatacgtcg atatagataa      540
taatgataat gacagcagga ttatcgtaat acgtaatagt tgaaaatctc aaaaatgtgt     600
gggtcattac gtaaataatg ataggaatgg gattcttcta tttttccttt ttccattcta     660
gcagccgtcg ggaaaacgtg gcatcctctc tttcgggctc aattggagtc acgctgccgt     720
gagcatcctc tctttccata tctaacaact gagcacgtaa ccaatggaaa agcatgagct     780
tagcgttgct ccaaaaaagt attggatggt taataccatt tgtctgttct cttctgactt     840
tgactcctca aaaaaaaaaa atctacaatc aacagatcgc ttcaattacg ccctcacaaa     900 aactttttc cttcttcttc gcccacgtta aattttatcc ctcatgttgt ctaacggatt       960
tctgcacttg attattata aaagacaaa gacataatac ttctctatca atttcagtta      1020
ttgttcttcc ttgcgttatt cttctgttct tcttttttctt ttgtcatata taaccataac    1080
caagtaatac atattcaaat ctagagctga ggatgacctt ggcaccccta gacgcctcca    1140
aagttaagat aactaccaca caacatgcat ctaagccaaa accgaacagt gagttagtgt    1200
ttggcaagag cttcacggac cacatgttaa ctgcggaatg gacagctgaa aaagggtggg    1260
gtaccccaga gattaaacct tatcaaaatc tgtctttaga cccttccgcg gtggttttcc     1320
attatgcttt tgagctattc gaagggatga aggcttacag aacggtggac aacaaaatta    1380
caatgtttcg tccagatatg aatatgaagc gcatgaataa gtctgctcag agaatctgtt    1440
tgccaacgtt cgacccagaa gagttgatta ccctaattgg gaaactgatc cagcaagata    1500
agtgcttagt tcctgaagga aaaggttact ctttatatat caggcctaca ttaatcggca    1560
ctacggccgg tttagggggtt tccacgcctg atagagcctt gctatatgtc atttgctgcc    1620
ctgtgggtcc ttattacaaa actggattta aggcggtcag actggaagcc actgattatg    1680
ccacaagagc ttggccagga ggctgtggtg acaagaaact aggtgcaaac tacgcccccct    1740 gcgtcctgcc acaattgcaa gctgcttcaa ggggttacca acaaaattta tggctatttg    1800
gtccaaataa caacattact gaagtcggca ccatgaatgc ttttttcgtg tttaaagata    1860
gtaaaacggg caagaaggaa ctagttactg ctccactaga cggtaccatt ttggaaggtg    1920
ttactaggga ttccattta aatcttgcta agaaagact cgaaccaagt gaatggacca      1980
ttagtgaacg ctacttcact ataggcgaag ttactgagag atccaagaac ggtgaactac    2040
ttgaagcctt tggttctggt actgctgcga ttgtttctcc cattaaggaa atcggctgga    2100
aaggcgaaca aattaatatt ccgttgttgc ccggcgaaca aaccggtcca ttggccaaag    2160
aagttgcaca atggattaat ggaatccaat atggcgagac tgagcatggc aattggtcaa    2220
gggttgttac tgatttgaac tgattaatta atcatgtaat tagttatgtc acgcttacat    2280
tcacgccctc cccccacatc cgctctaacc gaaaaggaag gagttagaca acctgaagtc    2340
taggtcccta tttatttttt tatagttatg ttagtattaa gaacgttatt tatatttcaa    2400
```

```
attttcttt tttttctgta cagacgcgtg tacgcatgta acattatact gaaaaccttg    2460
cttgagaagg ttttgggacg ctcgaaggct ttaatttagg ttttgggacg ctcgaaggct    2520
ttaatttgga tccgcattgc ggattacgta ttctaatgtt cagtaccgtt cgtataatgt    2580
atgctatacg aagttatgca gattgtactg agagtgcacc ataccacagc ttttcaattc    2640
aattcatcat tttttttta ttcttttttt tgatttcggt ttctttgaaa ttttttttgat    2700 tcggtaatct ccgaacagaa ggaagaacga aggaaggagc acagacttag attggtatat    2760
atacgcatat gtagtgttga agaaacatga aattgcccag tattcttaac ccaactgcac    2820
agaacaaaaa cctgcaggaa acgaagataa atcatgtcga aagctacata taaggaacgt    2880
gctgctactc atcctagtcc tgttgctgcc aagctattta atatcatgca cgaaaagcaa    2940
acaaacttgt gtgcttcatt ggatgttcgt accaccaagg aattactgga gttagttgaa    3000
gcattaggtc ccaaaatttg tttactaaaa acacatgtgg atatcttgac tgatttttcc    3060
atggagggca cagttaagcc gctaaaggca ttatccgcca agtacaattt tttactcttc    3120
gaagacagaa aatttgctga cattggtaat acagtcaaat tgcagtactc tgcgggtgta    3180
tacagaatag cagaatgggc agacattacg aatgcacacg gtgtggtggg cccaggtatt    3240
gttagcggtt tgaagcaggc ggcagaagaa gtaacaaagg aacctagagg ccttttgatg    3300
ttagcagaat tgtcatgcaa gggctcccta tctactggag aatatactaa gggtactgtt    3360
gacattgcga agagcgacaa agattttgtt atcggcttta ttgctcaaag agacatgggt    3420
ggaagagatg aaggttacga ttggttgatt atgacacccg gtgtgggttt agatgacaag    3480
ggagacgcat tgggtcaaca gtatagaacc gtggatgatg tggtctctac aggatctgac    3540
attattattg ttggaagagg actatttgca aagggaaggg atgctaaggt agagggtgaa    3600
cgttacagaa aagcaggctg ggaagcatat ttgagaagat gcggccagca aaactaaaaa    3660
actgtattat aagtaaatgc atgtatacta aactcacaaa ttagagcttc aatttaatta    3720
tatcagttat taccctatgc ggtgtgaaat accgcacaga tgcgtaagga gaaaataccg    3780
catcaggaaa ttgtaaacgt taatattttg ttaaaattcg cgttaaattt ttgttaaatc    3840
agctcatttt ttaaccaata ggccgaaatc ggcaaaatcc cttataaatc aaaagaatag    3900
accgagatag ggttgagtgt tgttccagtt tggaacaaga gtccactatt aaagaacgtg    3960
gactccaacg tcaaagggcg aaaaaccgtc tatcagggcg atggcccact acgtgaacca    4020
tcaccctaat caagataact tcgtataatg tatgctatac gaacggtacc agtgatgata    4080
caacgagtta gccaaggtga attcactggc cgtcgtttta caacgtcgtg actgggaaaa    4140
ccctggcgtt acccaactta atcgccttgc agcacatccc cctttcgcca gctggcgtaa    4200
tagcgaagag gcccgcaccg atcgcccttc ccaacagttg cgcagcctga atggcgaatg    4260
gcgcctgatg cggtattttc tccttacgca tctgtgcggt atttcacacc gcatatggtg    4320
cactctcagt acaatctgct ctgatgccgc atagttaagc cagccccgac acccgccaac    4380
acccgctgac gcgccctgac gggcttgtct gctcccggca tccgcttaca gacaagctgt    4440
gaccgtctcc gggagctgca tgtgtcagag gttttcaccg tcatcaccga acgcgcgag    4500 acgaaagggc ctcgtgatac gcctattttt ataggttaat gtcatgataa taatggtttc    4560
ttagacgtca ggtggcactt ttcggggaaa tgtgcgcgga acccctattt gtttattttt    4620
ctaaatacat tcaaatatgt atccgctcat gagacaataa ccctgataaa tgcttcaata    4680
atattgaaaa aggaagagta tgagtattca acatttccgt gtcgccctta ttccctttt    4740
```

```
tgcggcattt tgccttcctg tttttgctca cccagaaacg ctggtgaaag taaaagatgc    4800
tgaagatcag ttgggtgcac gagtgggtta catcgaactg gatctcaaca gcggtaagat    4860
ccttgagagt tttcgccccg aagaacgttt tccaatgatg agcactttta aagttctgct    4920
atgtggcgcg gtattatccc gtattgacgc cgggcaagag caactcggtc gccgcataca    4980
ctattctcag aatgacttgg ttgagtactc accagtcaca gaaaagcatc ttacggatgg    5040
catgacagta agagaattat gcagtgctgc cataaccatg agtgataaca ctgcggccaa    5100
cttacttctg acaacgatcg gaggaccgaa ggagctaacc gcttttttgc acaacatggg    5160
ggatcatgta actcgccttg atcgttggga accggagctg aatgaagcca taccaaacga    5220
cgagcgtgac accacgatgc ctgtagcaat ggcaacaacg ttgcgcaaac tattaactgg    5280
cgaactactt actctagctt cccggcaaca attaatagac tggatggagg cggataaagt    5340
tgcaggacca cttctgcgct cggcccttcc ggctggctgg tttattgctg ataaatctgg    5400
agccggtgag cgtgggtctc gcggtatcat tgcagcactg gggccagatg gtaagccctc    5460
ccgtatcgta gttatctaca cgacggggag tcaggcaact atggatgaac gaaatagaca    5520
gatcgctgag ataggtgcct cactgattaa gcattggtaa ctgtcagacc aagtttactc    5580
atatatactt tagattgatt taaaacttca ttttttaattt aaaaggatct aggtgaagat    5640 ccttttttgat aatctcatga ccaaaatccc ttaacgtgag ttttcgttcc actgagcgtc    5700 agacccgta gaaaagatca aaggatcttc ttgagatcct ttttttctgc gcgtaatctg    5760
ctgcttgcaa acaaaaaaac caccgctacc agcggtggtt tgtttgccgg atcaagagct    5820
accaactctt tttccgaagg taactggctt cagcagagcg cagataccaa atactgtcct    5880
tctagtgtag ccgtagttag gccaccactt caagaactct gtagcaccgc ctacatacct    5940
cgctctgcta atcctgttac cagtggctgc tgccagtggc gataagtcgt gtcttaccgg    6000
gttggactca agacgatagt taccggataa ggcgcagcgg tcgggctgaa cggggggttc    6060
gtgcacacag cccagcttgg agcgaacgac ctacaccgaa ctgagatacc tacagcgtga    6120
gctatgagaa agcgccacgc ttcccgaagg agaaaggcg gacaggtatc cggtaagcgg    6180
cagggtcgga acaggagagc gcacgaggga gcttccaggg ggaaacgcct ggtatcttta    6240
tagtcctgtc gggtttcgcc acctctgact tgagcgtcga ttttttgtgat gctcgtcagg    6300 ggggcggagc ctatggaa                                                  6318
```

<210> SEQ ID NO 119
<211> LENGTH: 6682
<212> TYPE: DNA
<213> ORGANISM: Artificial Sequence
<220> FEATURE:
<223> OTHER INFORMATION: Plasmid pLA59::TDH3p-ARO8-ADH1t

<400> SEQUENCE: 119

```
aaacgccagc aacgcggcct ttttacggtt cctggccttt tgctggcctt ttgctcacat      60
gttctttcct gcgttatccc ctgattctgt ggataaccgt attaccgcct ttgagtgagc     120
tgataccgct cgccgcagcc gaacgaccga gcgcagcgag tcagtgagcg aggaagcgga     180
agagcgccca atacgcaaac cgcctctccc cgcgcgttgg ccgattcatt aatgcagctg     240
gcacgacagg tttcccgact ggaaagcggg cagtgagcgc aacgcaatta atgtgagtta     300
gctcactcat taggcacccc aggctttaca ctttatgctt ccggctcgta tgttgtgtgg     360
aattgtgagc ggataacaat ttcacacagg aaacagctat gaccatgatt acgccaatac     420
tgccatttca aagaatacgt aaataattaa tagtagtgat tttcctaact ttatttagtc     480
```

```
aaaaaattag ccttttaatt ctgctgtaac ccgtacatgc ccaaaatagg gggcgggtta    540
cacagaatat ataacatcgt aggtgtctgg gtgaacagtt tattcctggc atccactaaa    600
tataatggag cccgcttttt aagctggcat ccagaaaaaa aaagaatccc agcaccaaaa    660
tattgttttc ttcaccaacc atcagttcat aggtccattc tcttagcgca actacagaga    720 acagggcac  aaacaggcaa aaacgggca  caacctcaat ggagtgatgc aacctgcctg    780
gagtaaatga tgacacaagg caattgaccc acgcatgtat ctatctcatt tcttacacc     840 ttctattacc ttctgctctc tctgatttgg aaaaagctga aaaaaaggt  tgaaaccagt    900 tccctgaaat tattccccta cttgactaat aagtatataa agacggtagg tattgattgt    960
aattctgtaa atctatttct taaacttctt aaattctact tttatagtta gtctttttt    1020 tagttttaaa acaccaagaa cttagtttcg aataaacaca cataaactag taaacaaaat   1080
gactttacct gaatcaaaag acttttctta cttgttttcg gatgaaacca atgctcgtaa   1140
accatcccca ttgaaaacct gcatccatct tttccaagat cctaacatta tcttttgggg   1200
tggtggcctg ccattaaaag attatttccc atgggataat ctatctgtag attcacccaa   1260
gcctcctttt ccccagggta ttggagctcc aattgacgag cagaattgca taaaatacac   1320
cgtcaacaaa gattacgctg ataaaagtgc caatccttcc aacgatattc ctttgtcaag   1380
agctttgcaa tacgggttca gtgctggtca acctgaacta ttaaacttca ttagagatca   1440
taccaagatt atccacgatt tgaagtataa ggactgggac gttttagcca ctgcaggtaa   1500
cacaaatgcc tgggaatcta cttttaagagt cttttgtaac cgaggtgatg tcatcttagt   1560
tgaggcacat tctttttcct cttcattggc ttctgcagag gctcaaggtg tcattacctt   1620
ccccgtgcca attgacgctg atggtatcat tcctgaaaaa ttagctaaag tcatggaaaa   1680
ctggacacct ggtgctccta accaaagtt  gttatacact attccaacgg ccaaaatcc    1740 aactggtact tccattgcag accatagaaa ggaggcaatt tacaagatcg ctcaaaagta   1800
cgacttccta attgtggaag atgaacctta ttatttctta caaatgaatc cctacatcaa   1860
agacttgaag gaaagagaga aggcacaaag ttctccaaag caggaccatg acgaattttt   1920
gaagtccttg gcaaacactt tccttttcctt ggatacagaa ggccgtgtta ttagaatgga   1980
ttccttttca aaagttttgg ccccagggac aagattgggt tggattactg gttcatccaa   2040
aatcttgaag ccttacttga gtttgcatga aatgacgatt caagcccag  caggttttac   2100 acaagttttg gtcaacgcta cgctatccag gtggggtcaa aagggttact tggactggtt   2160
gcttggcctg cgtcatgaat acactttgaa acgtgactgt gccatcgatg ccctttacaa   2220
gtatctacca caatctgatg ctttcgtgat caatcctcca attgcaggta tgttttcac    2280 cgtgaacatt gacgcatctg tccaccctga gtttaaaaca aaatacaact cagacccttta  2340 ccagctagaa cagagtcttt accacaaagt ggttgaacgt ggtgttttag tggttcccgg   2400
ttcttggttc aagagtgagg gtgagacgga acctcctcaa cccgctgaat ctaaagaagt   2460
cagtaatcca aacataaattt tcttcagagg tacctatgca gctgtctctc ctgagaaact  2520
gactgaaggt ctgaagagat taggtgatac tttatacgaa gaatttggta tttccaaata   2580
gaccacaggt gttgtcctct gaggacataa aatacacacc gagattcatc aactcattgc    2640
tggagttagc atatctacaa ttgggtgaaa tggggagcga tttgcaggca tttgctcggc   2700
atgccggtag aggtgtggtc aataagagcg acctcatgct atacctgaga aagcaacctg   2760
acctacagga aagagttact caagaataag aattttcgtt ttaaaaccta agagtcactt   2820
```

```
taaaatttgt atacacttat ttttttttata acttatttaa taataaaaat cataaatcat    2880
aagaaattcg cttactccaa gcttgcattg cggattacgt attctaatgt tcagtaccgt    2940
tcgtataatg tatgctatac gaagttatgc agattgtact gagagtgcac cataccacct    3000
tttcaattca tcattttttt tttattcttt tttttgattt cggtttcctt gaaattttt     3060 tgattcggta atctccgaac agaaggaaga acgaaggaag gagcacagac ttagattggt    3120
atatatacgc atatgtagtg ttgaagaaac atgaaattgc ccagtattct taacccaact    3180
gcacagaaca aaaacctgca ggaaacgaag ataaatcatg tcgaaagcta catataagga    3240
acgtgctgct actcatccta gtcctgttgc tgccaagcta tttaatatca tgcacgaaaa    3300
gcaaacaaac ttgtgtgctt cattggatgt tcgtaccacc aaggaattac tggagttagt    3360
tgaagcatta ggtcccaaaa tttgtttact aaaaacacat gtggatatct tgactgattt    3420
ttccatggag ggcacagtta agccgctaaa ggcattatcc gccaagtaca atttttttact  3480 cttcgaagac agaaaatttg ctgacattgg taatacagtc aaattgcagt actctgcggg    3540
tgtatacaga atagcagaat gggcagacat tacgaatgca cacggtgtgg tgggcccagg    3600
tattgttagc ggtttgaagc aggcggcaga agaagtaaca aaggaaccta gaggccttt    3660 gatgttagca gaattgtcat gcaagggctc cctatctact ggagaatata ctaagggtac    3720
tgttgacatt gcgaagagcg acaaagattt tgttatcggc tttattgctc aaagagacat    3780
gggtggaaga gatgaaggtt acgattggtt gattatgaca cccggtgtgg gtttagatga    3840
caagggagac gcattgggtc aacagtatag aaccgtggat gatgtggtct ctacaggatc    3900
tgacattatt attgttggaa gaggactatt tgcaaaggga agggatgcta aggtagaggg    3960
tgaacgttac agaaaagcag gctgggaagc atatttgaga agatgcggcc agcaaaacta    4020
aaaaactgta ttataagtaa atgcatgtat actaaactca caaattagag cttcaattta    4080
attatatcag ttattaccct atgcggtgtg aaataccgca cagatgcgta aggagaaaat    4140
accgcatcag gaaattgtaa acgttaatat tttgttaaaa ttcgcgttaa attttttgtta   4200 aatcagctca ttttttaacc aataggccga atcggcaaa atcccttata aatcaaaaga    4260
atagaccgag atagggttga gtgttgttcc agtttggaac aagagtccac tattaaagaa    4320
cgtggactcc aacgtcaaag ggcgaaaaac cgtctatcag ggcgatggcc cactacgtga    4380
accatcaccc taatcaagat aacttcgtat aatgtatgct atacgaacgg taccagtgat    4440
gatacaacga gttagccaag gtgaattcac tggccgtcgt tttacaacgt cgtgactggg    4500
aaaaccctgg cgttacccaa cttaatcgcc ttgcagcaca tccccctttc gccagctggc    4560
gtaatagcga agaggcccgc accgatcgcc cttcccaaca gttgcgcagc ctgaatggcg    4620
aatggcgcct gatgcggtat tttctcctta cgcatctgtg cggtatttca caccgcatat    4680
ggtgcactct cagtacaatc tgctctgatg ccgcatagtt aagccagccc cgacacccgc    4740
caacacccgc tgacgcgccc tgacgggctt gtctgctccc ggcatccgct tacagacaag    4800
ctgtgaccgt ctccgggagc tgcatgtgtc agaggttttc accgtcatca ccgaaacgcg    4860
cgagacgaaa gggcctcgtg atacgcctat ttttataggt taatgtcatg ataataatgg    4920
tttcttagac gtcaggtggc acttttcggg gaaatgtgcg cggaacccct atttgtttat    4980
ttttctaaat acattcaaat atgtatccgc tcatgagaca ataaccctga taaatgcttc    5040
aataatattg aaaaaggaag agtatgagta ttcaacattt ccgtgtcgcc cttattccct    5100
tttttgcggc attttgcctt cctgtttttg ctcacccaga aacgctggtg aaagtaaaag    5160
atgctgaaga tcagttgggt gcacgagtgg gttacatcga actggatctc aacagcggta    5220
```

```
agatccttga gagttttcgc cccgaagaac gttttccaat gatgagcact tttaaagttc    5280
tgctatgtgg cgcggtatta tcccgtattg acgccgggca agagcaactc ggtcgccgca    5340
tacactattc tcagaatgac ttggttgagt actcaccagt cacagaaaag catcttacgg    5400
atggcatgac agtaagagaa ttatgcagtg ctgccataac catgagtgat aacactgcgg    5460
ccaacttact tctgacaacg atcggaggac cgaaggagct aaccgctttt ttgcacaaca    5520
tgggggatca tgtaactcgc cttgatcgtt gggaaccgga gctgaatgaa gccataccaa    5580
acgacgagcg tgacaccacg atgcctgtag caatggcaac aacgttgcgc aaactattaa    5640
ctggcgaact acttactcta gcttcccggc aacaattaat agactggatg gaggcggata    5700
aagttgcagg accacttctg cgctcggccc ttccggctgg ctggtttatt gctgataaat    5760
ctggagccgg tgagcgtggg tctcgcggta tcattgcagc actggggcca gatggtaagc    5820
cctcccgtat cgtagttatc tacacgacgg ggagtcaggc aactatggat gaacgaaata    5880
gacagatcgc tgagataggt gcctcactga ttaagcattg gtaactgtca gaccaagttt    5940
actcatatat actttagatt gatttaaaac ttcatttttt atttaaaagg atctaggtga    6000 agatccttttt tgataatctc atgaccaaaa tcccttaacg tgagttttcg ttccactgag    6060
cgtcagaccc cgtagaaaag atcaaaggat cttcttgaga tcctttttt ctgcgcgtaa    6120 tctgctgctt gcaaacaaaa aaaccaccgc taccagcggt ggtttgtttg ccggatcaag    6180
agctaccaac tcttttttccg aaggtaactg gcttcagcag agcgcagata ccaaatactg    6240
tccttctagt gtagccgtag ttaggccacc acttcaagaa ctctgtagca ccgcctacat    6300
acctcgctct gctaatcctg ttaccagtgg ctgctgccag tggcgataag tcgtgtctta    6360
ccgggttgga ctcaagacga tagttaccgg ataaggcgca gcggtcgggc tgaacggggg    6420
gttcgtgcac acagcccagc ttggagcgaa cgacctacac cgaactgaga tacctacagc    6480
gtgagctatg agaaagcgcc acgcttcccg aagggagaaa ggcggacagg tatccggtaa    6540
gcggcagggt cggaacagga gagcgcacga gggagcttcc agggggaaac gcctggtatc    6600
tttatagtcc tgtcgggttt cgccacctct gacttgagcg tcgatttttg tgatgctcgt    6660
caggggggcg gagcctatgg aa                                            6682
```

<210> SEQ ID NO 120
<211> LENGTH: 6721
<212> TYPE: DNA
<213> ORGANISM: Artificial Sequence
<220> FEATURE:
<223> OTHER INFORMATION: Plasmid pHR59::TDH3p-ARO9-ADHt1

<400> SEQUENCE: 120

```
aaacgccagc aacgcggcct ttttacggtt cctggccttt tgctggcctt ttgctcacat      60
gttctttcct gcgttatccc ctgattctgt ggataaccgt attaccgcct ttgagtgagc     120
tgataccgct cgccgcagcc gaacgaccga gcgcagcgag tcagtgagcg aggaagcgga     180
agagcgccca atacgcaaac cgcctctccc cgcgcgttgg ccgattcatt aatgcagctg     240
gcacgacagg tttcccgact ggaaagcggg cagtgagcgc aacgcaatta atgtgagtta     300
gctcactcat taggcacccc aggctttaca ctttatgctt ccggctcgta tgttgtgtgg     360
aattgtgagc ggataacaat ttcacacagg aaacagctat gaccatgatt acgccaatac     420
tgccatttca aagaatacgt aaataattaa tagtagtgat tttcctaact ttatttagtc     480
aaaaaattag ccttttaatt ctgctgtaac ccgtacatgc ccaaaatagg gggcgggtta     540
```

```
cacagaatat ataacatcgt aggtgtctgg gtgaacagtt tattcctggc atccactaaa    600
tataatggag cccgcttttt aagctggcat ccagaaaaaa aaagaatccc agcaccaaaa    660
tattgttttc ttcaccaacc atcagttcat aggtccattc tcttagcgca actacagaga    720 acagggcac aaacaggcaa aaacgggca caacctcaat ggagtgatgc aacctgcctg      780
gagtaaatga tgacacaagg caattgaccc acgcatgtat ctatctcatt ttcttacacc    840
ttctattacc ttctgctctc tctgatttgg aaaaagctga aaaaaaggt tgaaaccagt     900 tccctgaaat tattccccta cttgactaat aagtatataa agacggtagg tattgattgt    960
aattctgtaa atctatttct taaacttctt aaattctact tttatagtta gtctttttt   1020 tagttttaaa acaccaagaa cttagtttcg aataaacaca cataaactag taaacaaaat   1080
gactgctggt tctgccccc ctgttgatta cacttcctta aagaagaact tccaaccgtt    1140
tctctccaga agagtagaaa atagatctct gaaaagcttt tgggatgctt ctgatatctc   1200
agatgacgtc attgagctag ctggtggaat gccaaacgag agatttttc ctatcgaatc    1260 tatggatttg aaaatatcaa aagttccttt taatgataac ccaaaatggc ataattcgtt   1320
taccacggcg catttggact tgggatcccc cagtgagcta cccattgcac gttctttcca   1380
atatgcagaa accaagggtt tacccctct cttacatttt gttaaagatt ttgtgtccag    1440
aattaatcgc ccagccttt ccgatgagac ggagtctaac tgggatgtca tcctttctgg    1500
cgggtccaac gattcaatgt ttaaggtttt tgaaacaatt tgcgacgaat cgaccactgt   1560
gatgattgaa gagtttactt tcaccccggc tatgtccaat gtggaggcta caggagcaaa   1620
agtcatcccc atcaagatga acctgacctt cgacagagag tcccagggta ttgatgtcga   1680
atatctaacg cagttgctcg ataattggtc aactggacca tacaaagact taaacaagcc   1740
aagggtccta tataccattg caacgggcca aaatcctacc gggatgtctg tcccccagtg   1800
gaaaagagag aaaatttacc agttggccca agacacgat ttcctcattg ttgaagatga    1860
tccctacggt tatctgtact ttccttccta taatccgcaa gagccattag aaaaccctta   1920
ccattctagc gacctgacta ctgaacggta tttgaatgat tttttaatga aatcattctt   1980
gactttggat acagatgccc gtgtcatccg tttggagact ttttctaaaa ttttgctcc    2040 tggattaagg ttatccttca tcgttgctaa taaattcctt ttgcaaaaaa tcttggattt   2100
ggccgacatt actacaaggg cccccagtgg tacctcacaa gctattgttt attctacaat   2160
aaaggcaatg gctgagtcca acttatcgtc ctctcttttct atgaaagaag caatgtttga   2220
gggttggata agatggataa tgcagattgc ttctaaatac aatcatagga aaaatcttac   2280
tttgaaagcc ttatacgaaa cagaatctta ccaagctggt cagtttaccg ttatggaacc   2340
ctccgcgggt atgttcatca ttattaaaat caattggggg aatttcgata gacctgacga   2400
tttgccgcaa cagatggata ttttagataa gttcttgctg aagaatggtg ttaaagtagt   2460
gcttggttat aaaatggctg tttgcccaaa ttattcaaag cagaattcag attttctaag   2520
actcaccatc gcctatgcaa gggatgatga tcagttgatt gaagcttcca aaagaatcgg   2580
tagtggcata aaagaatttt ttgacaacta taaagttga accacaggtg ttgtcctctg    2640
aggacataaa atacacaccg agattcatca actcattgct ggagttagca tatctacaat   2700
tgggtgaaat ggggagcgat ttgcaggcat ttgctcggca tgccggtaga ggtgtggtca   2760
ataagagcga cctcatgcta tacctgagaa agcaacctga cctacaggaa agagttactc   2820
aagaataaga atttttcgttt taaaacctaa gagtcacttt aaaatttgta tacacttatt   2880 tttttataa cttatttaat aataaaaatc ataaatcata agaaattcgc ttactccaag   2940
```

```
cttgcattgc ggattacgta ttctaatgtt cagtaccgtt cgtataatgt atgctatacg   3000
aagttatgca gattgtactg agagtgcacc ataccaccrt ttcaattcat cattttrttt   3060
ttattctttt ttttgatttc ggtttccttg aaatttttt gattcggtaa tctccgaaca    3120
gaaggaagaa cgaaggaagg agcacagact tagattggta tatatacgca tatgtagtgt   3180
tgaagaaaca tgaaattgcc cagtattctt aacccaactg cacagaacaa aaacctgcag   3240
gaaacgaaga taaatcatgt cgaaagctac atataaggaa cgtgctgcta ctcatcctag   3300
tcctgttgct gccaagctat ttaatatcat gcacgaaaag caaacaaact tgtgtgcttc   3360
attggatgtt cgtaccacca aggaattact ggagttagtt gaagcattag gtcccaaaat   3420
ttgtttacta aaaacacatg tggatatctt gactgatttt tccatggagg gcacagttaa   3480
gccgctaaag gcattatccg ccaagtacaa tttttractc ttcgaagaca gaaaatttgc    3540
tgacattggt aatacagtca aattgcagta ctctgcgggt gtatacagaa tagcagaatg   3600
ggcagacatt acgaatgcac acggtgtggt gggcccaggt attgttagcg gtttgaagca   3660
ggcggcagaa gaagtaacaa aggaacctag aggccttttg atgttagcag aattgtcatg   3720
caagggctcc ctatctactg gagaatatac taagggtact gttgacattg cgaagagcga   3780
caaagatttt gttatcggct ttattgctca aagagacatg ggtggaagag atgaaggtta   3840
cgattggttg attatgacac ccggtgtggg tttagatgac aagggagacg cattgggtca   3900
acagtataga accgtggatg atgtggtctc tacaggatct gacattatta ttgttggaag   3960
aggactattt gcaaagggaa gggatgctaa ggtagagggt gaacgttaca gaaaagcagg   4020
ctgggaagca tatttgagaa gatgcggcca gcaaaactaa aaaactgtat tataagtaaa   4080
tgcatgtata ctaaactcac aaattagagc ttcaatttaa ttatatcagt tattacccta   4140
tgcggtgtga ataccgcac agatgcgtaa ggagaaaata ccgcatcagg aaattgtaaa     4200
cgttaatatt ttgttaaaat tcgcgttaaa ttttgttaa atcagctcat tttttaacca   4260
ataggccgaa atcggcaaaa tcccttataa atcaaaagaa tagaccgaga tagggttgag    4320
tgttgttcca gtttggaaca agagtccact attaaagaac gtggactcca acgtcaaagg   4380
gcgaaaaacc gtctatcagg gcgatggccc actacgtgaa ccatcaccct aatcaagata   4440
acttcgtata atgtatgcta tacgaacggt accagtgatg atacaacgag ttagccaagg   4500
tgaattcact ggccgtcgtt ttacaacgtc gtgactggga aaaccctggc gttacccaac   4560
ttaatcgcct tgcagcacat ccccctttcg ccagctggcg taatagcgaa gaggcccgca   4620
ccgatcgccc ttcccaacag ttgcgcagcc tgaatggcga atggcgcctg atgcggtatt   4680
ttctccttac gcatctgtgc ggtatttcac accgcatatg gtgcactctc agtacaatct   4740
gctctgatgc cgcatagtta agccagcccc gacacccgcc aacacccgct gacgcgccct   4800
gacgggcttg tctgctcccg gcatccgctt acagacaagc tgtgaccgtc tccgggagct   4860
gcatgtgtca gaggttttca ccgtcatcac cgaaacgcgc gagacgaaag gcctcgtga    4920 tacgcctatt tttataggtt aatgtcatga taataatggt ttcttagacg tcaggtggca   4980
cttttcgggg aaatgtgcgc ggaaccccta tttgtttatt tttctaaata cattcaaata   5040
tgtatccgct catgagacaa taaccctgat aaatgcttca ataatattga aaaggaaga    5100 gtatgagtat tcaacatttc cgtgtcgccc ttattccctt ttttgcggca ttttgccttc    5160 ctgttttgc tcacccagaa acgctggtga agtaaaaga tgctgaagat cagttgggtg     5220
cacgagtggg ttacatcgaa ctggatctca acagcggtaa gatccttgag agttttcgcc   5280
```

```
ccgaagaacg tttccaatg atgagcactt ttaaagttct gctatgtggc gcggtattat   5340
cccgtattga cgccgggcaa gagcaactcg gtcgccgcat acactattct cagaatgact   5400
tggttgagta ctcaccagtc acagaaaagc atcttacgga tggcatgaca gtaagagaat   5460
tatgcagtgc tgccataacc atgagtgata acactgcggc caacttactt ctgacaacga   5520
tcggaggacc gaaggagcta accgcttttt tgcacaacat gggggatcat gtaactcgcc   5580
ttgatcgttg ggaaccggag ctgaatgaag ccataccaaa cgacgagcgt gacaccacga   5640
tgcctgtagc aatggcaaca acgttgcgca aactattaac tggcgaacta cttactctag   5700
cttcccggca acaattaata gactggatgg aggcggataa agttgcagga ccacttctgc   5760
gctcggccct tccggctggc tggtttattg ctgataaatc tggagccggt gagcgtgggt   5820
ctcgcggtat cattgcagca ctggggccag atggtaagcc ctcccgtatc gtagttatct   5880
acacgacggg gagtcaggca actatggatg aacgaaatag acagatcgct gagataggtg   5940
cctcactgat taagcattgg taactgtcag accaagttta ctcatatata ctttagattg   6000
atttaaaact tcatttttaa tttaaaagga tctaggtgaa gatcctttt gataatctca   6060
tgaccaaaat cccttaacgt gagttttcgt tccactgagc gtcagacccc gtagaaaaga   6120
tcaaaggatc ttcttgagat cctttttttc tgcgcgtaat ctgctgcttg caaacaaaaa   6180
aaccaccgct accagcggtg tttgtttgc cggatcaaga gctaccaact cttttttccga   6240
aggtaactgg cttcagcaga gcgcagatac caaatactgt ccttctagtg tagccgtagt   6300
taggccacca cttcaagaac tctgtagcac cgcctacata cctcgctctg ctaatcctgt   6360
taccagtggc tgctgccagt ggcgataagt cgtgtcttac cgggttggac tcaagacgat   6420
agttaccgga taaggcgcag cggtcgggct gaacggggggg ttcgtgcaca gcccagct   6480
tggagcgaac gacctacacc gaactgagat acctacagcg tgagctatga gaaagcgcca   6540
cgcttcccga agggagaaag gcggacaggt atccggtaag cggcagggtc ggaacaggag   6600
agcgcacgag ggagcttcca gggggaaacg cctggtatct ttatagtcct gtcgggttc   6660
gccacctctg acttgagcgt cgatttttgt gatgctcgtc agggggggcgg agcctatgga   6720
a                                                                   6721
```

<210> SEQ ID NO 121
<211> LENGTH: 7087
<212> TYPE: DNA
<213> ORGANISM: Artificial Sequence
<220> FEATURE:
<223> OTHER INFORMATION: Plasmid pLA59::TDH3p-ARO10-ADH1t

<400> SEQUENCE: 121

```
aaacgccagc aacgcggcct ttttacggtt cctggccttt tgctggcctt ttgctcacat     60
gttctttcct gcgttatccc ctgattctgt ggataaccgt attaccgcct ttgagtgagc    120
tgataccgct cgccgcagcc gaacgaccga gcgcagcgag tcagtgagcg aggaagcgga    180
agagcgccca atacgcaaac cgcctctccc cgcgcgttgg ccgattcatt aatgcagctg    240
gcacgacagg tttcccgact ggaaagcggg cagtgagcgc aacgcaatta atgtgagtta    300
gctcactcat taggcacccc aggctttaca ctttatgctt ccggctcgta tgttgtgtgg    360
aattgtgagc ggataacaat ttcacacagg aaacagctat gaccatgatt acgccaatac    420
tgccatttca agaatacgt aaataattaa tagtagtgat tttcctaact ttatttagtc    480
aaaaaattag cctttaatt ctgctgtaac ccgtacatgc ccaaataggg ggcgggtta    540
cacagaatat ataacatcgt aggtgtctgg gtgaacagtt tattcctggc atccactaaa    600
```

```
tataatggag cccgcttttt aagctggcat ccagaaaaaa aaagaatccc agcaccaaaa      660
tattgttttc ttcaccaacc atcagttcat aggtccattc tcttagcgca actacagaga      720 acagggcac aaacaggcaa aaacgggca caacctcaat ggagtgatgc aacctgcctg        780
gagtaaatga tgcacaagg caattgaccc acgcatgtat ctatctcatt ttcttacacc       840
ttctattacc ttctgctctc tctgatttgg aaaaagctga aaaaaaggt tgaaaccagt       900 tccctgaaat tattcccta cttgactaat aagtatataa agacggtagg tattgattgt       960
aattctgtaa atctatttct taaacttctt aaattctact tttatagtta gtcttttttt     1020
tagttttaaa acaccaagaa cttagtttcg aataaacaca cataaactag taaacaaaat     1080
ggcacctgtt acaattgaaa agttcgtaaa tcaagaagaa cgacaccttg tttccaaccg     1140
atcagcaaca attccgtttg gtgaatacat atttaaaaga ttgttgtcca tcgatacgaa     1200
atcagttttc ggtgttcctg gtgacttcaa cttatctcta ttagaatatc tctattcacc     1260
tagtgttgaa tcagctggcc taagatgggt cggcacgtgt aatgaactga acgccgctta     1320
tgcggccgac ggatattccc gttactctaa taagattggc tgtttaataa ccacgtatgg     1380
cgttggtgaa ttaagcgcct tgaacggtat agccggttcg ttcgctgaaa atgtcaaagt     1440
tttgcacatt gttggtgtgg ccaagtccat agattcgcgt tcaagtaact ttagtgatcg     1500
gaacctacat catttggtcc cacagctaca tgattcaaat tttaaagggc caaatcataa     1560
agtatatcat gatatggtaa aagatagagt cgcttgctcg gtagcctact ggaggatat     1620 tgaaactgca tgtgaccaag tcgataatgt tatccgcgat atttacaagt attctaaacc     1680
tggttatatt tttgttcctg cagattttgc ggatatgtct gttacatgtg ataatttggt     1740
taatgttcca cgtatatctc aacaagattg tatagtatac ccttctgaaa accaattgtc     1800
tgacataatc aacaagatta ctagttggat atattccagt aaaacacctg cgatccttgg     1860
agacgtactg actgataggt atggtgtgag taacttttg aacaagctta tctgcaaaac     1920
tgggatttgg aattttttcca ctgttatggg aaaatctgta attgatgagt caaacccaac    1980
ttatatgggt caatataatg gtaaagaagg tttaaaacaa gtctatgaac attttgaact    2040
gtgcgacttg gtcttgcatt ttggagtcga catcaatgaa attaataatg gcattatac     2100 ttttacttat aaaccaaatg ctaaaatcat tcaatttcat ccgaattata ttcgccttgt    2160
ggacactagg cagggcaatg agcaaatgtt caaggaatc aattttgccc ctattttaaa     2220
agaactatac aagcgcattg acgtttctaa actttctttg caatatgatt caaatgtaac    2280
tcaatatacg aacgaaacaa tgcggttaga agatcctacc aatggacaat caagcattat    2340
tacacaagtt cacttacaaa agacgatgcc taaatttttg aaccctggtg atgttgtcgt    2400
ttgtgaaaca ggctctttc aattctctgt tcgtgatttc gcgtttcctt cgcaattaaa     2460
atatatatcg caaggatttt tcctttccat tggcatggcc cttcctgccg ccctaggtgt    2520
tggaattgcc atgcaagacc actcaaacgc tcacatcaat ggtggcaacg taaaagagga    2580
ctataagcca agattaattt tgtttgaagg tgacggtgca gcacagatga caatccaaga    2640
actgagcacc attctgaagt gcaatattcc actagaagtt atcatttgga acaataacgg    2700
ctacactatt gaaagagcca tcatgggccc taccaggtcg tataacgacg ttatgtcttg    2760
gaaatggacc aaactatttg aagcattcgg agacttcgac ggaaagtata ctaatagcac    2820
tctcattcaa tgtccctcta aattagcact gaaattggag gagcttaaga attcaaacaa    2880
aagaagcggg atagaacttt tagaagtcaa attaggcgaa ttggattcc ccgaacagct     2940
```

```
aaagtgcatg gttgaagcag cggcacttaa aagaaataaa aaatagacca caggtgttgt    3000
cctctgagga cataaaatac acaccgagat tcatcaactc attgctggag ttagcatatc    3060
tacaattggg tgaaatgggg agcgatttgc aggcatttgc tcggcatgcc ggtagaggtg    3120
tggtcaataa gagcgacctc atgctatacc tgagaaagca acctgaccta caggaaagag    3180
ttactcaaga ataagaattt tcgttttaaa acctaagagt cactttaaaa tttgtataca    3240 cttattttt ttataactta tttaataata aaaatcataa atcataagaa attcgcttac    3300
tccaagcttg cattgcggat tacgtattct aatgttcagt accgttcgta taatgtatgc    3360
tatacgaagt tatgcagatt gtactgagag tgcaccatac cacctttca attcatcatt    3420 ttttttttat tctttttttt gatttcggtt tccttgaaat ttttttgatt cggtaatctc    3480
cgaacagaag gaagaacgaa ggaaggagca cagacttaga ttggtatata tacgcatatg    3540
tagtgttgaa gaaacatgaa attgcccagt attcttaacc caactgcaca gaacaaaaac    3600
ctgcaggaaa cgaagataaa tcatgtcgaa agctacatat aaggaacgtg ctgctactca    3660
tcctagtcct gttgctgcca agctatttaa tatcatgcac gaaaagcaaa caaacttgtg    3720
tgcttcattg gatgttcgta ccaccaagga attactggag ttagttgaag cattaggtcc    3780
caaaatttgt ttactaaaaa cacatgtgga tatcttgact gatttttcca tggagggcac    3840
agttaagccg ctaaaggcat tatccgccaa gtacaatttt ttactcttcg aagacagaaa    3900
atttgctgac attggtaata cagtcaaatt gcagtactct gcgggtgtat acagaatagc    3960
agaatgggca gacattacga atgcacacgg tgtggtgggc ccaggtattg ttagcggttt    4020
gaagcaggcg gcagaagaag taacaaagga acctagaggc cttttgatgt tagcagaatt    4080
gtcatgcaag ggctccctat ctactggaga atatactaag ggtactgttg acattgcgaa    4140
gagcgacaaa gattttgtta tcggctttat tgctcaaaga gacatgggtg aagagatga    4200 aggttacgat tggttgatta tgacacccgg tgtgggttta gatgacaagg gagacgcatt    4260
gggtcaacag tatagaaccg tggatgatgt ggtctctaca ggatctgaca ttattattgt    4320
tggaagagga ctatttgcaa agggaaggga tgctaaggta gagggtgaac gttacagaaa    4380
agcaggctgg gaagcatatt tgagaagatg cggccagcaa aactaaaaaa ctgtattata    4440
agtaaatgca tgtatactaa actcacaaat tagagcttca atttaattat atcagttatt    4500
accctatgcg gtgtgaaata ccgcacagat gcgtaaggag aaaataccgc atcaggaaat    4560
tgtaaacgtt aatattttgt taaaattcgc gttaaatttt tgttaaatca gctcattttt    4620
taaccaatag gccgaaatcg gcaaaatccc ttataaatca aaagaataga ccgagatagg    4680
gttgagtgtt gttccagttt ggaacaagag tccactatta agaacgtgg actccaacgt     4740 caaagggcga aaaccgtct atcagggcga tggcccacta cgtgaaccat cacctaatc      4800 aagataactt cgtataatgt atgctatacg aacggtacca gtgatgatac aacgagttag    4860
ccaaggtgaa ttcactggcc gtcgttttac aacgtcgtga ctgggaaaac cctggcgtta    4920
cccaacttaa tcgccttgca gcacatcccc ctttcgccag ctggcgtaat agcgaagagg    4980
cccgcaccga tcgcccttcc caacagttgc gcagcctgaa tggcgaatgg cgcctgatgc    5040
ggtattttct ccttacgcat ctgtgcggta tttcacaccg catatggtgc actctcagta    5100
caatctgctc tgatgccgca tagttaagcc agccccgaca cccgccaaca cccgctgacg    5160
cgccctgacg ggcttgtctg ctcccggcat ccgcttacag acaagctgtg accgtctccg    5220
ggagctgcat gtgtcagagg ttttcaccgt catcaccgaa acgcgcgaga cgaaagggcc    5280
tcgtgatacg cctatttta taggttaatg tcatgataat aatggtttct tagacgtcag    5340
```

```
gtggcacttt tcggggaaat gtgcgcggaa ccctatttg tttattttc taaatacatt      5400
caaatatgta tccgctcatg agacaataac cctgataaat gcttcaataa tattgaaaaa    5460
ggaagagtat gagtattcaa catttccgtg tcgcccttat tccctttttt gcggcatttt    5520
gccttcctgt ttttgctcac ccagaaacgc tggtgaaagt aaaagatgct gaagatcagt    5580
tgggtgcacg agtgggttac atcgaactgg atctcaacag cggtaagatc cttgagagtt    5640
ttcgccccga agaacgtttt ccaatgatga gcacttttaa agttctgcta tgtggcgcgg    5700
tattatcccg tattgacgcc gggcaagagc aactcggtcg ccgcatacac tattctcaga    5760
atgacttggt tgagtactca ccagtcacag aaaagcatct tacgatggc atgacagtaa     5820
gagaattatg cagtgctgcc ataaccatga gtgataacac tgcggccaac ttacttctga    5880
caacgatcgg aggaccgaag gagctaaccg cttttttgca caacatgggg gatcatgtaa    5940
ctcgccttga tcgttgggaa ccggagctga atgaagccat accaaacgac gagcgtgaca    6000
ccacgatgcc tgtagcaatg gcaacaacgt tgcgcaaact attaactggc gaactactta    6060
ctctagcttc ccggcaacaa ttaatagact ggatggaggc ggataaagtt gcaggaccac    6120
ttctgcgctc ggcccttccg gctggctggt ttattgctga taaatctgga gccggtgagc    6180
gtgggtctcg cggtatcatt gcagcactgg ggccagatgg taagccctcc cgtatcgtag    6240
ttatctacac gacggggagt caggcaacta tggatgaacg aaatagacag atcgctgaga    6300
taggtgcctc actgattaag cattggtaac tgtcagacca gtttactca tatatacttt     6360
agattgattt aaaacttcat ttttaattta aaaggatcta ggtgaagatc cttttttgata  6420
atctcatgac caaaatccct aacgtgagt tttcgttcca ctgagcgtca gacccgtag      6480
aaaagatcaa aggatcttct tgagatcctt ttttctgcg cgtaatctgc tgcttgcaaa     6540
caaaaaaacc accgctacca gcggtggttt gtttgccgga tcaagagcta ccaactcttt   6600
ttccgaaggt aactggcttc agcagagcgc agataccaaa tactgtcctt ctagtgtagc   6660
cgtagttagg ccaccacttc aagaactctg tagcaccgcc tacatacctc gctctgctaa   6720
tcctgttacc agtggctgct gccagtggcg ataagtcgtg tcttaccggg ttggactcaa   6780
gacgatagtt accggataag gcgcagcggt cgggctgaac ggggggttcg tgcacacagc   6840
ccagcttgga gcgaacgacc tacaccgaac tgagatacct acagcgtgag ctatgagaaa   6900
gcgccacgct tcccgaaggg agaaaggcgg acaggtatcc ggtaagcggc agggtcggaa   6960
caggagagcg cacgagggag cttccagggg gaaacgcctg gtatctttat agtcctgtcg   7020
ggtttcgcca cctctgactt gagcgtcgat ttttgtgatg ctcgtcaggg gggcggagcc   7080
tatggaa                                                              7087
```

<210> SEQ ID NO 122
<211> LENGTH: 9613
<212> TYPE: DNA
<213> ORGANISM: Artificial sequence
<220> FEATURE:
<223> OTHER INFORMATION: pHR81-ILV5p-K9SB2

<400> SEQUENCE: 122

```
aaacagtatg aagaatgta agatggctaa gatttactac caagaagact gtaacttgtc       60
cttgttggat ggtaagacta tcgccgttat cggttacggt tctcaaggtc acgctcatgc     120
cctgaatgct aaggaatccg gttgtaacgt tatcattggt ttattcgaag gtgcggagga    180
gtggaaaaga gctgaagaac aaggtttcga agtctacacc gctgctgaag ctgctaagaa    240
```

```
ggctgacatc attatgatct tgatcccaga tgaaaagcag gctaccatgt acaaaaacga    300
catcgaacca aacttggaag ccggtaacat gttgatgttc gctcacggtt tcaacatcca    360
tttcggttgt attgttccac caaaggacgt tgatgtcact atgatcgctc caaagggtcc    420
aggtcacacc gttagatccg aatacgaaga aggtaaaggt gtcccatgct ggttgctgt     480 cgaacaagac gctactggca aggctttgga tatggctttg gcctacgctt tagccatcgg    540
tggtgctaga gccggtgtct tggaaactac cttcagaacc gaaactgaaa ccgacttgtt    600
cggtgaacaa gctgttttat gtggtggtgt ctgcgctttg atgcaggccg ttttgaaac    660 cttggttgaa gccggttacg acccaagaaa cgcttacttc gaatgtatcc acgaaatgaa    720
gttgatcgtt gacttgatct accaatctgg tttctccggt atgcgttact ctatctccaa    780
cactgctgaa tacggtgact acattaccgg tccaaagatc attactgaag ataccaagaa    840
ggctatgaag aagattttgt ctgacattca agatggtacc tttgccaagg acttcttggt    900
tgacatgtct gatgctggtt cccaggtcca cttcaaggct atgagaaagt tggcctccga    960
acacccagct gaagttgtcg gtgaagaaat tagatccttg tactcctggt ccgacgaaga   1020
caagttgatt aacaactgag gccctgcagg ccagaggaaa ataatatcaa gtgctggaaa   1080 cttttttctct tggaatttttt gcaacatcaa gtcatagtca attgaattga cccaatttca   1140
catttaagat ttttttttttt tcatccgaca tacatctgta cactaggaag ccctgttttt   1200
ctgaagcagc ttcaaatata tatattttt acatatttat tatgattcaa tgaacaatct    1260
aattaaatcg aaaacaagaa ccgaaacgcg aataaataat ttatttagat ggtgacaagt   1320
gtataagtcc tcatcgggac agctacgatt tctctttcgg ttttggctga gctactggtt   1380
gctgtgacgc agcggcatta gcgcggcgtt atgagctacc ctcgtggcct gaaagatggc   1440
gggaataaag cggaactaaa aattactgac tgagccatat tgaggtcaat ttgtcaactc   1500
gtcaagtcac gtttggtgga cggcccctt ccaacgaatc gtatatacta acatgcgcgc    1560
gcttcctata tacacatata catatatata tatatatata tgtgtgcgtg tatgtgtaca    1620
cctgtattta atttccttac tcgcgggttt ttcttttttc tcaattcttg gcttcctctt    1680
tctcgagcgg accggatcct ccgcggtgcc ggcagatcta tttaaatggc gcgccgacgt   1740
caggtggcac ttttcgggga atgtgcgcg gaacccctat tgtttatttt ttctaaatac    1800
attcaaatat gtatccgctc atgagacaat aaccctgata aatgcttcaa taatattgaa   1860
aaaggaagag tatgagtatt caacatttcc gtgtcgccct tattccctt tttgcggcat    1920 tttgccttcc tgtttttgct cacccagaaa cgctggtgaa agtaaaagat gctgaagatc   1980
agttgggtgc acgagtgggt tacatcgaac tggatctcaa cagcggtaag atccttgaga   2040
gttttcgccc cgaagaacgt tttccaatga tgagcacttt taaagttctg ctatgtggcg   2100
cggtattatc ccgtattgac gccgggcaag agcaactcgg tcgccgcata cactattctc   2160
agaatgactt ggttgagtac tcaccagtca cagaaaagca tcttacggat ggcatgacag   2220
taagagaatt atgcagtgct gccataacca tgagtgataa cactgcggcc aacttacttc   2280
tgacaacgat cggaggaccg aaggagctaa ccgcttttttt gcacaacatg gggatcatg    2340 taactcgcct tgatcgttgg aaccggagc tgaatgaagc cataccaaac gacgagcgtg    2400
acaccacgat gcctgtagca atggcaacaa cgttgcgcaa actattaact ggcgaactac    2460
ttactctagc ttcccggcaa caattaatag actggatgga ggcggataaa gttgcaggac   2520
cacttctgcg ctcggccctt ccggctggct ggtttattgc tgataaatct ggagccggtg   2580
agcgtgggtc tcgcggtatc attgcagcac tggggccaga tggtaagccc tcccgtatcg   2640
```

```
tagttatcta cacgacgggg agtcaggcaa ctatggatga acgaaataga cagatcgctg    2700
agataggtgc ctcactgatt aagcattggt aactgtcaga ccaagtttac tcatatatac    2760
tttagattga tttaaaactt cattttaat ttaaaaggat ctaggtgaag atcctttttg     2820
ataatctcat gaccaaaatc ccttaacgtg agttttcgtt ccactgagcg tcagaccccg    2880
tagaaaagat caaaggatct tcttgagatc ctttttttct gcgcgtaatc tgctgcttgc    2940
aaacaaaaaa accaccgcta ccagcggtgg tttgtttgcc ggatcaagag ctaccaactc    3000
tttttccgaa ggtaactggc ttcagcagag cgcagatacc aaatactgtt cttctagtgt    3060
agccgtagtt aggccaccac ttcaagaact ctgtagcacc gcctacatac ctcgctctgc    3120
taatcctgtt accagtggct gctgccagtg gcgataagtc gtgtcttacc gggttggact    3180
caagacgata gttaccggat aaggcgcagc ggtcgggctg aacggggggt tcgtgcacac    3240
agcccagctt ggagcgaacg acctacaccg aactgagata cctacagcgt gagctatgag    3300
aaagcgccac gcttcccgaa gggagaaagg cggacaggta tccggtaagc ggcagggtcg    3360
gaacaggaga gcgcacgagg gagcttccag ggggaaacgc ctggtatctt tatagtcctg    3420
tcgggtttcg ccacctctga cttgagcgtc gatttttgtg atgctcgtca gggggggcgga   3480
gcctatggaa aaacgccagc aacgcggcct ttttacggtt cctggccttt tgctggcctt    3540
ttgctcacat gttctttcct gcgttatccc ctgattctgt ggataaccgt attaccgcct    3600
ttgagtgagc tgataccgct cgccgcagcc gaacgaccga gcgcagcgag tcagtgagcg    3660
aggaagcgga agagcgccca atacgcaaac cgcctctccc cgcgcgttgg ccgattcatt    3720
aatgcagctg gcacgacagg tttcccgact ggaaagcggg cagtgagcgc aacgcaatta    3780
atgtgagtta gctcactcat taggcacccc aggctttaca ctttatgctt ccggctcgta    3840
tgttgtgtgg aattgtgagc ggataacaat ttcacacagg aaacagctat gaccatgatt    3900
acgccaagct ttttctttcc aattttttt ttttcgtcat tataaaaatc attacgaccg     3960
agattcccgg gtaataactg atataattaa attgaagctc taatttgtga gtttagtata    4020
catgcattta cttataatac agttttttag ttttgctggc cgcatcttct caaatatgct    4080
tcccagcctg cttttctgta acgttcaccc tctaccttag catcccttcc ctttgcaaat    4140
agtcctcttc caacaataat aatgtcagat cctgtagaga ccacatcatc cacggttcta    4200
tactgttgac ccaatgcgtc tcccttgtca tctaaaccca caccgggtgt cataatcaac    4260
caatcgtaac cttcatctct tccacccatg tctctttgag caataaagcc gataacaaaa    4320
tctttgtcgc tcttcgcaat gtcaacagta cccttagtat attctccagt agataggag    4380
cccttgcatg acaattctgc taacatcaaa aggcctctag gttcctttgt tacttcttct    4440
gccgcctgct tcaaaccgct aacaatacct gggcccacca caccgtgtgc attcgtaatg   4500
tctgcccatt ctgctattct gtatacaccc gcagagtact gcaatttgac tgtattacca    4560
atgtcagcaa attttctgtc ttcgaagagt aaaaaattgt acttggcgga taatgccttt    4620
agcggcttaa ctgtgccctc catggaaaaa tcagtcaaga tatccacatg tgtttttagt    4680
aaacaaattt tgggacctaa tgcttcaact aactccagta attccttggt ggtacgaaca    4740
tccaatgaag cacacaagtt tgtttgcttt tcgtgcatga tattaaatag cttggcagca    4800
acaggactag gatgagtagc agcacgttcc ttatatgtag ctttcgacat gatttatctt    4860
cgtttcctgc aggttttgt tctgtgcagt tgggttaaga atactgggca atttcatgtt    4920
tcttcaacac tacatatgcg tatatatacc aatctaagtc tgtgctcctt ccttcgttct    4980
```

```
tccttctgtt cggagattac cgaatcaaaa aaatttcaag gaaaccgaaa tcaaaaaaaa      5040
gaataaaaaa aaaatgatga attgaaaagc ttgcatgcct gcaggtcgac tctagtatac      5100
tccgtctact gtacgataca cttccgctca ggtccttgtc ctttaacgag gccttaccac      5160
tcttttgtta ctctattgat ccagctcagc aaaggcagtg tgatctaaga ttctatcttc      5220
gcgatgtagt aaaactagct agaccgagaa agagactaga aatgcaaaag gcacttctac      5280
aatggctgcc atcattatta tccgatgtga cgctgcattt tttttttttt tttttttttt      5340
tttttttttt tttttttttt tttttttttg tacaaatatc ataaaaaaag agaatctttt      5400
taagcaagga ttttcttaac ttcttcggcg acagcatcac cgacttcggt ggtactgttg      5460
gaaccaccta aatcaccagt tctgatacct gcatccaaaa cctttttaac tgcatcttca      5520
atggctttac cttcttcagg caagttcaat gacaatttca acatcattgc agcagacaag      5580
atagtggcga tagggttgac cttattcttt ggcaaatctg gagcggaacc atggcatggt      5640
tcgtacaaac caaatgcggt gttcttgtct ggcaaagagg ccaaggacgc agatggcaac      5700
aaacccaagg agcctgggat aacgaggct tcatcggaga tgatatcacc aaacatgttg      5760
ctggtgatta aataccatt taggtgggtt gggttcttaa ctaggatcat ggcggcagaa      5820
tcaatcaatt gatgttgaac tttcaatgta gggaattcgt tcttgatggt ttcctccaca      5880 gttttctcc ataatcttga agaggccaaa acattagctt tatccaagga ccaaataggc      5940
aatggtggct catgttgtag ggccatgaaa gcggccattc ttgtgattct ttgcacttct      6000
ggaacggtgt attgttcact atcccaagcg acaccatcac catcgtcttc ctttctctta      6060
ccaaagtaaa tacctcccac taattctcta acaacaacga agtcagtacc tttagcaaat      6120
tgtggcttga ttggagataa gtctaaaaga gagtcggatg caaagttaca tggtcttaag      6180
ttggcgtaca attgaagttc tttacggatt tttagtaaac cttgttcagg tctaacacta      6240
ccggtacccc atttaggacc acccacagca cctaacaaaa cggcatcagc cttcttggag      6300
gcttccagcg cctcatctgg aagtggaaca cctgtagcat cgatagcagc accaccaatt      6360
aaatgatttt cgaaatcgaa cttgacattg aacgaacat cagaaatagc tttaagaacc      6420
ttaatggctt cggctgtgat ttcttgacca acgtggtcac ctggcaaaac gacgatcttc      6480
ttaggggcag acattacaat ggtatatcct tgaaatatat ataaaaaaa aaaaaaaaa       6540 aaaaaaaaaa aatgcagctt ctcaatgata ttcgaatacg ctttgaggag atacagccta      6600
atatccgaca aactgtttta cagatttacg atcgtacttg ttacccatca ttgaattttg      6660
aacatccgaa cctgggagtt ttccctgaaa cagatagtat atttgaacct gtataataat      6720
atatagtcta gcgctttacg gaagacaatg tatgtatttc ggttcctgga gaaactattg      6780
catctattgc ataggtaatc ttgcacgtcg catcccgt tcattttctg cgtttccatc       6840
ttgcacttca atagcatatc tttgttaacg aagcatctgt gcttcatttt gtagaacaaa      6900
aatgcaacgc gagagcgcta attttcaaa caaagaatct gagctgcatt tttacagaac       6960
agaaatgcaa cgcgaaagcg ctattttacc aacgaagaat ctgtgcttca ttttttgtaaa      7020 acaaaaatgc aacgcgagag cgctaatttt tcaaacaaag aatctgagct gcattttac       7080 agaacagaaa tgcaacgcga gagcgctatt ttaccaacaa gaatctata cttcttttt        7140 gttctacaaa aatgcatccc gagagcgcta ttttctaac aaagcatctt agattacttt       7200
ttttctcctt tgtgcgctct ataatgcagt ctcttgataa cttttgcac tgtaggtccg       7260 ttaaggttag aagaaggcta ctttggtgtc tattttctct tccataaaaa aagcctgact      7320
ccacttcccg cgtttactga ttactagcga agctgcgggt gcattttttc aagataaagg      7380
```

```
catccccgat tatattctat accgatgtgg attgcgcata ctttgtgaac agaaagtgat    7440
agcgttgatg attcttcatt ggtcagaaaa ttatgaacgg tttcttctat tttgtctcta    7500
tatactacgt ataggaaatg tttacatttt cgtattgttt tcgattcact ctatgaatag    7560
ttcttactac aattttttg tctaaagagt aatactagag ataaacataa aaatgtaga     7620 ggtcgagttt agatgcaagt tcaaggagcg aaaggtggat gggtaggtta tatagggata    7680
tagcacagag atatatagca aagagatact tttgagcaat gtttgtggaa gcggtattcg    7740
caatatttta gtagctcgtt acagtccggt gcgttttgg ttttttgaaa gtgcgtcttc     7800
agagcgcttt tggttttcaa aagcgctctg aagttcctat actttctaga gaataggaac    7860
ttcggaatag gaacttcaaa gcgtttccga aaacgagcgc ttccgaaaat gcaacgcgag    7920
ctgcgcacat acagctcact gttcacgtcg cacctatatc tgcgtgttgc ctgtatatat    7980
atatacatga agaacggc atagtgcgtg tttatgctta aatgcgtact tatatgcgtc      8040
tatttatgta ggatgaaagg tagtctagta cctcctgtga tattatccca ttccatgcgg    8100
ggtatcgtat gcttccttca gcactaccct ttagctgttc tatatgctgc cactcctcaa    8160
ttggattagt ctcatccttc aatgctatca tttccttga tattggatca tatgcatagt      8220
accgagaaac tagaggatct cccattaccg acatttgggc gctatacgtg catatgttca    8280
tgtatgtatc tgtatttaaa acactttgt attattttc ctcatatatg tgtataggtt       8340
tatacggatg atttaattat tacttcacca ccctttattt caggctgata tcttagcctt    8400
gttactagtc accggtggcg gccgcacctg gtaaaacctc tagtggagta gtagatgtaa    8460
tcaatgaagc ggaagccaaa agaccagagt agaggcctat agaagaaact gcgataccttt   8520 ttgtgatggc taaacaaaca gacatctttt tatatgttt tacttctgta tatcgtgaag     8580
tagtaagtga taagcgaatt tggctaagaa cgttgtaagt gaacaaggga cctcttttgc    8640
ctttcaaaaa aggattaaat ggagttaatc attgagattt agttttcgtt agattctgta    8700
tccctaaata actcccttac ccgacgggaa ggcacaaaag acttgaataa tagcaaacgg    8760
ccagtagcca agaccaaata atactagagt taactgatgg tcttaaacag gcattacgtg    8820
gtgaactcca agaccaatat acaaaatatc gataagttat tcttgcccac caatttaagg    8880
agcctacatc aggacagtag taccattcct cagagaagag gtatacataa caagaaaatc    8940
gcgtgaacac cttatataac ttagcccgtt attgagctaa aaaaccttgc aaaatttcct    9000
atgaataaga atacttcaga cgtgataaaa atttactttc taactcttct cacgctgccc    9060
ctatctgttc ttccgctcta ccgtgagaaa taaagcatcg agtacggcag ttcgctgtca   9120
ctgaactaaa acaataaggc tagttcgaat gatgaacttg cttgctgtca aacttctgag    9180
ttgccgctga tgtgacactg tgacaataaa ttcaaaccgg ttatagcggt ctcctccggt    9240
accggttctg ccacctccaa tagagctcag taggagtcag aacctctgcg gtggctgtca    9300
gtgactcatc cgcgtttcgt aagttgtgcg cgtgcacatt tcgcccgttc ccgctcatct    9360
tgcagcaggc ggaaattttc atcacgctgt aggacgcaaa aaaaaataa ttaatcgtac      9420 aagaatcttg gaaaaaaaat tgaaaaattt tgtataaaag ggatgaccta acttgactca     9480 atggcttta cacccagtat tttccctttc cttgtttgtt acaattatag aagcaagaca      9540
aaaacatata gacaacctat tcctaggagt tatattttt tacccctacca gcaatataag    9600 taaaaaactg ttt                                                      9613
```

<210> SEQ ID NO 123

-continued

<211> LENGTH: 13022
<212> TYPE: DNA
<213> ORGANISM: Artificial sequence
<220> FEATURE:
<223> OTHER INFORMATION: pLA84

<400> SEQUENCE: 123

| | | | | | |
|---|---|---|---|---|---|
| ccagcttttg | ttccctttag | tgagggttaa | ttgcgcgctt | ggcgtaatca | tggtcatagc | 60 |
| tgtttcctgt | gtgaaattgt | tatccgctca | caattccaca | caacatacga | gccgaagca | 120 |
| taaagtgtaa | agcctggggt | gcctaatgag | tgagctaact | cacattaatt | gcgttgcgct | 180 |
| cactgcccgc | tttccagtcg | ggaaacctgt | cgtgccagct | gcattaatga | atcggccaac | 240 |
| gcgcggggag | aggcggtttg | cgtattgggc | gctcttccgc | ttcctcgctc | actgactcgc | 300 |
| tgcgctcggt | cgttcggctg | cggcgagcgg | tatcagctca | ctcaaaggcg | gtaatacggt | 360 |
| tatccacaga | atcaggggat | aacgcaggaa | agaacatgtg | agcaaaaggc | cagcaaaagg | 420 |
| ccaggaaccg | taaaaaggcc | gcgttgctgg | cgtttttcca | taggctccgc | ccccctgacg | 480 |
| agcatcacaa | aaatcgacgc | tcaagtcaga | ggtggcgaaa | cccgacagga | ctataaagat | 540 |
| accaggcgtt | tccccctgga | agctccctcg | tgcgctctcc | tgttccgacc | ctgccgctta | 600 |
| ccggatacct | gtccgccttt | ctcccttcgg | gaagcgtggc | gctttctcat | agctcacgct | 660 |
| gtaggtatct | cagttcggtg | taggtcgttc | gctccaagct | gggctgtgtg | cacgaacccc | 720 |
| ccgttcagcc | cgaccgctgc | gccttatccg | gtaactatcg | tcttgagtcc | aacccggtaa | 780 |
| gacacgactt | atcgccactg | gcagcagcca | ctggtaacag | gattagcaga | gcgaggtatg | 840 |
| taggcggtgc | tacagagttc | ttgaagtggt | ggcctaacta | cggctacact | agaagaacag | 900 |
| tatttggtat | ctgcgctctg | ctgaagccag | ttaccttcgg | aaaaagagtt | ggtagctctt | 960 |
| gatccggcaa | acaaaccacc | gctggtagcg | gtggtttttt | tgtttgcaag | cagcagatta | 1020 |
| cgcgcagaaa | aaaaggatct | caagaagatc | ctttgatctt | ttctacgggg | tctgacgctc | 1080 |
| agtggaacga | aaactcacgt | taagggattt | tggtcatgag | attatcaaaa | aggatcttca | 1140 |
| cctagatcct | tttaaattaa | aaatgaagtt | ttaaatcaat | ctaaagtata | tatgagtaaa | 1200 |
| cttggtctga | cagttaccaa | tgcttaatca | gtgaggcacc | tatctcagcg | atctgtctat | 1260 |
| ttcgttcatc | catagttgcc | tgactccccg | tcgtgtagat | aactacgata | cgggagggct | 1320 |
| taccatctgg | ccccagtgct | gcaatgatac | cgcgagaccc | acgctcaccg | gctccagatt | 1380 |
| tatcagcaat | aaaccagcca | gccggaaggg | ccgagcgcag | aagtggtcct | gcaactttat | 1440 |
| ccgcctccat | ccagtctatt | aattgttgcc | gggaagctag | agtaagtagt | tcgccagtta | 1500 |
| atagtttgcg | caacgttgtt | gccattgcta | caggcatcgt | ggtgtcacgc | tcgtcgtttg | 1560 |
| gtatggcttc | attcagctcc | ggttcccaac | gatcaaggcg | agttacatga | tcccccatgt | 1620 |
| tgtgcaaaaa | agcggttagc | tccttcggtc | ctccgatcgt | tgtcagaagt | aagttggccg | 1680 |
| cagtgttatc | actcatggtt | atggcagcac | tgcataattc | tcttactgtc | atgccatccg | 1740 |
| taagatgctt | ttctgtgact | ggtgagtact | caaccaagtc | attctgagaa | tagtgtatgc | 1800 |
| ggcgaccgag | ttgctcttgc | ccggcgtcaa | tacgggataa | taccgcgcca | catagcagaa | 1860 |
| ctttaaaagt | gctcatcatt | ggaaaacgtt | cttcggggcg | aaaactctca | aggatcttac | 1920 |
| cgctgttgag | atccagttcg | atgtaaccca | ctcgtgcacc | caactgatct | tcagcatctt | 1980 |
| ttactttcac | cagcgtttct | gggtgagcaa | aaacaggaag | gcaaaatgcc | gcaaaaaagg | 2040 |
| gaataagggc | gacacggaaa | tgttgaatac | tcatactctt | cctttttcaa | tattattgaa | 2100 |
| gcatttatca | gggttattgt | ctcatgagcg | gatacatatt | tgaatgtatt | tagaaaaata | 2160 |

```
aacaaatagg ggttccgcgc acatttcccc gaaaagtgcc acctgaacga agcatctgtg    2220
cttcattttg tagaacaaaa atgcaacgcg agagcgctaa ttttcaaac aaagaatctg    2280 agctgcattt ttacagaaca gaaatgcaac gcgaaagcgc tattttacca acgaagaatc    2340
tgtgcttcat ttttgtaaaa caaaaatgca acgcgagagc gctaattttt caaacaaaga    2400
atctgagctg cattttaca gaacagaaat gcaacgcgag agcgctattt taccaacaaa    2460
gaatctatac ttcttttttg ttctacaaaa atgcatcccg agagcgctat ttttctaaca    2520
aagcatctta gattactttt tttctccttt gtgcgctcta taatgcagtc tcttgataac    2580 ttttttgcact gtaggtccgt taaggttaga agaaggctac tttggtgtct attttctctt    2640
ccataaaaaa agcctgactc cacttcccgc gtttactgat tactagcgaa gctgcgggtg    2700
cattttttca agataaaggc atccccgatt atattctata ccgatgtgga ttgcgcatac    2760
tttgtgaaca gaaagtgata gcgttgatga ttcttcattg gtcagaaaat tatgaacggt    2820
ttcttctatt ttgtctctat atactacgta taggaaatgt ttacattttc gtattgtttt    2880
cgattcactc tatgaatagt tcttactaca atttttttgt ctaaagagta atactagaga    2940
taaacataaa aaatgtagag gtcgagttta gatgcaagtt caaggagcga aggtggatg    3000 ggtaggttat atagggatat agcacagaga tatatagcaa agagatactt tgagcaatg    3060 tttgtgaag cggtattcgc aatattttag tagctcgtta cagtccggtg cgttttggt    3120 tttttgaaag tgcgtcttca gagcgctttt ggttttcaaa agcgctctga agttcctata    3180
ctttctagag aataggaact tcggaatagg aacttcaaag cgtttccgaa acgagcgct    3240 tccgaaaatg caacgcgagc tgcgcacata cagctcactg ttcacgtcgc acctatatct    3300
gcgtgttgcc tgtatatata tatacatgag aagaacggca tagtgcgtgt ttatgcttaa    3360
atgcgtactt atatgcgtct atttatgtag gatgaaaggt agtctagtac ctcctgtgat    3420
attatcccat tccatgcggg gtatcgtatg cttccttcag cactacccctt tagctgttct    3480 atatgctgcc actcctcaat tggattagtc tcatccttca atgctatcat ttcctttgat    3540
attggatcat actaagaaac cattattatc atgacattaa cctataaaaa taggcgtatc    3600
acgaggccct ttcgtctcgc gcgtttcggt gatgacggtg aaaacctctg acacatgcag    3660
ctcccggaga cggtcacagc ttgtctgtaa gcggatgccg ggagcagaca agcccgtcag    3720
ggcgcgtcag cgggtgttgg cgggtgtcgg ggctggctta actatgcggc atcagagcag    3780
attgtactga gagtgcacca taaattcccg ttttaagagc ttggtgagcg ctaggagtca    3840
ctgccaggta tcgtttgaac acggcattag tcagggaagt cataacacag tcctttcccg    3900
caattttctt tttctattac tcttggcctc ctctagtaca ctctatattt ttttatgcct    3960
cggtaatgat tttcattttt tttttccac ctagcggatg actctttttt tttcttagcg    4020
attggcatta tcacataatg aattatacat tatataaagt aatgtgattt cttcgaagaa    4080
tatactaaaa aatgagcagg caagataaac gaaggcaaag atgacagagc agaaagccct    4140
agtaaagcgt attacaaatg aaaccaagat tcagattgcg atctctttaa agggtggtcc    4200
cctagcgata gagcactcga tcttcccaga aaaagaggca gaagcagtag cagaacaggc    4260
cacacaatcg caagtgatta acgtccacac aggtataggg tttctggacc atatgataca    4320
tgctctggcc aagcattccg gctggtcgct aatcgttgag tgcattggtg acttacacat    4380
agacgaccat cacaccactg aagactgcgg gattgctctc ggtcaagctt ttaaagaggc    4440
cctaggggcc gtgcgtggag taaaaaggtt tggatcagga tttgcgcctt tggatgaggc    4500
```

```
actttccaga gcggtggtag atctttcgaa caggccgtac gcagttgtcg aacttggttt    4560
gcaaagggag aaagtaggag atctctcttg cgagatgatc ccgcattttc ttgaaagctt    4620
tgcagaggct agcagaatta ccctccacgt tgattgtctg cgaggcaaga atgatcatca    4680
ccgtagtgag agtgcgttca aggctcttgc ggttgccata agagaagcca cctcgcccaa    4740
tggtaccaac gatgttccct ccaccaaagg tgttcttatg tagtgacacc gattatttaa    4800
agctgcagca tacgatatat atacatgtgt atatatgtat acctatgaat gtcagtaagt    4860
atgtatacga acagtatgat actgaagatg acaaggtaat gcatcattct atacgtgtca    4920
ttctgaacga ggcgcgcttt ccttttttct ttttgctttt tctttttttt tctccttgaac   4980 tcgacggatc tatgcggtgt gaaataccgc acagatgcgt aaggagaaaa taccgcatca    5040
ggaaattgta agcgttaata ttttgttaaa attcgcgtta aatttttgtt aaatcagctc    5100
attttttaac caataggccg aaatcggcaa aatcccttat aaatcaaaag aatagaccga    5160
gatagggttg agtgttgttc cagtttggaa caagagtcca ctattaaaga acgtggactc    5220
caacgtcaaa gggcgaaaaa ccgtctatca gggcgatggc ccactacgtg gccggcttca    5280
catacgttgc atacgtcgat atagataata atgataatga cagcaggatt atcgtaatac    5340
gtaatagctg aaaatctcaa aaatgtgtgg gtcattacgt aaataatgat aggaatggga    5400
ttcttctatt tttccttttt ccattctagc agccgtcggg aaaacgtggc atcctctctt    5460
tcgggctcaa ttggagtcac gctgccgtga gcatcctctc tttccatatc taacaactga    5520
gcacgtaacc aatggaaaag catgagctta gcgttgctcc aaaaaagtat tggatggtta    5580
ataccatttg tctgttctct tctgactttg actcctcaaa aaaaaaaatc tacaatcaac    5640
agatcgcttc aattacgccc tcacaaaaac tttttccctt cttcttcgcc cacgttaaat    5700
tttatccctc atgttgtcta acggatttct gcacttgatt tattataaaa agacaaagac    5760
ataatacttc tctatcaatt tcagttattg ttcttccttg cgttattctt ctgttcttct    5820
ttttcttttg tcatatataa ccataaccaa gtaatacata ttcaaacacg tgagtatgac    5880
tgacaaaaaa actcttaaag acttaagaaa tcgtagttct gtttacgatt caatggttaa    5940
atcacctaat cgtgctatgt tgcgtgcaac tggtatgcaa gatgaagact ttgaaaaacc    6000
tatcgtcggt gtcatttcaa cttgggctga aaacacacct tgtaatatcc acttacatga    6060
ctttggtaaa ctagccaaag tcggtgttaa ggaagctggt gcttggccag ttcagttcgg    6120
aacaatcacg gtttctgatg gaatcgccat gggaacccaa ggaatgcgtt tctccttgac    6180
atctcgtgat attattgcag attctattga agcagccatg ggaggtcata atgcggatgc    6240
ttttgtagcc attggcggtt gtgataaaaa catgcccggt tctgttatcg ctatggctaa    6300
catggatatc ccagccattt ttgcttacgg cggaacaatt gcacctggta atttagacgg    6360
caaagatatc gatttagtct ctgtctttga aggtgtcggc cattggaacc acggcgatat    6420
gaccaaagaa gaagttaaag ctttggaatg taatgcttgt cccggtcctg gaggctgcgg    6480
tggtatgtat actgctaaca caatggcgac agctattgaa gttttgggac ttagccttcc    6540
gggttcatct tctcacccgg ctgaatccgc agaaagaaa gcagatattg aagaagctgg    6600
tcgcgctgtt gtcaaaatgc tcgaaatggg cttaaaacct tctgacattt taacgcgtga    6660
agcttttgaa gatgctatta ctgtaactat ggctctggga ggttcaacca actcaaccct    6720
tcacctctta gctattgccc atgctgctaa tgtggaattg acacttgatg atttcaatac    6780
tttccaagaa aaagttcctc atttggctga tttgaaacct tctggtcaat atgtattcca    6840
agacctttac aaggtcggag gggtaccagc agttatgaaa tatctcctta aaaatggctt    6900
```

```
ccttcatggt gaccgtatca cttgtactgg caaaacagtc gctgaaaatt tgaaggcttt    6960
tgatgattta acacctggtc aaaaggttat tatgccgctt gaaaatccta aacgtgaaga    7020
tggtccgctc attattctcc atggtaactt ggctccagac ggtgccgttg ccaaagtttc    7080
tggtgtaaaa gtgcgtcgtc atgtcggtcc tgctaaggtc tttaattctg aagaagaagc    7140
cattgaagct gtcttgaatg atgatattgt tgatggtgat gttgttgtcg tacgttttgt    7200
aggaccaaag ggcggtcctg gtatgcctga aatgcttttc ctttcatcaa tgattgttgg    7260
taaagggcaa ggtgaaaaag ttgcccttct gacagatggc cgcttctcag gtggtactta    7320
tggtcttgtc gtgggtcata tcgctcctga agcacaagat ggcggtccaa tcgcctacct    7380
gcaaacagga gacatagtca ctattgacca agacactaag gaattacact tgatatctc    7440 cgatgaagag ttaaaacatc gtcaagagac cattgaattg ccaccgctct attcacgcgg    7500
tatccttggt aaatatgctc acatcgtttc gtctgcttct aggggagccg taacagactt    7560
ttggaagcct gaagaaactg gcaaaaaatg ttgtcctggt tgctgtggtt aagcggccgc    7620
gttaattcaa attaattgat atagtttttt aatgagtatt gaatctgttt agaaataatg    7680
gaatattatt tttatttatt tatttatatt attggtcggc tcttttcttc tgaaggtcaa    7740
tgacaaaatg atatgaagga aataatgatt tctaaaattt tacaacgtaa gatattttta    7800
caaaagccta gctcatcttt tgtcatgcac tattttactc acgcttgaaa ttaacggcca    7860
gtccactgcg gagtcatttc aaagtcatcc taatcgatct atcgtttttg atagctcatt    7920
ttggagttcg cgaggatcca ctagttctag agcggccgct ctagaactag taccacaggt    7980
gttgtcctct gaggacataa aatacacacc gagattcatc aactcattgc tggagttagc    8040
atatctacaa ttgggtgaaa tggggagcga tttgcaggca tttgctcggc atgccggtag    8100
aggtgtggtc aataagagcg acctcatgct ataccgtgaga aagcaacctg acctacagga    8160
aagagttact caagaataag aatttttcgtt ttaaaaccta agagtcactt taaaatttgt    8220
atacacttat tttttttata acttatttaa taataaaaat cataaatcat aagaaattcg    8280
cttactctta attaatcaag cctccatcga aatgatgact tttagtgctt gagtagacgc    8340
agcttggcca aaagtttcat atgcgtccaa gatctggtcc aggctgaatc tatgtgttat    8400
caatctagat ggatctagct tgtgactttg aacagttttc agtaacatcg gggtggtagc    8460
cgtgtcaacc aaccttgtag taatcgtgac attatgggac cataaacttt caagatgcaa    8520
atcaactttg ctaccgtgaa cgccgacatt agcgatagtt ccaccgggag ctacgatatt    8580
ctgacacaat tcaaatgtag caggtatccc aactgcttca atcgcagtat caacacctaa    8640
gccttcagta agagctttca cttcggctgc ggcgttacca cccgtggagt ttactgttct    8700
ggtggcacca aattgtttgg ctaatcccag cctgttatca tcaagatcga tcattatgat    8760
ttcagctggg gagtagaatt gtgctgtcag taaggcggcc aaaccaacgg gaccagcacc    8820
tactatagcc accgaagaac caggtgcgac tttgccgttt aggactccgc actcaaaacc    8880
cgttggtaga atatctgata acatgactaa ggcctcttca tccgcacctg ccggaatacg    8940
ataaagggat gtgtcagcat gtggtactct tacgtactct gcttgggtac catcaatttc    9000
gttgcccaga atccaacccc cggtcgtaca gtgactgaac attcctcttc tacaaaatga    9060
gcactttccg caactcgata tacatgatat caaaactcta tcgcctggtt ggaaagcagt    9120 aacccccagat ccgactgatt caataacccc cactccttca tgccctaata cacgaccggg    9180
tttacaagtc gcaacgtcac ctttaagaat gtgtagatcg gttccgcaaa ttgtagtctt    9240
```

```
tgttaccttc actatagcgt caccaggttc cttaagctct ggcttctgtc tctcttccac   9300
caacttctgg cctgggcccc tatacactaa tgctttcatc ctcagctagc tattgtaata   9360
tgtgtgtttg tttggattat taagaagaat aattacaaaa aaaattacaa aggaaggtaa   9420
ttacaacaga attaagaaag gacaagaagg aggaagagaa tcagttcatt atttcttctt   9480
tgttatataa caaacccaag tagcgatttg gccatacatt aaaagttgag aaccaccctc   9540
cctggcaaca gccacaactc gttaccattg ttcatcacga tcatgaaact cgctgtcagc   9600
tgaaatttca cctcagtgga tctctctttt tattcttcat cgttccacta acctttttcc   9660
atcagctggc agggaacgga aagtggaatc ccatttagcg agcttcctct tttcttcaag   9720
aaaagacgaa gcttgtgtgt gggtgcgcgc gctagtatct ttccacatta agaaatatac   9780
cataaaggtt acttagacat cactatggct atatatatat atatatatat atgtaactta   9840
gcaccatcgc gcgtgcatca ctgcatgtgt taaccgaaaa gtttggcgaa cacttcaccg   9900
acacggtcat ttagatctgt cgtctgcatt gcacgtccct tagccttaaa tcctaggcgg   9960
gagcattctc gtgtaattgt gcagcctgcg tagcaactca acatagcgta gtctacccag  10020
tttttcaagg gtttatcgtt agaagattct cccttttctt cctgctcaca aatcttaaag  10080
tcatacattg cacgactaaa tgcaagcgac gtcagggaaa gatatgagct atacagcgga  10140
atttccatat cactcagatt ttgttatcta attttttcct tcccacgtcc gcgggaatct  10200
gtgtatatta ctgcatctag atatatgtta tcttatcttg gcgcgtacat ttaattttca  10260
acgtattcta taagaaattg cgggagtttt tttcatgtag atgatactga ctgcacgcaa  10320
atataggcat gatttatagg catgatttga tggctgtacc gataggaacg ctaagagtaa  10380
cttcagaatc gttatcctgg cggaaaaaat tcatttgtaa actttaaaaa aaaaagccaa  10440
tatccccaaa attattaaga gcgcctccat tattaactaa aatttcactc agcatccaca  10500
atgtatcagg tatctactac agatattaca tgtggcgaaa aagacaagaa caatgcaata  10560
gcgcatcaag aaaaaacaca aagctttcaa tcaatgaatc gaaaatgtca ttaaaatagt  10620
atataaattg aaactaagtc ataaagctat aaaaagaaaa tttatttaaa tgcaagattt  10680
aaagtaaaatt cacggccctg caggccttaa gagttttgct tagataaggc taagccaatc  10740
tgtctcaatg attctggcat atccatttgt tccatatgaa cttcaacgac atgtgctttt  10800
tgaggagtag catcgatagc agctaaagta ttagcgaagt ctgtttctgt gaaaacgttg  10860
tgagtgtcga cagtttcggc atcaccacca aatgtttcag caactaattg caagttccaa  10920
gttggtatat cattgtaact ctcatcctct ccatggatgg ctctttcgac tgtatagcca  10980
tcgttattga taatgaatat cactggtgtc aatttctctc tgaagatggt ggacatttcc  11040
tgtgctgtca gttgaaaaga tccatcaccg atggataaga tgtgtctcct ttctggggca  11100
gcaatttgtg aaccaatcat agcaggtaat gtgtatccta tggagcccca taatgtttga  11160
ctgatcaaat tcatacccct tttcagaggt gccaacatca aaccgaaaga tgatgtcccc  11220
tgctcagtga ccaacacatc atcagcttgc aaaaagttca taacagcttg gtgaaatctg  11280
tcttgcttta gtggtgtttc ggcctgtggt tcgaaaacag ctaattcagc ttgtttagca  11340
gcagtatcag caaagtaaa gtttagtttt tccagctctg ccaaaagacc gttaagagaa  11400
atcccagagt aagtagaccc atctggcagc ataatgatgt catttgcagc ggttaaagtg  11460
ttttcagtct taaagccttg agaaaatgag gaggtagaat tgtcaatgat tttcccacca  11520
aaatgtaaaa cgaagtcact attgtcaacg taatccagaa cgttttttgtc agaaaaagct  11580
gggtaatagg taccaatgaa atgttcgttc tcttcattga aagagccttt gccatatgcc  11640
```

```
aaattggtta ctggcaactt tgtttggttt atccagtttt caaatctttc tcttatctgg  11700
aaacgggcga tctcatgacc ggcgattacg ataggttgag cggccttttc taagtgtgat  11760
agtatgattt ctgcaagttg tgcctctctc tcaccagatg atttctctgt ttgtagtgct  11820
tttgcaggtt taactattgc tttatgagct atatcaattg gaagattgat gtatactggc  11880
ctcttttcca acaaggctgt ttctaatact ctgtcgatct ctgaagctgc attctcttca  11940
gtaagcatgg ttgtagcggc agtgacttcc ttagccattt cactaaagtt atgaaagtta  12000
cccattccta aggaatgatg aaccagcttt tgttggatt gcacattcat agttggagaa   12060
cccacgatgt ggatgacagg gacttgttct gcaaaactac cagctgttcc gttaatggct  12120
gacagttcac ccactccgaa tgtagtaaca agagctgata cgcctctttc acgggcgtag  12180
ccatctgctg catatgctgc gtttagttca ttagtattcc cttgccagga aagtccttcg  12240
tgattttgaa tgtaatctag aaaagtcaaa ttgtaatccc ctggcacacc gaaaacctta  12300
tcgataccaa tctcttctag tctatctacc aagtactgtc ctacggtata cattttgttt  12360
actagtttat gtgtgtttat tcgaaactaa gttcttggtg ttttaaaact aaaaaaaaga  12420
ctaactataa aagtagaatt taagaagttt aagaaataga tttacagaat tacaatcaat  12480
acctaccgtc tttatatact tattagtcaa gtaggggaat aatttcaggg aactggtttc  12540
aaccttttt ttcagctttt tccaaatcag agagagcaga aggtaataga aggtgtaaga  12600
aaatgagata gatacatgcg tgggtcaatt gccttgtgtc atcatttact ccaggcaggt  12660
tgcatcactc cattgaggtt gtgcccgttt tttgcctgtt tgtgccctg ttctctgtag    12720
ttgcgctaag agaatggacc tatgaactga tggttggtga agaaaacaat attttggtgc  12780
tgggattctt ttttttctg gatgccagct taaaaagcgg gctccattat atttagtgga    12840
tgccaggaat aaactgttca cccagacacc tacgatgtta tatattctgt gtaacccgcc  12900
ccctattttg ggcatgtacg ggttacagca gaattaaaag gctaattttt tgactaaata  12960
aagttaggaa aatcactact attaattatt tacgtattct ttgaaatggc agtattggag  13020
ct                                                                 13022
```

<210> SEQ ID NO 124
<211> LENGTH: 343
<212> TYPE: PRT
<213> ORGANISM: Artificial sequence
<220> FEATURE:
<223> OTHER INFORMATION: Anaerostipes caccae KARI variant- K9SB2

<400> SEQUENCE: 124

```
Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Phe Glu Gly Ala Glu Glu Trp Lys Arg Ala Glu Glu
    50                  55                  60

Gln Gly Phe Glu Val Tyr Thr Ala Ala Glu Ala Ala Lys Lys Ala Asp
65                  70                  75                  80

Ile Ile Met Ile Leu Ile Pro Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110
```

```
His Gly Phe Asn Ile His Phe Gly Cys Ile Val Pro Pro Lys Asp Val
            115                 120                 125

Asp Val Thr Met Ile Ala Pro Lys Gly Pro Gly His Thr Val Arg Ser
        130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
                180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
        210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
                260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
        290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340
```

<210> SEQ ID NO 125
<211> LENGTH: 1713
<212> TYPE: DNA
<213> ORGANISM: Streptococcus mutans
<220> FEATURE:
<221> NAME/KEY: CDS
<222> LOCATION: (1)..(1713)

<400> SEQUENCE: 125

```
atg act gac aaa aaa act ctt aaa gac tta aga aat cgt agt tct gtt        48
Met Thr Asp Lys Lys Thr Leu Lys Asp Leu Arg Asn Arg Ser Ser Val
1               5                   10                  15 tac gat tca atg gtt aaa tca cct aat cgt gct atg ttg cgt gca act        96
Tyr Asp Ser Met Val Lys Ser Pro Asn Arg Ala Met Leu Arg Ala Thr
            20                  25                  30 ggt atg caa gat gaa gac ttt gaa aaa cct atc gtc ggt gtc att tca       144
Gly Met Gln Asp Glu Asp Phe Glu Lys Pro Ile Val Gly Val Ile Ser
        35                  40                  45 act tgg gct gaa aac aca cct tgt aat atc cac tta cat gac ttt ggt       192
Thr Trp Ala Glu Asn Thr Pro Cys Asn Ile His Leu His Asp Phe Gly
    50                  55                  60 aaa cta gcc aaa gtc ggt gtt aag gaa gct ggt gct tgg cca gtt cag       240
Lys Leu Ala Lys Val Gly Val Lys Glu Ala Gly Ala Trp Pro Val Gln
65                  70                  75                  80 ttc gga aca atc acg gtt tct gat gga atc gcc atg gga acc caa gga       288
Phe Gly Thr Ile Thr Val Ser Asp Gly Ile Ala Met Gly Thr Gln Gly
```

```
                          85                  90                  95
atg cgt ttc tcc ttg aca tct cgt gat att att gca gat tct att gaa       336
Met Arg Phe Ser Leu Thr Ser Arg Asp Ile Ile Ala Asp Ser Ile Glu
            100                 105                 110 gca gcc atg gga ggt cat aat gcg gat gct ttt gta gcc att ggc ggt       384
Ala Ala Met Gly Gly His Asn Ala Asp Ala Phe Val Ala Ile Gly Gly
            115                 120                 125 tgt gat aaa aac atg ccc ggt tct gtt atc gct atg gct aac atg gat       432
Cys Asp Lys Asn Met Pro Gly Ser Val Ile Ala Met Ala Asn Met Asp
130                 135                 140 atc cca gcc att ttt gct tac ggc gga aca att gca cct ggt aat tta       480
Ile Pro Ala Ile Phe Ala Tyr Gly Gly Thr Ile Ala Pro Gly Asn Leu
145                 150                 155                 160 gac ggc aaa gat atc gat tta gtc tct gtc ttt gaa ggt gtc ggc cat       528
Asp Gly Lys Asp Ile Asp Leu Val Ser Val Phe Glu Gly Val Gly His
                165                 170                 175 tgg aac cac ggc gat atg acc aaa gaa gaa gtt aaa gct ttg gaa tgt       576
Trp Asn His Gly Asp Met Thr Lys Glu Glu Val Lys Ala Leu Glu Cys
            180                 185                 190 aat gct tgt ccc ggt cct gga ggc tgc ggt ggt atg tat act gct aac       624
Asn Ala Cys Pro Gly Pro Gly Gly Cys Gly Gly Met Tyr Thr Ala Asn
            195                 200                 205 aca atg gcg aca gct att gaa gtt ttg gga ctt agc ctt ccg ggt tca       672
Thr Met Ala Thr Ala Ile Glu Val Leu Gly Leu Ser Leu Pro Gly Ser
210                 215                 220 tct tct cac ccg gct gaa tcc gca gaa aag aaa gca gat att gaa gaa       720
Ser Ser His Pro Ala Glu Ser Ala Glu Lys Lys Ala Asp Ile Glu Glu
225                 230                 235                 240 gct ggt cgc gct gtt gtc aaa atg ctc gaa atg ggc tta aaa cct tct       768
Ala Gly Arg Ala Val Val Lys Met Leu Glu Met Gly Leu Lys Pro Ser
                245                 250                 255 gac att tta acg cgt gaa gct ttt gaa gat gct att act gta act atg       816
Asp Ile Leu Thr Arg Glu Ala Phe Glu Asp Ala Ile Thr Val Thr Met
            260                 265                 270 gct ctg gga ggt tca acc aac tca acc ctt cac ctc tta gct att gcc       864
Ala Leu Gly Gly Ser Thr Asn Ser Thr Leu His Leu Leu Ala Ile Ala
            275                 280                 285 cat gct gct aat gtg gaa ttg aca ctt gat gat ttc aat act ttc caa       912
His Ala Ala Asn Val Glu Leu Thr Leu Asp Asp Phe Asn Thr Phe Gln
            290                 295                 300 gaa aaa gtt cct cat ttg gct gat ttg aaa cct tct ggt caa tat gta       960
Glu Lys Val Pro His Leu Ala Asp Leu Lys Pro Ser Gly Gln Tyr Val
305                 310                 315                 320 ttc caa gac ctt tac aag gtc gga ggg gta cca gca gtt atg aaa tat      1008
Phe Gln Asp Leu Tyr Lys Val Gly Gly Val Pro Ala Val Met Lys Tyr
                325                 330                 335 ctc ctt aaa aat ggc ttc ctt cat ggt gac cgt atc act tgt act ggc      1056
Leu Leu Lys Asn Gly Phe Leu His Gly Asp Arg Ile Thr Cys Thr Gly
            340                 345                 350 aaa aca gtc gct gaa aat ttg aag gct ttt gat gat tta aca cct ggt      1104
Lys Thr Val Ala Glu Asn Leu Lys Ala Phe Asp Asp Leu Thr Pro Gly
            355                 360                 365 caa aag gtt att atg ccg ctt gaa aat cct aaa cgt gaa gat ggt ccg      1152
Gln Lys Val Ile Met Pro Leu Glu Asn Pro Lys Arg Glu Asp Gly Pro
370                 375                 380 ctc att att ctc cat ggt aac ttg gct cca gac ggt gcc gtt gcc aaa      1200
Leu Ile Ile Leu His Gly Asn Leu Ala Pro Asp Gly Ala Val Ala Lys
385                 390                 395                 400 gtt tct ggt gta aaa gtg cgt cgt cat gtc ggt cct gct aag gtc ttt      1248
```

```
Val Ser Gly Val Lys Val Arg Arg His Val Gly Pro Ala Lys Val Phe
                405                 410                 415 aat tct gaa gaa gaa gcc att gaa gct gtc ttg aat gat gat att gtt      1296
Asn Ser Glu Glu Glu Ala Ile Glu Ala Val Leu Asn Asp Asp Ile Val
                420                 425                 430 gat ggt gat gtt gtt gtc gta cgt ttt gta gga cca aag ggc ggt cct      1344
Asp Gly Asp Val Val Val Arg Phe Val Gly Pro Lys Gly Gly Pro
            435                 440                 445 ggt atg cct gaa atg ctt tcc ctt tca tca atg att gtt ggt aaa ggg      1392
Gly Met Pro Glu Met Leu Ser Leu Ser Ser Met Ile Val Gly Lys Gly
        450                 455                 460 caa ggt gaa aaa gtt gcc ctt ctg aca gat ggc cgc ttc tca ggt ggt      1440
Gln Gly Glu Lys Val Ala Leu Leu Thr Asp Gly Arg Phe Ser Gly Gly
465                 470                 475                 480 act tat ggt ctt gtc gtg ggt cat atc gct cct gaa gca caa gat ggc      1488
Thr Tyr Gly Leu Val Val Gly His Ile Ala Pro Glu Ala Gln Asp Gly
                485                 490                 495 ggt cca atc gcc tac ctg caa aca gga gac ata gtc act att gac caa      1536
Gly Pro Ile Ala Tyr Leu Gln Thr Gly Asp Ile Val Thr Ile Asp Gln
            500                 505                 510 gac act aag gaa tta cac ttt gat atc tcc gat gaa gag tta aaa cat      1584
Asp Thr Lys Glu Leu His Phe Asp Ile Ser Asp Glu Glu Leu Lys His
        515                 520                 525 cgt caa gag acc att gaa ttg cca ccg ctc tat tca cgc ggt atc ctt      1632
Arg Gln Glu Thr Ile Glu Leu Pro Pro Leu Tyr Ser Arg Gly Ile Leu
530                 535                 540 ggt aaa tat gct cac atc gtt tcg tct gct tct agg gga gcc gta aca      1680
Gly Lys Tyr Ala His Ile Val Ser Ser Ala Ser Arg Gly Ala Val Thr
545                 550                 555                 560 gac ttt tgg aag cct gaa gaa act ggc aaa aaa                          1713
Asp Phe Trp Lys Pro Glu Glu Thr Gly Lys Lys
                565                 570

<210> SEQ ID NO 126
<211> LENGTH: 571
<212> TYPE: PRT
<213> ORGANISM: Streptococcus mutans

<400> SEQUENCE: 126

Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
```

```
            145                 150                 155                 160
Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570
```

```
<210> SEQ ID NO 127
<211> LENGTH: 1647
<212> TYPE: DNA
<213> ORGANISM: Artificial sequence
<220> FEATURE:
<223> OTHER INFORMATION: Listeria grayi 2-ketoisovalerate decarboxylase
      (kivD)
<220> FEATURE:
<221> NAME/KEY: CDS
<222> LOCATION: (1)..(1647)

<400> SEQUENCE: 127
```

| | | | | | | | | | | | | | | | | |
|---|---|---|---|---|---|---|---|---|---|---|---|---|---|---|---|---|
| atg | tac | acc | gtc | ggc | caa | tac | tta | gta | gac | cgc | tta | gaa | gag | atc | ggc | 48 |
| Met | Tyr | Thr | Val | Gly | Gln | Tyr | Leu | Val | Asp | Arg | Leu | Glu | Glu | Ile | Gly | |
| 1 | | | | 5 | | | | | 10 | | | | | 15 | | |
| atc | gat | aag | gtt | ttt | ggt | gtc | ccg | ggt | gac | tac | aac | ctg | acc | ttt | ttg | 96 |
| Ile | Asp | Lys | Val | Phe | Gly | Val | Pro | Gly | Asp | Tyr | Asn | Leu | Thr | Phe | Leu | |
| | | | 20 | | | | | 25 | | | | | 30 | | | |
| gac | tac | atc | cag | aac | cac | gaa | ggt | ctg | agc | tgg | caa | ggt | aat | acg | aat | 144 |
| Asp | Tyr | Ile | Gln | Asn | His | Glu | Gly | Leu | Ser | Trp | Gln | Gly | Asn | Thr | Asn | |
| | | | | 35 | | | | | 40 | | | | | 45 | | |
| gaa | ctg | aat | gcc | gcg | tac | gca | gct | gat | ggc | tat | gct | cgt | gaa | cgc | ggt | 192 |
| Glu | Leu | Asn | Ala | Ala | Tyr | Ala | Ala | Asp | Gly | Tyr | Ala | Arg | Glu | Arg | Gly | |
| | 50 | | | | | 55 | | | | | 60 | | | | | |
| gtt | agc | gct | ttg | gtc | acg | acc | ttc | ggc | gtt | ggt | gag | ctg | tcc | gca | atc | 240 |
| Val | Ser | Ala | Leu | Val | Thr | Thr | Phe | Gly | Val | Gly | Glu | Leu | Ser | Ala | Ile | |
| 65 | | | | | 70 | | | | | 75 | | | | | 80 | |
| aat | ggc | acc | gca | ggt | agc | ttc | gcg | gag | caa | gtt | ccg | gtg | att | cat | atc | 288 |
| Asn | Gly | Thr | Ala | Gly | Ser | Phe | Ala | Glu | Gln | Val | Pro | Val | Ile | His | Ile | |
| | | | | 85 | | | | | 90 | | | | | 95 | | |
| gtg | ggc | agc | ccg | acc | atg | aat | gtt | cag | agc | aac | aag | aaa | ctg | gtt | cat | 336 |
| Val | Gly | Ser | Pro | Thr | Met | Asn | Val | Gln | Ser | Asn | Lys | Lys | Leu | Val | His | |
| | | | 100 | | | | | 105 | | | | | 110 | | | |
| cac | agc | ctg | ggt | atg | ggc | aac | ttt | cac | aac | ttc | agc | gag | atg | gcg | aaa | 384 |
| His | Ser | Leu | Gly | Met | Gly | Asn | Phe | His | Asn | Phe | Ser | Glu | Met | Ala | Lys | |
| | | 115 | | | | | 120 | | | | | 125 | | | | |
| gaa | gtc | acc | gcc | gca | acc | acg | atg | ctg | acg | gaa | gag | aat | gcg | gcg | tcg | 432 |
| Glu | Val | Thr | Ala | Ala | Thr | Thr | Met | Leu | Thr | Glu | Glu | Asn | Ala | Ala | Ser | |
| | 130 | | | | | 135 | | | | | 140 | | | | | |
| gag | att | gat | cgt | gtt | ctg | gaa | acc | gcc | ctg | ctg | gag | aaa | cgc | cca | gtg | 480 |
| Glu | Ile | Asp | Arg | Val | Leu | Glu | Thr | Ala | Leu | Leu | Glu | Lys | Arg | Pro | Val | |
| 145 | | | | | 150 | | | | | 155 | | | | | 160 | |
| tac | atc | aat | ctg | ccg | atc | gac | att | gct | cac | aag | gcg | atc | gtc | aag | ccg | 528 |
| Tyr | Ile | Asn | Leu | Pro | Ile | Asp | Ile | Ala | His | Lys | Ala | Ile | Val | Lys | Pro | |
| | | | | 165 | | | | | 170 | | | | | 175 | | |
| gcg | aaa | gcc | ctg | caa | acc | gag | aag | agc | tct | ggc | gag | cgt | gag | gca | caa | 576 |
| Ala | Lys | Ala | Leu | Gln | Thr | Glu | Lys | Ser | Ser | Gly | Glu | Arg | Glu | Ala | Gln | |
| | | | 180 | | | | | 185 | | | | | 190 | | | |
| ctg | gcg | gag | atc | att | ctg | agc | cat | ctg | gag | aag | gct | gca | cag | ccg | att | 624 |
| Leu | Ala | Glu | Ile | Ile | Leu | Ser | His | Leu | Glu | Lys | Ala | Ala | Gln | Pro | Ile | |
| | | 195 | | | | | 200 | | | | | 205 | | | | |
| gtg | att | gcg | ggt | cac | gag | atc | gcg | cgc | ttc | cag | atc | cgt | gag | cgt | ttc | 672 |
| Val | Ile | Ala | Gly | His | Glu | Ile | Ala | Arg | Phe | Gln | Ile | Arg | Glu | Arg | Phe | |
| | 210 | | | | | 215 | | | | | 220 | | | | | |
| gag | aat | tgg | att | aat | caa | acg | aaa | ctg | ccg | gtg | acc | aat | ctg | gcc | tac | 720 |
| Glu | Asn | Trp | Ile | Asn | Gln | Thr | Lys | Leu | Pro | Val | Thr | Asn | Leu | Ala | Tyr | |
| 225 | | | | | 230 | | | | | 235 | | | | | 240 | |
| ggc | aag | ggt | agc | ttc | aac | gaa | gaa | aac | gag | cat | ttc | att | ggt | acc | tat | 768 |
| Gly | Lys | Gly | Ser | Phe | Asn | Glu | Glu | Asn | Glu | His | Phe | Ile | Gly | Thr | Tyr | |
| | | | | 245 | | | | | 250 | | | | | 255 | | |

```
tat cct gca ttt agc gat aag aac gtg ctg gac tac gtg gat aac tcc      816
Tyr Pro Ala Phe Ser Asp Lys Asn Val Leu Asp Tyr Val Asp Asn Ser
            260                 265                 270 gac ttt gtc ctg cac ttt ggt ggt aaa atc att gat aac agc acc tcc      864
Asp Phe Val Leu His Phe Gly Gly Lys Ile Ile Asp Asn Ser Thr Ser
            275                 280                 285 agc ttc tcc caa ggc ttc aaa acc gag aac acc ctg act gcg gcg aac      912
Ser Phe Ser Gln Gly Phe Lys Thr Glu Asn Thr Leu Thr Ala Ala Asn
        290                 295                 300 gat atc att atg ctg ccg gac ggt agc acg tat tct ggt att agc ctg      960
Asp Ile Ile Met Leu Pro Asp Gly Ser Thr Tyr Ser Gly Ile Ser Leu
305                 310                 315                 320 aat ggc ctg ctg gcc gag ctg gaa aaa ctg aat ttc acg ttt gcc gac     1008
Asn Gly Leu Leu Ala Glu Leu Glu Lys Leu Asn Phe Thr Phe Ala Asp
                325                 330                 335 acc gca gca aag cag gcg gag ttg gcg gtg ttt gag ccg cag gct gaa     1056
Thr Ala Ala Lys Gln Ala Glu Leu Ala Val Phe Glu Pro Gln Ala Glu
            340                 345                 350 acc ccg ttg aaa cag gac cgt ttt cac cag gcg gtg atg aat ttt ctg     1104
Thr Pro Leu Lys Gln Asp Arg Phe His Gln Ala Val Met Asn Phe Leu
        355                 360                 365 caa gct gac gat gtc ctg gtt acg gaa cag ggc acc tct tct ttt ggc     1152
Gln Ala Asp Asp Val Leu Val Thr Glu Gln Gly Thr Ser Ser Phe Gly
370                 375                 380 ttg atg ctg gcg cct ctg aaa aag ggt atg aac ttg atc tcg caa acg     1200
Leu Met Leu Ala Pro Leu Lys Lys Gly Met Asn Leu Ile Ser Gln Thr
385                 390                 395                 400 ctg tgg ggt agc att ggt tac acg ttg ccg gcg atg att ggt agc caa     1248
Leu Trp Gly Ser Ile Gly Tyr Thr Leu Pro Ala Met Ile Gly Ser Gln
                405                 410                 415 att gcg gca ccg gag cgt cgt cat atc ctg agc att ggt gat ggt agc     1296
Ile Ala Ala Pro Glu Arg Arg His Ile Leu Ser Ile Gly Asp Gly Ser
            420                 425                 430 ttt cag ctg act gcg cag gaa atg agc acc att ttc cgt gag aaa ctg     1344
Phe Gln Leu Thr Ala Gln Glu Met Ser Thr Ile Phe Arg Glu Lys Leu
        435                 440                 445 acc cca gtc atc ttc atc att aac aat gat ggc tat acc gtt gag cgt     1392
Thr Pro Val Ile Phe Ile Ile Asn Asn Asp Gly Tyr Thr Val Glu Arg
450                 455                 460 gcg atc cat ggc gaa gat gaa agc tat aac gac att ccg acg tgg aac     1440
Ala Ile His Gly Glu Asp Glu Ser Tyr Asn Asp Ile Pro Thr Trp Asn
465                 470                 475                 480 ttg caa ctg gtg gcg gaa acc ttc ggt ggt gac gcc gaa acc gtc gac     1488
Leu Gln Leu Val Ala Glu Thr Phe Gly Gly Asp Ala Glu Thr Val Asp
                485                 490                 495 act cac aat gtg ttc acg gag act gat ttc gcc aac acc ctg gcg gca     1536
Thr His Asn Val Phe Thr Glu Thr Asp Phe Ala Asn Thr Leu Ala Ala
            500                 505                 510 att gac gcg acg ccg cag aaa gca cac gtt gtg gaa gtt cac atg gaa     1584
Ile Asp Ala Thr Pro Gln Lys Ala His Val Val Glu Val His Met Glu
        515                 520                 525 caa atg gat atg ccg gag agc ctg cgc cag atc ggt ctg gca ctg tcc     1632
Gln Met Asp Met Pro Glu Ser Leu Arg Gln Ile Gly Leu Ala Leu Ser
530                 535                 540 aag cag aat agc taa                                                  1647
Lys Gln Asn Ser
545

<210> SEQ ID NO 128
<211> LENGTH: 548
```

```
<212> TYPE: PRT
<213> ORGANISM: Artificial sequence
<220> FEATURE:
<223> OTHER INFORMATION: Synthetic Construct

<400> SEQUENCE: 128

Met Tyr Thr Val Gly Gln Tyr Leu Val Asp Arg Leu Glu Glu Ile Gly
1               5                   10                  15

Ile Asp Lys Val Phe Gly Val Pro Gly Asp Tyr Asn Leu Thr Phe Leu
            20                  25                  30

Asp Tyr Ile Gln Asn His Glu Gly Leu Ser Trp Gln Gly Asn Thr Asn
        35                  40                  45

Glu Leu Asn Ala Ala Tyr Ala Ala Asp Gly Tyr Ala Arg Glu Arg Gly
    50                  55                  60

Val Ser Ala Leu Val Thr Thr Phe Gly Val Gly Glu Leu Ser Ala Ile
65                  70                  75                  80

Asn Gly Thr Ala Gly Ser Phe Ala Glu Gln Val Pro Val Ile His Ile
                85                  90                  95

Val Gly Ser Pro Thr Met Asn Val Gln Ser Asn Lys Lys Leu Val His
            100                 105                 110

His Ser Leu Gly Met Gly Asn Phe His Asn Phe Ser Glu Met Ala Lys
        115                 120                 125

Glu Val Thr Ala Ala Thr Thr Met Leu Thr Glu Glu Asn Ala Ala Ser
    130                 135                 140

Glu Ile Asp Arg Val Leu Glu Thr Ala Leu Leu Glu Lys Arg Pro Val
145                 150                 155                 160

Tyr Ile Asn Leu Pro Ile Asp Ile Ala His Lys Ala Ile Val Lys Pro
                165                 170                 175

Ala Lys Ala Leu Gln Thr Glu Lys Ser Ser Gly Glu Arg Glu Ala Gln
            180                 185                 190

Leu Ala Glu Ile Ile Leu Ser His Leu Glu Lys Ala Ala Gln Pro Ile
        195                 200                 205

Val Ile Ala Gly His Glu Ile Ala Arg Phe Gln Ile Arg Glu Arg Phe
    210                 215                 220

Glu Asn Trp Ile Asn Gln Thr Lys Leu Pro Val Thr Asn Leu Ala Tyr
225                 230                 235                 240

Gly Lys Gly Ser Phe Asn Glu Glu Asn Glu His Phe Ile Gly Thr Tyr
                245                 250                 255

Tyr Pro Ala Phe Ser Asp Lys Asn Val Leu Asp Tyr Val Asp Asn Ser
            260                 265                 270

Asp Phe Val Leu His Phe Gly Gly Lys Ile Ile Asp Asn Ser Thr Ser
        275                 280                 285

Ser Phe Ser Gln Gly Phe Lys Thr Glu Asn Thr Leu Thr Ala Ala Asn
    290                 295                 300

Asp Ile Ile Met Leu Pro Asp Gly Ser Thr Tyr Ser Gly Ile Ser Leu
305                 310                 315                 320

Asn Gly Leu Leu Ala Glu Leu Glu Lys Leu Asn Phe Thr Phe Ala Asp
                325                 330                 335

Thr Ala Ala Lys Gln Ala Glu Leu Ala Val Phe Glu Pro Gln Ala Glu
            340                 345                 350

Thr Pro Leu Lys Gln Asp Arg Phe His Gln Ala Val Met Asn Phe Leu
        355                 360                 365

Gln Ala Asp Asp Val Leu Val Thr Glu Gln Gly Thr Ser Ser Phe Gly
    370                 375                 380
```

```
Leu Met Leu Ala Pro Leu Lys Lys Gly Met Asn Leu Ile Ser Gln Thr
385                 390                 395                 400

Leu Trp Gly Ser Ile Gly Tyr Thr Leu Pro Ala Met Ile Gly Ser Gln
            405                 410                 415

Ile Ala Ala Pro Glu Arg Arg His Ile Leu Ser Ile Gly Asp Gly Ser
            420                 425                 430

Phe Gln Leu Thr Ala Gln Glu Met Ser Thr Ile Phe Arg Glu Lys Leu
            435                 440                 445

Thr Pro Val Ile Phe Ile Ile Asn Asn Asp Gly Tyr Thr Val Glu Arg
            450                 455                 460

Ala Ile His Gly Glu Asp Glu Ser Tyr Asn Asp Ile Pro Thr Trp Asn
465                 470                 475                 480

Leu Gln Leu Val Ala Glu Thr Phe Gly Gly Asp Ala Glu Thr Val Asp
                485                 490                 495

Thr His Asn Val Phe Thr Glu Thr Asp Phe Ala Asn Thr Leu Ala Ala
                500                 505                 510

Ile Asp Ala Thr Pro Gln Lys Ala His Val Val Glu Val His Met Glu
                515                 520                 525

Gln Met Asp Met Pro Glu Ser Leu Arg Gln Ile Gly Leu Ala Leu Ser
530                 535                 540

Lys Gln Asn Ser
545

<210> SEQ ID NO 129
<211> LENGTH: 347
<212> TYPE: PRT
<213> ORGANISM: Artificial sequence
<220> FEATURE:
<223> OTHER INFORMATION: Beijerinkia indica alcohol dehydrogenase (ADH)

<400> SEQUENCE: 129

Met Lys Ala Leu Val Tyr Arg Gly Pro Gly Gln Lys Leu Val Glu Glu
1               5                   10                  15

Arg Gln Lys Pro Glu Leu Lys Glu Pro Gly Asp Ala Ile Val Lys Val
                20                  25                  30

Thr Lys Thr Thr Ile Cys Gly Thr Asp Leu His Ile Leu Lys Gly Asp
            35                  40                  45

Val Ala Thr Cys Lys Pro Gly Arg Val Leu Gly His Glu Gly Val Gly
    50                  55                  60

Val Ile Glu Ser Val Gly Ser Gly Val Thr Ala Phe Gln Pro Gly Asp
65                  70                  75                  80

Arg Val Leu Ile Ser Cys Ile Ser Ser Cys Gly Lys Cys Ser Phe Cys
                85                  90                  95

Arg Arg Gly Met Phe Ser His Cys Thr Thr Gly Gly Trp Ile Leu Gly
            100                 105                 110

Asn Glu Ile Asp Gly Thr Gln Ala Glu Tyr Val Arg Val Pro His Ala
        115                 120                 125

Asp Thr Ser Leu Tyr Arg Ile Pro Ala Gly Ala Asp Glu Glu Ala Leu
    130                 135                 140

Val Met Leu Ser Asp Ile Leu Pro Thr Gly Phe Glu Cys Gly Val Leu
145                 150                 155                 160

Asn Gly Lys Val Ala Pro Gly Ser Ser Val Ala Ile Val Gly Ala Gly
                165                 170                 175

Pro Val Gly Leu Ala Ala Leu Leu Thr Ala Gln Phe Tyr Ser Pro Ala
            180                 185                 190
```

```
Glu Ile Ile Met Ile Asp Leu Asp Asp Asn Arg Leu Gly Leu Ala Lys
            195                 200                 205

Gln Phe Gly Ala Thr Arg Thr Val Asn Ser Thr Gly Gly Asn Ala Ala
        210                 215                 220

Ala Glu Val Lys Ala Leu Thr Glu Gly Leu Gly Val Asp Thr Ala Ile
225                 230                 235                 240

Glu Ala Val Gly Ile Pro Ala Thr Phe Glu Leu Cys Gln Asn Ile Val
                245                 250                 255

Ala Pro Gly Gly Thr Ile Ala Asn Val Gly Val His Gly Ser Lys Val
            260                 265                 270

Asp Leu His Leu Glu Ser Leu Trp Ser His Asn Val Thr Ile Thr Thr
        275                 280                 285

Arg Leu Val Asp Thr Ala Thr Thr Pro Met Leu Leu Lys Thr Val Gln
    290                 295                 300

Ser His Lys Leu Asp Pro Ser Arg Leu Ile Thr His Arg Phe Ser Leu
305                 310                 315                 320

Asp Gln Ile Leu Asp Ala Tyr Glu Thr Phe Gly Gln Ala Ala Ser Thr
                325                 330                 335

Gln Ala Leu Lys Val Ile Ile Ser Met Glu Ala
            340                 345

<210> SEQ ID NO 130
<211> LENGTH: 1713
<212> TYPE: DNA
<213> ORGANISM: Lactococcus lactis
<220> FEATURE:
<221> NAME/KEY: CDS
<222> LOCATION: (1)..(1713)
<223> OTHER INFORMATION: dihydroxy-acid dehydratase

<400> SEQUENCE: 130 atg gaa ttc aaa tat aac gga aaa gtt gaa tca ata gag ctc aat aag      48
Met Glu Phe Lys Tyr Asn Gly Lys Val Glu Ser Ile Glu Leu Asn Lys
1               5                   10                  15 tat tca aaa aca ttg aca caa gac cca aca cag cca gcg acc caa gcc      96
Tyr Ser Lys Thr Leu Thr Gln Asp Pro Thr Gln Pro Ala Thr Gln Ala
            20                  25                  30 atg cac tat ggc att ggt ttt aaa gat gag gac ttc aaa aaa gct cag     144
Met His Tyr Gly Ile Gly Phe Lys Asp Glu Asp Phe Lys Lys Ala Gln
        35                  40                  45 gtc gga atc gtc agc atg gat tgg gac gga aat ccc tgt aac atg cac     192
Val Gly Ile Val Ser Met Asp Trp Asp Gly Asn Pro Cys Asn Met His
    50                  55                  60 ttg ggc aca ctc ggt agt aaa atc aaa aat tct gtc aat caa act gac     240
Leu Gly Thr Leu Gly Ser Lys Ile Lys Asn Ser Val Asn Gln Thr Asp
65                  70                  75                  80 gga ctg att ggg ctt caa ttt cac acg att ggg gtt tct gac gga att     288
Gly Leu Ile Gly Leu Gln Phe His Thr Ile Gly Val Ser Asp Gly Ile
                85                  90                  95 gcc aac gga aag ctt ggc atg aga tat tcc ttg gtc agt cgt gaa gtt     336
Ala Asn Gly Lys Leu Gly Met Arg Tyr Ser Leu Val Ser Arg Glu Val
            100                 105                 110 att gct gac agt att gaa acc aac gct ggc gcc gaa tat tac gat gca     384
Ile Ala Asp Ser Ile Glu Thr Asn Ala Gly Ala Glu Tyr Tyr Asp Ala
        115                 120                 125 att gtc gct gtt ccc ggt tgt gac aaa aat atg cca ggc tca atc att     432
Ile Val Ala Val Pro Gly Cys Asp Lys Asn Met Pro Gly Ser Ile Ile
    130                 135                 140 ggc atg gct cgg ctc aat cgt ccg tca att atg gtt tat ggt gga acg     480
```

|  |  |
|---|---|
| Gly Met Ala Arg Leu Asn Arg Pro Ser Ile Met Val Tyr Gly Gly Thr<br>145                             150                     155                      160 |  |
| att gaa cat ggc gaa tac aaa ggc gaa aag tta aat att gtt tcg gct<br>Ile Glu His Gly Glu Tyr Lys Gly Glu Lys Leu Asn Ile Val Ser Ala<br>                  165                     170                     175 | 528 |
| ttt gaa gcg ctt gga caa aaa atc act gga aat att tcc gag gaa gat<br>Phe Glu Ala Leu Gly Gln Lys Ile Thr Gly Asn Ile Ser Glu Glu Asp<br>          180                     185                     190 | 576 |
| tat cac ggc gtc att tgt aat gcc att ccg gga cag ggt gct tgt ggg<br>Tyr His Gly Val Ile Cys Asn Ala Ile Pro Gly Gln Gly Ala Cys Gly<br>             195                     200                   205 | 624 |
| ggc atg tat aca gca aat aca ctg gct tcg gca att gaa act ttg gga<br>Gly Met Tyr Thr Ala Asn Thr Leu Ala Ser Ala Ile Glu Thr Leu Gly<br>210                           215                     220 | 672 |
| atg agt ttg cct tat tcg gct tca aat cca gcg gtc agt caa gaa aaa<br>Met Ser Leu Pro Tyr Ser Ala Ser Asn Pro Ala Val Ser Gln Glu Lys<br>225                         230                     235                   240 | 720 |
| gaa gac gaa tgt gat gaa att ggt ctg gca atc aaa aat ttg cta gaa<br>Glu Asp Glu Cys Asp Glu Ile Gly Leu Ala Ile Lys Asn Leu Leu Glu<br>                     245                     250                     255 | 768 |
| aaa gac atc aaa cca agc gat atc atg acc aag gaa gct ttt gaa aat<br>Lys Asp Ile Lys Pro Ser Asp Ile Met Thr Lys Glu Ala Phe Glu Asn<br>             260                     265                     270 | 816 |
| gcc ata acg atc gtc atg gtt ctc ggt ggt tca act aat gct gtg ctt<br>Ala Ile Thr Ile Val Met Val Leu Gly Gly Ser Thr Asn Ala Val Leu<br>          275                     280                     285 | 864 |
| cat atc att gcc atg gct aat gcc atc ggt gtc gaa att acg caa gat<br>His Ile Ile Ala Met Ala Asn Ala Ile Gly Val Glu Ile Thr Gln Asp<br>290                           295                     300 | 912 |
| gat ttt caa cgt att tcc gat gtc acg cct gtg ctt ggc gac ttc aag<br>Asp Phe Gln Arg Ile Ser Asp Val Thr Pro Val Leu Gly Asp Phe Lys<br>305                         310                     315                   320 | 960 |
| cca agt ggc aag tac atg atg gaa gat ttg cac aaa att ggt ggc gtg<br>Pro Ser Gly Lys Tyr Met Met Glu Asp Leu His Lys Ile Gly Gly Val<br>                     325                     330                   335 | 1008 |
| cct gct gtt ttg aaa tat ttg ctc aaa gag ggc aag ctt cat ggc gac<br>Pro Ala Val Leu Lys Tyr Leu Leu Lys Glu Gly Lys Leu His Gly Asp<br>          340                     345                     350 | 1056 |
| tgt ttg aca gtt act ggt aaa act cta gct gaa aat gtt gaa aca gca<br>Cys Leu Thr Val Thr Gly Lys Thr Leu Ala Glu Asn Val Glu Thr Ala<br>             355                     360                     365 | 1104 |
| ctg gat ttg gac ttt gac agc caa gac att att cga cca ctt gaa aat<br>Leu Asp Leu Asp Phe Asp Ser Gln Asp Ile Ile Arg Pro Leu Glu Asn<br>370                           375                     380 | 1152 |
| cct atc aaa gca aca ggt cat ttg caa att ctc tat ggc aat ctt gct<br>Pro Ile Lys Ala Thr Gly His Leu Gln Ile Leu Tyr Gly Asn Leu Ala<br>385                         390                     395                   400 | 1200 |
| gaa ggt ggt tct gtg gca aaa att tct gga aaa gaa ggg gaa ttt ttc<br>Glu Gly Gly Ser Val Ala Lys Ile Ser Gly Lys Glu Gly Glu Phe Phe<br>                   405                     410                   415 | 1248 |
| aaa gga aca gct cgt gtc ttt gat ggc gaa caa cat ttt att gac gga<br>Lys Gly Thr Ala Arg Val Phe Asp Gly Glu Gln His Phe Ile Asp Gly<br>             420                     425                   430 | 1296 |
| att gag tca ggt cgt ttg cac gca gga gat gtc gct gtc att cgt aat<br>Ile Glu Ser Gly Arg Leu His Ala Gly Asp Val Ala Val Ile Arg Asn<br>                   435                     440                   445 | 1344 |
| atc ggt cca gtc gga ggc cca gga atg cca gaa atg tta aaa ccg acc<br>Ile Gly Pro Val Gly Gly Pro Gly Met Pro Glu Met Leu Lys Pro Thr<br>450                           455                     460 | 1392 |

-continued

```
tca gcc ttg att gga gca ggt ctt gga aaa tct tgt gct ttg att act        1440
Ser Ala Leu Ile Gly Ala Gly Leu Gly Lys Ser Cys Ala Leu Ile Thr
465             470                 475                 480 gac gga cgt ttc tct ggt ggc aca cat ggc ttt gtg gtt ggc cac att        1488
Asp Gly Arg Phe Ser Gly Gly Thr His Gly Phe Val Val Gly His Ile
            485                 490                 495 gtc ccc gaa gcg gtt gag ggt gga ttg att ggc ttg gtc gaa gat gat        1536
Val Pro Glu Ala Val Glu Gly Gly Leu Ile Gly Leu Val Glu Asp Asp
500                 505                 510 gat att atc gag att gat gcg gtc aat aac agc att agt ttg aaa gtt        1584
Asp Ile Ile Glu Ile Asp Ala Val Asn Asn Ser Ile Ser Leu Lys Val
            515                 520                 525 gct gac gat gag att gct aga cga cgt gcc aat tat caa aaa cct gct        1632
Ala Asp Asp Glu Ile Ala Arg Arg Arg Ala Asn Tyr Gln Lys Pro Ala
530                 535                 540 cct aaa gca acg cgt ggg gtt ctt gct aaa ttt gct aaa ctc acg cgc        1680
Pro Lys Ala Thr Arg Gly Val Leu Ala Lys Phe Ala Lys Leu Thr Arg
545                 550                 555                 560 cca gcc agt gaa ggc tgt gtg act gat tta tag                            1713
Pro Ala Ser Glu Gly Cys Val Thr Asp Leu
                565                 570

<210> SEQ ID NO 131
<211> LENGTH: 570
<212> TYPE: PRT
<213> ORGANISM: Lactococcus lactis

<400> SEQUENCE: 131

Met Glu Phe Lys Tyr Asn Gly Lys Val Glu Ser Ile Glu Leu Asn Lys
1               5                   10                  15

Tyr Ser Lys Thr Leu Thr Gln Asp Pro Thr Gln Pro Ala Thr Gln Ala
            20                  25                  30

Met His Tyr Gly Ile Gly Phe Lys Asp Glu Asp Phe Lys Lys Ala Gln
        35                  40                  45

Val Gly Ile Val Ser Met Asp Trp Asp Gly Asn Pro Cys Asn Met His
    50                  55                  60

Leu Gly Thr Leu Gly Ser Lys Ile Lys Asn Ser Val Asn Gln Thr Asp
65                  70                  75                  80

Gly Leu Ile Gly Leu Gln Phe His Thr Ile Gly Val Ser Asp Gly Ile
                85                  90                  95

Ala Asn Gly Lys Leu Gly Met Arg Tyr Ser Leu Val Ser Arg Glu Val
            100                 105                 110

Ile Ala Asp Ser Ile Glu Thr Asn Ala Gly Ala Glu Tyr Tyr Asp Ala
        115                 120                 125

Ile Val Ala Val Pro Gly Cys Asp Lys Asn Met Pro Gly Ser Ile Ile
    130                 135                 140

Gly Met Ala Arg Leu Asn Arg Pro Ser Ile Met Val Tyr Gly Gly Thr
145                 150                 155                 160

Ile Glu His Gly Glu Tyr Lys Gly Glu Lys Leu Asn Ile Val Ser Ala
                165                 170                 175

Phe Glu Ala Leu Gly Gln Lys Ile Thr Gly Asn Ile Ser Glu Glu Asp
            180                 185                 190

Tyr His Gly Val Ile Cys Asn Ala Ile Pro Gly Gln Gly Ala Cys Gly
        195                 200                 205

Gly Met Tyr Thr Ala Asn Thr Leu Ala Ser Ala Ile Glu Thr Leu Gly
    210                 215                 220

Met Ser Leu Pro Tyr Ser Ala Ser Asn Pro Ala Val Ser Gln Glu Lys
```

```
                225                 230                 235                 240
Glu Asp Glu Cys Asp Glu Ile Gly Leu Ala Ile Lys Asn Leu Leu Glu
                    245                 250                 255
Lys Asp Ile Lys Pro Ser Asp Ile Met Thr Lys Glu Ala Phe Glu Asn
                260                 265                 270
Ala Ile Thr Ile Val Met Val Leu Gly Gly Ser Thr Asn Ala Val Leu
                275                 280                 285
His Ile Ile Ala Met Ala Asn Ala Ile Gly Val Glu Ile Thr Gln Asp
            290                 295                 300
Asp Phe Gln Arg Ile Ser Asp Val Thr Pro Val Leu Gly Asp Phe Lys
305                 310                 315                 320
Pro Ser Gly Lys Tyr Met Met Glu Asp Leu His Lys Ile Gly Gly Val
                        325                 330                 335
Pro Ala Val Leu Lys Tyr Leu Leu Lys Glu Gly Lys Leu His Gly Asp
                    340                 345                 350
Cys Leu Thr Val Thr Gly Lys Thr Leu Ala Glu Asn Val Glu Thr Ala
                355                 360                 365
Leu Asp Leu Asp Phe Asp Ser Gln Asp Ile Ile Arg Pro Leu Glu Asn
        370                 375                 380
Pro Ile Lys Ala Thr Gly His Leu Gln Ile Leu Tyr Gly Asn Leu Ala
385                 390                 395                 400
Glu Gly Gly Ser Val Ala Lys Ile Ser Gly Lys Glu Gly Glu Phe Phe
                    405                 410                 415
Lys Gly Thr Ala Arg Val Phe Asp Gly Glu Gln His Phe Ile Asp Gly
                420                 425                 430
Ile Glu Ser Gly Arg Leu His Ala Gly Asp Val Ala Val Ile Arg Asn
            435                 440                 445
Ile Gly Pro Val Gly Gly Pro Gly Met Pro Glu Met Leu Lys Pro Thr
        450                 455                 460
Ser Ala Leu Ile Gly Ala Gly Leu Gly Lys Ser Cys Ala Leu Ile Thr
465                 470                 475                 480
Asp Gly Arg Phe Ser Gly Gly Thr His Gly Phe Val Val Gly His Ile
                    485                 490                 495
Val Pro Glu Ala Val Glu Gly Gly Leu Ile Gly Leu Val Glu Asp Asp
                500                 505                 510
Asp Ile Ile Glu Ile Asp Ala Val Asn Asn Ser Ile Ser Leu Lys Val
            515                 520                 525
Ala Asp Asp Glu Ile Ala Arg Arg Arg Ala Asn Tyr Gln Lys Pro Ala
        530                 535                 540
Pro Lys Ala Thr Arg Gly Val Leu Ala Lys Phe Ala Lys Leu Thr Arg
545                 550                 555                 560
Pro Ala Ser Glu Gly Cys Val Thr Asp Leu
                    565                 570

<210> SEQ ID NO 132
<211> LENGTH: 1641
<212> TYPE: DNA
<213> ORGANISM: Artificial sequence
<220> FEATURE:
<223> OTHER INFORMATION: Macrococcus caseolyticus 2-ketoisovalerate
      decarboxylase
<220> FEATURE:
<221> NAME/KEY: CDS
<222> LOCATION: (1)..(1641)

<400> SEQUENCE: 132
```

```
atg aaa caa cgt atc ggg caa tac ttg atc gat gcc cta cac gtt aat      48
Met Lys Gln Arg Ile Gly Gln Tyr Leu Ile Asp Ala Leu His Val Asn
1               5                   10                  15 ggt gtc gat aag atc ttt gga gtc cca ggt gat ttc act tta gcc ttt      96
Gly Val Asp Lys Ile Phe Gly Val Pro Gly Asp Phe Thr Leu Ala Phe
                20                  25                  30 ttg gac gat atc ata aga cat gac aac gtg gaa tgg gtg gga aat act     144
Leu Asp Asp Ile Ile Arg His Asp Asn Val Glu Trp Val Gly Asn Thr
            35                  40                  45 aat gag ttg aac gcc gct tac gcc gct gat ggt tac gct aga gtt aat     192
Asn Glu Leu Asn Ala Ala Tyr Ala Ala Asp Gly Tyr Ala Arg Val Asn
        50                  55                  60 gga tta gcc gct gta tct acc act ttt ggg gtt ggc gag tta tct gct     240
Gly Leu Ala Ala Val Ser Thr Thr Phe Gly Val Gly Glu Leu Ser Ala
65                  70                  75                  80 gtg aat ggt att gct gga agt tac gca gag cgt gtt cct gta atc aaa     288
Val Asn Gly Ile Ala Gly Ser Tyr Ala Glu Arg Val Pro Val Ile Lys
                85                  90                  95 atc tca ggc ggt cct tca tca gtt gct caa caa gag ggt aga tat gtc     336
Ile Ser Gly Gly Pro Ser Ser Val Ala Gln Gln Glu Gly Arg Tyr Val
            100                 105                 110 cac cat tca ttg ggt gaa gga atc ttt gat tca tat tca aag atg tac     384
His His Ser Leu Gly Glu Gly Ile Phe Asp Ser Tyr Ser Lys Met Tyr
        115                 120                 125 gct cac ata acc gca aca act aca atc tta tcc gtt gac aac gca gtc     432
Ala His Ile Thr Ala Thr Thr Thr Ile Leu Ser Val Asp Asn Ala Val
130                 135                 140 gac gaa att gat aga gtt att cat tgt gct ttg aag gaa aag agg cca     480
Asp Glu Ile Asp Arg Val Ile His Cys Ala Leu Lys Glu Lys Arg Pro
145                 150                 155                 160 gtg cat att cat ttg cct att gac gta gcc tta act gag att gaa atc     528
Val His Ile His Leu Pro Ile Asp Val Ala Leu Thr Glu Ile Glu Ile
                165                 170                 175 cct cat gca cca aaa gtt tac aca cac gaa tcc cag aac gtc gat gct     576
Pro His Ala Pro Lys Val Tyr Thr His Glu Ser Gln Asn Val Asp Ala
            180                 185                 190 tac att caa gct gtt gag aaa aag tta atg tct gca aaa caa cca gta     624
Tyr Ile Gln Ala Val Glu Lys Lys Leu Met Ser Ala Lys Gln Pro Val
        195                 200                 205 atc ata gca ggt cat gaa atc aat tca ttc aag ttg cac gaa caa ctg     672
Ile Ile Ala Gly His Glu Ile Asn Ser Phe Lys Leu His Glu Gln Leu
210                 215                 220 gaa cag ttt gtc aat cag aca aac atc cct gtt gca caa ctt tcc ttg     720
Glu Gln Phe Val Asn Gln Thr Asn Ile Pro Val Ala Gln Leu Ser Leu
225                 230                 235                 240 ggt aag tct gct ttc aat gaa gag aat gaa cat tac ctt ggt atc tac     768
Gly Lys Ser Ala Phe Asn Glu Glu Asn Glu His Tyr Leu Gly Ile Tyr
                245                 250                 255 gat ggc aaa atc gca aag gaa aat gtg aga gag tac gtc gac aat gct     816
Asp Gly Lys Ile Ala Lys Glu Asn Val Arg Glu Tyr Val Asp Asn Ala
            260                 265                 270 gat gtc ata ttg aac ata ggt gcc aaa ctg act gat tct gct aca gct     864
Asp Val Ile Leu Asn Ile Gly Ala Lys Leu Thr Asp Ser Ala Thr Ala
        275                 280                 285 gga ttt tcc tac aag ttc gat aca aac aac ata atc tac att aac cat     912
Gly Phe Ser Tyr Lys Phe Asp Thr Asn Asn Ile Ile Tyr Ile Asn His
290                 295                 300 aat gac ttc aaa gct gaa gat gtg att tct gat aat gtt tca ctg att     960
Asn Asp Phe Lys Ala Glu Asp Val Ile Ser Asp Asn Val Ser Leu Ile
305                 310                 315                 320
```

```
gat ctt gtg aat ggc ctg aat tct att gac tat aga aat gaa aca cac    1008
Asp Leu Val Asn Gly Leu Asn Ser Ile Asp Tyr Arg Asn Glu Thr His
            325                 330                 335 tac cca tct tat caa aga tct gat atg aaa tac gaa ttg aat gac gca    1056
Tyr Pro Ser Tyr Gln Arg Ser Asp Met Lys Tyr Glu Leu Asn Asp Ala
        340                 345                 350 cca ctt aca caa tct aac tat ttc aaa atg atg aac gct ttt cta gaa    1104
Pro Leu Thr Gln Ser Asn Tyr Phe Lys Met Met Asn Ala Phe Leu Glu
    355                 360                 365 aaa gat gac atc cta cta gct gaa caa ggt aca tcc ttt ttc ggc gca    1152
Lys Asp Asp Ile Leu Leu Ala Glu Gln Gly Thr Ser Phe Phe Gly Ala
370                 375                 380 tat gac tta tcc cta tac aag gga aat cag ttt atc ggt cag cct tta    1200
Tyr Asp Leu Ser Leu Tyr Lys Gly Asn Gln Phe Ile Gly Gln Pro Leu
385                 390                 395                 400 tgg ggg tca ata ggg tat act ttt cca tct tta cta gga agt caa cta    1248
Trp Gly Ser Ile Gly Tyr Thr Phe Pro Ser Leu Leu Gly Ser Gln Leu
            405                 410                 415 gca gac atg cat agg aga aac att ttg ctt ata ggc gat ggt agt tta    1296
Ala Asp Met His Arg Arg Asn Ile Leu Leu Ile Gly Asp Gly Ser Leu
        420                 425                 430 caa ctt act gtt caa gcc cta agt aca atg att aga aag gat atc aaa    1344
Gln Leu Thr Val Gln Ala Leu Ser Thr Met Ile Arg Lys Asp Ile Lys
    435                 440                 445 cca atc att ttc gtt atc aat aac gac ggt tac acc gtc gaa aga ctt    1392
Pro Ile Ile Phe Val Ile Asn Asn Asp Gly Tyr Thr Val Glu Arg Leu
450                 455                 460 atc cac ggc atg gaa gag cca tac aat gat atc caa atg tgg aac tac    1440
Ile His Gly Met Glu Glu Pro Tyr Asn Asp Ile Gln Met Trp Asn Tyr
465                 470                 475                 480 aag caa ttg cca gaa gta ttt ggt gga aaa gat act gta aaa gtt cat    1488
Lys Gln Leu Pro Glu Val Phe Gly Gly Lys Asp Thr Val Lys Val His
            485                 490                 495 gat gct aaa acc tcc aac gaa ctg aaa act gta atg gat tct gtt aaa    1536
Asp Ala Lys Thr Ser Asn Glu Leu Lys Thr Val Met Asp Ser Val Lys
        500                 505                 510 gca gac aaa gat cac atg cat ttc att gaa gtg cat atg gca gta gag    1584
Ala Asp Lys Asp His Met His Phe Ile Glu Val His Met Ala Val Glu
    515                 520                 525 gac gcc cca aag aag ttg att gat ata gct aaa gcc ttt agt gat gct    1632
Asp Ala Pro Lys Lys Leu Ile Asp Ile Ala Lys Ala Phe Ser Asp Ala
530                 535                 540 aac aag taa                                                        1641
Asn Lys
545

<210> SEQ ID NO 133
<211> LENGTH: 546
<212> TYPE: PRT
<213> ORGANISM: Artificial sequence
<220> FEATURE:
<223> OTHER INFORMATION: Synthetic Construct

<400> SEQUENCE: 133

Met Lys Gln Arg Ile Gly Gln Tyr Leu Ile Asp Ala Leu His Val Asn
1               5                   10                  15

Gly Val Asp Lys Ile Phe Gly Val Pro Gly Asp Phe Thr Leu Ala Phe
            20                  25                  30

Leu Asp Asp Ile Ile Arg His Asp Asn Val Glu Trp Val Gly Asn Thr
        35                  40                  45
```

```
Asn Glu Leu Asn Ala Ala Tyr Ala Ala Asp Gly Tyr Ala Arg Val Asn
     50                  55                  60

Gly Leu Ala Ala Val Ser Thr Thr Phe Gly Val Gly Glu Leu Ser Ala
 65              70                  75                  80

Val Asn Gly Ile Ala Gly Ser Tyr Ala Glu Arg Val Pro Val Ile Lys
                 85                  90                  95

Ile Ser Gly Gly Pro Ser Ser Val Ala Gln Gln Glu Gly Arg Tyr Val
                100                 105                 110

His His Ser Leu Gly Glu Gly Ile Phe Asp Ser Tyr Ser Lys Met Tyr
            115                 120                 125

Ala His Ile Thr Ala Thr Thr Thr Ile Leu Ser Val Asp Asn Ala Val
            130                 135                 140

Asp Glu Ile Asp Arg Val Ile His Cys Ala Leu Lys Glu Lys Arg Pro
145                 150                 155                 160

Val His Ile His Leu Pro Ile Asp Val Ala Leu Thr Glu Ile Glu Ile
                165                 170                 175

Pro His Ala Pro Lys Val Tyr Thr His Glu Ser Gln Asn Val Asp Ala
                180                 185                 190

Tyr Ile Gln Ala Val Glu Lys Lys Leu Met Ser Ala Lys Gln Pro Val
        195                 200                 205

Ile Ile Ala Gly His Glu Ile Asn Ser Phe Lys Leu His Glu Gln Leu
        210                 215                 220

Glu Gln Phe Val Asn Gln Thr Asn Ile Pro Val Ala Gln Leu Ser Leu
225                 230                 235                 240

Gly Lys Ser Ala Phe Asn Glu Glu Asn Glu His Tyr Leu Gly Ile Tyr
                245                 250                 255

Asp Gly Lys Ile Ala Lys Glu Asn Val Arg Glu Tyr Val Asp Asn Ala
                260                 265                 270

Asp Val Ile Leu Asn Ile Gly Ala Lys Leu Thr Asp Ser Ala Thr Ala
        275                 280                 285

Gly Phe Ser Tyr Lys Phe Asp Thr Asn Asn Ile Ile Tyr Ile Asn His
        290                 295                 300

Asn Asp Phe Lys Ala Glu Asp Val Ile Ser Asp Asn Val Ser Leu Ile
305                 310                 315                 320

Asp Leu Val Asn Gly Leu Asn Ser Ile Asp Tyr Arg Asn Glu Thr His
                325                 330                 335

Tyr Pro Ser Tyr Gln Arg Ser Asp Met Lys Tyr Glu Leu Asn Asp Ala
                340                 345                 350

Pro Leu Thr Gln Ser Asn Tyr Phe Lys Met Met Asn Ala Phe Leu Glu
        355                 360                 365

Lys Asp Asp Ile Leu Leu Ala Glu Gln Gly Thr Ser Phe Phe Gly Ala
        370                 375                 380

Tyr Asp Leu Ser Leu Tyr Lys Gly Asn Gln Phe Ile Gly Gln Pro Leu
385                 390                 395                 400

Trp Gly Ser Ile Gly Tyr Thr Phe Pro Ser Leu Leu Gly Ser Gln Leu
                405                 410                 415

Ala Asp Met His Arg Arg Asn Ile Leu Leu Ile Gly Asp Gly Ser Leu
                420                 425                 430

Gln Leu Thr Val Gln Ala Leu Ser Thr Met Ile Arg Lys Asp Ile Lys
        435                 440                 445

Pro Ile Ile Phe Val Ile Asn Asn Asp Gly Tyr Thr Val Glu Arg Leu
        450                 455                 460
```

```
Ile His Gly Met Glu Glu Pro Tyr Asn Asp Ile Gln Met Trp Asn Tyr
465                 470                 475                 480

Lys Gln Leu Pro Glu Val Phe Gly Gly Lys Asp Thr Val Lys Val His
            485                 490                 495

Asp Ala Lys Thr Ser Asn Glu Leu Lys Thr Val Met Asp Ser Val Lys
        500                 505                 510

Ala Asp Lys Asp His Met His Phe Ile Glu Val His Met Ala Val Glu
    515                 520                 525

Asp Ala Pro Lys Lys Leu Ile Asp Ile Ala Lys Ala Phe Ser Asp Ala
530                 535                 540

Asn Lys
545

<210> SEQ ID NO 134
<211> LENGTH: 348
<212> TYPE: PRT
<213> ORGANISM: Artificial sequence
<220> FEATURE:
<223> OTHER INFORMATION: Achromobacter xylosoxidans alcohol
      dehydrogenase

<400> SEQUENCE: 134

Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
            35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270
```

-continued

```
Phe Glu Ile Gln Lys Leu Trp Ile Lys Asn Leu Thr Ile Thr Thr Gly
            275                 280                 285

Leu Val Asn Thr Asn Thr Thr Pro Met Leu Met Lys Val Ala Ser Thr
290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345

<210> SEQ ID NO 135
<211> LENGTH: 571
<212> TYPE: PRT
<213> ORGANISM: Artificial Sequence
<220> FEATURE:
<223> OTHER INFORMATION: Bacillus subtilis

<400> SEQUENCE: 135

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285
```

```
Pro Ile Glu Tyr Asp Pro Lys Phe Trp Asn Ile Asn Gly Asp Arg Thr
            290                 295                 300
Ile Ile His Leu Asp Glu Ile Ile Ala Asp Ile Asp His Ala Tyr Gln
305                 310                 315                 320
Pro Asp Leu Glu Leu Ile Gly Asp Ile Pro Ser Thr Ile Asn His Ile
                325                 330                 335
Glu His Asp Ala Val Lys Val Glu Phe Ala Glu Arg Glu Gln Lys Ile
            340                 345                 350
Leu Ser Asp Leu Lys Gln Tyr Met His Glu Gly Glu Gln Val Pro Ala
                355                 360                 365
Asp Trp Lys Ser Asp Arg Ala His Pro Leu Glu Ile Val Lys Glu Leu
370                 375                 380
Arg Asn Ala Val Asp Asp His Val Thr Val Thr Cys Asp Ile Gly Ser
385                 390                 395                 400
His Ala Ile Trp Met Ser Arg Tyr Phe Arg Ser Tyr Glu Pro Leu Thr
                405                 410                 415
Leu Met Ile Ser Asn Gly Met Gln Thr Leu Gly Val Ala Leu Pro Trp
                420                 425                 430
Ala Ile Gly Ala Ser Leu Val Lys Pro Gly Glu Lys Val Val Ser Val
            435                 440                 445
Ser Gly Asp Gly Gly Phe Leu Phe Ser Ala Met Glu Leu Glu Thr Ala
450                 455                 460
Val Arg Leu Lys Ala Pro Ile Val His Ile Val Trp Asn Asp Ser Thr
465                 470                 475                 480
Tyr Asp Met Val Ala Phe Gln Gln Leu Lys Lys Tyr Asn Arg Thr Ser
                485                 490                 495
Ala Val Asp Phe Gly Asn Ile Asp Ile Val Lys Tyr Ala Glu Ser Phe
                500                 505                 510
Gly Ala Thr Gly Leu Arg Val Glu Ser Pro Asp Gln Leu Ala Asp Val
            515                 520                 525
Leu Arg Gln Gly Met Asn Ala Glu Gly Pro Val Ile Ile Asp Val Pro
                530                 535                 540
Val Asp Tyr Ser Asp Asn Ile Asn Leu Ala Ser Asp Lys Leu Pro Lys
545                 550                 555                 560
Glu Phe Gly Glu Leu Met Lys Thr Lys Ala Leu
                565                 570

<210> SEQ ID NO 136
<211> LENGTH: 491
<212> TYPE: PRT
<213> ORGANISM: Artificial sequence
<220> FEATURE:
<223> OTHER INFORMATION: Escherichia coli ketol-acid reductoisomerase

<400> SEQUENCE: 136

Met Ala Asn Tyr Phe Asn Thr Leu Asn Leu Arg Gln Gln Leu Ala Gln
1               5                   10                  15
Leu Gly Lys Cys Arg Phe Met Gly Arg Asp Glu Phe Ala Asp Gly Ala
            20                  25                  30
Ser Tyr Leu Gln Gly Lys Lys Val Val Ile Val Gly Cys Gly Ala Gln
        35                  40                  45
Gly Leu Asn Gln Gly Leu Asn Met Arg Asp Ser Gly Leu Asp Ile Ser
    50                  55                  60
Tyr Ala Leu Arg Lys Glu Ala Ile Ala Glu Lys Arg Ala Ser Trp Arg
65                  70                  75                  80
```

```
Lys Ala Thr Glu Asn Gly Phe Lys Val Gly Thr Tyr Glu Glu Leu Ile
                85                  90                  95
Pro Gln Ala Asp Leu Val Ile Asn Leu Thr Pro Asp Lys Gln His Ser
            100                 105                 110
Asp Val Val Arg Thr Val Gln Pro Leu Met Lys Asp Gly Ala Ala Leu
        115                 120                 125
Gly Tyr Ser His Gly Phe Asn Ile Val Glu Val Gly Glu Gln Ile Arg
    130                 135                 140
Lys Asp Ile Thr Val Val Met Val Ala Pro Lys Cys Pro Gly Thr Glu
145                 150                 155                 160
Val Arg Glu Glu Tyr Lys Arg Gly Phe Gly Val Pro Thr Leu Ile Ala
                165                 170                 175
Val His Pro Glu Asn Asp Pro Lys Gly Glu Gly Met Ala Ile Ala Lys
            180                 185                 190
Ala Trp Ala Ala Ala Thr Gly Gly His Arg Ala Gly Val Leu Glu Ser
        195                 200                 205
Ser Phe Val Ala Glu Val Lys Ser Asp Leu Met Gly Glu Gln Thr Ile
    210                 215                 220
Leu Cys Gly Met Leu Gln Ala Gly Ser Leu Leu Cys Phe Asp Lys Leu
225                 230                 235                 240
Val Glu Glu Gly Thr Asp Pro Ala Tyr Ala Glu Lys Leu Ile Gln Phe
                245                 250                 255
Gly Trp Glu Thr Ile Thr Glu Ala Leu Lys Gln Gly Gly Ile Thr Leu
            260                 265                 270
Met Met Asp Arg Leu Ser Asn Pro Ala Lys Leu Arg Ala Tyr Ala Leu
        275                 280                 285
Ser Glu Gln Leu Lys Glu Ile Met Ala Pro Leu Phe Gln Lys His Met
    290                 295                 300
Asp Asp Ile Ile Ser Gly Glu Phe Ser Ser Gly Met Met Ala Asp Trp
305                 310                 315                 320
Ala Asn Asp Asp Lys Lys Leu Leu Thr Trp Arg Glu Thr Gly Lys
                325                 330                 335
Thr Ala Phe Glu Thr Ala Pro Gln Tyr Glu Gly Lys Ile Gly Glu Gln
            340                 345                 350
Glu Tyr Phe Asp Lys Gly Val Leu Met Ile Ala Met Val Lys Ala Gly
        355                 360                 365
Val Glu Leu Ala Phe Glu Thr Met Val Asp Ser Gly Ile Ile Glu Glu
    370                 375                 380
Ser Ala Tyr Tyr Glu Ser Leu His Glu Leu Pro Leu Ile Ala Asn Thr
385                 390                 395                 400
Ile Ala Arg Lys Arg Leu Tyr Glu Met Asn Val Val Ile Ser Asp Thr
                405                 410                 415
Ala Glu Tyr Gly Asn Tyr Leu Phe Ser Tyr Ala Cys Val Pro Leu Leu
            420                 425                 430
Lys Pro Phe Met Ala Glu Leu Gln Pro Gly Asp Leu Gly Lys Ala Ile
        435                 440                 445
Pro Glu Gly Ala Val Asp Asn Gly Gln Leu Arg Asp Val Asn Glu Ala
    450                 455                 460
Ile Arg Ser His Ala Ile Glu Gln Val Gly Lys Lys Leu Arg Gly Tyr
465                 470                 475                 480
Met Thr Asp Met Lys Arg Ile Ala Val Ala Gly
                485                 490
```

<210> SEQ ID NO 137
<211> LENGTH: 338
<212> TYPE: PRT
<213> ORGANISM: Artificial sequence
<220> FEATURE:
<223> OTHER INFORMATION: Pseudomonas fluorescens ketol-acid reductoisomerase

<400> SEQUENCE: 137

```
Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
                20                  25                  30

Cys Asn Leu Lys Asp Ser Gly Val Asp Val Thr Val Gly Leu Arg Lys
            35                  40                  45

Gly Ser Ala Thr Val Ala Lys Ala Glu Ala His Gly Leu Lys Val Thr
        50                  55                  60

Asp Val Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Gly Glu Gln Leu
305                 310                 315                 320

Arg Ser Met Met Pro Trp Ile Gly Ala Asn Lys Ile Val Asp Lys Ala
                325                 330                 335

Lys Asn
```